US007045529B2

(12) United States Patent
Wilde et al.

(10) Patent No.: US 7,045,529 B2
(45) Date of Patent: *May 16, 2006

(54) IMIDAZOPYRIMIDINYL AND IMIDAZOPYRIDINYL DERIVATIVES

(75) Inventors: Richard G. Wilde, Newark, DE (US); Rajagopal Bakthavatchalam, Wilmington, DE (US); James P. Beck, Kalamazoo, MI (US); Argyrios Arvanitis, Kennett Square, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 315 days.

This patent is subject to a terminal disclaimer.

(21) Appl. No.: 09/738,666

(22) Filed: Dec. 15, 2000

(65) Prior Publication Data

US 2004/0229887 A1 Nov. 18, 2004

Related U.S. Application Data

(60) Provisional application No. 60/172,262, filed on Dec. 17, 1999.

(51) Int. Cl.
*A61K 31/437* (2006.01)
*C07D 471/04* (2006.01)

(52) U.S. Cl. ...................... 514/303; 546/118

(58) Field of Classification Search ................ 514/303; 546/118
See application file for complete search history.

(56) References Cited

U.S. PATENT DOCUMENTS

| 4,950,802 | A | | 8/1990 | Nader ........................ 568/655 |
| 5,446,160 | A | * | 8/1995 | Stucky et al. ............... 546/118 |
| 6,362,180 | B1 | * | 3/2002 | Wilde et al. ............. 514/234.2 |
| 6,642,230 | B1 | * | 11/2003 | Wilde et al. ............. 514/234.2 |

FOREIGN PATENT DOCUMENTS

| WO | WO 95/10506 | 4/1995 |
| WO | WO 95/33727 | 12/1995 |
| WO | WO 95/33750 | 12/1995 |
| WO | WO 95/34563 | 12/1995 |
| WO | WO 98/35967 | 8/1998 |

OTHER PUBLICATIONS

Arató, M., et al., "Elevated CSF CRF in suicide victims," *Biol. Psychiatry*, 1989, 25, 355–359.
Banki, C.M., et al., "CSF corticotrophin–releasing factor–like immunoreactivity in depression and schizophrenia," *Am. J. Psychiatry*, 1987, 144(7), 873–877.
Berridge, C.W., et al., "A corticotrophin–releasing factor antagonist reverses the stress–induced changes of exploratory behavior in mice," *Horm. & Behav.*, 1987, 21, 393–401.

Berridge, C.W., et al., "Corticotropin–releasingfactor elicits naloxone sensitive stress–like alterations in exploratory behavior in mice," *Regul. Peptides*, 1986, 16, 83–93.
Blalock, J.E., "A molecular basis for bidirectional communication between the immune and neuroendocrine systems," *Physiological Reviews*, 1989, 69(1), 1–32.
Britton, D.R., et al., "Intraventricular corticotrophin–releasing factor enhances behavioral effects of novelty," *Life Sci.*, 1982, 31, 363–367.
Britton, K.T., et al., "Chlordiazepoxide attenuates response suppression induced by corticotrophin–releasing factor in the conflict test," *Psychopharmacology*, 1985, 86, 170–174.
Britton, K.T., et al., "Corticotropin releasing factor and amphetamine exaggerate partial agonist properties of benzodiazepine antagonist Ro 15–1788," *Psychopharmacology*, 1988, 94, 306–311.
Brown, D.J., et al., "Purine studies. Part XI. Condensation of tetraethoxymethanine and similar orthocarbonates with *ortho*–diamines to give 8–ethoxypurines and related fused imidazoles," *J. Chem. Soc., Perkin Trans.*, 1974, 1, 349–352.
Camps, F., et al., "A simple method for preparation of Aryl 2,2,2–Tri–fluoroethyl ethers," *Synthesis*, 1980, pp. 727–728.
De Souza, E.B., et al., "Corticotropin–releasing factor receptors and widely distributed within the rat central nervous system: an autoradiographic study," *J. Neurosci.*, 1985, 5(12), 3189–3203.

(Continued)

*Primary Examiner*—Patricia L. Morris
(74) *Attorney, Agent, or Firm*—Shah R. Makujina

(57) ABSTRACT

Provided herein are compounds of the formula (I):

(I)

$$\begin{array}{c} R^1 \\ | \\ N \\ R^2-X-\underset{N}{\overset{}{\diagdown}}\underset{}{\overset{A}{\diagdown}}R^3 \\ \phantom{R^2-X-}B \\ \phantom{R^2-X-}D \end{array}$$

as well as stereoisomers and pharmaceutically acceptable salts thereof. Such compounds are, because of their ability to antagonize CRF, useful in the treatment of a variety of disorders characterized by execssive CRF expression. These include, for example: affective disorder, anxiety, depression, headache, irritable bowel syndrome, post-traumatic stress disorder, supranuclear palsy, immune suppression, Alzheimer's disease, Huntington's disease, Parkinson's disease, amyotrophic lateral sclerosis, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis and hypoglycemia.

21 Claims, No Drawings

OTHER PUBLICATIONS

De Souza, E.B., "CRH defects in alzheimer's and other neurologic diseases," *Hosp. Practice,* 1988, 23, 59–71.

Dunn, A.J., et al., "Physiological and behavioral responses to corticotrophin–releasing factor administration: is CRF a mediator of anxiety or stress responses?, " *Brain Res. Rev.,* 1990, 15, 71–100.

France, R.D., et al., "CSF corticotrophin–releasing factor–like immunoactivity in chronic pain patients with and without major depression," *Biol. Psychiatry,* 1988, 23, 86–88.

Gold, P.W., et al., "Psychiatric implications of basic and clinical studies with corticotrophin–releasing factor," *Am. J. Psychiatry,* 1984, 141(5), 619–627.

Gold., P.W., et al., "responses to corticotrophin–releasing hormone in the hypercortisolism of depression and cushing's disease," *New Eng. J. Med.,* 1986, 314(21), 1329–1335.

Grigoriadis, D.E., et al., "Effects of chronic antidepressant and benzodiazepine treatment on corticotrophin–releasing–factor receptors in rat brain and pituitary," *Neuropsychopharmacology,* 1989, 2(1), 53–60.

Grimmett, M.R., "Imidazoles and their benzo derivatives: (iii) synthesis and applications," *Comprehensive Heterocyclic Chemistry, Pergamon Press,* 1984, vol. 5, Part 4A, Katritzky A.R., et al. (Eds.),457–498.

Grinberg, V.A., et al., "Electrochemical perfluoroalkoxylation of aromatic compounds," Russian Chem. Bull., 1997, 46(8), 1441–1444.

Holsboer, F., et al., "Acth and multisteroid responses to corticotrophin–releasing factor in depressive illness: relationship to multisteroid responses after acth stimulation and dexamethasone suppression," *Psychoneuroendocrinology,* 1984, 9(2), 147–160.

Huynh, C., et al., "Copper–catalysed reactions of grignard reagents with epoxides and oxetane," *Tetrah. Letts.,* 1979, 17, 1503–1506.

Koob, G.F., et al., in *Corticotropin–Releasing Factor: Basic and Clinical Studies of a Neuropeptide,* De Souza, E.B., et al. (Eds.), CRC Press, 1990, 17, 253–265.

Koob, G.F., "Stress, corticotrophin–releasing factor, and behavior," *Persp. On Behav. Med.,* 1985, 2, 39–52.

Kuroboshi, M., et al., "Oxidative desulfurization–fluorination of xanthates. A convenient synthesis of trifluoromethyl ethers and difluoro(methylthio)methyl ethers," *Tetrah. Letts.,* 1992, 33(29), 4173–4176.

Mathey, F., et al., "Reaction De $MoF_6$ avec les chlorothioformiates d'aryle nouvelle synthese des aryl trifluoromethylethers $ArOCF_3$, " *Tetrah. Letts.,* 1973, 25, 2253–2256.

Mitsunobu, O., "The use of diethyl azodicarboxylate and triphenylphosphine in synthesis and transformation of natural products," *Synthesis,* 1981, 1–28.

Montgomery, J.A., et al., "Synthesis of potential anticancer agents. XXII. Reactions of orthoesters with 4,5–diaminopyrimidines," *J. Org. Chem.,* 1960, 25, 395–399.

Morley, J.E., "Minireview—neuropeptides: conductors of the immune orchestra," *Life Sci.,* 1987, 41, 527–544.

Negishi, E.–I., et al., "Selective carbon–carbon bond formation via transition metal catalysis 3. [1] A highly selective synthesis of unsymmetrical biaryls and diarylmethanes by the nickel–or palladium–catalyzed reaction of aryl–and benzylzinc derivaives with aryl halides," *J. Org. Chem.,* 1977, 42(10), 1821–1823.

Nemeroff, C.B., et al., "Elevated concentrations of SF corticotrophin–releasing factor–like immunoreactivity in depressed patients," *Science,* 1984, 226, 1342–1344.

Nemeroff, C.B., et al., "Reduced corticotrophin releasing factor binding sites in the frontal cortex of suicide victims," *Arch. Gen. Psychiatry,* 1988, 45, 577–579.

Preschler, D., et al., "Various synthetic approaches to fluoroalkyl p–nitrophenyl ethers," *J. Fluorine Chem.,* 1996, 79, 145–148.

*Remington's Pharmaceutical Sciences,* $17^{th}$ Ed., Mack Publishing Co., 1985, p. 1418.

Rivier, J., et al., "Characterization of rat hypothalamic corticotrophin–releasing factor," *Proc. Nat. Acad. Sci. USA,* 1983, 80, 4851–4855.

Sapolsky, R.M., "Hypercortisolism among socially subordinate wild baboons originates at the CNS level," *Arch. Gen. Psychiatry,* 1989, 46, 1047–1051.

Sato, M., et al., "Cross–coupling reaction of alkyl– or arylboronic acid esters with organic halides induced by thallium(I) salts and palladium–catalyst," *Chem. Letts.,* 1989, 1405–1408.

Shelyazhenko, S.V., et al., "Synthesis and reactions of difluromethoxy– and difluorochloromethoxy derivatives of benzene," *J. Org. Chem. (Russia),* 1992, 28(8), 1317–1323.

Swerdlow, N.R., et al., "Corticotropin–releasing factor potentiates acoustic startle in rats: blockade by chlordiazepoxide," *Psychopharmacology,* 1986, 88, 147–152.

Vale, W., et al., "Chemical and biological characterization of corticotrophin releasing factor," *Rec. Prog. Horm. Res.,* 1983, 39, 245–270.

Vale, W., et al., "Characterization of a 41–residue ovine hypothalamic peptide that stimulates secretion of corticotrophin and β–endorphin," *Science,* 1981, 213, 1394–1397.

* cited by examiner

IMIDAZOPYRIMIDINYL AND IMIDAZOPYRIDINYL DERIVATIVES

This application claims the benefit of U.S. Provisional Application No. 60/172,262, filed Dec. 17,1999.

FIELD OF THE INVENTION

The invention presented herein is directed to novel imidazopyrimidinyl and imidazopyridinyl derivatives, and to their use as CRF antagonists in the treatment of a variety of neurological and psychiatric disorders.

BACKGROUND OF THE INVENTION

Corticotropin releasing factor (herein referred to as CRF), a 41 amino acid peptide, is the primary physiological regulator of proopiomelanocortin (POMC)—derived peptide secretion from the anterior pituitary gland [J. Rivier et al., *Proc. Nat. Acad. Sci. (USA)* 80:4851 (1983); W. Vale et al., *Science* 213:1394 (1981)]. In addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in the brain [W. Vale et al., *Rec. Prog. Horm. Res.* 39:245 (1983); G. F. Koob, *Persp. Behav. Med.* 2:39 (1985); E. B. De Souza et al., *J. Neurosci.* 5:3189 (1985)]. There is also evidence that CRF plays a significant role in integrating the response of the immune system to physiological, psychological, and immunological stressors [J. E. Blalock, *Physiological Reviews* 69:1 (1989); J. E. Morley, *Life Sci.* 41:527 (1987)].

Clinical data provides evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis, as they relate to the dysfunction of CRF neurons in the central nervous system [for review see E. B. De Souza, *Hosp. Practice* 23:59 (1988)].

In affective disorder, or major depression, the concentration of CRF is significantly increased in the cerebral spinal fluid (CSF) of drug-free individuals [C. B. Nemeroff et al., *Science* 226:1342 (1984); C. M. Banki et al., *Am. J. Psychiatry* 144:873 (1987); R.D. France et al., *Biol. Psychiatry* 28:86 (1988); M. Arato et al., *Biol Psychiatry* 25:355 (1989)]. Furthermore, the density of CRF receptors is significantly decreased in the frontal cortex of suicide victims, consistent with a hypersecretion of CRF [C. B. Nemeroff et al., *Arch. Gen. Psychiatry* 45:577 (1988)]. In addition, there is a blunted adrenocorticotropin (ACTH) response to CRF (i.v. administered) observed in depressed patients [P. W. Gold et al., *Am J. Psychiatry* 141:619 (1984); F. Holsboer et al., *Psychoneuroendocrinology* 9:147 (1984); P. W. Gold et al., *New Eng. J. Med.* 314:1129 (1986)]. Preclinical studies in rats and non-human primates provide additional support for the hypothesis that hypersecretion of CRF may be involved in the symptoms seen in human depression [R. M. Sapolsky, *Arch. Gen. Psychiatry* 46:1047 (1989)]. There is preliminary evidence that tricyclic antidepressants can alter CRF levels and thus modulate the numbers of CRF receptors in the brain [Grigoriadis et al., *Neuropsychopharmacology* 2:53 (1989)].

Furthermore, CRF has been postulated to have a role in the etiology of anxiety-related disorders, and is known to produce anxiogenic effects in animals. Moreover, interactions between benzodiazepine/non-benzodiazepine anxiolytics and CRF have been demonstrated in a variety of behavioral anxiety models [D. R. Britton et al., *Life Sci.* 31:363 (1982); C. W. Berridge and A. J. Dunn *Regul. Peptides* 16:83 (1986)]. Preliminary studies using the putative CRF receptor antagonist α-helical ovine CRF (9–41) in a variety of behavioral paradigms demonstrate that the antagonist produces "anxiolytic-like" effects that are qualitatively similar to the benzodiazepines [C. W. Berridge and A. J. Dunn *Horm. Behav.* 21:393 (1987), *Brain Research Reviews* 15:71 (1990)].

Neurochemical, endocrine and receptor binding studies have all demonstrated interactions between CRF and benzodiazepine anxiolytics, providing further evidence for the involvement of CRF in these disorders. Chlordiazepoxide attenuates the "anxiogenic" effects of CRF in both the conflict test [K. T. Britton et al., *Psychopharmacology* 86:170 (1985); K. T. Britton et al., *Psychopharmacology* 94:306 (1988)] and in the acoustic startle test [N. R. Swerdlow et al., *Psychopharmacology* 88:147 (1986)] in rats. The benzodiazepine receptor antagonist (Ro15-1788), which was without behavioral activity alone in the operant conflict test, reversed the effects of CRF in a dose-dependent manner while the benzodiazepine inverse agonist (FG7142) enhanced the actions of CRF [K. T. Britton et al., *Psychopharmacology* 94:306 (1988)].

It has been further postulated that CRF has a role in immunological, cardiovascular or heart-related diseases such as hypertension, tachycardia and congestive heart failure, stroke, osteoporosis, premature birth, psychosocial dwarfism, stress-induced fever, ulcer, diarrhea, postoperative ileus and colonic hypersensitivity associated with psychopathological disturbance and stress.

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist (alpha helical CRF9–41) in a variety of behavioral paradigms have demonstrated that the CRF antagonist produces "anxiolytic-like" effects qualitatively similar to the benzodiazepines [for review see G. F. Koob and K. T. Britton, In: *Corticotropin-Releasing Factor: Basic and Clinical Studies of a Neuropeptide*, E. B. De Souza and C. B. Nemeroff eds., CRC Press p221 (1990)].

DuPont Merck PCT application US94/11050 describes corticotropin releasing factor antagonist compounds, and their use in treating psychiatric disorders and neurological diseases; however, said compounds do not have the same structures as do the compounds provided herein. Other compounds reported to have activity as corticotropin releasing factors are disclosed in WO 95/33750, WO 95/34563 and WO 95/33727; these compounds also do not have the structures of the compounds provided herein.

SUMMARY OF THE INVENTION

This invention provides compounds of the formula (I)

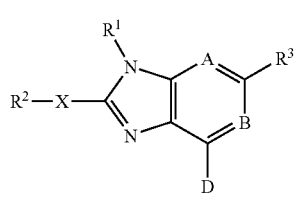

(I)

as well as stereoisomers and pharmaceutically acceptable salts thereof.

Preferably, A is N and B is CH, A is CH and B is N, or A and B are each N. D is preferably phenyl or 3-pyridyl. Each of these rings is substituted with 1–2 haloalkoxy groups, such substitution being at any available position of the ring. Most preferably, the haloalkoxy substitution is at least on the carbon atom of ring D which is furthest away on the ring from the carbon by which the ring is attached to the imidazopyridine or imidazopyrimidine ring (e.g., at the 4 position of the phenyl ring where ring D is phenyl). The haloalkoxy group is $C_{1-4}$ haloalkoxy, preferably —OCHF$_2$ or —OCF$_3$, and most preferably, —OCHF$_2$.

Most preferably, ring D has at least one substitution in addition to the single haloalkoxy substituent, said substitution being at any available position on the ring. Most preferably, said additional substitution is on that carbon atom of ring D which is adjacent to the carbon atom of ring D that is the point of attachment of ring D to the imidazopyridine or imidazopyrimidine ring (e.g., at the 2 position of the phenyl ring wherein ring D is phenyl); said additional substituent is preferably Cl or CH$_3$. Optionally, Ring D may also have a third substitution, said substitution being at any of the available positions on the ring.

Preferably, $R^2$ is CH$_3$ or C$_2$H$_5$, $R^3$ is H or CH$_3$, X is CH$_2$ or O, and $R^1$ is 2-butyl, 2-pentyl, 2-hexyl, 2-heptyl, 3-pentyl, 3-hexyl, 3-heptyl, 1-methoxy-3-pentyl, 4-heptyl, 1-cyclopropyl-1-ethyl, 1-cyclopropyl-1-propyl, 1-cyclopropyl-1-butyl, 1-cyclopropyl-3-methoxy-1-propyl, 1-cyclobutyl-1-ethyl, 1-cyclobutyl-1-propyl, 1-cyclobutyl-1-butyl, 1-cyclobutyl-3-methoxy-1-propyl, 1-cyclopentyl-1-ethyl, 1-cyclopentyl-1-propyl, 1-cyclopentyl-1-butyl, 1-cyclopentyl-3-methoxy-1-propyl, alpha-cyclopropylbenzyl, 1-phenyl-2-butyn-1-yl, 1-cyclopropyl-2-butyn-1-yl or dicyclopropylmethyl.

Also provided herein are compositions containing the compound of this invention, particularly pharmaceutical compositions comprising a pharmaceutically acceptable carrier and a therapeutically effective amount of the compound. Said compositions are useful, for example, in the alleviation of disorders the treatment of which can be effected or facilitated by antagonizing CRF. Such disorders include, without limitation: affective disorder, anxiety, depression, headache, irritable bowel syndrome, post-traumatic stress disorder, immune suppression, Huntington's disease, Parkinson's disease, progressive supranuclear palsy, amyotrophic lateral sclerosis, Alzheimer's disease, gastrointestinal diseases, anorexia nervosa or other feeding disorders, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis and hypoglycemia.

DETAILED DESCRIPTION OF THE INVENTION

This invention provides certain compounds, as well as stereoisomers thereof. Accordingly, compounds provided herein can have one or more asymmetric centers or planes, and all chiral (enantiomeric and diastereomeric) and racemic forms of the compounds are included in the present invention. Many geometric isomers of olefins, C═N double bonds, and the like can also be present in the compounds, and all such stable isomers are contemplated in the present invention. Compounds are isolated in either the racemic form, or in the optically pure form, for example, by resolution of the racemic form.

Pharmaceutically acceptable salts of compounds of this invention are also provided herein. The phrase "pharmaceutically acceptable" is employed to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, or alkali or organic salts of acidic residues such as carboxylic acids. Pharmaceutically acceptable salts include the conventional non-toxic salts or the quaternary ammonium salts of the parent compound formed, for example, from non-toxic inorganic or organic acids. Such conventional nontoxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

Pharmaceutically acceptable salt forms of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

In the compounds of this invention, "alkyl", means saturated hydrocarbon chains, branched or unbranched, having the specified number of carbon atoms. "Alkenyl" means hydrocarbon chains of either a straight or branched configuration and one or more unsaturated carbon-carbon bonds which may occur in any stable point along the chain, such as ethenyl, propenyl, and the like. "Alkynyl" means hydrocarbon chains of either a straight or branched configuration and one or more triple carbon-carbon bonds which may occur in any stable point along the chain, such as ethynyl, propynyl and the like. "Alkoxy" means an alkyl group of indicated number of carbon atoms attached through an oxygen bridge. "Cycloalkyl" means saturated ring groups, including mono-, bi- or polycyclic ring systems, such as cyclopropyl, cyclobutyl, cyclopentyl, cyclohexyl, and so forth. "Halo" or "halogen" means fluoro, chloro, bromo, and iodo. "Haloalkyl" means both branched and straight-chain alkyls having the specified number of carbon atoms, substituted with 1 or more halogen. "Haloalkoxy" means an alkoxy group substituted by at least one halogen atom.

"Substituted" means that one or more hydrogen on the designated atom is replaced with a selection from the indicated group, provided that the designated atom's normal valency is not exceeded, and that the substitution results in a stable compound. "Unsubstituted" atoms bear all of the hydrogen atoms dictated by their valency. When a substituent is keto, then 2 hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

Compounds provided herein are of the formula I:

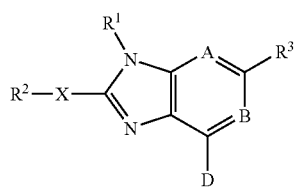

(I)

wherein A is N or C—$R^7$ and B is N or C—$R^8$, provided that at least one of A and B is N. $R^7$ and $R^8$ are each independently selected from H, $C_{1-4}$ alkyl, $C_{3-8}$ cycloalkyl, $C_{1-4}$ alkoxy, $C_{1-4}$ alkylthio, $C_{1-4}$ alkylsulfinyl, $C_{1-4}$ alkylsulfonyl, amino, $C_{1-4}$ alkylamino, $C_{2-8}$ dialkylamino, phenyl and phenyl substituted by 1–3 groups selected from $C_{1-7}$ alkyl, $C_{3-8}$ cycloalkyl, halogen, nitro, $C_{1-4}$ alkoxy, $C_{1-4}$ alkylthio and $C_{2-8}$ dialkylamino. In preferred embodiments of this invention, A is N and B is C—$R^8$, A is C—$R^8$ and B is N, or A and B are both N; where B is C—$R^8$, it is most preferably CH.

D is an aryl ring or a heteroaryl ring, aryl rings being 6-carbon, substituted or unsubstituted aromatic rings, or multiple condensed, substituted or unsubstituted 6-carbon rings, and heteroaryl rings being substituted or unsubstituted 5–10 membered mono or bicyclic aromatic rings containing from one to three heteroatoms selected from the group consisting of O, N or S. Aryl ring D is selected herein from phenyl, naphthyl, indanyl and indenyl. Heteroaryl ring D is selected herein from pyridyl, pyrimidyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzofuranyl, 2,3-dihydrobenzothienyl, the S-oxide of 2,3-dihydrobenzothienyl, the S,S-dioxide of 2,3-dihydrobenzothienyl, indolinyl, benzoxazolin-2-one-yl, benzodioxolanyl, and benzodioxanyl. Most preferably, ring D is either a phenyl ring or a 3-pyridyl ring.

Ring D herein is substituted by a $C_{1-4}$ alkoxy group, said substitution being at any of the available positions on the ring. Most preferably, where there is a single haloalkoxy substitution of ring D, the substitution is on the carbon atom of ring D which is furthest away on the ring from the carbon atom of ring D by which the ring is attached to the imidazopyridine or imidazopyrimidine ring (e.g., at the 4 position of the phenyl ring where ring D is phenyl). Alternatively, where there are multiple haloalkoxy substitutions of ring D, one of such substituents is preferably located on said carbon atom. The haloalkoxy group is $C_{1-4}$ haloalkoxy, preferably —$OCHF_2$ or —$OCF_3$, and most preferably, —$OCHF_2$.

Ring member atoms unoccupied by a haloalkoxy group can be unsubstituted or, optionally, substituted with 1–3 additional moieties; preferably at least one ring member in addition to the atom substituted with haloalkoxy is also substituted. Most preferably, the first of said additional substitutions is on the carbon atom adjacent to the carbon of ring D which is the point by which the ring is attached to the imidazopyridine or imidazopyrimidine ring (e.g., at the 2 position of the phenyl ring wherein ring D is phenyl). Such additional substituents are preferably selected independently from $C_{1-6}$ alkyl, $C_{3-6}$ cycloalkyl, $C_{2-6}$ alkenyl, $C_{2-6}$ alkynyl, halogen, $C_{1-4}$ haloalkyl, OH, $C_{1-4}$ alkoxy, ($C_{1-4}$ alkoxy)-$C_{1-4}$ alkoxy, CN, SH, $C_{1-4}$ alkylthio, $C_{1-4}$ alkylsulfinyl, $C_{1-4}$ alkylsulfonyl, $CR^{17}$, $CO_2R^{17}$ and $NR^{17}R^{19}$. $R^{17}$, $R^{18}$ and $R^{19}$ are independently selected at each occurrence thereof H, $C_{1-6}$ alkyl, $C_{3-10}$ cycloalkyl or $C_{4-16}$ cycloalkylalkyl.

Optionally, Ring D may also have a third substitution, or a second substitution in addition to the haloalkoxy substituent, said additional substitution being at any of the available positions on the ring. Preferably, said additional substitution is on a carbon atom between: (1) the carbon atom to which the haloalkoxy is preferably attached (e.g., the 4 position of the phenyl ring when ring D is phenyl) and, (2) the point of attachment of ring D to the imidazopyridine or imidazopyrimidine rings, and is also preferably further along the ring than is the haloalkoxy substituent (e.g., at the 5 or 6 position of the phenyl ring where ring D is phenyl). More preferably, the additional substitution is also on a carbon atom adjacent to the preferred haloalkoxy location (e.g., at the 5 position of the phenyl ring where ring D is phenyl).

Accordingly, ring D's most preferred herein have the following structures:

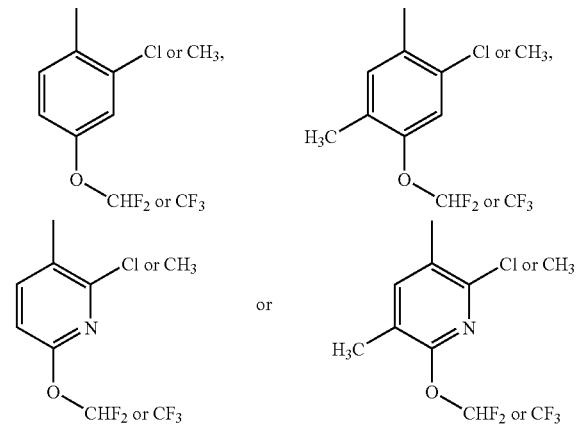

$R^1$ is selected from H, $C_{1-10}$ alkyl, $C_{2-10}$ alkenyl, $C_{2-10}$ alkynyl, $C_{3-8}$ cycloalkyl, $C_{4-12}$ cycloalkylalkyl and ($C_{1-4}$ alkoxy)-$C_{1-4}$ alkyl, each of these being optionally substituted with 1 to 3 substituents selected independently from $C_{1-6}$ alkyl, $C_{3-6}$ cycloalkyl, $C_{4-8}$ cycloalkyl, $C_{4-8}$ cycloalkyl comprising a ring-member oxygen, aryl, heteroaryl, heterocyclyl, halogen, $C_{1-4}$ haloalkyl, cyano, —$OR^{13}$, —$S(O)_mR^{14}$, —$COR^{13}$, —$CO_2R^{13}$, —$NR_{15}COR^{13}$, $N(COR^{13})_2$, —$NR^{15}CONR^{13}R^{16}$, —$NR^{15}CO_2R^{14}$, —$NR^{13}R^{16}$, —$CONR^{13}R^{16}$ and the cyclic groups morpholinyl, 1-piperidinyl, 1-piperazinyl and 1-piperazinyl having an N4 substituted with methyl, acetyl or methylsulfonyl. $R^{13}$ and $R^{16}$ are selected independently at each occurrence thereof from H, $C_{1-4}$ alkyl, $C_{1-4}$ haloalkyl, $C_{2-8}$ alkoxyalkyl, $C_{3-6}$ cycloalkyl, $C_{4-12}$ cycloalkylalkyl, aryl, (aryl)$C_{1-4}$ alkyl, heteroaryl and (heteroaryl)-$C_{1-4}$ alkyl. $R^{14}$ is selected from $C_{1-4}$ alkyl, $C_{1-4}$ haloalkyl, $C_{2-8}$ alkoxyalkyl, $C_{3-6}$ cycloalkyl, $C_{4-12}$ cycloalkylalkyl, aryl, (aryl)$C_{1-4}$ alkyl, heteroaryl and (heteroaryl)$C_{1-4}$ alkyl. $R^{15}$ is selected independently from H, $C_{1-4}$ alkyl, $C_{3-7}$ cycloalkyl, $C_{4-12}$ cycloalkylalkyl and benzyl (optionally substituted with 1–3 groups chosen from $C_{1-4}$ alkyl, halogen, nitro, $C_{1-4}$ alkoxy, or dimethylamino) and m is equal to 0, 1, or 2.

Preferably, $R^1$ is $C_{1-7}$ alkyl, $C_{5-7}$ cycloalkyl, or $C_{2-7}$ alkynyl, and $R^1$ is substituted with $C_{3-5}$ cycloalkyl, $C_{1-2}$ alkoxy, phenyl or phenyl substituted with 1–3 CN, $C_{1-3}$ alkoxy, or $C_{1-3}$ alkyl groups. Most preferably, $R^1$ is 2-butyl, 2-pentyl, 2-hexyl, 2-heptyl, 3-pentyl, 3-hexyl, 3-heptyl, 1-methoxy-3-pentyl, 4-heptyl, 1-cyclopropyl-1-ethyl, 1-cyclopropyl-1-propyl, 1-cyclopropyl-1-butyl, 1-cyclopropyl-3-methoxy-1-propyl, 1-cyclobutyl-1-ethyl, 1-dihydrobenzothienyl, cyclobutyl-1-propyl, 1-cyclobutyl-1-butyl, 1-cyclobutyl-3-methoxy-1-propyl, 1-cyclopentyl-1-ethyl, 1-cyclopentyl-1-propyl, 1-cyclopentyl-1-butyl, 1-cyclopentyl-3-methoxy-1-propyl, alpha-cyclopropylbenzyl, 1-phenyl-2-butyn-1-yl, 1-cyclopropyl-2-butyn-1-yl or dicyclopropylmethyl.

X is CH—$R^9$, N—$R^{10}$, O, S(O)$_n$ or a bond, wherein $R^9$ and $R^{10}$ are each independently H, $C_{1-4}$ alkyl or $C_{3-8}$ cycloalkyl and n is equal to 0, 2 or 3. Most preferably, X is O or CH—$R^9$, wherein $R^9$ is H.

$R^2$ is $C_{1-4}$ alkyl or $C_{3-8}$ cycloalkyl, each optionally substituted with 1–3 substituents selected from hydroxy, halo and $C_{1-4}$ alkoxy, or where X is a bond, $R^2$ is optionally also cyano. Most preferably, $R^2$ is $CH_3$ or $C_2H_5$.

$R^3$ is selected from H, $C_{1-4}$ alkyl, $C_{3-8}$ cycloalkyl, $C_{1-4}$ alkoxy, $C_{1-4}$ alkylthio, $C_{1-4}$ alkylsulfinyl, $C_{1-4}$ alkylsulfonyl, amino, $C_{1-4}$ alkylamino, $C_{2-8}$ dialkylamino, phenyl and phenyl substituted by 1–3 groups selected from $C_{1-7}$ alkyl, $C_{3-8}$ cycloalkyl, halogen, nitro, $C_{1-4}$ alkoxy, $C_{1-4}$ alkylthio and $C_{2-8}$ dialkylamino. Most preferably, $R^3$ is H or $CH_3$.

Accordingly, compounds are provided having the following structures:

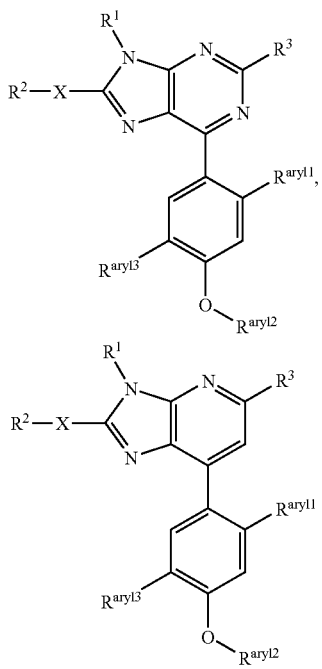

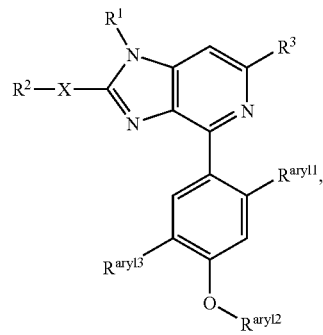

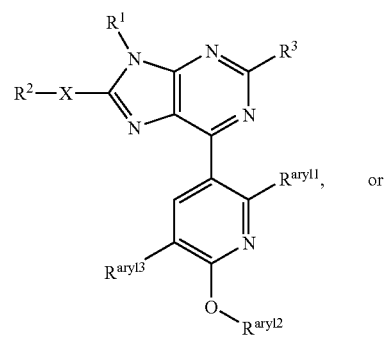

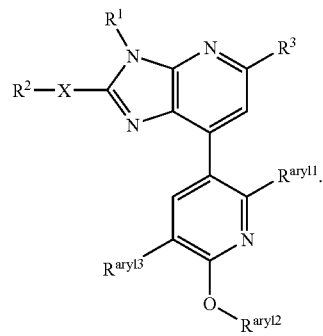

Preferably: $R^1$ is 2-butyl, 2-pentyl, 2-hexyl, 2-heptyl, 3-pentyl, 3-hexyl, 3-heptyl, 1-methoxy-3-pentyl, 4-heptyl, 1-cyclopropyl-1-ethyl, 1-cyclopropyl-1-propyl, 1-cyclopropyl-1-butyl, 1-cyclopropyl-3-methoxy-1-propyl, 1-cyclobutyl-1-ethyl, 1-cyclobutyl-1-propyl, 1-cyclobutyl-1-butyl, 1-cyclobutyl-3-methoxy-1-propyl, 1-cyclopentyl-1-ethyl, 1-cyclopentyl-1-propyl, 1-cyclopentyl-1-butyl, 1-cyclopentyl-3-methoxy-1-propyl, alpha-cyclopropylbenzyl, 1-phenyl-2-butyn-1-yl, 1-cyclopropyl-2-butyn-1-yl or dicyclopropylmethyl; $R^2$ is $CH_3$ or $C_2H_5$; $R^3$ is H or $CH_3$; X is $CH_2$ or O; A is N; B is N or CH; and, D is phenyl or 3-pyridyl. Preferred compounds of this invention include compounds with any combination of the above described substituents at the various positions.

Particularly preferred compounds provided herein are those having the following structure, with the substituents being given in the table following thereafter.

TABLE A

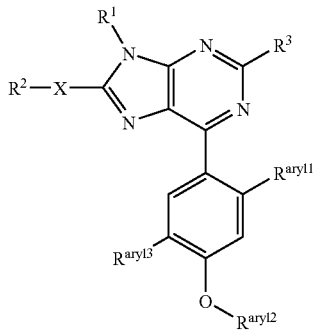

| R$^{1(a)}$ | X | R$^2$ | R$^3$ | R$^{aryl1}$ | R$^{aryl2}$ | R$^{aryl3}$ |
|---|---|---|---|---|---|---|
| A | CH$_2$ | CH$_3$ | H | Cl | CF$_3$ | H |
| B | CH$_2$ | CH$_3$ | H | Cl | CF$_3$ | H |
| C | CH$_2$ | CH$_3$ | H | Cl | CF$_3$ | H |
| D | CH$_2$ | CH$_3$ | H | Cl | CF$_3$ | H |
| E | CH$_2$ | CH$_3$ | H | Cl | CF$_3$ | H |
| F | CH$_2$ | CH$_3$ | H | Cl | CF$_3$ | H |
| G | CH$_2$ | CH$_3$ | H | Cl | CF$_3$ | H |
| H | CH$_2$ | CH$_3$ | H | Cl | CF$_3$ | H |
| I | CH$_2$ | CH$_3$ | H | Cl | CF$_3$ | H |
| J | CH$_2$ | CH$_3$ | H | Cl | CF$_3$ | H |
| K | CH$_2$ | CH$_3$ | H | Cl | CF$_3$ | H |
| L | CH$_2$ | CH$_3$ | H | Cl | CF$_3$ | H |
| N | CH$_2$ | CH$_3$ | H | Cl | CF$_3$ | H |
| N | CH$_2$ | CH$_3$ | H | Cl | CF$_3$ | H |
| O | CH$_2$ | CH$_3$ | H | Cl | CF$_3$ | H |
| P | CH$_2$ | CH$_3$ | H | Cl | CF$_3$ | H |
| Q | CH$_2$ | CH$_3$ | H | Cl | CF$_3$ | H |
| R | CH$_2$ | CH$_3$ | H | Cl | CF$_3$ | H |
| S | CH$_2$ | CH$_3$ | H | Cl | CF$_3$ | H |
| T | CH$_2$ | CH$_3$ | H | Cl | CF$_3$ | H |
| U | CH$_2$ | CH$_3$ | H | Cl | CF$_3$ | H |
| V | CH$_2$ | CH$_3$ | H | Cl | CF$_3$ | H |
| W | CH$_2$ | CH$_3$ | H | Cl | CF$_3$ | H |
| X | CH$_2$ | CH$_3$ | H | Cl | CF$_3$ | H |
| Y | CH$_2$ | CH$_3$ | H | Cl | CF$_3$ | H |
| A | O | CH$_3$ | H | Cl | CF$_3$ | H |
| B | O | CH$_3$ | H | Cl | CF$_3$ | H |
| C | O | CH$_3$ | H | Cl | CF$_3$ | H |
| D | O | CH$_3$ | H | Cl | CF$_3$ | H |
| E | O | CH$_3$ | H | Cl | CF$_3$ | H |
| F | O | CH$_3$ | H | Cl | CF$_3$ | H |
| G | O | CH$_3$ | H | Cl | CF$_3$ | H |
| H | O | CH$_3$ | H | Cl | CF$_3$ | H |
| I | O | CH$_3$ | H | Cl | CF$_3$ | H |
| J | O | CH$_3$ | H | Cl | CF$_3$ | H |
| K | O | CH$_3$ | H | Cl | CF$_3$ | H |
| L | O | CH$_3$ | H | Cl | CF$_3$ | H |
| M | O | CH$_3$ | H | Cl | CF$_3$ | H |
| N | O | CH$_3$ | H | Cl | CF$_3$ | H |
| O | O | CH$_3$ | H | Cl | CF$_3$ | H |
| P | O | CH$_3$ | H | Cl | CF$_3$ | H |
| Q | O | CH$_3$ | H | Cl | CF$_3$ | H |
| R | O | CH$_3$ | H | Cl | CF$_3$ | H |
| S | O | CH$_3$ | H | Cl | CF$_3$ | H |
| T | O | CH$_3$ | H | Cl | CF$_3$ | H |
| U | O | CH$_3$ | H | Cl | CF$_3$ | H |
| V | O | CH$_3$ | H | Cl | CF$_3$ | H |
| W | O | CH$_3$ | H | Cl | CF$_3$ | H |
| X | O | CH$_3$ | H | Cl | CF$_3$ | H |
| Y | O | CH$_3$ | H | Cl | CF$_3$ | H |
| A | O | C$_2$H$_5$ | H | Cl | CF$_3$ | H |
| B | O | C$_2$H$_5$ | H | Cl | CF$_3$ | H |
| C | O | C$_2$H$_5$ | H | Cl | CF$_3$ | H |
| D | O | C$_2$H$_5$ | H | Cl | CF$_3$ | H |
| E | O | C$_2$H$_5$ | H | Cl | CF$_3$ | H |
| F | O | C$_2$H$_5$ | H | Cl | CF$_3$ | H |
| G | O | C$_2$H$_5$ | H | Cl | CF$_3$ | H |
| H | O | C$_2$H$_5$ | H | Cl | CF$_3$ | H |
| I | O | C$_2$H$_5$ | H | Cl | CF$_3$ | H |
| J | O | C$_2$H$_5$ | H | Cl | CF$_3$ | H |

TABLE A-continued

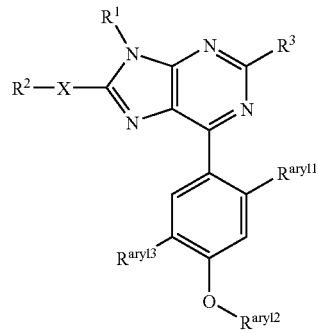

| R$^{1(a)}$ | X | R$^2$ | R$^3$ | R$^{aryl1}$ | R$^{aryl2}$ | R$^{aryl3}$ |
|---|---|---|---|---|---|---|
| K | O | C$_2$H$_5$ | H | Cl | CF$_3$ | H |
| L | O | C$_2$H$_5$ | H | Cl | CF$_3$ | H |
| M | O | C$_2$H$_5$ | H | Cl | CF$_3$ | H |
| N | O | C$_2$H$_5$ | H | Cl | CF$_3$ | H |
| O | O | C$_2$H$_5$ | H | Cl | CF$_3$ | H |
| P | O | C$_2$H$_5$ | H | Cl | CF$_3$ | H |
| Q | O | C$_2$H$_5$ | H | Cl | CF$_3$ | H |
| R | O | C$_2$H$_5$ | H | Cl | CF$_3$ | H |
| S | O | C$_2$H$_5$ | H | Cl | CF$_3$ | H |
| T | O | C$_2$H$_5$ | H | Cl | CF$_3$ | H |
| U | O | C$_2$H$_5$ | H | Cl | CF$_3$ | H |
| V | O | C$_2$H$_5$ | H | Cl | CF$_3$ | H |
| W | O | C$_2$H$_5$ | H | Cl | CF$_3$ | H |
| X | O | C$_2$H$_5$ | H | Cl | CF$_3$ | H |
| Y | O | C$_2$H$_5$ | H | Cl | CF$_3$ | H |
| A | CH$_2$ | CH$_3$ | CH$_3$ | Cl | CF$_3$ | H |
| B | CH$_2$ | CH$_3$ | CH$_3$ | Cl | CF$_3$ | H |
| C | CH$_2$ | CH$_3$ | CH$_3$ | Cl | CF$_3$ | H |
| D | CH$_2$ | CH$_3$ | CH$_3$ | Cl | CF$_3$ | H |
| E | CH$_2$ | CH$_3$ | CH$_3$ | Cl | CF$_3$ | H |
| F | CH$_2$ | CH$_3$ | CH$_3$ | Cl | CF$_3$ | H |
| G | CH$_2$ | CH$_3$ | CH$_3$ | Cl | CF$_3$ | H |
| H | CH$_2$ | CH$_3$ | CH$_3$ | Cl | CF$_3$ | H |
| I | CH$_2$ | CH$_3$ | CH$_3$ | Cl | CF$_3$ | H |
| J | CH$_2$ | CH$_3$ | CH$_3$ | Cl | CF$_3$ | H |
| K | CH$_2$ | CH$_3$ | CH$_3$ | Cl | CF$_3$ | H |
| L | CH$_2$ | CH$_3$ | CH$_3$ | Cl | CF$_3$ | H |
| M | CH$_2$ | CH$_3$ | CH$_3$ | Cl | CF$_3$ | H |
| N | CH$_2$ | CH$_3$ | CH$_3$ | Cl | CF$_3$ | H |
| O | CH$_2$ | CH$_3$ | CH$_3$ | Cl | CF$_3$ | H |
| P | CH$_2$ | CH$_3$ | CH$_3$ | Cl | CF$_3$ | H |
| Q | CH$_2$ | CH$_3$ | CH$_3$ | Cl | CF$_3$ | H |
| R | CH$_2$ | CH$_3$ | CH$_3$ | Cl | CF$_3$ | H |
| S | CH$_2$ | CH$_3$ | CH$_3$ | Cl | CF$_3$ | H |
| T | CH$_2$ | CH$_3$ | CH$_3$ | Cl | CF$_3$ | H |
| U | CH$_2$ | CH$_3$ | CH$_3$ | Cl | CF$_3$ | H |
| V | CH$_2$ | CH$_3$ | CH$_3$ | Cl | CF$_3$ | H |
| W | CH$_2$ | CH$_3$ | CH$_3$ | Cl | CF$_3$ | H |
| X | CH$_2$ | CH$_3$ | CH$_3$ | Cl | CF$_3$ | H |
| Y | CH$_2$ | CH$_3$ | CH$_3$ | Cl | CF$_3$ | H |
| A | CH$_2$ | CH$_3$ | H | CH$_3$ | CF$_3$ | H |
| B | CH$_2$ | CH$_3$ | H | CH$_3$ | CF$_3$ | H |
| C | CH$_2$ | CH$_3$ | H | CH$_3$ | CF$_3$ | H |
| D | CH$_2$ | CH$_3$ | H | CH$_3$ | CF$_3$ | H |
| E | CH$_2$ | CH$_3$ | H | CH$_3$ | CF$_3$ | H |
| F | CH$_2$ | CH$_3$ | H | CH$_3$ | CF$_3$ | H |
| G | CH$_2$ | CH$_3$ | H | CH$_3$ | CF$_3$ | H |
| H | CH$_2$ | CH$_3$ | H | CH$_3$ | CF$_3$ | H |
| I | CH$_2$ | CH$_3$ | H | CH$_3$ | CF$_3$ | H |
| J | CH$_2$ | CH$_3$ | H | CH$_3$ | CF$_3$ | H |
| K | CH$_2$ | CH$_3$ | H | CH$_3$ | CF$_3$ | H |
| L | CH$_2$ | CH$_3$ | H | CH$_3$ | CF$_3$ | H |
| M | CH$_2$ | CH$_3$ | H | CH$_3$ | CF$_3$ | H |
| N | CH$_2$ | CH$_3$ | H | CH$_3$ | CF$_3$ | H |
| O | CH$_2$ | CH$_3$ | H | CH$_3$ | CF$_3$ | H |
| P | CH$_2$ | CH$_3$ | H | CH$_3$ | CF$_3$ | H |
| Q | CH$_2$ | CH$_3$ | H | CH$_3$ | CF$_3$ | H |
| R | CH$_2$ | CH$_3$ | H | CH$_3$ | CF$_3$ | H |
| S | CH$_2$ | CH$_3$ | H | CH$_3$ | CF$_3$ | H |
| T | CH$_2$ | CH$_3$ | H | CH$_3$ | CF$_3$ | H |

TABLE A-continued

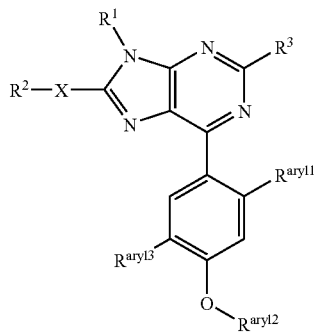

| R$^{1(a)}$ | X | R$^2$ | R$^3$ | R$^{aryl}$ | R$^{aryl2}$ | R$^{aryl3}$ |
|---|---|---|---|---|---|---|
| U | CH$_2$ | CH$_3$ | H | CH$_3$ | CF$_3$ | H |
| V | CH$_2$ | CH$_3$ | H | CH$_3$ | CF$_3$ | H |
| W | CH$_2$ | CH$_3$ | H | CH$_3$ | CF$_3$ | H |
| X | CH$_2$ | CH$_3$ | H | CH$_3$ | CF$_3$ | H |
| Y | CH$_2$ | CH$_3$ | H | CH$_3$ | CF$_3$ | H |
| A | O | CH$_3$ | H | CH$_3$ | CF$_3$ | H |
| B | O | CH$_3$ | H | CH$_3$ | CF$_3$ | H |
| C | O | CH$_3$ | H | CH$_3$ | CF$_3$ | H |
| D | O | CH$_3$ | H | CH$_3$ | CF$_3$ | H |
| E | O | CH$_3$ | H | CH$_3$ | CF$_3$ | H |
| F | O | CH$_3$ | H | CH$_3$ | CF$_3$ | H |
| G | O | CH$_3$ | H | CH$_3$ | CF$_3$ | H |
| H | O | CH$_3$ | H | CH$_3$ | CF$_3$ | H |
| I | O | CH$_3$ | H | CH$_3$ | CF$_3$ | H |
| J | O | CH$_3$ | H | CH$_3$ | CF$_3$ | H |
| K | O | CH$_3$ | H | CH$_3$ | CF$_3$ | H |
| L | O | CH$_3$ | H | CH$_3$ | CF$_3$ | H |
| H | O | CH$_3$ | H | CH$_3$ | CF$_3$ | H |
| N | O | CH$_3$ | H | CH$_3$ | CF$_3$ | H |
| O | O | CH$_3$ | H | CH$_3$ | CF$_3$ | H |
| P | O | CH$_3$ | H | CH$_3$ | CF$_3$ | H |
| Q | O | CH$_3$ | H | CH$_3$ | CF$_3$ | H |
| R | O | CH$_3$ | H | CH$_3$ | CF$_3$ | H |
| S | O | CH$_3$ | H | CH$_3$ | CF$_3$ | H |
| T | O | CH$_3$ | H | CH$_3$ | CF$_3$ | H |
| U | O | CH$_3$ | H | CH$_3$ | CF$_3$ | H |
| V | O | CH$_3$ | H | CH$_3$ | CF$_3$ | H |
| W | O | CH$_3$ | H | CH$_3$ | CF$_3$ | H |
| X | O | CH$_3$ | H | CH$_3$ | CF$_3$ | H |
| Y | O | CH$_3$ | H | CH$_3$ | CF$_3$ | H |
| A | O | C$_2$H$_5$ | H | CH$_3$ | CF$_3$ | H |
| B | O | C$_2$H$_5$ | H | CH$_3$ | CF$_3$ | H |
| C | O | C$_2$H$_5$ | H | CH$_3$ | CF$_3$ | H |
| D | O | C$_2$H$_5$ | H | CH$_3$ | CF$_3$ | H |
| E | O | C$_2$H$_5$ | H | CH$_3$ | CF$_3$ | H |
| F | O | C$_2$H$_5$ | H | CH$_3$ | CF$_3$ | H |
| G | O | C$_2$H$_5$ | H | CH$_3$ | CF$_3$ | H |
| H | O | C$_2$H$_5$ | H | CH$_3$ | CF$_3$ | H |
| I | O | C$_2$H$_5$ | H | CH$_3$ | CF$_3$ | H |
| J | O | C$_2$H$_5$ | H | CH$_3$ | CF$_3$ | H |
| K | O | C$_2$H$_5$ | H | CH$_3$ | CF$_3$ | H |
| L | O | C$_2$H$_5$ | H | CH$_3$ | CF$_3$ | H |
| H | O | C$_2$H$_5$ | H | CH$_3$ | CF$_3$ | H |
| N | O | C$_2$H$_5$ | H | CH$_3$ | CF$_3$ | H |
| O | O | C$_2$H$_5$ | H | CH$_3$ | CF$_3$ | H |
| P | O | C$_2$H$_5$ | H | CH$_3$ | CF$_3$ | H |
| Q | O | C$_2$H$_5$ | H | CH$_3$ | CF$_3$ | H |
| R | O | C$_2$H$_5$ | H | CH$_3$ | CF$_3$ | H |
| S | O | C$_2$H$_5$ | H | CH$_3$ | CF$_3$ | H |
| T | O | C$_2$H$_5$ | H | CH$_3$ | CF$_3$ | H |
| U | O | C$_2$H$_5$ | H | CH$_3$ | CF$_3$ | H |
| V | O | C$_2$H$_5$ | H | CH$_3$ | CF$_3$ | H |
| W | O | C$_2$H$_5$ | H | CH$_3$ | CF$_3$ | H |
| X | O | C$_2$H$_5$ | H | CH$_3$ | CF$_3$ | H |
| Y | O | C$_2$H$_5$ | H | CH$_3$ | CF$_3$ | H |
| A | CH$_2$ | CH$_3$ | CH$_3$ | CH$_3$ | CF$_3$ | H |
| B | CH$_2$ | CH$_3$ | CH$_3$ | CH$_3$ | CF$_3$ | H |
| C | CH$_2$ | CH$_3$ | CH$_3$ | CH$_3$ | CF$_3$ | H |
| D | CH$_2$ | CH$_3$ | CH$_3$ | CH$_3$ | CF$_3$ | H |
| E | CH$_2$ | CH$_3$ | CH$_3$ | CH$_3$ | CF$_3$ | H |

TABLE A-continued

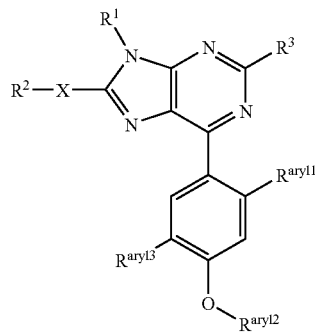

| R$^{1(a)}$ | X | R$^2$ | R$^3$ | R$^{aryl}$ | R$^{aryl2}$ | R$^{aryl3}$ |
|---|---|---|---|---|---|---|
| F | CH$_2$ | CH$_3$ | CH$_3$ | CH$_3$ | CF$_3$ | H |
| G | CH$_2$ | CH$_3$ | CH$_3$ | CH$_3$ | CF$_3$ | H |
| H | CH$_2$ | CH$_3$ | CH$_3$ | CH$_3$ | CF$_3$ | H |
| I | CH$_2$ | CH$_3$ | CH$_3$ | CH$_3$ | CF$_3$ | H |
| J | CH$_2$ | CH$_3$ | CH$_3$ | CH$_3$ | CF$_3$ | H |
| K | CH$_2$ | CH$_3$ | CH$_3$ | CH$_3$ | CF$_3$ | H |
| L | CH$_2$ | CH$_3$ | CH$_3$ | CH$_3$ | CF$_3$ | H |
| M | CH$_2$ | CH$_3$ | CH$_3$ | CH$_3$ | CF$_3$ | H |
| N | CH$_2$ | CH$_3$ | CH$_3$ | CH$_3$ | CF$_3$ | H |
| O | CH$_2$ | CH$_3$ | CH$_3$ | CH$_3$ | CF$_3$ | H |
| P | CH$_2$ | CH$_3$ | CH$_3$ | CH$_3$ | CF$_3$ | H |
| Q | CH$_2$ | CH$_3$ | CH$_3$ | CH$_3$ | CF$_3$ | H |
| R | CH$_2$ | CH$_3$ | CH$_3$ | CH$_3$ | CF$_3$ | H |
| S | CH$_2$ | CH$_3$ | CH$_3$ | CH$_3$ | CF$_3$ | H |
| T | CH$_2$ | CH$_3$ | CH$_3$ | CH$_3$ | CF$_3$ | H |
| U | CH$_2$ | CH$_3$ | CH$_3$ | CH$_3$ | CF$_3$ | H |
| V | CH$_2$ | CH$_3$ | CH$_3$ | CH$_3$ | CF$_3$ | H |
| W | CH$_2$ | CH$_3$ | CH$_3$ | CH$_3$ | CF$_3$ | H |
| X | CH$_2$ | CH$_3$ | CH$_3$ | CH$_3$ | CF$_3$ | H |
| Y | CH$_2$ | CH$_3$ | CH$_3$ | CH$_3$ | CF$_3$ | H |
| A | CH$_2$ | CH$_3$ | H | Cl | CHF$_2$ | H |
| B | CH$_2$ | CH$_3$ | H | Cl | CHF$_2$ | H |
| C | CH$_2$ | CH$_3$ | H | Cl | CHF$_2$ | H |
| D | CH$_2$ | CH$_3$ | H | Cl | CHF$_2$ | H |
| E | CH$_2$ | CH$_3$ | H | Cl | CHF$_2$ | H |
| F | CH$_2$ | CH$_3$ | H | Cl | CHF$_2$ | H |
| G | CH$_2$ | CH$_3$ | H | Cl | CHF$_2$ | H |
| H | CH$_2$ | CH$_3$ | H | Cl | CHF$_2$ | H |
| I | CH$_2$ | CH$_3$ | H | Cl | CHF$_2$ | H |
| J | CH$_2$ | CH$_3$ | H | Cl | CHF$_2$ | H |
| K | CH$_2$ | CH$_3$ | H | Cl | CHF$_2$ | H |
| L | CH$_2$ | CH$_3$ | H | Cl | CHF$_2$ | H |
| M | CH$_2$ | CH$_3$ | H | Cl | CHF$_2$ | H |
| N | CH$_2$ | CH$_3$ | H | Cl | CHF$_2$ | H |
| O | CH$_2$ | CH$_3$ | H | Cl | CHF$_2$ | H |
| P | CH$_2$ | CH$_3$ | H | Cl | CHF$_2$ | H |
| Q | CH$_2$ | CH$_3$ | H | Cl | CHF$_2$ | H |
| R | CH$_2$ | CH$_3$ | H | Cl | CHF$_2$ | H |
| S | CH$_2$ | CH$_3$ | H | Cl | CHF$_2$ | H |
| T | CH$_2$ | CH$_3$ | H | Cl | CHF$_2$ | H |
| U | CH$_2$ | CH$_3$ | H | Cl | CHF$_2$ | H |
| V | CH$_2$ | CH$_3$ | H | Cl | CHF$_2$ | H |
| W | CH$_2$ | CH$_3$ | H | Cl | CHF$_2$ | H |
| X | CH$_2$ | CH$_3$ | H | Cl | CHF$_2$ | H |
| Y | CH$_2$ | CH$_3$ | H | Cl | CHF$_2$ | H |
| A | O | CH$_3$ | H | Cl | CHF$_2$ | H |
| B | O | CH$_3$ | H | Cl | CHF$_2$ | H |
| C | O | CH$_3$ | H | Cl | CHF$_2$ | H |
| D | O | CH$_3$ | H | Cl | CHF$_2$ | H |
| E | O | CH$_3$ | H | Cl | CHF$_2$ | H |
| F | O | CH$_3$ | H | Cl | CHF$_2$ | H |
| G | O | CH$_3$ | H | Cl | CHF$_2$ | H |
| H | O | CH$_3$ | H | Cl | CHF$_2$ | H |
| I | O | CH$_3$ | H | Cl | CHF$_2$ | H |
| J | O | CH$_3$ | H | Cl | CHF$_2$ | H |
| K | O | CH$_3$ | H | Cl | CHF$_2$ | H |
| L | O | CH$_3$ | H | Cl | CHF$_2$ | H |
| M | O | CH$_3$ | H | Cl | CHF$_2$ | H |
| N | O | CH$_3$ | H | Cl | CHF$_2$ | H |
| O | O | CH$_3$ | H | Cl | CHF$_2$ | H |

TABLE A-continued

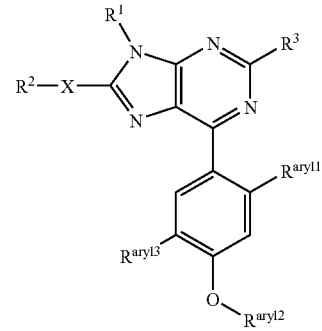

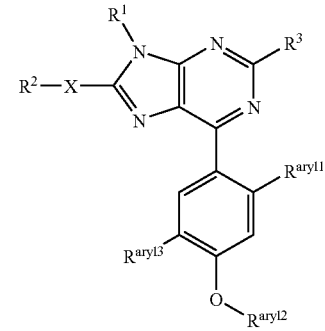

| R[1(a)] | X | R[2] | R[3] | R[aryl1] | R[aryl2] | R[aryl3] |
|---|---|---|---|---|---|---|
| P | O | CH$_3$ | H | Cl | CHF$_2$ | H |
| Q | O | CH$_3$ | H | Cl | CHF$_2$ | H |
| R | O | CH$_3$ | H | Cl | CHF$_2$ | H |
| S | O | CH$_3$ | H | Cl | CHF$_2$ | H |
| T | O | CH$_3$ | H | Cl | CHF$_2$ | H |
| U | O | CH$_3$ | H | Cl | CHF$_2$ | H |
| V | O | CH$_3$ | H | Cl | CHF$_2$ | H |
| W | O | CH$_3$ | H | Cl | CHF$_2$ | H |
| X | O | CH$_3$ | H | Cl | CHF$_2$ | H |
| Y | O | CH$_3$ | H | Cl | CHF$_2$ | H |
| A | O | C$_2$H$_5$ | H | Cl | CHF$_2$ | H |
| B | O | C$_2$H$_5$ | H | Cl | CHF$_2$ | H |
| C | O | C$_2$H$_5$ | H | Cl | CHF$_2$ | H |
| D | O | C$_2$H$_5$ | H | Cl | CHF$_2$ | H |
| E | O | C$_2$H$_5$ | H | Cl | CHF$_2$ | H |
| F | O | C$_2$H$_5$ | H | Cl | CHF$_2$ | H |
| G | O | C$_2$H$_5$ | H | Cl | CHF$_2$ | H |
| H | O | C$_2$H$_5$ | H | Cl | CHF$_2$ | H |
| I | O | C$_2$H$_5$ | H | Cl | CHF$_2$ | H |
| J | O | C$_2$H$_5$ | H | Cl | CHF$_2$ | H |
| K | O | C$_2$H$_5$ | H | Cl | CHF$_2$ | H |
| L | O | C$_2$H$_5$ | H | Cl | CHF$_2$ | H |
| M | O | C$_2$H$_5$ | H | Cl | CHF$_2$ | H |
| N | O | C$_2$H$_5$ | H | Cl | CHF$_2$ | H |
| O | O | C$_2$H$_5$ | H | Cl | CHF$_2$ | H |
| P | O | C$_2$H$_5$ | H | Cl | CHF$_2$ | H |
| Q | O | C$_2$H$_5$ | H | Cl | CHF$_2$ | H |
| R | O | C$_2$H$_5$ | H | Cl | CHF$_2$ | H |
| S | O | C$_2$H$_5$ | H | Cl | CHF$_2$ | H |
| T | O | C$_2$H$_5$ | H | Cl | CHF$_2$ | H |
| U | O | C$_2$H$_5$ | H | Cl | CHF$_2$ | H |
| V | O | C$_2$H$_5$ | H | Cl | CHF$_2$ | H |
| W | O | C$_2$H$_5$ | H | Cl | CHF$_2$ | H |
| X | O | C$_2$H$_5$ | H | Cl | CHF$_2$ | H |
| Y | O | C$_2$H$_5$ | H | Cl | CHF$_2$ | H |
| A | CH$_2$ | CH$_3$ | CH$_3$ | Cl | CHF$_2$ | H |
| B | CH$_2$ | CH$_3$ | CH$_3$ | Cl | CHF$_2$ | H |
| C | CH$_2$ | CH$_3$ | CH$_3$ | Cl | CHF$_2$ | H |
| D | CH$_2$ | CH$_3$ | CH$_3$ | Cl | CHF$_2$ | H |
| E | CH$_2$ | CH$_3$ | CH$_3$ | Cl | CHF$_2$ | H |
| F | CH$_2$ | CH$_3$ | CH$_3$ | Cl | CHF$_2$ | H |
| G | CH$_2$ | CH$_3$ | CH$_3$ | Cl | CHF$_2$ | H |
| H | CH$_2$ | CH$_3$ | CH$_3$ | Cl | CHF$_2$ | H |
| I | CH$_2$ | CH$_3$ | CH$_3$ | Cl | CHF$_2$ | H |
| J | CH$_2$ | CH$_3$ | CH$_3$ | Cl | CHF$_2$ | H |
| K | CH$_2$ | CH$_3$ | CH$_3$ | Cl | CHF$_2$ | H |
| L | CH$_2$ | CH$_3$ | CH$_3$ | Cl | CHF$_2$ | H |
| M | CH$_2$ | CH$_3$ | CH$_3$ | Cl | CHF$_2$ | H |
| N | CH$_2$ | CH$_3$ | CH$_3$ | Cl | CHF$_2$ | H |
| O | CH$_2$ | CH$_3$ | CH$_3$ | Cl | CHF$_2$ | H |
| P | CH$_2$ | CH$_3$ | CH$_3$ | Cl | CHF$_2$ | H |
| Q | CH$_2$ | CH$_3$ | CH$_3$ | Cl | CHF$_2$ | H |
| R | CH$_2$ | CH$_3$ | CH$_3$ | Cl | CHF$_2$ | H |
| S | CH$_2$ | CH$_3$ | CH$_3$ | Cl | CHF$_2$ | H |
| T | CH$_2$ | CH$_3$ | CH$_3$ | Cl | CHF$_2$ | H |
| U | CH$_2$ | CH$_3$ | CH$_3$ | Cl | CHF$_2$ | H |
| V | CH$_2$ | CH$_3$ | CH$_3$ | Cl | CHF$_2$ | H |
| W | CH$_2$ | CH$_3$ | CH$_3$ | Cl | CHF$_2$ | H |
| X | CH$_2$ | CH$_3$ | CH$_3$ | Cl | CHF$_2$ | H |
| Y | CH$_2$ | CH$_3$ | CH$_3$ | Cl | CHF$_2$ | H |
| A | CH$_2$ | CH$_3$ | H | CH$_3$ | CHF$_2$ | H |
| B | CH$_2$ | CH$_3$ | H | CH$_3$ | CHF$_2$ | H |
| O | CH$_2$ | CH$_3$ | H | CH$_3$ | CHF$_2$ | H |
| D | CH$_2$ | CH$_3$ | H | CH$_3$ | CHF$_2$ | H |
| E | CH$_2$ | CH$_3$ | H | CH$_3$ | CHF$_2$ | H |
| F | CH$_2$ | CH$_3$ | H | CH$_3$ | CHF$_2$ | H |
| G | CH$_2$ | CH$_3$ | H | CH$_3$ | CHF$_2$ | H |
| H | CH$_2$ | CH$_3$ | H | CH$_3$ | CHF$_2$ | H |
| I | CH$_2$ | CH$_3$ | H | CH$_3$ | CHF$_2$ | H |
| J | CH$_2$ | CH$_3$ | H | CH$_3$ | CHF$_2$ | H |
| K | CH$_2$ | CH$_3$ | H | CH$_3$ | CHF$_2$ | H |
| L | CH$_2$ | CH$_3$ | H | CH$_3$ | CHF$_2$ | H |
| M | CH$_2$ | CH$_3$ | H | CH$_3$ | CHF$_2$ | H |
| N | CH$_2$ | CH$_3$ | H | CH$_3$ | CHF$_2$ | H |
| O | CH$_2$ | CH$_3$ | H | CH$_3$ | CHF$_2$ | H |
| P | CH$_2$ | CH$_3$ | H | CH$_3$ | CHF$_2$ | H |
| Q | CH$_2$ | CH$_3$ | H | CH$_3$ | CHF$_2$ | H |
| R | CH$_2$ | CH$_3$ | H | CH$_3$ | CHF$_2$ | H |
| S | CH$_2$ | CH$_3$ | H | CH$_3$ | CHF$_2$ | H |
| T | CH$_2$ | CH$_3$ | H | CH$_3$ | CHF$_2$ | H |
| U | CH$_2$ | CH$_3$ | H | CH$_3$ | CHF$_2$ | H |
| V | CH$_2$ | CH$_3$ | H | CH$_3$ | CHF$_2$ | H |
| W | CH$_2$ | CH$_3$ | H | CH$_3$ | CHF$_2$ | H |
| X | CH$_2$ | CH$_3$ | H | CH$_3$ | CHF$_2$ | H |
| Y | CH$_2$ | CH$_3$ | H | CH$_3$ | CHF$_2$ | H |
| A | O | CH$_3$ | H | CH$_3$ | CHF$_2$ | H |
| B | O | CH$_3$ | H | CH$_3$ | CHF$_2$ | H |
| C | O | CH$_3$ | H | CH$_3$ | CHF$_2$ | H |
| D | O | CH$_3$ | H | CH$_3$ | CHF$_2$ | H |
| E | O | CH$_3$ | H | CH$_3$ | CHF$_2$ | H |
| F | O | CH$_3$ | H | CH$_3$ | CHF$_2$ | H |
| G | O | CH$_3$ | H | CH$_3$ | CHF$_2$ | H |
| H | O | CH$_3$ | H | CH$_3$ | CHF$_2$ | H |
| I | O | CH$_3$ | H | CH$_3$ | CHF$_2$ | H |
| J | O | CH$_3$ | H | CH$_3$ | CHF$_2$ | H |
| K | O | CH$_3$ | H | CH$_3$ | CHF$_2$ | H |
| L | O | CH$_3$ | H | CH$_3$ | CHF$_2$ | H |
| N | O | CH$_3$ | H | CH$_3$ | CHF$_2$ | H |
| N | O | CH$_3$ | H | CH$_3$ | CHF$_2$ | H |
| O | O | CH$_3$ | H | CH$_3$ | CHF$_2$ | H |
| P | O | CH$_3$ | H | CH$_3$ | CHF$_2$ | H |
| Q | O | CH$_3$ | H | CH$_3$ | CHF$_2$ | H |
| R | O | CH$_3$ | H | CH$_3$ | CHF$_2$ | H |
| S | O | CH$_3$ | H | CH$_3$ | CHF$_2$ | H |
| T | O | CH$_3$ | H | CH$_3$ | CHF$_2$ | H |
| U | O | CH$_3$ | H | CH$_3$ | CHF$_2$ | H |
| V | O | CH$_3$ | H | CH$_3$ | CHF$_2$ | H |
| W | O | CH$_3$ | H | CH$_3$ | CHF$_2$ | H |
| X | O | CH$_3$ | H | CH$_3$ | CHF$_2$ | H |
| Y | O | CH$_3$ | H | CH$_3$ | CHF$_2$ | H |
| A | O | C$_2$H$_5$ | H | CH$_3$ | CHF$_2$ | H |
| B | O | C$_2$H$_5$ | H | CH$_3$ | CHF$_2$ | H |
| C | O | C$_2$H$_5$ | H | CH$_3$ | CHF$_2$ | H |
| D | O | C$_2$H$_5$ | H | CH$_3$ | CHF$_2$ | H |
| E | O | C$_2$H$_5$ | H | CH$_3$ | CHF$_2$ | H |
| F | O | C$_2$H$_5$ | H | CH$_3$ | CHF$_2$ | H |
| G | O | C$_2$H$_5$ | H | CH$_3$ | CHF$_2$ | H |
| H | O | C$_2$H$_5$ | H | CH$_3$ | CHF$_2$ | H |
| I | O | C$_2$H$_5$ | H | CH$_3$ | CHF$_2$ | H |
| J | O | C$_2$H$_5$ | H | CH$_3$ | CHF$_2$ | H |

TABLE A-continued

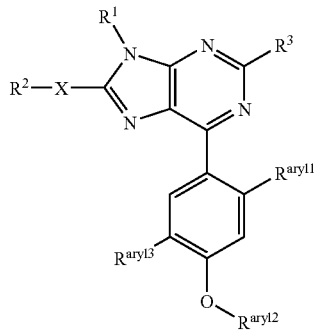

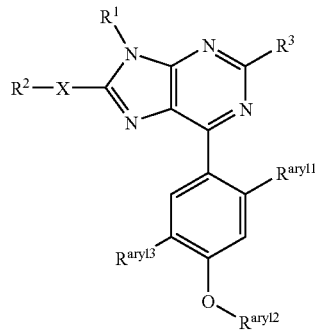

| $R^{1(a)}$ | X | $R^2$ | $R^3$ | $R^{aryl1}$ | $R^{aryl2}$ | $R^{aryl3}$ | $R^{1(a)}$ | X | $R^2$ | $R^3$ | $R^{aryl1}$ | $R^{aryl2}$ | $R^{aryl3}$ |
|---|---|---|---|---|---|---|---|---|---|---|---|---|---|
| K | O | $C_2H_5$ | H | $CH_3$ | $CHF_2$ | H | U | $CH_2$ | $CH_3$ | H | Cl | $CF_3$ | $CH_3$ |
| L | O | $C_2H_5$ | H | $CH_3$ | $CHF_2$ | H | V | $CH_2$ | $CH_3$ | H | Cl | $CF_3$ | $CH_3$ |
| M | O | $C_2H_5$ | H | $CH_3$ | $CHF_2$ | H | W | $CH_2$ | $CH_3$ | H | Cl | $CF_3$ | $CH_3$ |
| N | O | $C_2H_5$ | H | $CH_3$ | $CHF_2$ | H | X | $CH_2$ | $CH_3$ | H | Cl | $CF_3$ | $CH_3$ |
| O | O | $C_2H_5$ | H | $CH_3$ | $CHF_2$ | H | Y | $CH_2$ | $CH_3$ | H | Cl | $CF_3$ | $CH_3$ |
| P | O | $C_2H_5$ | H | $CH_3$ | $CHF_2$ | H | A | O | $CH_3$ | H | Cl | $CF_3$ | $CH_3$ |
| Q | O | $C_2H_5$ | H | $CH_3$ | $CHF_2$ | H | B | O | $CH_3$ | H | Cl | $CF_3$ | $CH_3$ |
| R | O | $C_2H_5$ | H | $CH_3$ | $CHF_2$ | H | C | O | $CH_3$ | H | Cl | $CF_3$ | $CH_3$ |
| S | O | $C_2H_5$ | H | $CH_3$ | $CHF_2$ | H | D | O | $CH_3$ | H | Cl | $CF_3$ | $CH_3$ |
| T | O | $C_2H_5$ | H | $CH_3$ | $CHF_2$ | H | E | O | $CH_3$ | H | Cl | $CF_3$ | $CH_3$ |
| U | O | $C_2H_5$ | H | $CH_3$ | $CHF_2$ | H | F | O | $CH_3$ | H | Cl | $CF_3$ | $CH_3$ |
| V | O | $C_2H_5$ | H | $CH_3$ | $CHF_2$ | H | G | O | $CH_3$ | H | Cl | $CF_3$ | $CH_3$ |
| W | O | $C_2H_5$ | H | $CH_3$ | $CHF_2$ | H | H | O | $CH_3$ | H | Cl | $CF_3$ | $CH_3$ |
| X | O | $C_2H_5$ | H | $CH_3$ | $CHF_2$ | H | I | O | $CH_3$ | H | Cl | $CF_3$ | $CH_3$ |
| Y | O | $C_2H_5$ | H | $CH_3$ | $CHF_2$ | H | J | O | $CH_3$ | H | Cl | $CF_3$ | $CH_3$ |
| A | $CH_2$ | $CH_3$ | $CH_3$ | $CH_3$ | $CHF_2$ | H | K | O | $CH_3$ | H | Cl | $CF_3$ | $CH_3$ |
| B | $CH_2$ | $CH_3$ | $CH_3$ | $CH_3$ | $CHF_2$ | H | L | O | $CH_3$ | H | Cl | $CF_3$ | $CH_3$ |
| C | $CH_2$ | $CH_3$ | $CH_3$ | $CH_3$ | $CHF_2$ | H | M | O | $CH_3$ | H | Cl | $CF_3$ | $CH_3$ |
| D | $CH_2$ | $CH_3$ | $CH_3$ | $CH_3$ | $CHF_2$ | H | N | O | $CH_3$ | H | Cl | $CF_3$ | $CH_3$ |
| E | $CH_2$ | $CH_3$ | $CH_3$ | $CH_3$ | $CHF_2$ | H | O | O | $CH_3$ | H | Cl | $CF_3$ | $CH_3$ |
| F | $CH_2$ | $CH_3$ | $CH_3$ | $CH_3$ | $CHF_2$ | H | P | O | $CH_3$ | H | Cl | $CF_3$ | $CH_3$ |
| G | $CH_2$ | $CH_3$ | $CH_3$ | $CH_3$ | $CHF_2$ | H | Q | O | $CH_3$ | H | Cl | $CF_3$ | $CH_3$ |
| H | $CH_2$ | $CH_3$ | $CH_3$ | $CH_3$ | $CHF_2$ | H | R | O | $CH_3$ | H | Cl | $CF_3$ | $CH_3$ |
| I | $CH_2$ | $CH_3$ | $CH_3$ | $CH_3$ | $CHF_2$ | H | S | O | $CH_3$ | H | Cl | $CF_3$ | $CH_3$ |
| J | $CH_2$ | $CH_3$ | $CH_3$ | $CH_3$ | $CHF_2$ | H | T | O | $CH_3$ | H | Cl | $CF_3$ | $CH_3$ |
| K | $CH_2$ | $CH_3$ | $CH_3$ | $CH_3$ | $CHF_2$ | H | U | O | $CH_3$ | H | Cl | $CF_3$ | $CH_3$ |
| L | $CH_2$ | $CH_3$ | $CH_3$ | $CH_3$ | $CHF_2$ | H | V | O | $CH_3$ | H | Cl | $CF_3$ | $CH_3$ |
| N | $CH_2$ | $CH_3$ | $CH_3$ | $CH_3$ | $CHF_2$ | H | W | O | $CH_3$ | H | Cl | $CF_3$ | $CH_3$ |
| N | $CH_2$ | $CH_3$ | $CH_3$ | $CH_3$ | $CHF_2$ | H | X | O | $CH_3$ | H | Cl | $CF_3$ | $CH_3$ |
| O | $CH_2$ | $CH_3$ | $CH_3$ | $CH_3$ | $CHF_2$ | H | Y | O | $CH_3$ | H | Cl | $CF_3$ | $CH_3$ |
| P | $CH_2$ | $CH_3$ | $CH_3$ | $CH_3$ | $CHF_2$ | H | A | O | $C_2H_5$ | H | Cl | $CF_3$ | $CH_3$ |
| Q | $CH_2$ | $CH_3$ | $CH_3$ | $CH_3$ | $CHF_2$ | H | B | O | $C_2H_5$ | H | Cl | $CF_3$ | $CH_3$ |
| R | $CH_2$ | $CH_3$ | $CH_3$ | $CH_3$ | $CHF_2$ | H | C | O | $C_2H_5$ | H | Cl | $CF_3$ | $CH_3$ |
| S | $CH_2$ | $CH_3$ | $CH_3$ | $CH_3$ | $CHF_2$ | H | D | O | $C_2H_5$ | H | Cl | $CF_3$ | $CH_3$ |
| T | $CH_2$ | $CH_3$ | $CH_3$ | $CH_3$ | $CHF_2$ | H | E | O | $C_2H_5$ | H | Cl | $CF_3$ | $CH_3$ |
| U | $CH_2$ | $CH_3$ | $CH_3$ | $CH_3$ | $CHF_2$ | H | F | O | $C_2H_5$ | H | Cl | $CF_3$ | $CH_3$ |
| V | $CH_2$ | $CH_3$ | $CH_3$ | $CH_3$ | $CHF_2$ | H | G | O | $C_2H_5$ | H | Cl | $CF_3$ | $CH_3$ |
| W | $CH_2$ | $CH_3$ | $CH_3$ | $CH_3$ | $CHF_2$ | H | H | O | $C_2H_5$ | H | Cl | $CF_3$ | $CH_3$ |
| X | $CH_2$ | $CH_3$ | $CH_3$ | $CH_3$ | $CHF_2$ | H | I | O | $C_2H_5$ | H | Cl | $CF_3$ | $CH_3$ |
| Y | $CH_2$ | $CH_3$ | $CH_3$ | $CH_3$ | $CHF_2$ | H | J | O | $C_2H_5$ | H | Cl | $CF_3$ | $CH_3$ |
| A | $CH_2$ | $CH_3$ | H | Cl | $CF_3$ | $CH_3$ | K | O | $C_2H_5$ | H | Cl | $CF_3$ | $CH_3$ |
| B | $CH_2$ | $CH_3$ | H | Cl | $CF_3$ | $CH_3$ | L | O | $C_2H_5$ | H | Cl | $CF_3$ | $CH_3$ |
| C | $CH_2$ | $CH_3$ | H | Cl | $CF_3$ | $CH_3$ | M | O | $C_2H_5$ | H | Cl | $CF_3$ | $CH_3$ |
| D | $CH_2$ | $CH_3$ | H | Cl | $CF_3$ | $CH_3$ | N | O | $C_2H_5$ | H | Cl | $CF_3$ | $CH_3$ |
| E | $CH_2$ | $CH_3$ | H | Cl | $CF_3$ | $CH_3$ | O | O | $C_2H_5$ | H | Cl | $CF_3$ | $CH_3$ |
| F | $CH_2$ | $CH_3$ | H | Cl | $CF_3$ | $CH_3$ | P | O | $C_2H_5$ | H | Cl | $CF_3$ | $CH_3$ |
| G | $CH_2$ | $CH_3$ | H | Cl | $CF_3$ | $CH_3$ | Q | O | $C_2H_5$ | H | Cl | $CF_3$ | $CH_3$ |
| H | $CH_2$ | $CH_3$ | H | Cl | $CF_3$ | $CH_3$ | R | O | $C_2H_5$ | H | Cl | $CF_3$ | $CH_3$ |
| I | $CH_2$ | $CH_3$ | H | Cl | $CF_3$ | $CH_3$ | S | O | $C_2H_5$ | H | Cl | $CF_3$ | $CH_3$ |
| J | $CH_2$ | $CH_3$ | H | Cl | $CF_3$ | $CH_3$ | T | O | $C_2H_5$ | H | Cl | $CF_3$ | $CH_3$ |
| K | $CH_2$ | $CH_3$ | H | Cl | $CF_3$ | $CH_3$ | U | O | $C_2H_5$ | H | Cl | $CF_3$ | $CH_3$ |
| L | $CH_2$ | $CH_3$ | H | Cl | $CF_3$ | $CH_3$ | V | O | $C_2H_5$ | H | Cl | $CF_3$ | $CH_3$ |
| M | $CH_2$ | $CH_3$ | H | Cl | $CF_3$ | $CH_3$ | W | O | $C_2H_5$ | H | Cl | $CF_3$ | $CH_3$ |
| N | $CH_2$ | $CH_3$ | H | Cl | $CF_3$ | $CH_3$ | X | O | $C_2H_5$ | H | Cl | $CF_3$ | $CH_3$ |
| O | $CH_2$ | $CH_3$ | H | Cl | $CF_3$ | $CH_3$ | Y | O | $C_2H_5$ | H | Cl | $CF_3$ | $CH_3$ |
| P | $CH_2$ | $CH_3$ | H | Cl | $CF_3$ | $CH_3$ | A | $CH_2$ | $CH_3$ | $CH_3$ | Cl | $CF_3$ | $CH_3$ |
| Q | $CH_2$ | $CH_3$ | H | Cl | $CF_3$ | $CH_3$ | B | $CH_2$ | $CH_3$ | $CH_3$ | Cl | $CF_3$ | $CH_3$ |
| R | $CH_2$ | $CH_3$ | H | Cl | $CF_3$ | $CH_3$ | C | $CH_2$ | $CH_3$ | $CH_3$ | Cl | $CF_3$ | $CH_3$ |
| S | $CH_2$ | $CH_3$ | H | Cl | $CF_3$ | $CH_3$ | D | $CH_2$ | $CH_3$ | $CH_3$ | Cl | $CF_3$ | $CH_3$ |
| T | $CH_2$ | $CH_3$ | H | Cl | $CF_3$ | $CH_3$ | E | $CH_2$ | $CH_3$ | $CH_3$ | Cl | $CF_3$ | $CH_3$ |

TABLE A-continued

| R[1(a)] | X | R[2] | R[3] | R[aryl1] | R[aryl2] | R[aryl3] |
|---|---|---|---|---|---|---|
| F | $CH_2$ | $CH_3$ | $CH_3$ | Cl | $CF_3$ | $CH_3$ |
| G | $CH_2$ | $CH_3$ | $CH_3$ | Cl | $CF_3$ | $CH_3$ |
| H | $CH_2$ | $CH_3$ | $CH_3$ | Cl | $CF_3$ | $CH_3$ |
| I | $CH_2$ | $CH_3$ | $CH_3$ | Cl | $CF_3$ | $CH_3$ |
| J | $CH_2$ | $CH_3$ | $CH_3$ | Cl | $CF_3$ | $CH_3$ |
| K | $CH_2$ | $CH_3$ | $CH_3$ | Cl | $CF_3$ | $CH_3$ |
| L | $CH_2$ | $CH_3$ | $CH_3$ | Cl | $CF_3$ | $CH_3$ |
| M | $CH_2$ | $CH_3$ | $CH_3$ | Cl | $CF_3$ | $CH_3$ |
| N | $CH_2$ | $CH_3$ | $CH_3$ | Cl | $CF_3$ | $CH_3$ |
| O | $CH_2$ | $CH_3$ | $CH_3$ | Cl | $CF_3$ | $CH_3$ |
| P | $CH_2$ | $CH_3$ | $CH_3$ | Cl | $CF_3$ | $CH_3$ |
| Q | $CH_2$ | $CH_3$ | $CH_3$ | Cl | $CF_3$ | $CH_3$ |
| R | $CH_2$ | $CH_3$ | $CH_3$ | Cl | $CF_3$ | $CH_3$ |
| S | $CH_2$ | $CH_3$ | $CH_3$ | Cl | $CF_3$ | $CH_3$ |
| T | $CH_2$ | $CH_3$ | $CH_3$ | Cl | $CF_3$ | $CH_3$ |
| U | $CH_2$ | $CH_3$ | $CH_3$ | Cl | $CF_3$ | $CH_3$ |
| V | $CH_2$ | $CH_3$ | $CH_3$ | Cl | $CF_3$ | $CH_3$ |
| W | $CH_2$ | $CH_3$ | $CH_3$ | Cl | $CF_3$ | $CH_3$ |
| X | $CH_2$ | $CH_3$ | $CH_3$ | Cl | $CF_3$ | $CH_3$ |
| Y | $CH_2$ | $CH_3$ | $CH_3$ | Cl | $CF_3$ | $CH_3$ |
| A | $CH_2$ | $CH_3$ | H | $CH_3$ | $CF_3$ | $CH_3$ |
| B | $CH_2$ | $CH_3$ | H | $CH_3$ | $CF_3$ | $CH_3$ |
| C | $CH_2$ | $CH_3$ | H | $CH_3$ | $CF_3$ | $CH_3$ |
| D | $CH_2$ | $CH_3$ | H | $CH_3$ | $CF_3$ | $CH_3$ |
| E | $CH_2$ | $CH_3$ | H | $CH_3$ | $CF_3$ | $CH_3$ |
| F | $CH_2$ | $CH_3$ | H | $CH_3$ | $CF_3$ | $CH_3$ |
| G | $CH_2$ | $CH_3$ | H | $CH_3$ | $CF_3$ | $CH_3$ |
| H | $CH_2$ | $CH_3$ | H | $CH_3$ | $CF_3$ | $CH_3$ |
| I | $CH_2$ | $CH_3$ | H | $CH_3$ | $CF_3$ | $CH_3$ |
| J | $CH_2$ | $CH_3$ | H | $CH_3$ | $CF_3$ | $CH_3$ |
| K | $CH_2$ | $CH_3$ | H | $CH_3$ | $CF_3$ | $CH_3$ |
| L | $CH_2$ | $CH_3$ | H | $CH_3$ | $CF_3$ | $CH_3$ |
| M | $CH_2$ | $CH_3$ | H | $CH_3$ | $CF_3$ | $CH_3$ |
| N | $CH_2$ | $CH_3$ | H | $CH_3$ | $CF_3$ | $CH_3$ |
| O | $CH_2$ | $CH_3$ | H | $CH_3$ | $CF_3$ | $CH_3$ |
| P | $CH_2$ | $CH_3$ | H | $CH_3$ | $CF_3$ | $CH_3$ |
| Q | $CH_2$ | $CH_3$ | H | $CH_3$ | $CF_3$ | $CH_3$ |
| R | $CH_2$ | $CH_3$ | H | $CH_3$ | $CF_3$ | $CH_3$ |
| S | $CH_2$ | $CH_3$ | H | $CH_3$ | $CF_3$ | $CH_3$ |
| T | $CH_2$ | $CH_3$ | H | $CH_3$ | $CF_3$ | $CH_3$ |
| U | $CH_2$ | $CH_3$ | H | $CH_3$ | $CF_3$ | $CH_3$ |
| V | $CH_2$ | $CH_3$ | H | $CH_3$ | $CF_3$ | $CH_3$ |
| W | $CH_2$ | $CH_3$ | H | $CH_3$ | $CF_3$ | $CH_3$ |
| X | $CH_2$ | $CH_3$ | H | $CH_3$ | $CF_3$ | $CH_3$ |
| Y | $CH_2$ | $CH_3$ | H | $CH_3$ | $CF_3$ | $CH_3$ |
| A | O | $CH_3$ | H | $CH_3$ | $CF_3$ | $CH_3$ |
| B | O | $CH_3$ | H | $CH_3$ | $CF_3$ | $CH_3$ |
| C | O | $CH_3$ | H | $CH_3$ | $CF_3$ | $CH_3$ |
| D | O | $CH_3$ | H | $CH_3$ | $CF_3$ | $CH_3$ |
| E | O | $CH_3$ | H | $CH_3$ | $CF_3$ | $CH_3$ |
| F | O | $CH_3$ | H | $CH_3$ | $CF_3$ | $CH_3$ |
| G | O | $CH_3$ | H | $CH_3$ | $CF_3$ | $CH_3$ |
| H | O | $CH_3$ | H | $CH_3$ | $CF_3$ | $CH_3$ |
| I | O | $CH_3$ | H | $CH_3$ | $CF_3$ | $CH_3$ |
| J | O | $CH_3$ | H | $CH_3$ | $CF_3$ | $CH_3$ |
| K | O | $CH_3$ | H | $CH_3$ | $CF_3$ | $CH_3$ |
| L | O | $CH_3$ | H | $CH_3$ | $CF_3$ | $CH_3$ |
| M | O | $CH_3$ | H | $CH_3$ | $CF_3$ | $CH_3$ |
| N | O | $CH_3$ | H | $CH_3$ | $CF_3$ | $CH_3$ |
| O | O | $CH_3$ | H | $CH_3$ | $CF_3$ | $CH_3$ |
| P | O | $CH_3$ | H | $CH_3$ | $CF_3$ | $CH_3$ |
| Q | O | $CH_3$ | H | $CH_3$ | $CF_3$ | $CH_3$ |
| R | O | $CH_3$ | H | $CH_3$ | $CF_3$ | $CH_3$ |
| S | O | $CH_3$ | H | $CH_3$ | $CF_3$ | $CH_3$ |
| T | O | $CH_3$ | H | $CH_3$ | $CF_3$ | $CH_3$ |
| U | O | $CH_3$ | H | $CH_3$ | $CF_3$ | $CH_3$ |
| V | O | $CH_3$ | H | $CH_3$ | $CF_3$ | $CH_3$ |
| W | O | $CH_3$ | H | $CH_3$ | $CF_3$ | $CH_3$ |
| X | O | $CH_3$ | H | $CH_3$ | $CF_3$ | $CH_3$ |
| Y | O | $CH_3$ | H | $CH_3$ | $CF_3$ | $CH_3$ |
| A | O | $C_2H_5$ | H | $CH_3$ | $CF_3$ | $CH_3$ |
| B | O | $C_2H_5$ | H | $CH_3$ | $CF_3$ | $CH_3$ |
| C | O | $C_2H_5$ | H | $CH_3$ | $CF_3$ | $CH_3$ |
| D | O | $C_2H_5$ | H | $CH_3$ | $CF_3$ | $CH_3$ |
| E | O | $C_2H_5$ | H | $CH_3$ | $CF_3$ | $CH_3$ |
| F | O | $C_2H_5$ | H | $CH_3$ | $CF_3$ | $CH_3$ |
| G | O | $C_2H_5$ | H | $CH_3$ | $CF_3$ | $CH_3$ |
| H | O | $C_2H_5$ | H | $CH_3$ | $CF_3$ | $CH_3$ |
| I | O | $C_2H_5$ | H | $CH_3$ | $CF_3$ | $CH_3$ |
| J | O | $C_2H_5$ | H | $CH_3$ | $CF_3$ | $CH_3$ |
| K | O | $C_2H_5$ | H | $CH_3$ | $CF_3$ | $CH_3$ |
| L | O | $C_2H_5$ | H | $CH_3$ | $CF_3$ | $CH_3$ |
| M | O | $C_2H_5$ | H | $CH_3$ | $CF_3$ | $CH_3$ |
| N | O | $C_2H_5$ | H | $CH_3$ | $CF_3$ | $CH_3$ |
| O | O | $C_2H_5$ | H | $CH_3$ | $CF_3$ | $CH_3$ |
| P | O | $C_2H_5$ | H | $CH_3$ | $CF_3$ | $CH_3$ |
| Q | O | $C_2H_5$ | H | $CH_3$ | $CF_3$ | $CH_3$ |
| R | O | $C_2H_5$ | H | $CH_3$ | $CF_3$ | $CH_3$ |
| S | O | $C_2H_5$ | H | $CH_3$ | $CF_3$ | $CH_3$ |
| T | O | $C_2H_5$ | H | $CH_3$ | $CF_3$ | $CH_3$ |
| U | O | $C_2H_5$ | H | $CH_3$ | $CF_3$ | $CH_3$ |
| V | O | $C_2H_5$ | H | $CH_3$ | $CF_3$ | $CH_3$ |
| W | O | $C_2H_5$ | H | $CH_3$ | $CF_3$ | $CH_3$ |
| X | O | $C_2H_5$ | H | $CH_3$ | $CF_3$ | $CH_3$ |
| Y | O | $C_2H_5$ | H | $CH_3$ | $CF_3$ | $CH_3$ |
| A | $CH_2$ | $CH_3$ | $CH_3$ | $CH_3$ | $CF_3$ | $CH_3$ |
| B | $CH_2$ | $CH_3$ | $CH_3$ | $CH_3$ | $CF_3$ | $CH_3$ |
| C | $CH_2$ | $CH_3$ | $CH_3$ | $CH_3$ | $CF_3$ | $CH_3$ |
| D | $CH_2$ | $CH_3$ | $CH_3$ | $CH_3$ | $CF_3$ | $CH_3$ |
| E | $CH_2$ | $CH_3$ | $CH_3$ | $CH_3$ | $CF_3$ | $CH_3$ |
| F | $CH_2$ | $CH_3$ | $CH_3$ | $CH_3$ | $CF_3$ | $CH_3$ |
| G | $CH_2$ | $CH_3$ | $CH_3$ | $CH_3$ | $CF_3$ | $CH_3$ |
| H | $CH_2$ | $CH_3$ | $CH_3$ | $CH_3$ | $CF_3$ | $CH_3$ |
| I | $CH_2$ | $CH_3$ | $CH_3$ | $CH_3$ | $CF_3$ | $CH_3$ |
| J | $CH_2$ | $CH_3$ | $CH_3$ | $CH_3$ | $CF_3$ | $CH_3$ |
| K | $CH_2$ | $CH_3$ | $CH_3$ | $CH_3$ | $CF_3$ | $CH_3$ |
| L | $CH_2$ | $CH_3$ | $CH_3$ | $CH_3$ | $CF_3$ | $CH_3$ |
| M | $CH_2$ | $CH_3$ | $CH_3$ | $CH_3$ | $CF_3$ | $CH_3$ |
| N | $CH_2$ | $CH_3$ | $CH_3$ | $CH_3$ | $CF_3$ | $CH_3$ |
| O | $CH_2$ | $CH_3$ | $CH_3$ | $CH_3$ | $CF_3$ | $CH_3$ |
| P | $CH_2$ | $CH_3$ | $CH_3$ | $CH_3$ | $CF_3$ | $CH_3$ |
| Q | $CH_2$ | $CH_3$ | $CH_3$ | $CH_3$ | $CF_3$ | $CH_3$ |
| R | $CH_2$ | $CH_3$ | $CH_3$ | $CH_3$ | $CF_3$ | $CH_3$ |
| S | $CH_2$ | $CH_3$ | $CH_3$ | $CH_3$ | $CF_3$ | $CH_3$ |
| T | $CH_2$ | $CH_3$ | $CH_3$ | $CH_3$ | $CF_3$ | $CH_3$ |
| U | $CH_2$ | $CH_3$ | $CH_3$ | $CH_3$ | $CF_3$ | $CH_3$ |
| V | $CH_2$ | $CH_3$ | $CH_3$ | $CH_3$ | $CF_3$ | $CH_3$ |
| W | $CH_2$ | $CH_3$ | $CH_3$ | $CH_3$ | $CF_3$ | $CH_3$ |
| X | $CH_2$ | $CH_3$ | $CH_3$ | $CH_3$ | $CF_3$ | $CH_3$ |
| Y | $CH_2$ | $CH_3$ | $CH_3$ | $CH_3$ | $CF_3$ | $CH_3$ |

TABLE A-continued

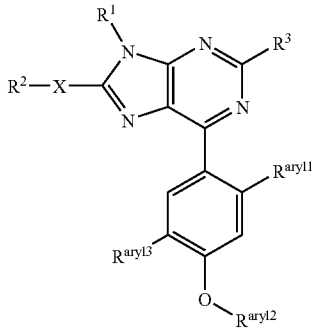

| $R^{1(a)}$ | X | $R^2$ | $R^3$ | $R^{aryl1}$ | $R^{aryl2}$ | $R^{aryl3}$ |
|---|---|---|---|---|---|---|
| A | $CH_2$ | $CH_3$ | H | Cl | $CHF_2$ | $CH_3$ |
| B | $CH_2$ | $CH_3$ | H | Cl | $CHF_2$ | $CH_3$ |
| C | $CH_2$ | $CH_3$ | H | Cl | $CHF_2$ | $CH_3$ |
| D | $CH_2$ | $CH_3$ | H | Cl | $CHF_2$ | $CH_3$ |
| E | $CH_2$ | $CH_3$ | H | Cl | $CHF_2$ | $CH_3$ |
| F | $CH_2$ | $CH_3$ | H | Cl | $CHF_2$ | $CH_3$ |
| G | $CH_2$ | $CH_3$ | H | Cl | $CHF_2$ | $CH_3$ |
| H | $CH_2$ | $CH_3$ | H | Cl | $CHF_2$ | $CH_3$ |
| I | $CH_2$ | $CH_3$ | H | Cl | $CHF_2$ | $CH_3$ |
| J | $CH_2$ | $CH_3$ | H | Cl | $CHF_2$ | $CH_3$ |
| K | $CH_2$ | $CH_3$ | H | Cl | $CHF_2$ | $CH_3$ |
| L | $CH_2$ | $CH_3$ | H | Cl | $CHF_2$ | $CH_3$ |
| M | $CH_2$ | $CH_3$ | H | Cl | $CHF_2$ | $CH_3$ |
| N | $CH_2$ | $CH_3$ | H | Cl | $CHF_2$ | $CH_3$ |
| O | $CH_2$ | $CH_3$ | H | Cl | $CHF_2$ | $CH_3$ |
| P | $CH_2$ | $CH_3$ | H | Cl | $CHF_2$ | $CH_3$ |
| Q | $CH_2$ | $CH_3$ | H | Cl | $CHF_2$ | $CH_3$ |
| R | $CH_2$ | $CH_3$ | H | Cl | $CHF_2$ | $CH_3$ |
| S | $CH_2$ | $CH_3$ | H | Cl | $CHF_2$ | $CH_3$ |
| T | $CH_2$ | $CH_3$ | H | Cl | $CHF_2$ | $CH_3$ |
| U | $CH_2$ | $CH_3$ | H | Cl | $CHF_2$ | $CH_3$ |
| V | $CH_2$ | $CH_3$ | H | Cl | $CHF_2$ | $CH_3$ |
| W | $CH_2$ | $CH_3$ | H | Cl | $CHF_2$ | $CH_3$ |
| X | $CH_2$ | $CH_3$ | H | Cl | $CHF_2$ | $CH_3$ |
| Y | $CH_2$ | $CH_3$ | H | Cl | $CHF_2$ | $CH_3$ |
| A | O | $CH_3$ | H | Cl | $CHF_2$ | $CH_3$ |
| B | O | $CH_3$ | H | Cl | $CHF_2$ | $CH_3$ |
| C | O | $CH_3$ | H | Cl | $CHF_2$ | $CH_3$ |
| D | O | $CH_3$ | H | Cl | $CHF_2$ | $CH_3$ |
| E | O | $CH_3$ | H | Cl | $CHF_2$ | $CH_3$ |
| F | O | $CH_3$ | H | Cl | $CHF_2$ | $CH_3$ |
| G | O | $CH_3$ | H | Cl | $CHF_2$ | $CH_3$ |
| H | O | $CH_3$ | H | Cl | $CHF_2$ | $CH_3$ |
| I | O | $CH_3$ | H | Cl | $CHF_2$ | $CH_3$ |
| J | O | $CH_3$ | H | Cl | $CHF_2$ | $CH_3$ |
| K | O | $CH_3$ | H | Cl | $CHF_2$ | $CH_3$ |
| L | O | $CH_3$ | H | Cl | $CHF_2$ | $CH_3$ |
| M | O | $CH_3$ | H | Cl | $CHF_2$ | $CH_3$ |
| N | O | $CH_3$ | H | Cl | $CHF_2$ | $CH_3$ |
| O | O | $CH_3$ | H | Cl | $CHF_2$ | $CH_3$ |
| P | O | $CH_3$ | H | Cl | $CHF_2$ | $CH_3$ |
| Q | O | $CH_3$ | H | Cl | $CHF_2$ | $CH_3$ |
| R | O | $CH_3$ | H | Cl | $CHF_2$ | $CH_3$ |
| S | O | $CH_3$ | H | Cl | $CHF_2$ | $CH_3$ |
| T | O | $CH_3$ | H | Cl | $CHF_2$ | $CH_3$ |
| U | O | $CH_3$ | H | Cl | $CHF_2$ | $CH_3$ |
| V | O | $CH_3$ | H | Cl | $CHF_2$ | $CH_3$ |
| W | O | $CH_3$ | H | Cl | $CHF_2$ | $CH_3$ |
| X | O | $CH_3$ | H | Cl | $CHF_2$ | $CH_3$ |
| Y | O | $CH_3$ | H | Cl | $CHF_2$ | $CH_3$ |
| A | O | $C_2H_5$ | H | Cl | $CHF_2$ | $CH_3$ |
| B | O | $C_2H_5$ | H | Cl | $CHF_2$ | $CH_3$ |
| C | O | $C_2H_5$ | H | Cl | $CHF_2$ | $CH_3$ |
| D | O | $C_2H_5$ | H | Cl | $CHF_2$ | $CH_3$ |
| E | O | $C_2H_5$ | H | Cl | $CHF_2$ | $CH_3$ |
| F | O | $C_2H_5$ | H | Cl | $CHF_2$ | $CH_3$ |
| G | O | $C_2H_5$ | H | Cl | $CHF_2$ | $CH_3$ |
| H | O | $C_2H_5$ | H | Cl | $CHF_2$ | $CH_3$ |
| I | O | $C_2H_5$ | H | Cl | $CHF_2$ | $CH_3$ |
| J | O | $C_2H_5$ | H | Cl | $CHF_2$ | $CH_3$ |
| K | O | $C_2H_5$ | H | Cl | $CHF_2$ | $CH_3$ |
| L | O | $C_2H_5$ | H | Cl | $CHF_2$ | $CH_3$ |
| M | O | $C_2H_5$ | H | Cl | $CHF_2$ | $CH_3$ |
| N | O | $C_2H_5$ | H | Cl | $CHF_2$ | $CH_3$ |
| O | O | $C_2H_5$ | H | Cl | $CHF_2$ | $CH_3$ |
| P | O | $C_2H_5$ | H | Cl | $CHF_2$ | $CH_3$ |
| Q | O | $C_2H_5$ | H | Cl | $CHF_2$ | $CH_3$ |
| R | O | $C_2H_5$ | H | Cl | $CHF_2$ | $CH_3$ |
| S | O | $C_2H_5$ | H | Cl | $CHF_2$ | $CH_3$ |
| T | O | $C_2H_5$ | H | Cl | $CHF_2$ | $CH_3$ |
| U | O | $C_2H_5$ | H | Cl | $CHF_2$ | $CH_3$ |
| V | O | $C_2H_5$ | H | Cl | $CHF_2$ | $CH_3$ |
| W | O | $C_2H_5$ | H | Cl | $CHF_2$ | $CH_3$ |
| X | O | $C_2H_5$ | H | Cl | $CHF_2$ | $CH_3$ |
| Y | O | $C_2H_5$ | H | Cl | $CHF_2$ | $CH_3$ |
| A | $CH_2$ | $CH_3$ | $CH_3$ | Cl | $CHF_2$ | $CH_3$ |
| B | $CH_2$ | $CH_3$ | $CH_3$ | Cl | $CHF_2$ | $CH_3$ |
| C | $CH_2$ | $CH_3$ | $CH_3$ | Cl | $CHF_2$ | $CH_3$ |
| D | $CH_2$ | $CH_3$ | $CH_3$ | Cl | $CHF_2$ | $CH_3$ |
| E | $CH_2$ | $CH_3$ | $CH_3$ | Cl | $CHF_2$ | $CH_3$ |
| F | $CH_2$ | $CH_3$ | $CH_3$ | Cl | $CHF_2$ | $CH_3$ |
| G | $CH_2$ | $CH_3$ | $CH_3$ | Cl | $CHF_2$ | $CH_3$ |
| H | $CH_2$ | $CH_3$ | $CH_3$ | Cl | $CHF_2$ | $CH_3$ |
| I | $CH_2$ | $CH_3$ | $CH_3$ | Cl | $CHF_2$ | $CH_3$ |
| J | $CH_2$ | $CH_3$ | $CH_3$ | Cl | $CHF_2$ | $CH_3$ |
| K | $CH_2$ | $CH_3$ | $CH_3$ | Cl | $CHF_2$ | $CH_3$ |
| L | $CH_2$ | $CH_3$ | $CH_3$ | Cl | $CHF_2$ | $CH_3$ |
| M | $CH_2$ | $CH_3$ | $CH_3$ | Cl | $CHF_2$ | $CH_3$ |
| N | $CH_2$ | $CH_3$ | $CH_3$ | Cl | $CHF_2$ | $CH_3$ |
| O | $CH_2$ | $CH_3$ | $CH_3$ | Cl | $CHF_2$ | $CH_3$ |
| P | $CH_2$ | $CH_3$ | $CH_3$ | Cl | $CHF_2$ | $CH_3$ |
| Q | $CH_2$ | $CH_3$ | $CH_3$ | Cl | $CHF_2$ | $CH_3$ |
| R | $CH_2$ | $CH_3$ | $CH_3$ | Cl | $CHF_2$ | $CH_3$ |
| S | $CH_2$ | $CH_3$ | $CH_3$ | Cl | $CHF_2$ | $CH_3$ |
| T | $CH_2$ | $CH_3$ | $CH_3$ | Cl | $CHF_2$ | $CH_3$ |
| U | $CH_2$ | $CH_3$ | $CH_3$ | Cl | $CHF_2$ | $CH_3$ |
| V | $CH_2$ | $CH_3$ | $CH_3$ | Cl | $CHF_2$ | $CH_3$ |
| W | $CH_2$ | $CH_3$ | $CH_3$ | Cl | $CHF_2$ | $CH_3$ |
| X | $CH_2$ | $CH_3$ | $CH_3$ | Cl | $CHF_2$ | $CH_3$ |
| Y | $CH_2$ | $CH_3$ | $CH_3$ | Cl | $CHF_2$ | $CH_3$ |
| A | $CH_2$ | $CH_3$ | H | $CH_3$ | $CHF_2$ | $CH_3$ |
| B | $CH_2$ | $CH_3$ | H | $CH_3$ | $CHF_2$ | $CH_3$ |
| C | $CH_2$ | $CH_3$ | H | $CH_3$ | $CHF_2$ | $CH_3$ |
| D | $CH_2$ | $CH_3$ | H | $CH_3$ | $CHF_2$ | $CH_3$ |
| E | $CH_2$ | $CH_3$ | H | $CH_3$ | $CHF_2$ | $CH_3$ |
| F | $CH_2$ | $CH_3$ | H | $CH_3$ | $CHF_2$ | $CH_3$ |
| G | $CH_2$ | $CH_3$ | H | $CH_3$ | $CHF_2$ | $CH_3$ |
| H | $CH_2$ | $CH_3$ | H | $CH_3$ | $CHF_2$ | $CH_3$ |
| I | $CH_2$ | $CH_3$ | H | $CH_3$ | $CHF_2$ | $CH_3$ |
| J | $CH_2$ | $CH_3$ | H | $CH_3$ | $CHF_2$ | $CH_3$ |
| K | $CH_2$ | $CH_3$ | H | $CH_3$ | $CHF_2$ | $CH_3$ |
| L | $CH_2$ | $CH_3$ | H | $CH_3$ | $CHF_2$ | $CH_3$ |
| M | $CH_2$ | $CH_3$ | H | $CH_3$ | $CHF_2$ | $CH_3$ |
| N | $CH_2$ | $CH_3$ | H | $CH_3$ | $CHF_2$ | $CH_3$ |
| O | $CH_2$ | $CH_3$ | H | $CH_3$ | $CHF_2$ | $CH_3$ |
| P | $CH_2$ | $CH_3$ | H | $CH_3$ | $CHF_2$ | $CH_3$ |
| Q | $CH_2$ | $CH_3$ | H | $CH_3$ | $CHF_2$ | $CH_3$ |
| R | $CH_2$ | $CH_3$ | H | $CH_3$ | $CHF_2$ | $CH_3$ |
| S | $CH_2$ | $CH_3$ | H | $CH_3$ | $CHF_2$ | $CH_3$ |
| T | $CH_2$ | $CH_3$ | H | $CH_3$ | $CHF_2$ | $CH_3$ |

TABLE A-continued

| R[1(a)] | X | R[2] | R[3] | R[aryl1] | R[aryl2] | R[aryl3] |
|---|---|---|---|---|---|---|
| U | $CH_2$ | $CH_3$ | H | $CH_3$ | $CHF_2$ | $CH_3$ |
| V | $CH_2$ | $CH_3$ | H | $CH_3$ | $CHF_2$ | $CH_3$ |
| W | $CH_2$ | $CH_3$ | H | $CH_3$ | $CHF_2$ | $CH_3$ |
| X | $CH_2$ | $CH_3$ | H | $CH_3$ | $CHF_2$ | $CH_3$ |
| Y | $CH_2$ | $CH_3$ | H | $CH_3$ | $CHF_2$ | $CH_3$ |
| A | O | $CH_3$ | H | $CH_3$ | $CHF_2$ | $CH_3$ |
| B | O | $CH_3$ | H | $CH_3$ | $CHF_2$ | $CH_3$ |
| C | O | $CH_3$ | H | $CH_3$ | $CHF_2$ | $CH_3$ |
| D | O | $CH_3$ | H | $CH_3$ | $CHF_2$ | $CH_3$ |
| E | O | $CH_3$ | H | $CH_3$ | $CHF_2$ | $CH_3$ |
| F | O | $CH_3$ | H | $CH_3$ | $CHF_2$ | $CH_3$ |
| G | O | $CH_3$ | H | $CH_3$ | $CHF_2$ | $CH_3$ |
| H | O | $CH_3$ | H | $CH_3$ | $CHF_2$ | $CH_3$ |
| I | O | $CH_3$ | H | $CH_3$ | $CHF_2$ | $CH_3$ |
| J | O | $CH_3$ | H | $CH_3$ | $CHF_2$ | $CH_3$ |
| K | O | $CH_3$ | H | $CH_3$ | $CHF_2$ | $CH_3$ |
| L | O | $CH_3$ | H | $CH_3$ | $CHF_2$ | $CH_3$ |
| M | O | $CH_3$ | H | $CH_3$ | $CHF_2$ | $CH_3$ |
| N | O | $CH_3$ | H | $CH_3$ | $CHF_2$ | $CH_3$ |
| O | O | $CH_3$ | H | $CH_3$ | $CHF_2$ | $CH_3$ |
| P | O | $CH_3$ | H | $CH_3$ | $CHF_2$ | $CH_3$ |
| Q | O | $CH_3$ | H | $CH_3$ | $CHF_2$ | $CH_3$ |
| R | O | $CH_3$ | H | $CH_3$ | $CHF_2$ | $CH_3$ |
| S | O | $CH_3$ | H | $CH_3$ | $CHF_2$ | $CH_3$ |
| T | O | $CH_3$ | H | $CH_3$ | $CHF_2$ | $CH_3$ |
| U | O | $CH_3$ | H | $CH_3$ | $CHF_2$ | $CH_3$ |
| V | O | $CH_3$ | H | $CH_3$ | $CHF_2$ | $CH_3$ |
| W | O | $CH_3$ | H | $CH_3$ | $CHF_2$ | $CH_3$ |
| X | O | $CH_3$ | H | $CH_3$ | $CHF_2$ | $CH_3$ |
| Y | O | $CH_3$ | H | $CH_3$ | $CHF_2$ | $CH_3$ |
| A | O | $C_2H_5$ | H | $CH_3$ | $CHF_2$ | $CH_3$ |
| B | O | $C_2H_5$ | H | $CH_3$ | $CHF_2$ | $CH_3$ |
| C | O | $C_2H_5$ | H | $CH_3$ | $CHF_2$ | $CH_3$ |
| D | O | $C_2H_5$ | H | $CH_3$ | $CHF_2$ | $CH_3$ |
| E | O | $C_2H_5$ | H | $CH_3$ | $CHF_2$ | $CH_3$ |
| F | O | $C_2H_5$ | H | $CH_3$ | $CHF_2$ | $CH_3$ |
| G | O | $C_2H_5$ | H | $CH_3$ | $CHF_2$ | $CH_3$ |
| H | O | $C_2H_5$ | H | $CH_3$ | $CHF_2$ | $CH_3$ |
| I | O | $C_2H_5$ | H | $CH_3$ | $CHF_2$ | $CH_3$ |
| J | O | $C_2H_5$ | H | $CH_3$ | $CHF_2$ | $CH_3$ |
| K | O | $C_2H_5$ | H | $CH_3$ | $CHF_2$ | $CH_3$ |
| L | O | $C_2H_5$ | H | $CH_3$ | $CHF_2$ | $CH_3$ |
| M | O | $C_2H_5$ | H | $CH_3$ | $CHF_2$ | $CH_3$ |
| N | O | $C_2H_5$ | H | $CH_3$ | $CHF_2$ | $CH_3$ |
| O | O | $C_2H_5$ | H | $CH_3$ | $CHF_2$ | $CH_3$ |
| P | O | $C_2H_5$ | H | $CH_3$ | $CHF_2$ | $CH_3$ |
| Q | O | $C_2H_5$ | H | $CH_3$ | $CHF_2$ | $CH_3$ |
| R | O | $C_2H_5$ | H | $CH_3$ | $CHF_2$ | $CH_3$ |
| S | O | $C_2H_5$ | H | $CH_3$ | $CHF_2$ | $CH_3$ |
| T | O | $C_2H_5$ | H | $CH_3$ | $CHF_2$ | $CH_3$ |
| U | O | $C_2H_5$ | H | $CH_3$ | $CHF_2$ | $CH_3$ |
| V | O | $C_2H_5$ | H | $CH_3$ | $CHF_2$ | $CH_3$ |
| W | O | $C_2H_5$ | H | $CH_3$ | $CHF_2$ | $CH_3$ |
| X | O | $C_2H_5$ | H | $CH_3$ | $CHF_2$ | $CH_3$ |
| Y | O | $C_2H_5$ | H | $CH_3$ | $CHF_2$ | $CH_3$ |
| A | $CH_2$ | $CH_3$ | $CH_3$ | $CH_3$ | $CHF_2$ | $CH_3$ |
| B | $CH_2$ | $CH_3$ | $CH_3$ | $CH_3$ | $CHF_2$ | $CH_3$ |
| C | $CH_2$ | $CH_3$ | $CH_3$ | $CH_3$ | $CHF_2$ | $CH_3$ |
| D | $CH_2$ | $CH_3$ | $CH_3$ | $CH_3$ | $CHF_2$ | $CH_3$ |
| E | $CH_2$ | $CH_3$ | $CH_3$ | $CH_3$ | $CHF_2$ | $CH_3$ |
| F | $CH_2$ | $CH_3$ | $CH_3$ | $CH_3$ | $CHF_2$ | $CH_3$ |
| G | $CH_2$ | $CH_3$ | $CH_3$ | $CH_3$ | $CHF_2$ | $CH_3$ |
| H | $CH_2$ | $CH_3$ | $CH_3$ | $CH_3$ | $CHF_2$ | $CH_3$ |
| I | $CH_2$ | $CH_3$ | $CH_3$ | $CH_3$ | $CHF_2$ | $CH_3$ |
| J | $CH_2$ | $CH_3$ | $CH_3$ | $CH_3$ | $CHF_2$ | $CH_3$ |
| K | $CH_2$ | $CH_3$ | $CH_3$ | $CH_3$ | $CHF_2$ | $CH_3$ |
| L | $CH_2$ | $CH_3$ | $CH_3$ | $CH_3$ | $CHF_2$ | $CH_3$ |
| M | $CH_2$ | $CH_3$ | $CH_3$ | $CH_3$ | $CHF_2$ | $CH_3$ |
| N | $CH_2$ | $CH_3$ | $CH_3$ | $CH_3$ | $CHF_2$ | $CH_3$ |
| O | $CH_2$ | $CH_3$ | $CH_3$ | $CH_3$ | $CHF_2$ | $CH_3$ |
| P | $CH_2$ | $CH_3$ | $CH_3$ | $CH_3$ | $CHF_2$ | $CH_3$ |
| Q | $CH_2$ | $CH_3$ | $CH_3$ | $CH_3$ | $CHF_2$ | $CH_3$ |
| R | $CH_2$ | $CH_3$ | $CH_3$ | $CH_3$ | $CHF_2$ | $CH_3$ |
| S | $CH_2$ | $CH_3$ | $CH_3$ | $CH_3$ | $CHF_2$ | $CH_3$ |
| T | $CH_2$ | $CH_3$ | $CH_3$ | $CH_3$ | $CHF_2$ | $CH_3$ |
| U | $CH_2$ | $CH_3$ | $CH_3$ | $CH_3$ | $CHF_2$ | $CH_3$ |
| V | $CH_2$ | $CH_3$ | $CH_3$ | $CH_3$ | $CHF_2$ | $CH_3$ |
| W | $CH_2$ | $CH_3$ | $CH_3$ | $CH_3$ | $CHF_2$ | $CH_3$ |
| X | $CH_2$ | $CH_3$ | $CH_3$ | $CH_3$ | $CHF_2$ | $CH_3$ |
| Y | $CH_2$ | $CH_3$ | $CH_3$ | $CH_3$ | $CHF_2$ | $CH_3$ |
| Z | $CH_2$ | $CH_3$ | H | Cl | $CF_3$ | H |
| Z | O | $CH_3$ | H | Cl | $CF_3$ | H |
| Z | O | $C_2H_5$ | H | Cl | $CF_3$ | H |
| Z | $CH_2$ | $CH_3$ | H | $CH_3$ | $CF_3$ | H |
| Z | O | $CH_3$ | H | $CH_3$ | $CF_3$ | H |
| Z | O | $C_2H_5$ | H | $CH_3$ | $CF_3$ | H |
| Z | $CH_2$ | $CH_3$ | H | Cl | $CHF_2$ | H |
| Z | O | $CH_3$ | H | Cl | $CHF_2$ | H |
| Z | O | $C_2H_5$ | H | Cl | $CHF_2$ | H |
| Z | $CH_2$ | $CH_3$ | H | $CH_3$ | $CHF_2$ | H |
| Z | O | $CH_3$ | H | $CH_3$ | $CHF_2$ | H |
| Z | O | $C_2H_5$ | H | $CH_3$ | $CHF_2$ | H |
| AA | $CH_2$ | $CH_3$ | H | Cl | $CHF_2$ | H |
| BB | $CH_2$ | $CH_3$ | H | Cl | $CHF_2$ | H |
| N | O | $CH_3$ | H | H | $CHF_2$ | H |

[(a)] A = 2-butyl; B = 2-pentyl; C = 2-hexyl; D = 2-heptyl; E = 3-pentyl; F = 3-hexyl; G = 3-heptyl; H = 1-methoxy-3-pentyl; I = 4-heptyl; J = 1-cyclopropyl-1-ethyl; K = 1-cyclopropyl-1-propyl; L = 1-cyclopropyl-1-butyl; M = 1-cyclopropyl-3-methoxy-1-propyl; N = 1-cyclobutyl-1-ethyl; O = 1-cyclobutyl-1-propyl; P = 1-cyclobutyl-1-butyl; Q = 1-cyclobutyl-3-methoxy-1-propyl; R = 1-cyclopentyl-1-ethyl; S = 1-cyclopentyl-1-propyl; T = 1-cyclopentyl-1-butyl; U = 1-cyclopentyl-3-methoxy-1-propyl; V = ?-cyclopropylbenzyl; W = 1-phenyl-2-butyn-1-yl; X = 1-cyclopropyl-2-butyn-1-yl; Y = dicyclopropylmethyl; Z = 2-hexyn-3-yl; AA = cyclopentyl; BB = 1-cyclopropyl-2-propyl.

Particular compounds provided herein also include those of the following structure, with the substituents thereof being set forth in the table.

TABLE B

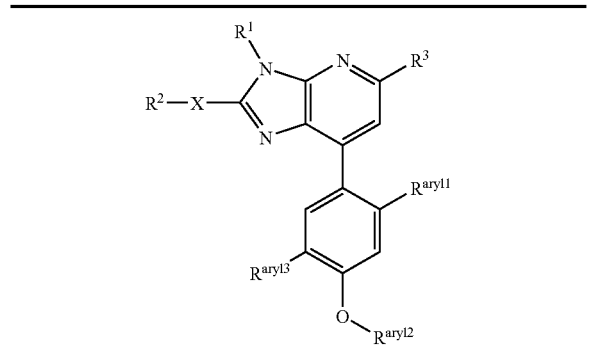

| R$^{1(a)}$ | X | R$^2$ | R$^3$ | R$^{aryl1}$ | R$^{aryl2}$ | R$^{aryl3}$ |
|---|---|---|---|---|---|---|
| A | CH$_2$ | CH$_3$ | H | Cl | CF$_3$ | H |
| B | CH$_2$ | CH$_3$ | H | Cl | CF$_3$ | H |
| C | CH$_2$ | CH$_3$ | H | Cl | CF$_3$ | H |
| D | CH$_2$ | CH$_3$ | H | Cl | CF$_3$ | H |
| E | CH$_2$ | CH$_3$ | H | Cl | CF$_3$ | H |
| F | CH$_2$ | CH$_3$ | H | Cl | CF$_3$ | H |
| G | CH$_2$ | CH$_3$ | H | Cl | CF$_3$ | H |
| H | CH$_2$ | CH$_3$ | H | Cl | CF$_3$ | H |
| I | CH$_2$ | CH$_3$ | H | Cl | CF$_3$ | H |
| J | CH$_2$ | CH$_3$ | H | Cl | CF$_3$ | H |
| K | CH$_2$ | CH$_3$ | H | Cl | CF$_3$ | H |
| L | CH$_2$ | CH$_3$ | H | Cl | CF$_3$ | H |
| M | CH$_2$ | CH$_3$ | H | Cl | CF$_3$ | H |
| N | CH$_2$ | CH$_3$ | H | Cl | CF$_3$ | H |
| O | CH$_2$ | CH$_3$ | H | Cl | CF$_3$ | H |
| P | CH$_2$ | CH$_3$ | H | Cl | CF$_3$ | H |
| Q | CH$_2$ | CH$_3$ | H | Cl | CF$_3$ | H |
| R | CH$_2$ | CH$_3$ | H | Cl | CF$_3$ | H |
| S | CH$_2$ | CH$_3$ | H | Cl | CF$_3$ | H |
| T | CH$_2$ | CH$_3$ | H | Cl | CF$_3$ | H |
| U | CH$_2$ | CH$_3$ | H | Cl | CF$_3$ | H |
| V | CH$_2$ | CH$_3$ | H | Cl | CF$_3$ | H |
| W | CH$_2$ | CH$_3$ | H | Cl | CF$_3$ | H |
| X | CH$_2$ | CH$_3$ | H | Cl | CF$_3$ | H |
| Y | CH$_2$ | CH$_3$ | H | Cl | CF$_3$ | H |
| A | O | CH$_3$ | H | Cl | CF$_3$ | H |
| B | O | CH$_3$ | H | Cl | CF$_3$ | H |
| C | O | CH$_3$ | H | Cl | CF$_3$ | H |
| D | O | CH$_3$ | H | Cl | CF$_3$ | H |
| E | O | CH$_3$ | H | Cl | CF$_3$ | H |
| F | O | CH$_3$ | H | Cl | CF$_3$ | H |
| G | O | CH$_3$ | H | Cl | CF$_3$ | H |
| H | O | CH$_3$ | H | Cl | CF$_3$ | H |
| I | O | CH$_3$ | H | Cl | CF$_3$ | H |
| J | O | CH$_3$ | H | Cl | CF$_3$ | H |
| K | O | CH$_3$ | H | Cl | CF$_3$ | H |
| L | O | CH$_3$ | H | Cl | CF$_3$ | H |
| N | O | CH$_3$ | H | Cl | CF$_3$ | H |
| N | O | CH$_3$ | H | Cl | CF$_3$ | H |
| O | O | CH$_3$ | H | Cl | CF$_3$ | H |
| P | O | CH$_3$ | H | Cl | CF$_3$ | H |
| Q | O | CH$_3$ | H | Cl | CF$_3$ | H |
| R | O | CH$_3$ | H | Cl | CF$_3$ | H |
| S | O | CH$_3$ | H | Cl | CF$_3$ | H |
| T | O | CH$_3$ | H | Cl | CF$_3$ | H |
| U | O | CH$_3$ | H | Cl | CF$_3$ | H |
| V | O | CH$_3$ | H | Cl | CF$_3$ | H |
| W | O | CH$_3$ | H | Cl | CF$_3$ | H |
| X | O | CH$_3$ | H | Cl | CF$_3$ | H |
| Y | O | CH$_3$ | H | Cl | CF$_3$ | H |
| A | O | C$_2$H$_5$ | H | Cl | CF$_3$ | H |
| B | O | C$_2$H$_5$ | H | Cl | CF$_3$ | H |
| C | O | C$_2$H$_5$ | H | Cl | CF$_3$ | H |
| D | O | C$_2$H$_5$ | H | Cl | CF$_3$ | H |
| E | O | C$_2$H$_5$ | H | Cl | CF$_3$ | H |
| F | O | C$_2$H$_5$ | H | Cl | CF$_3$ | H |
| G | O | C$_2$H$_5$ | H | Cl | CF$_3$ | H |
| H | O | C$_2$H$_5$ | H | Cl | CF$_3$ | H |
| I | O | C$_2$H$_5$ | H | Cl | CF$_3$ | H |
| J | O | C$_2$H$_5$ | H | Cl | CF$_3$ | H |
| K | O | C$_2$H$_5$ | H | Cl | CF$_3$ | H |
| L | O | C$_2$H$_5$ | H | Cl | CF$_3$ | H |
| M | O | C$_2$H$_5$ | H | Cl | CF$_3$ | H |
| N | O | C$_2$H$_5$ | H | Cl | CF$_3$ | H |
| O | O | C$_2$H$_5$ | H | Cl | CF$_3$ | H |
| P | O | C$_2$H$_5$ | H | Cl | CF$_3$ | H |
| Q | O | C$_2$H$_5$ | H | Cl | CF$_3$ | H |
| R | O | C$_2$H$_5$ | H | Cl | CF$_3$ | H |
| S | O | C$_2$H$_5$ | H | Cl | CF$_3$ | H |
| T | O | C$_2$H$_5$ | H | Cl | CF$_3$ | H |
| U | O | C$_2$H$_5$ | H | Cl | CF$_3$ | H |
| V | O | C$_2$H$_5$ | H | Cl | CF$_3$ | H |
| W | O | C$_2$H$_5$ | H | Cl | CF$_3$ | H |
| X | O | C$_2$H$_5$ | H | Cl | CF$_3$ | H |
| Y | O | C$_2$H$_5$ | H | Cl | CF$_3$ | H |
| A | CH$_2$ | CH$_3$ | CH$_3$ | Cl | CF$_3$ | H |
| B | CH$_2$ | CH$_3$ | CH$_3$ | Cl | CF$_3$ | H |
| C | CH$_2$ | CH$_3$ | CH$_3$ | Cl | CF$_3$ | H |
| D | CH$_2$ | CH$_3$ | CH$_3$ | Cl | CF$_3$ | H |
| E | CH$_2$ | CH$_3$ | CH$_3$ | Cl | CF$_3$ | H |
| F | CH$_2$ | CH$_3$ | CH$_3$ | Cl | CF$_3$ | H |
| G | CH$_2$ | CH$_3$ | CH$_3$ | Cl | CF$_3$ | H |
| H | CH$_2$ | CH$_3$ | CH$_3$ | Cl | CF$_3$ | H |
| I | CH$_2$ | CH$_3$ | CH$_3$ | Cl | CF$_3$ | H |
| J | CH$_2$ | CH$_3$ | CH$_3$ | Cl | CF$_3$ | H |
| K | CH$_2$ | CH$_3$ | CH$_3$ | Cl | CF$_3$ | H |
| L | CH$_2$ | CH$_3$ | CH$_3$ | Cl | CF$_3$ | H |
| M | CH$_2$ | CH$_3$ | CH$_3$ | Cl | CF$_3$ | H |
| N | CH$_2$ | CH$_3$ | CH$_3$ | Cl | CF$_3$ | H |
| O | CH$_2$ | CH$_3$ | CH$_3$ | Cl | CF$_3$ | H |
| P | CH$_2$ | CH$_3$ | CH$_3$ | Cl | CF$_3$ | H |
| Q | CH$_2$ | CH$_3$ | CH$_3$ | Cl | CF$_3$ | H |
| R | CH$_2$ | CH$_3$ | CH$_3$ | Cl | CF$_3$ | H |
| S | CH$_2$ | CH$_3$ | CH$_3$ | Cl | CF$_3$ | H |
| T | CH$_2$ | CH$_3$ | CH$_3$ | Cl | CF$_3$ | H |
| U | CH$_2$ | CH$_3$ | CH$_3$ | Cl | CF$_3$ | H |
| V | CH$_2$ | CH$_3$ | CH$_3$ | Cl | CF$_3$ | H |
| W | CH$_2$ | CH$_3$ | CH$_3$ | Cl | CF$_3$ | H |
| X | CH$_2$ | CH$_3$ | CH$_3$ | Cl | CF$_3$ | H |
| Y | CH$_2$ | CH$_3$ | CH$_3$ | Cl | CF$_3$ | H |
| A | CH$_2$ | CH$_3$ | H | CH$_3$ | CF$_3$ | H |
| B | CH$_2$ | CH$_3$ | H | CH$_3$ | CF$_3$ | H |
| C | CH$_2$ | CH$_3$ | H | CH$_3$ | CF$_3$ | H |
| D | CH$_2$ | CH$_3$ | H | CH$_3$ | CF$_3$ | H |
| E | CH$_2$ | CH$_3$ | H | CH$_3$ | CF$_3$ | H |
| F | CH$_2$ | CH$_3$ | H | CH$_3$ | CF$_3$ | H |
| G | CH$_2$ | CH$_3$ | H | CH$_3$ | CF$_3$ | H |
| H | CH$_2$ | CH$_3$ | H | CH$_3$ | CF$_3$ | H |
| I | CH$_2$ | CH$_3$ | H | CH$_3$ | CF$_3$ | H |
| J | CH$_2$ | CH$_3$ | H | CH$_3$ | CF$_3$ | H |
| K | CH$_2$ | CH$_3$ | H | CH$_3$ | CF$_3$ | H |
| L | CH$_2$ | CH$_3$ | H | CH$_3$ | CF$_3$ | H |
| M | CH$_2$ | CH$_3$ | H | CH$_3$ | CF$_3$ | H |
| N | CH$_2$ | CH$_3$ | H | CH$_3$ | CF$_3$ | H |
| O | CH$_2$ | CH$_3$ | H | CH$_3$ | CF$_3$ | H |
| P | CH$_2$ | CH$_3$ | H | CH$_3$ | CF$_3$ | H |
| Q | CH$_2$ | CH$_3$ | H | CH$_3$ | CF$_3$ | H |
| R | CH$_2$ | CH$_3$ | H | CH$_3$ | CF$_3$ | H |
| S | CH$_2$ | CH$_3$ | H | CH$_3$ | CF$_3$ | H |
| T | CH$_2$ | CH$_3$ | H | CH$_3$ | CF$_3$ | H |

TABLE B-continued

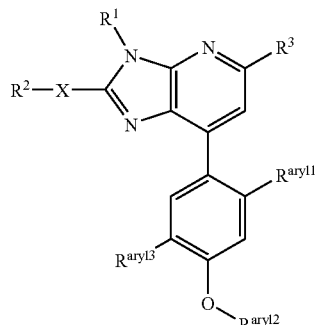

| R¹⁽ᵃ⁾ | X | R² | R³ | R^aryl1 | R^aryl2 | R^aryl3 |
|---|---|---|---|---|---|---|
| U | CH₂ | CH₃ | H | CH₃ | CF₃ | H |
| V | CH₂ | CH₃ | H | CH₃ | CF₃ | H |
| W | CH₂ | CH₃ | H | CH₃ | CF₃ | H |
| X | CH₂ | CH₃ | H | CH₃ | CF₃ | H |
| A | O | CH₃ | H | CH₃ | CF₃ | H |
| B | O | CH₃ | H | CH₃ | CF₃ | H |
| C | O | CH₃ | H | CH₃ | CF₃ | H |
| D | O | CH₃ | H | CH₃ | CF₃ | H |
| E | O | CH₃ | H | CH₃ | CF₃ | H |
| F | O | CH₃ | H | CH₃ | CF₃ | H |
| G | O | CH₃ | H | CH₃ | CF₃ | H |
| H | O | CH₃ | H | CH₃ | CF₃ | H |
| I | O | CH₃ | H | CH₃ | CF₃ | H |
| J | O | CH₃ | H | CH₃ | CF₃ | H |
| K | O | CH₃ | H | CH₃ | CF₃ | H |
| L | O | CH₃ | H | CH₃ | CF₃ | H |
| M | O | CH₃ | H | CH₃ | CF₃ | H |
| N | O | CH₃ | H | CH₃ | CF₃ | H |
| O | O | CH₃ | H | CH₃ | CF₃ | H |
| P | O | CH₃ | H | CH₃ | CF₃ | H |
| Q | O | CH₃ | H | CH₃ | CF₃ | H |
| R | O | CH₃ | H | CH₃ | CF₃ | H |
| S | O | CH₃ | H | CH₃ | CF₃ | H |
| T | O | CH₃ | H | CH₃ | CF₃ | H |
| U | O | CH₃ | H | CH₃ | CF₃ | H |
| V | O | CH₃ | H | CH₃ | CF₃ | H |
| W | O | CH₃ | H | CH₃ | CF₃ | H |
| X | O | CH₃ | H | CH₃ | CF₃ | H |
| Y | O | CH₃ | H | CH₃ | CF₃ | H |
| A | O | C₂H₅ | H | CH₃ | CF₃ | H |
| B | O | C₂H₅ | H | CH₃ | CF₃ | H |
| C | O | C₂H₅ | H | CH₃ | CF₃ | H |
| D | O | C₂H₅ | H | CH₃ | CF₃ | H |
| E | O | C₂H₅ | H | CH₃ | CF₃ | H |
| F | O | C₂H₅ | H | CH₃ | CF₃ | H |
| G | O | C₂H₅ | H | CH₃ | CF₃ | H |
| H | O | C₂H₅ | H | CH₃ | CF₃ | H |
| I | O | C₂H₅ | H | CH₃ | CF₃ | H |
| J | O | C₂H₅ | H | CH₃ | CF₃ | H |
| K | O | C₂H₅ | H | CH₃ | CF₃ | H |
| L | O | C₂H₅ | H | CH₃ | CF₃ | H |
| M | O | C₂H₅ | H | CH₃ | CF₃ | H |
| N | O | C₂H₅ | H | CH₃ | CF₃ | H |
| o | O | C₂H₅ | H | CH₃ | CF₃ | H |
| P | O | C₂H₅ | H | CH₃ | CF₃ | H |
| Q | O | C₂H₅ | H | CH₃ | CF₃ | H |
| R | O | C₂H₅ | H | CH₃ | CF₃ | H |
| S | O | C₂H₅ | H | CH₃ | CF₃ | H |
| T | O | C₂H₅ | H | CH₃ | CF₃ | H |
| U | O | C₂H₅ | H | CH₃ | CF₃ | H |
| V | O | C₂H₅ | H | CH₃ | CF₃ | H |
| W | O | C₂H₅ | H | CH₃ | CF₃ | H |
| X | O | C₂H₅ | H | CH₃ | CF₃ | H |
| Y | O | C₂H₅ | H | CH₃ | CF₃ | H |
| A | CH₂ | CH₃ | CH₃ | CH₃ | CF₃ | H |
| B | CH₂ | CH₃ | CH₃ | CH₃ | CF₃ | H |
| C | CH₂ | CH₃ | CH₃ | CH₃ | CF₃ | H |
| D | CH₂ | CH₃ | CH₃ | CH₃ | CF₃ | H |
| E | CH₂ | CH₃ | CH₃ | CH₃ | CF₃ | H |
| F | CH₂ | CH₃ | CH₃ | CH₃ | CF₃ | H |

TABLE B-continued

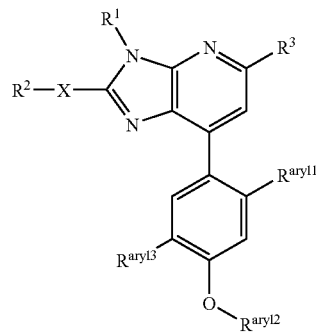

| R¹⁽ᵃ⁾ | X | R² | R³ | R^aryl1 | R^aryl2 | R^aryl3 |
|---|---|---|---|---|---|---|
| G | CH₂ | CH₃ | CH₃ | CH₃ | CF₃ | H |
| H | CH₂ | CH₃ | CH₃ | CH₃ | CF₃ | H |
| I | CH₂ | CH₃ | CH₃ | CH₃ | CF₃ | H |
| J | CH₂ | CH₃ | CH₃ | CH₃ | CF₃ | H |
| K | CH₂ | CH₃ | CH₃ | CH₃ | CF₃ | H |
| L | CH₂ | CH₃ | CH₃ | CH₃ | CF₃ | H |
| H | CH₂ | CH₃ | CH₃ | CH₃ | CF₃ | H |
| N | CH₂ | CH₃ | CH₃ | CH₃ | CF₃ | H |
| O | CH₂ | CH₃ | CH₃ | CH₃ | CF₃ | H |
| P | CH₂ | CH₃ | CH₃ | CH₃ | CF₃ | H |
| Q | CH₂ | CH₃ | CH₃ | CH₃ | CF₃ | H |
| R | CH₂ | CH₃ | CH₃ | CH₃ | CF₃ | H |
| S | CH₂ | CH₃ | CH₃ | CH₃ | CF₃ | H |
| T | CH₂ | CH₃ | CH₃ | CH₃ | CF₃ | H |
| U | CH₂ | CH₃ | CH₃ | CH₃ | CF₃ | H |
| V | CH₂ | CH₃ | CH₃ | CH₃ | CF₃ | H |
| W | CH₂ | CH₃ | CH₃ | CH₃ | CF₃ | H |
| X | CH₂ | CH₃ | CH₃ | CH₃ | CF₃ | H |
| Y | CH₂ | CH₃ | CH₃ | CH₃ | CF₃ | H |
| A | CH₂ | CH₃ | H | Cl | CHF₂ | H |
| B | CH₂ | CH₃ | H | Cl | CHF₂ | H |
| C | CH₂ | CH₃ | H | Cl | CHF₂ | H |
| D | CH₂ | CH₃ | H | Cl | CHF₂ | H |
| E | CH₂ | CH₃ | H | Cl | CHF₂ | H |
| F | CH₂ | CH₃ | H | Cl | CHF₂ | H |
| G | CH₂ | CH₃ | H | Cl | CHF₂ | H |
| H | CH₂ | CH₃ | H | Cl | CHF₂ | H |
| I | CH₂ | CH₃ | H | Cl | CHF₂ | H |
| J | CH₂ | CH₃ | H | Cl | CHF₂ | H |
| K | CH₂ | CH₃ | H | Cl | CHF₂ | H |
| L | CH₂ | CH₃ | H | Cl | CHF₂ | H |
| M | CH₂ | CH₃ | H | Cl | CHF₂ | H |
| N | CH₂ | CH₃ | H | Cl | CHF₂ | H |
| O | CH₂ | CH₃ | H | Cl | CHF₂ | H |
| P | CH₂ | CH₃ | H | Cl | CHF₂ | H |
| Q | CH₂ | CH₃ | H | Cl | CHF₂ | H |
| R | CH₂ | CH₃ | H | Cl | CHF₂ | H |
| S | CH₂ | CH₃ | H | Cl | CHF₂ | H |
| T | CH₂ | CH₃ | H | Cl | CHF₂ | H |
| U | CH₂ | CH₃ | H | Cl | CHF₂ | H |
| V | CH₂ | CH₃ | H | Cl | CHF₂ | H |
| W | CH₂ | CH₃ | H | Cl | CHF₂ | H |
| X | CH₂ | CH₃ | H | Cl | CHF₂ | H |
| Y | CH₂ | CH₃ | H | Cl | CHF₂ | H |
| A | O | CH₃ | H | Cl | CHF₂ | H |
| B | O | CH₃ | H | Cl | CHF₂ | H |
| C | O | CH₃ | H | Cl | CHF₂ | H |
| D | O | CH₃ | H | Cl | CHF₂ | H |
| E | O | CH₃ | H | Cl | CHF₂ | H |
| F | O | CH₃ | H | Cl | CHF₂ | H |
| G | O | CH₃ | H | Cl | CHF₂ | H |
| H | O | CH₃ | H | Cl | CHF₂ | H |
| I | O | CH₃ | H | Cl | CHF₂ | H |
| J | O | CH₃ | H | Cl | CHF₂ | H |
| K | O | CH₃ | H | Cl | CHF₂ | H |
| L | O | CH₃ | H | Cl | CHF₂ | H |
| M | O | CH₃ | H | Cl | CHF₂ | H |
| N | O | CH₃ | H | Cl | CHF₂ | H |
| O | O | CH₃ | H | Cl | CHF₂ | H |
| P | O | CH₃ | H | Cl | CHF₂ | H |

TABLE B-continued

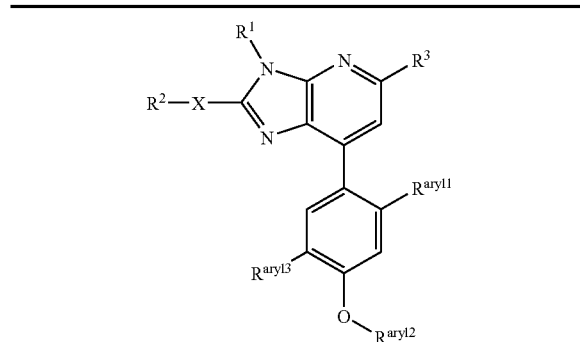

| R[1(a)] | X | R[2] | R[3] | R[aryl1] | R[aryl2] | R[aryl3] |
|---|---|---|---|---|---|---|
| Q | O | CH$_3$ | H | Cl | CHF$_2$ | H |
| R | O | CH$_3$ | H | Cl | CHF$_2$ | H |
| S | O | CH$_3$ | H | Cl | CHF$_2$ | H |
| T | O | CH$_3$ | H | Cl | CHF$_2$ | H |
| U | O | CH$_3$ | H | Cl | CHF$_2$ | H |
| V | O | CH$_3$ | H | Cl | CHF$_2$ | H |
| W | O | CH$_3$ | H | Cl | CHF$_2$ | H |
| X | O | CH$_3$ | H | Cl | CHF$_2$ | H |
| Y | O | CH$_3$ | H | Cl | CHF$_2$ | H |
| A | O | C$_2$H$_5$ | H | Cl | CHF$_2$ | H |
| B | O | C$_2$H$_5$ | H | Cl | CHF$_2$ | H |
| C | O | C$_2$H$_5$ | H | Cl | CHF$_2$ | H |
| D | O | C$_2$H$_5$ | H | Cl | CHF$_2$ | H |
| E | O | C$_2$H$_5$ | H | Cl | CHF$_2$ | H |
| F | O | C$_2$H$_5$ | H | Cl | CHF$_2$ | H |
| G | O | C$_2$H$_5$ | H | Cl | CHF$_2$ | H |
| H | O | C$_2$H$_5$ | H | Cl | CHF$_2$ | H |
| I | O | C$_2$H$_5$ | H | Cl | CHF$_2$ | H |
| J | O | C$_2$H$_5$ | H | Cl | CHF$_2$ | H |
| K | O | C$_2$H$_5$ | H | Cl | CHF$_2$ | H |
| L | O | C$_2$H$_5$ | H | Cl | CHF$_2$ | H |
| M | O | C$_2$H$_5$ | H | Cl | CHF$_2$ | H |
| N | O | C$_2$H$_5$ | H | Cl | CHF$_2$ | H |
| O | O | C$_2$H$_5$ | H | Cl | CHF$_2$ | H |
| P | O | C$_2$H$_5$ | H | Cl | CHF$_2$ | H |
| Q | O | C$_2$H$_5$ | H | Cl | CHF$_2$ | H |
| R | O | C$_2$H$_5$ | H | Cl | CHF$_2$ | H |
| S | O | C$_2$H$_5$ | H | Cl | CHF$_2$ | H |
| T | O | C$_2$H$_5$ | H | Cl | CHF$_2$ | H |
| U | O | C$_2$H$_5$ | H | Cl | CHF$_2$ | H |
| V | O | C$_2$H$_5$ | H | Cl | CHF$_2$ | H |
| W | O | C$_2$H$_5$ | H | Cl | CHF$_2$ | H |
| X | O | C$_2$H$_5$ | H | Cl | CHF$_2$ | H |
| Y | O | C$_2$H$_5$ | H | Cl | CHF$_2$ | H |
| A | CH$_2$ | CH$_3$ | CH$_3$ | Cl | CHF$_2$ | H |
| B | CH$_2$ | CH$_3$ | CH$_3$ | Cl | CHF$_2$ | H |
| C | CH$_2$ | CH$_3$ | CH$_3$ | Cl | CHF$_2$ | H |
| D | CH$_2$ | CH$_3$ | CH$_3$ | Cl | CHF$_2$ | H |
| E | CH$_2$ | CH$_3$ | CH$_3$ | Cl | CHF$_2$ | H |
| F | CH$_2$ | CH$_3$ | CH$_3$ | Cl | CHF$_2$ | H |
| G | CH$_2$ | CH$_3$ | CH$_3$ | Cl | CHF$_2$ | H |
| H | CH$_2$ | CH$_3$ | CH$_3$ | Cl | CHF$_2$ | H |
| I | CH$_2$ | CH$_3$ | CH$_3$ | Cl | CHF$_2$ | H |
| J | CH$_2$ | CH$_3$ | CH$_3$ | Cl | CHF$_2$ | H |
| K | CH$_2$ | CH$_3$ | CH$_3$ | Cl | CHF$_2$ | H |
| L | CH$_2$ | CH$_3$ | CH$_3$ | Cl | CHF$_2$ | H |
| M | CH$_2$ | CH$_3$ | CH$_3$ | Cl | CHF$_2$ | H |
| N | CH$_2$ | CH$_3$ | CH$_3$ | Cl | CHF$_2$ | H |
| O | CH$_2$ | CH$_3$ | CH$_3$ | Cl | CHF$_2$ | H |
| P | CH$_2$ | CH$_3$ | CH$_3$ | Cl | CHF$_2$ | H |
| Q | CH$_2$ | CH$_3$ | CH$_3$ | Cl | CHF$_2$ | H |
| R | CH$_2$ | CH$_3$ | CH$_3$ | Cl | CHF$_2$ | H |
| S | CH$_2$ | CH$_3$ | CH$_3$ | Cl | CHF$_2$ | H |
| T | CH$_2$ | CH$_3$ | CH$_3$ | Cl | CHF$_2$ | H |
| U | CH$_2$ | CH$_3$ | CH$_3$ | Cl | CHF$_2$ | H |
| V | CH$_2$ | CH$_3$ | CH$_3$ | Cl | CHF$_2$ | H |
| W | CH$_2$ | CH$_3$ | CH$_3$ | Cl | CHF$_2$ | H |
| X | CH$_2$ | CH$_3$ | CH$_3$ | Cl | CHF$_2$ | H |
| Y | CH$_2$ | CH$_3$ | CH$_3$ | Cl | CHF$_2$ | H |
| A | CH$_2$ | CH$_3$ | H | CH$_3$ | CHF$_2$ | H |

TABLE B-continued

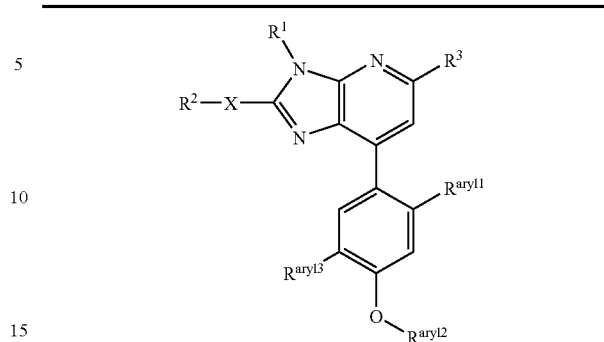

| R[1(a)] | X | R[2] | R[3] | R[aryl1] | R[aryl2] | R[aryl3] |
|---|---|---|---|---|---|---|
| B | CH$_2$ | CH$_3$ | H | CH$_3$ | CHF$_2$ | H |
| C | CH$_2$ | CH$_3$ | H | CH$_3$ | CHF$_2$ | H |
| D | CH$_2$ | CH$_3$ | H | CH$_3$ | CHF$_2$ | H |
| E | CH$_2$ | CH$_3$ | H | CH$_3$ | CHF$_2$ | H |
| F | CH$_2$ | CH$_3$ | H | CH$_3$ | CHF$_2$ | H |
| G | CH$_2$ | CH$_3$ | H | CH$_3$ | CHF$_2$ | H |
| H | CH$_2$ | CH$_3$ | H | CH$_3$ | CHF$_2$ | H |
| I | CH$_2$ | CH$_3$ | H | CH$_3$ | CHF$_2$ | H |
| J | CH$_2$ | CH$_3$ | H | CH$_3$ | CHF$_2$ | H |
| K | CH$_2$ | CH$_3$ | H | CH$_3$ | CHF$_2$ | H |
| L | CH$_2$ | CH$_3$ | H | CH$_3$ | CHF$_2$ | H |
| M | CH$_2$ | CH$_3$ | H | CH$_3$ | CHF$_2$ | H |
| N | CH$_2$ | CH$_3$ | H | CH$_3$ | CHF$_2$ | H |
| O | CH$_2$ | CH$_3$ | H | CH$_3$ | CHF$_2$ | H |
| P | CH$_2$ | CH$_3$ | H | CH$_3$ | CHF$_2$ | H |
| Q | CH$_2$ | CH$_3$ | H | CH$_3$ | CHF$_2$ | H |
| R | CH$_2$ | CH$_3$ | H | CH$_3$ | CHF$_2$ | H |
| S | CH$_2$ | CH$_3$ | H | CH$_3$ | CHF$_2$ | H |
| T | CH$_2$ | CH$_3$ | H | CH$_3$ | CHF$_2$ | H |
| U | CH$_2$ | CH$_3$ | H | CH$_3$ | CHF$_2$ | H |
| V | CH$_2$ | CH$_3$ | H | CH$_3$ | CHF$_2$ | H |
| W | CH$_2$ | CH$_3$ | H | CH$_3$ | CHF$_2$ | H |
| X | CH$_2$ | CH$_3$ | H | CH$_3$ | CHF$_2$ | H |
| Y | CH$_2$ | CH$_3$ | H | CH$_3$ | CHF$_2$ | H |
| A | O | CH$_3$ | H | CH$_3$ | CHF$_2$ | H |
| B | O | CH$_3$ | H | CH$_3$ | CHF$_2$ | H |
| C | O | CH$_3$ | H | CH$_3$ | CHF$_2$ | H |
| D | O | CH$_3$ | H | CH$_3$ | CHF$_2$ | H |
| E | O | CH$_3$ | H | CH$_3$ | CHF$_2$ | H |
| F | O | CH$_3$ | H | CH$_3$ | CHF$_2$ | H |
| G | O | CH$_3$ | H | CH$_3$ | CHF$_2$ | H |
| H | O | CH$_3$ | H | CH$_3$ | CHF$_2$ | H |
| I | O | CH$_3$ | H | CH$_3$ | CHF$_2$ | H |
| J | O | CH$_3$ | H | CH$_3$ | CHF$_2$ | H |
| K | O | CH$_3$ | H | CH$_3$ | CHF$_2$ | H |
| L | O | CH$_3$ | H | CH$_3$ | CHF$_2$ | H |
| M | O | CH$_3$ | H | CH$_3$ | CHF$_2$ | H |
| N | O | CH$_3$ | H | CH$_3$ | CHF$_2$ | H |
| O | O | CH$_3$ | H | CH$_3$ | CHF$_2$ | H |
| P | O | CH$_3$ | H | CH$_3$ | CHF$_2$ | H |
| Q | O | CH$_3$ | H | CH$_3$ | CHF$_2$ | H |
| R | O | CH$_3$ | H | CH$_3$ | CHF$_2$ | H |
| S | O | CH$_3$ | H | CH$_3$ | CHF$_2$ | H |
| T | O | CH$_3$ | H | CH$_3$ | CHF$_2$ | H |
| U | O | CH$_3$ | H | CH$_3$ | CHF$_2$ | H |
| V | O | CH$_3$ | H | CH$_3$ | CHF$_2$ | H |
| W | O | CH$_3$ | H | CH$_3$ | CHF$_2$ | H |
| X | O | CH$_3$ | H | CH$_3$ | CHF$_2$ | H |
| Y | O | CH$_3$ | H | CH$_3$ | CHF$_2$ | H |
| A | O | C$_2$H$_5$ | H | CH$_3$ | CHF$_2$ | H |
| B | O | C$_2$H$_5$ | H | CH$_3$ | CHF$_2$ | H |
| C | O | C$_2$H$_5$ | H | CH$_3$ | CHF$_2$ | H |
| D | O | C$_2$H$_5$ | H | CH$_3$ | CHF$_2$ | H |
| E | O | C$_2$H$_5$ | H | CH$_3$ | CHF$_2$ | H |
| F | O | C$_2$H$_5$ | H | CH$_3$ | CHF$_2$ | H |
| G | O | C$_2$H$_5$ | H | CH$_3$ | CHF$_2$ | H |
| H | O | C$_2$H$_5$ | H | CH$_3$ | CHF$_2$ | H |
| I | O | C$_2$H$_5$ | H | CH$_3$ | CHF$_2$ | H |
| J | O | C$_2$H$_5$ | H | CH$_3$ | CHF$_2$ | H |
| K | O | C$_2$H$_5$ | H | CH$_3$ | CHF$_2$ | H |

TABLE B-continued

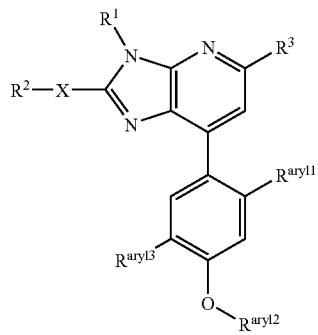

| R[1(a)] | X | R[2] | R[3] | R[aryl1] | R[aryl2] | R[aryl3] |
|---|---|---|---|---|---|---|
| L | O | C$_2$H$_5$ | H | CH$_3$ | CHF$_2$ | H |
| M | O | C$_2$H$_5$ | H | CH$_3$ | CHF$_2$ | H |
| N | O | C$_2$H$_5$ | H | CH$_3$ | CHF$_2$ | H |
| O | O | C$_2$H$_5$ | H | CH$_3$ | CHF$_2$ | H |
| P | O | C$_2$H$_5$ | H | CH$_3$ | CHF$_2$ | H |
| Q | O | C$_2$H$_5$ | H | CH$_3$ | CHF$_2$ | H |
| R | O | C$_2$H$_5$ | H | CH$_3$ | CHF$_2$ | H |
| S | O | C$_2$H$_5$ | H | CH$_3$ | CHF$_2$ | H |
| T | O | C$_2$H$_5$ | H | CH$_3$ | CHF$_2$ | H |
| U | O | C$_2$H$_5$ | H | CH$_3$ | CHF$_2$ | H |
| V | O | C$_2$H$_5$ | H | CH$_3$ | CHF$_2$ | H |
| W | O | C$_2$H$_5$ | H | CH$_3$ | CHF$_2$ | H |
| X | O | C$_2$H$_5$ | H | CH$_3$ | CHF$_2$ | H |
| Y | O | C$_2$H$_5$ | H | CH$_3$ | CHF$_2$ | H |
| A | CH$_2$ | CH$_3$ | CH$_3$ | CH$_3$ | CHF$_2$ | H |
| B | CH$_2$ | CH$_3$ | CH$_3$ | CH$_3$ | CHF$_2$ | H |
| C | CH$_2$ | CH$_3$ | CH$_3$ | CH$_3$ | CHF$_2$ | H |
| D | CH$_2$ | CH$_3$ | CH$_3$ | CH$_3$ | CHF$_2$ | H |
| E | CH$_2$ | CH$_3$ | CH$_3$ | CH$_3$ | CHF$_2$ | H |
| F | CH$_2$ | CH$_3$ | CH$_3$ | CH$_3$ | CHF$_2$ | H |
| G | CH$_2$ | CH$_3$ | CH$_3$ | CH$_3$ | CHF$_2$ | H |
| H | CH$_2$ | CH$_3$ | CH$_3$ | CH$_3$ | CHF$_2$ | H |
| I | CH$_2$ | CH$_3$ | CH$_3$ | CH$_3$ | CHF$_2$ | H |
| J | CH$_2$ | CH$_3$ | CH$_3$ | CH$_3$ | CHF$_2$ | H |
| K | CH$_2$ | CH$_3$ | CH$_3$ | CH$_3$ | CHF$_2$ | H |
| L | CH$_2$ | CH$_3$ | CH$_3$ | CH$_3$ | CHF$_2$ | H |
| M | CH$_2$ | CH$_3$ | CH$_3$ | CH$_3$ | CHF$_2$ | H |
| N | CH$_2$ | CH$_3$ | CH$_3$ | CH$_3$ | CHF$_2$ | H |
| O | CH$_2$ | CH$_3$ | CH$_3$ | CH$_3$ | CHF$_2$ | H |
| P | CH$_2$ | CH$_3$ | CH$_3$ | CH$_3$ | CHF$_2$ | H |
| Q | CH$_2$ | CH$_3$ | CH$_3$ | CH$_3$ | CHF$_2$ | H |
| R | CH$_2$ | CH$_3$ | CH$_3$ | CH$_3$ | CHF$_2$ | H |
| S | CH$_2$ | CH$_3$ | CH$_3$ | CH$_3$ | CHF$_2$ | H |
| T | CH$_2$ | CH$_3$ | CH$_3$ | CH$_3$ | CHF$_2$ | H |
| U | CH$_2$ | CH$_3$ | CH$_3$ | CH$_3$ | CHF$_2$ | H |
| V | CH$_2$ | CH$_3$ | CH$_3$ | CH$_3$ | CHF$_2$ | H |
| W | CH$_2$ | CH$_3$ | CH$_3$ | CH$_3$ | CHF$_2$ | H |
| X | CH$_2$ | CH$_3$ | CH$_3$ | CH$_3$ | CHF$_2$ | H |
| Y | CH$_2$ | CH$_3$ | CH$_3$ | CH$_3$ | CHF$_2$ | H |
| A | CH$_2$ | CH$_3$ | H | Cl | CF$_3$ | CH$_3$ |
| B | CH$_2$ | CH$_3$ | H | Cl | CF$_3$ | CH$_3$ |
| C | CH$_2$ | CH$_3$ | H | Cl | CF$_3$ | CH$_3$ |
| D | CH$_2$ | CH$_3$ | H | Cl | CF$_3$ | CH$_3$ |
| E | CH$_2$ | CH$_3$ | H | Cl | CF$_3$ | CH$_3$ |
| F | CH$_2$ | CH$_3$ | H | Cl | CF$_3$ | CH$_3$ |
| G | CH$_2$ | CH$_3$ | H | Cl | CF$_3$ | CH$_3$ |
| H | CH$_2$ | CH$_3$ | H | Cl | CF$_3$ | CH$_3$ |
| I | CH$_2$ | CH$_3$ | H | Cl | CF$_3$ | CH$_3$ |
| J | CH$_2$ | CH$_3$ | H | Cl | CF$_3$ | CH$_3$ |
| K | CH$_2$ | CH$_3$ | H | Cl | CF$_3$ | CH$_3$ |
| L | CH$_2$ | CH$_3$ | H | Cl | CF$_3$ | CH$_3$ |
| M | CH$_2$ | CH$_3$ | H | Cl | CF$_3$ | CH$_3$ |
| N | CH$_2$ | CH$_3$ | H | Cl | CF$_3$ | CH$_3$ |
| O | CH$_2$ | CH$_3$ | H | Cl | CF$_3$ | CH$_3$ |
| P | CH$_2$ | CH$_3$ | H | Cl | CF$_3$ | CH$_3$ |
| Q | CH$_2$ | CH$_3$ | H | Cl | CF$_3$ | CH$_3$ |
| R | CH$_2$ | CH$_3$ | H | Cl | CF$_3$ | CH$_3$ |
| S | CH$_2$ | CH$_3$ | H | Cl | CF$_3$ | CH$_3$ |
| T | CH$_2$ | CH$_3$ | H | Cl | CF$_3$ | CH$_3$ |
| U | CH$_2$ | CH$_3$ | H | Cl | CF$_3$ | CH$_3$ |

TABLE B-continued

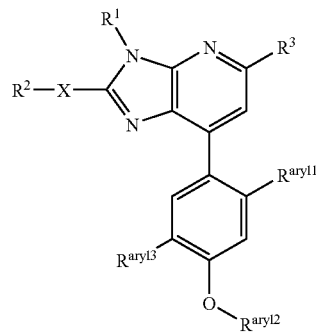

| R[1(a)] | X | R[2] | R[3] | R[aryl1] | R[aryl2] | R[aryl3] |
|---|---|---|---|---|---|---|
| V | CH$_2$ | CH$_3$ | H | Cl | CF$_3$ | CH$_3$ |
| W | CH$_2$ | CH$_3$ | H | Cl | CF$_3$ | CH$_3$ |
| X | CH$_2$ | CH$_3$ | H | Cl | CF$_3$ | CH$_3$ |
| Y | CH$_2$ | CH$_3$ | H | Cl | CF$_3$ | CH$_3$ |
| A | O | CH$_3$ | H | Cl | CF$_3$ | CH$_3$ |
| B | O | CH$_3$ | H | Cl | CF$_3$ | CH$_3$ |
| C | O | CH$_3$ | H | Cl | CF$_3$ | CH$_3$ |
| D | O | CH$_3$ | H | Cl | CF$_3$ | CH$_3$ |
| E | O | CH$_3$ | H | Cl | CF$_3$ | CH$_3$ |
| F | O | CH$_3$ | H | Cl | CF$_3$ | CH$_3$ |
| G | O | CH$_3$ | H | Cl | CF$_3$ | CH$_3$ |
| H | O | CH$_3$ | H | Cl | CF$_3$ | CH$_3$ |
| I | O | CH$_3$ | H | Cl | CF$_3$ | CH$_3$ |
| J | O | CH$_3$ | H | Cl | CF$_3$ | CH$_3$ |
| K | O | CH$_3$ | H | Cl | CF$_3$ | CH$_3$ |
| L | O | CH$_3$ | H | Cl | CF$_3$ | CH$_3$ |
| M | O | CH$_3$ | H | Cl | CF$_3$ | CH$_3$ |
| N | O | CH$_3$ | H | Cl | CF$_3$ | CH$_3$ |
| O | O | CH$_3$ | H | Cl | CF$_3$ | CH$_3$ |
| P | O | CH$_3$ | H | Cl | CF$_3$ | CH$_3$ |
| Q | O | CH$_3$ | H | Cl | CF$_3$ | CH$_3$ |
| R | O | CH$_3$ | H | Cl | CF$_3$ | CH$_3$ |
| S | O | CH$_3$ | H | Cl | CF$_3$ | CH$_3$ |
| T | O | CH$_3$ | H | Cl | CF$_3$ | CH$_3$ |
| U | O | CH$_3$ | H | Cl | CF$_3$ | CH$_3$ |
| V | O | CH$_3$ | H | Cl | CF$_3$ | CH$_3$ |
| W | O | CH$_3$ | H | Cl | CF$_3$ | CH$_3$ |
| X | O | CH$_3$ | H | Cl | CF$_3$ | CH$_3$ |
| Y | O | CH$_3$ | H | Cl | CF$_3$ | CH$_3$ |
| A | O | C$_2$H$_5$ | H | Cl | CF$_3$ | CH$_3$ |
| B | O | C$_2$H$_5$ | H | Cl | CF$_3$ | CH$_3$ |
| C | O | C$_2$H$_5$ | H | Cl | CF$_3$ | CH$_3$ |
| D | O | C$_2$H$_5$ | H | Cl | CF$_3$ | CH$_3$ |
| E | O | C$_2$H$_5$ | H | Cl | CF$_3$ | CH$_3$ |
| F | O | C$_2$H$_5$ | H | Cl | CF$_3$ | CH$_3$ |
| G | O | C$_2$H$_5$ | H | Cl | CF$_3$ | CH$_3$ |
| H | O | C$_2$H$_5$ | H | Cl | CF$_3$ | CH$_3$ |
| I | O | C$_2$H$_5$ | H | Cl | CF$_3$ | CH$_3$ |
| J | O | C$_2$H$_5$ | H | Cl | CF$_3$ | CH$_3$ |
| K | O | C$_2$H$_5$ | H | Cl | CF$_3$ | CH$_3$ |
| L | O | C$_2$H$_5$ | H | Cl | CF$_3$ | CH$_3$ |
| M | O | C$_2$H$_5$ | H | Cl | CF$_3$ | CH$_3$ |
| N | O | C$_2$H$_5$ | H | Cl | CF$_3$ | CH$_3$ |
| O | O | C$_2$H$_5$ | H | Cl | CF$_3$ | CH$_3$ |
| P | O | C$_2$H$_5$ | H | Cl | CF$_3$ | CH$_3$ |
| Q | O | C$_2$H$_5$ | H | Cl | CF$_3$ | CH$_3$ |
| R | O | C$_2$H$_5$ | H | Cl | CF$_3$ | CH$_3$ |
| S | O | C$_2$H$_5$ | H | Cl | CF$_3$ | CH$_3$ |
| T | O | C$_2$H$_5$ | H | Cl | CF$_3$ | CH$_3$ |
| U | O | C$_2$H$_5$ | H | Cl | CF$_3$ | CH$_3$ |
| V | O | C$_2$H$_5$ | H | Cl | CF$_3$ | CH$_3$ |
| W | O | C$_2$H$_5$ | H | Cl | CF$_3$ | CH$_3$ |
| X | O | C$_2$H$_5$ | H | Cl | CF$_3$ | CH$_3$ |
| Y | O | C$_2$H$_5$ | H | Cl | CF$_3$ | CH$_3$ |
| A | CH$_2$ | CH$_3$ | CH$_3$ | Cl | CF$_3$ | CH$_3$ |
| B | CH$_2$ | CH$_3$ | CH$_3$ | Cl | CF$_3$ | CH$_3$ |
| C | CH$_2$ | CH$_3$ | CH$_3$ | Cl | CF$_3$ | CH$_3$ |
| D | CH$_2$ | CH$_3$ | CH$_3$ | Cl | CF$_3$ | CH$_3$ |
| E | CH$_2$ | CH$_3$ | CH$_3$ | Cl | CF$_3$ | CH$_3$ |
| F | CH$_2$ | CH$_3$ | CH$_3$ | Cl | CF$_3$ | CH$_3$ |

TABLE B-continued

| R[1(a)] | X | R[2] | R[3] | R[aryl1] | R[aryl2] | R[aryl3] |
|---|---|---|---|---|---|---|
| G | CH$_2$ | CH$_3$ | CH$_3$ | Cl | CF$_3$ | CH$_3$ |
| H | CH$_2$ | CH$_3$ | CH$_3$ | Cl | CF$_3$ | CH$_3$ |
| I | CH$_2$ | CH$_3$ | CH$_3$ | Cl | CF$_3$ | CH$_3$ |
| J | CH$_2$ | CH$_3$ | CH$_3$ | Cl | CF$_3$ | CH$_3$ |
| K | CH$_2$ | CH$_3$ | CH$_3$ | Cl | CF$_3$ | CH$_3$ |
| L | CH$_2$ | CH$_3$ | CH$_3$ | Cl | CF$_3$ | CH$_3$ |
| M | CH$_2$ | CH$_3$ | CH$_3$ | Cl | CF$_3$ | CH$_3$ |
| N | CH$_2$ | CH$_3$ | CH$_3$ | Cl | CF$_3$ | CH$_3$ |
| O | CH$_2$ | CH$_3$ | CH$_3$ | Cl | CF$_3$ | CH$_3$ |
| P | CH$_2$ | CH$_3$ | CH$_3$ | Cl | CF$_3$ | CH$_3$ |
| Q | CH$_2$ | CH$_3$ | CH$_3$ | Cl | CF$_3$ | CH$_3$ |
| R | CH$_2$ | CH$_3$ | CH$_3$ | Cl | CF$_3$ | CH$_3$ |
| S | CH$_2$ | CH$_3$ | CH$_3$ | Cl | CF$_3$ | CH$_3$ |
| T | CH$_2$ | CH$_3$ | CH$_3$ | Cl | CF$_3$ | CH$_3$ |
| U | CH$_2$ | CH$_3$ | CH$_3$ | Cl | CF$_3$ | CH$_3$ |
| V | CH$_2$ | CH$_3$ | CH$_3$ | Cl | CF$_3$ | CH$_3$ |
| W | CH$_2$ | CH$_3$ | CH$_3$ | Cl | CF$_3$ | CH$_3$ |
| X | CH$_2$ | CH$_3$ | CH$_3$ | Cl | CF$_3$ | CH$_3$ |
| Y | CH$_2$ | CH$_3$ | CH$_3$ | Cl | CF$_3$ | CH$_3$ |
| A | CH$_2$ | CH$_3$ | H | CH$_3$ | CF$_3$ | CH$_3$ |
| B | CH$_2$ | CH$_3$ | H | CH$_3$ | CF$_3$ | CH$_3$ |
| C | CH$_2$ | CH$_3$ | H | CH$_3$ | CF$_3$ | CH$_3$ |
| D | CH$_2$ | CH$_3$ | H | CH$_3$ | CF$_3$ | CH$_3$ |
| E | CH$_2$ | CH$_3$ | H | CH$_3$ | CF$_3$ | CH$_3$ |
| F | CH$_2$ | CH$_3$ | H | CH$_3$ | CF$_3$ | CH$_3$ |
| G | CH$_2$ | CH$_3$ | H | CH$_3$ | CF$_3$ | CH$_3$ |
| H | CH$_2$ | CH$_3$ | H | CH$_3$ | CF$_3$ | CH$_3$ |
| I | CH$_2$ | CH$_3$ | H | CH$_3$ | CF$_3$ | CH$_3$ |
| J | CH$_2$ | CH$_3$ | H | CH$_3$ | CF$_3$ | CH$_3$ |
| K | CH$_2$ | CH$_3$ | H | CH$_3$ | CF$_3$ | CH$_3$ |
| L | CH$_2$ | CH$_3$ | H | CH$_3$ | CF$_3$ | CH$_3$ |
| M | CH$_2$ | CH$_3$ | H | CH$_3$ | CF$_3$ | CH$_3$ |
| N | CH$_2$ | CH$_3$ | H | CH$_3$ | CF$_3$ | CH$_3$ |
| O | CH$_2$ | CH$_3$ | H | CH$_3$ | CF$_3$ | CH$_3$ |
| P | CH$_2$ | CH$_3$ | H | CH$_3$ | CF$_3$ | CH$_3$ |
| Q | CH$_2$ | CH$_3$ | H | CH$_3$ | CF$_3$ | CH$_3$ |
| R | CH$_2$ | CH$_3$ | H | CH$_3$ | CF$_3$ | CH$_3$ |
| S | CH$_2$ | CH$_3$ | H | CH$_3$ | CF$_3$ | CH$_3$ |
| T | CH$_2$ | CH$_3$ | H | CH$_3$ | CF$_3$ | CH$_3$ |
| U | CH$_2$ | CH$_3$ | H | CH$_3$ | CF$_3$ | CH$_3$ |
| V | CH$_2$ | CH$_3$ | H | CH$_3$ | CF$_3$ | CH$_3$ |
| W | CH$_2$ | CH$_3$ | H | CH$_3$ | CF$_3$ | CH$_3$ |
| X | CH$_2$ | CH$_3$ | H | CH$_3$ | CF$_3$ | CH$_3$ |
| Y | CH$_2$ | CH$_3$ | H | CH$_3$ | CF$_3$ | CH$_3$ |
| A | O | CH$_3$ | H | CH$_3$ | CF$_3$ | CH$_3$ |
| B | O | CH$_3$ | H | CH$_3$ | CF$_3$ | CH$_3$ |
| C | O | CH$_3$ | H | CH$_3$ | CF$_3$ | CH$_3$ |
| D | O | CH$_3$ | H | CH$_3$ | CF$_3$ | CH$_3$ |
| E | O | CH$_3$ | H | CH$_3$ | CF$_3$ | CH$_3$ |
| F | O | CH$_3$ | H | CH$_3$ | CF$_3$ | CH$_3$ |
| G | O | CH$_3$ | H | CH$_3$ | CF$_3$ | CH$_3$ |
| H | O | CH$_3$ | H | CH$_3$ | CF$_3$ | CH$_3$ |
| I | O | CH$_3$ | H | CH$_3$ | CF$_3$ | CH$_3$ |
| J | O | CH$_3$ | H | CH$_3$ | CF$_3$ | CH$_3$ |
| K | O | CH$_3$ | H | CH$_3$ | CF$_3$ | CH$_3$ |
| L | O | CH$_3$ | H | CH$_3$ | CF$_3$ | CH$_3$ |
| M | O | CH$_3$ | H | CH$_3$ | CF$_3$ | CH$_3$ |
| N | O | CH$_3$ | H | CH$_3$ | CF$_3$ | CH$_3$ |
| O | O | CH$_3$ | H | CH$_3$ | CF$_3$ | CH$_3$ |
| P | O | CH$_3$ | H | CH$_3$ | CF$_3$ | CH$_3$ |
| Q | O | CH$_3$ | H | CH$_3$ | CF$_3$ | CH$_3$ |
| R | O | CH$_3$ | H | CH$_3$ | CF$_3$ | CH$_3$ |
| S | O | CH$_3$ | H | CH$_3$ | CF$_3$ | CH$_3$ |
| T | O | CH$_3$ | H | CH$_3$ | CF$_3$ | CH$_3$ |
| U | O | CH$_3$ | H | CH$_3$ | CF$_3$ | CH$_3$ |
| V | O | CH$_3$ | H | CH$_3$ | CF$_3$ | CH$_3$ |
| W | O | CH$_3$ | H | CH$_3$ | CF$_3$ | CH$_3$ |
| X | O | CH$_3$ | H | CH$_3$ | CF$_3$ | CH$_3$ |
| Y | O | CH$_3$ | H | CH$_3$ | CF$_3$ | CH$_3$ |
| A | O | C$_2$H$_5$ | H | CH$_3$ | CF$_3$ | CH$_3$ |
| B | O | C$_2$H$_5$ | H | CH$_3$ | CF$_3$ | CH$_3$ |
| C | O | C$_2$H$_5$ | H | CH$_3$ | CF$_3$ | CH$_3$ |
| D | O | C$_2$H$_5$ | H | CH$_3$ | CF$_3$ | CH$_3$ |
| E | O | C$_2$H$_5$ | H | CH$_3$ | CF$_3$ | CH$_3$ |
| F | O | C$_2$H$_5$ | H | CH$_3$ | CF$_3$ | CH$_3$ |
| G | O | C$_2$H$_5$ | H | CH$_3$ | CF$_3$ | CH$_3$ |
| H | O | C$_2$H$_5$ | H | CH$_3$ | CF$_3$ | CH$_3$ |
| I | O | C$_2$H$_5$ | H | CH$_3$ | CF$_3$ | CH$_3$ |
| J | O | C$_2$H$_5$ | H | CH$_3$ | CF$_3$ | CH$_3$ |
| K | O | C$_2$H$_5$ | H | CH$_3$ | CF$_3$ | CH$_3$ |
| L | O | C$_2$H$_5$ | H | CH$_3$ | CF$_3$ | CH$_3$ |
| M | O | C$_2$H$_5$ | H | CH$_3$ | CF$_3$ | CH$_3$ |
| N | O | C$_2$H$_5$ | H | CH$_3$ | CF$_3$ | CH$_3$ |
| O | O | C$_2$H$_5$ | H | CH$_3$ | CF$_3$ | CH$_3$ |
| P | O | C$_2$H$_5$ | H | CH$_3$ | CF$_3$ | CH$_3$ |
| Q | O | C$_2$H$_5$ | H | CH$_3$ | CF$_3$ | CH$_3$ |
| R | O | C$_2$H$_5$ | H | CH$_3$ | CF$_3$ | CH$_3$ |
| S | O | C$_2$H$_5$ | H | CH$_3$ | CF$_3$ | CH$_3$ |
| T | O | C$_2$H$_5$ | H | CH$_3$ | CF$_3$ | CH$_3$ |
| U | O | C$_2$H$_5$ | H | CH$_3$ | CF$_3$ | CH$_3$ |
| V | O | C$_2$H$_5$ | H | CH$_3$ | CF$_3$ | CH$_3$ |
| W | O | C$_2$H$_5$ | H | CH$_3$ | CF$_3$ | CH$_3$ |
| X | O | C$_2$H$_5$ | H | CH$_3$ | CF$_3$ | CH$_3$ |
| Y | O | C$_2$H$_5$ | H | CH$_3$ | CF$_3$ | CH$_3$ |
| A | CH$_2$ | CH$_3$ | CH$_3$ | CH$_3$ | CF$_3$ | CH$_3$ |
| B | CH$_2$ | CH$_3$ | CH$_3$ | CH$_3$ | CF$_3$ | CH$_3$ |
| C | CH$_2$ | CH$_3$ | CH$_3$ | CH$_3$ | CF$_3$ | CH$_3$ |
| D | CH$_2$ | CH$_3$ | CH$_3$ | CH$_3$ | CF$_3$ | CH$_3$ |
| E | CH$_2$ | CH$_3$ | CH$_3$ | CH$_3$ | CF$_3$ | CH$_3$ |
| F | CH$_2$ | CH$_3$ | CH$_3$ | CH$_3$ | CF$_3$ | CH$_3$ |
| G | CH$_2$ | CH$_3$ | CH$_3$ | CH$_3$ | CF$_3$ | CH$_3$ |
| H | CH$_2$ | CH$_3$ | CH$_3$ | CH$_3$ | CF$_3$ | CH$_3$ |
| I | CH$_2$ | CH$_3$ | CH$_3$ | CH$_3$ | CF$_3$ | CH$_3$ |
| J | CH$_2$ | CH$_3$ | CH$_3$ | CH$_3$ | CF$_3$ | CH$_3$ |
| K | CH$_2$ | CH$_3$ | CH$_3$ | CH$_3$ | CF$_3$ | CH$_3$ |
| L | CH$_2$ | CH$_3$ | CH$_3$ | CH$_3$ | CF$_3$ | CH$_3$ |
| M | CH$_2$ | CH$_3$ | CH$_3$ | CH$_3$ | CF$_3$ | CH$_3$ |
| N | CH$_2$ | CH$_3$ | CH$_3$ | CH$_3$ | CF$_3$ | CH$_3$ |
| O | CH$_2$ | CH$_3$ | CH$_3$ | CH$_3$ | CF$_3$ | CH$_3$ |
| P | CH$_2$ | CH$_3$ | CH$_3$ | CH$_3$ | CF$_3$ | CH$_3$ |
| Q | CH$_2$ | CH$_3$ | CH$_3$ | CH$_3$ | CF$_3$ | CH$_3$ |
| R | CH$_2$ | CH$_3$ | CH$_3$ | CH$_3$ | CF$_3$ | CH$_3$ |
| S | CH$_2$ | CH$_3$ | CH$_3$ | CH$_3$ | CF$_3$ | CH$_3$ |
| T | CH$_2$ | CH$_3$ | CH$_3$ | CH$_3$ | CF$_3$ | CH$_3$ |
| U | CH$_2$ | CH$_3$ | CH$_3$ | CH$_3$ | CF$_3$ | CH$_3$ |
| V | CH$_2$ | CH$_3$ | CH$_3$ | CH$_3$ | CF$_3$ | CH$_3$ |
| W | CH$_2$ | CH$_3$ | CH$_3$ | CH$_3$ | CF$_3$ | CH$_3$ |
| X | CH$_2$ | CH$_3$ | CH$_3$ | CH$_3$ | CF$_3$ | CH$_3$ |
| Y | CH$_2$ | CH$_3$ | CH$_3$ | CH$_3$ | CF$_3$ | CH$_3$ |
| A | CH$_2$ | CH$_3$ | H | Cl | CHF$_2$ | CH$_3$ |

TABLE B-continued

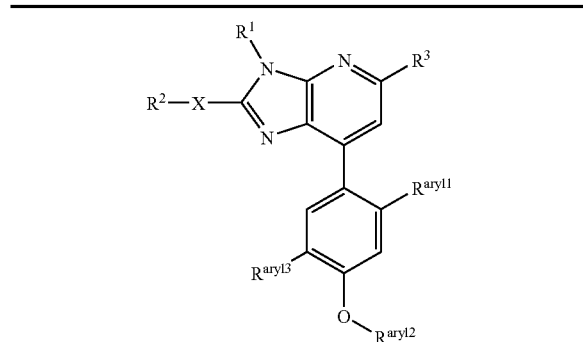

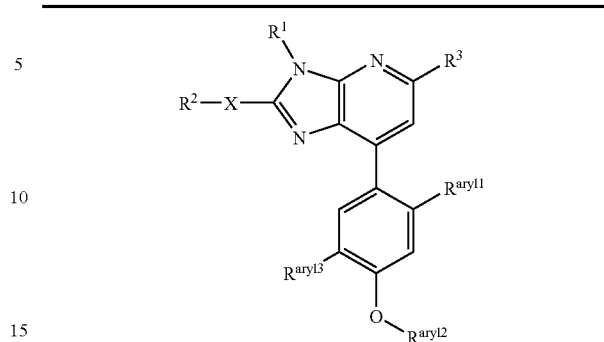

| R[1(a)] | X | R[2] | R[3] | R[aryl1] | R[aryl2] | R[aryl3] |
|---|---|---|---|---|---|---|
| B | CH₂ | CH₃ | H | Cl | CHF₂ | CH₃ |
| C | CH₂ | CH₃ | H | Cl | CHF₂ | CH₃ |
| D | CH₂ | CH₃ | H | Cl | CHF₂ | CH₃ |
| E | CH₂ | CH₃ | H | Cl | CHF₂ | CH₃ |
| F | CH₂ | CH₃ | H | Cl | CHF₂ | CH₃ |
| G | CH₂ | CH₃ | H | Cl | CHF₂ | CH₃ |
| H | CH₂ | CH₃ | H | Cl | CHF₂ | CH₃ |
| I | CH₂ | CH₃ | H | Cl | CHF₂ | CH₃ |
| J | CH₂ | CH₃ | H | Cl | CHF₂ | CH₃ |
| K | CH₂ | CH₃ | H | Cl | CHF₂ | CH₃ |
| L | CH₂ | CH₃ | H | Cl | CHF₂ | CH₃ |
| M | CH₂ | CH₃ | H | Cl | CHF₂ | CH₃ |
| N | CH₂ | CH₃ | H | Cl | CHF₂ | CH₃ |
| O | CH₂ | CH₃ | H | Cl | CHF₂ | CH₃ |
| P | CH₂ | CH₃ | H | Cl | CHF₂ | CH₃ |
| Q | CH₂ | CH₃ | H | Cl | CHF₂ | CH₃ |
| R | CH₂ | CH₃ | H | Cl | CHF₂ | CH₃ |
| S | CH₂ | CH₃ | H | Cl | CHF₂ | CH₃ |
| T | CH₂ | CH₃ | H | Cl | CHF₂ | CH₃ |
| U | CH₂ | CH₃ | H | Cl | CHF₂ | CH₃ |
| V | CH₂ | CH₃ | H | Cl | CHF₂ | CH₃ |
| W | CH₂ | CH₃ | H | Cl | CHF₂ | CH₃ |
| X | CH₂ | CH₃ | H | Cl | CHF₂ | CH₃ |
| Y | CH₂ | CH₃ | H | Cl | CHF₂ | CH₃ |
| A | O | CH₃ | H | Cl | CHF₂ | CH₃ |
| B | O | CH₃ | H | Cl | CHF₂ | CH₃ |
| C | O | CH₃ | H | Cl | CHF₂ | CH₃ |
| D | O | CH₃ | H | Cl | CHF₂ | CH₃ |
| E | O | CH₃ | H | Cl | CHF₂ | CH₃ |
| F | O | CH₃ | H | Cl | CHF₂ | CH₃ |
| G | O | CH₃ | H | Cl | CHF₂ | CH₃ |
| H | O | CH₃ | H | Cl | CHF₂ | CH₃ |
| I | O | CH₃ | H | Cl | CHF₂ | CH₃ |
| J | O | CH₃ | H | Cl | CHF₂ | CH₃ |
| K | O | CH₃ | H | Cl | CHF₂ | CH₃ |
| L | O | CH₃ | H | Cl | CHF₂ | CH₃ |
| M | O | CH₃ | H | Cl | CHF₂ | CH₃ |
| N | O | CH₃ | H | Cl | CHF₂ | CH₃ |
| O | O | CH₃ | H | Cl | CHF₂ | CH₃ |
| P | O | CH₃ | H | Cl | CHF₂ | CH₃ |
| Q | O | CH₃ | H | Cl | CHF₂ | CH₃ |
| R | O | CH₃ | H | Cl | CHF₂ | CH₃ |
| S | O | CH₃ | H | Cl | CHF₂ | CH₃ |
| T | O | CH₃ | H | Cl | CHF₂ | CH₃ |
| U | O | CH₃ | H | Cl | CHF₂ | CH₃ |
| V | O | CH₃ | H | Cl | CHF₂ | CH₃ |
| W | O | CH₃ | H | Cl | CHF₂ | CH₃ |
| X | O | CH₃ | H | Cl | CHF₂ | CH₃ |
| Y | O | CH₃ | H | Cl | CHF₂ | CH₃ |
| A | O | C₂H₅ | H | Cl | CHF₂ | CH₃ |
| B | O | C₂H₅ | H | Cl | CHF₂ | CH₃ |
| C | O | C₂H₅ | H | Cl | CHF₂ | CH₃ |
| D | O | C₂H₅ | H | Cl | CHF₂ | CH₃ |
| E | O | C₂H₅ | H | Cl | CHF₂ | CH₃ |
| F | O | C₂H₅ | H | Cl | CHF₂ | CH₃ |
| G | O | C₂H₅ | H | Cl | CHF₂ | CH₃ |
| H | O | C₂H₅ | H | Cl | CHF₂ | CH₃ |
| I | O | C₂H₅ | H | Cl | CHF₂ | CH₃ |
| J | O | C₂H₅ | H | Cl | CHF₂ | CH₃ |
| K | O | C₂H₅ | H | Cl | CHF₂ | CH₃ |
| L | O | C₂H₅ | H | Cl | CHF₂ | CH₃ |
| M | O | C₂H₅ | H | Cl | CHF₂ | CH₃ |
| N | O | C₂H₅ | H | Cl | CHF₂ | CH₃ |
| O | O | C₂H₅ | H | Cl | CHF₂ | CH₃ |
| P | O | C₂H₅ | H | Cl | CHF₂ | CH₃ |
| Q | O | C₂H₅ | H | Cl | CHF₂ | CH₃ |
| R | O | C₂H₅ | H | Cl | CHF₂ | CH₃ |
| S | O | C₂H₅ | H | Cl | CHF₂ | CH₃ |
| T | O | C₂H₅ | H | Cl | CHF₂ | CH₃ |
| U | O | C₂H₅ | H | Cl | CHF₂ | CH₃ |
| V | O | C₂H₅ | H | Cl | CHF₂ | CH₃ |
| W | O | C₂H₅ | H | Cl | CHF₂ | CH₃ |
| X | O | C₂H₅ | H | Cl | CHF₂ | CH₃ |
| Y | O | C₂H₅ | H | Cl | CHF₂ | CH₃ |
| A | CH₂ | CH₃ | CH₃ | Cl | CHF₂ | CH₃ |
| B | CH₂ | CH₃ | CH₃ | Cl | CHF₂ | CH₃ |
| C | CH₂ | CH₃ | CH₃ | Cl | CHF₂ | CH₃ |
| D | CH₂ | CH₃ | CH₃ | Cl | CHF₂ | CH₃ |
| E | CH₂ | CH₃ | CH₃ | Cl | CHF₂ | CH₃ |
| F | CH₂ | CH₃ | CH₃ | Cl | CHF₂ | CH₃ |
| G | CH₂ | CH₃ | CH₃ | Cl | CHF₂ | CH₃ |
| H | CH₂ | CH₃ | CH₃ | Cl | CHF₂ | CH₃ |
| I | CH₂ | CH₃ | CH₃ | Cl | CHF₂ | CH₃ |
| J | CH₂ | CH₃ | CH₃ | Cl | CHF₂ | CH₃ |
| K | CH₂ | CH₃ | CH₃ | Cl | CHF₂ | CH₃ |
| L | CH₂ | CH₃ | CH₃ | Cl | CHF₂ | CH₃ |
| M | CH₂ | CH₃ | CH₃ | Cl | CHF₂ | CH₃ |
| N | CH₂ | CH₃ | CH₃ | Cl | CHF₂ | CH₃ |
| O | CH₂ | CH₃ | CH₃ | Cl | CHF₂ | CH₃ |
| P | CH₂ | CH₃ | CH₃ | Cl | CHF₂ | CH₃ |
| Q | CH₂ | CH₃ | CH₃ | Cl | CHF₂ | CH₃ |
| R | CH₂ | CH₃ | CH₃ | Cl | CHF₂ | CH₃ |
| S | CH₂ | CH₃ | CH₃ | Cl | CHF₂ | CH₃ |
| T | CH₂ | CH₃ | CH₃ | Cl | CHF₂ | CH₃ |
| U | CH₂ | CH₃ | CH₃ | Cl | CHF₂ | CH₃ |
| V | CH₂ | CH₃ | CH₃ | Cl | CHF₂ | CH₃ |
| W | CH₂ | CH₃ | CH₃ | Cl | CHF₂ | CH₃ |
| X | CH₂ | CH₃ | CH₃ | Cl | CHF₂ | CH₃ |
| Y | CH₂ | CH₃ | CH₃ | Cl | CHF₂ | CH₃ |
| A | CH₂ | CH₃ | H | CH₃ | CHF₂ | CH₃ |
| B | CH₂ | CH₃ | H | CH₃ | CHF₂ | CH₃ |
| C | CH₂ | CH₃ | H | CH₃ | CHF₂ | CH₃ |
| D | CH₂ | CH₃ | H | CH₃ | CHF₂ | CH₃ |
| E | CH₂ | CH₃ | H | CH₃ | CHF₂ | CH₃ |
| F | CH₂ | CH₃ | H | CH₃ | CHF₂ | CH₃ |
| G | CH₂ | CH₃ | H | CH₃ | CHF₂ | CH₃ |
| H | CH₂ | CH₃ | H | CH₃ | CHF₂ | CH₃ |
| I | CH₂ | CH₃ | H | CH₃ | CHF₂ | CH₃ |
| J | CH₂ | CH₃ | H | CH₃ | CHF₂ | CH₃ |
| K | CH₂ | CH₃ | H | CH₃ | CHF₂ | CH₃ |
| L | CH₂ | CH₃ | H | CH₃ | CHF₂ | CH₃ |
| M | CH₂ | CH₃ | H | CH₃ | CHF₂ | CH₃ |
| N | CH₂ | CH₃ | H | CH₃ | CHF₂ | CH₃ |
| O | CH₂ | CH₃ | H | CH₃ | CHF₂ | CH₃ |
| P | CH₂ | CH₃ | H | CH₃ | CHF₂ | CH₃ |
| Q | CH₂ | CH₃ | H | CH₃ | CHF₂ | CH₃ |
| R | CH₂ | CH₃ | H | CH₃ | CHF₂ | CH₃ |
| S | CH₂ | CH₃ | H | CH₃ | CHF₂ | CH₃ |
| T | CH₂ | CH₃ | H | CH₃ | CHF₂ | CH₃ |
| U | CH₂ | CH₃ | H | CH₃ | CHF₂ | CH₃ |

TABLE B-continued

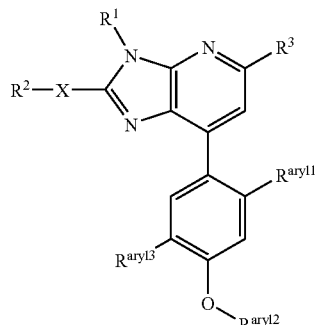

| R[1(a)] | X | R[2] | R[3] | R[aryl1] | R[aryl2] | R[aryl3] |
|---|---|---|---|---|---|---|
| V | $CH_2$ | $CH_3$ | H | $CH_3$ | $CHF_2$ | $CH_3$ |
| W | $CH_2$ | $CH_3$ | H | $CH_3$ | $CHF_2$ | $CH_3$ |
| X | $CH_2$ | $CH_3$ | H | $CH_3$ | $CHF_2$ | $CH_3$ |
| Y | $CH_2$ | $CH_3$ | H | $CH_3$ | $CHF_2$ | $CH_3$ |
| A | O | $CH_3$ | H | $CH_3$ | $CHF_2$ | $CH_3$ |
| B | O | $CH_3$ | H | $CH_3$ | $CHF_2$ | $CH_3$ |
| C | O | $CH_3$ | H | $CH_3$ | $CHF_2$ | $CH_3$ |
| D | O | $CH_3$ | H | $CH_3$ | $CHF_2$ | $CH_3$ |
| E | O | $CH_3$ | H | $CH_3$ | $CHF_2$ | $CH_3$ |
| F | O | $CH_3$ | H | $CH_3$ | $CHF_2$ | $CH_3$ |
| G | O | $CH_3$ | H | $CH_3$ | $CHF_2$ | $CH_3$ |
| H | O | $CH_3$ | H | $CH_3$ | $CHF_2$ | $CH_3$ |
| I | O | $CH_3$ | H | $CH_3$ | $CHF_2$ | $CH_3$ |
| J | O | $CH_3$ | H | $CH_3$ | $CHF_2$ | $CH_3$ |
| K | O | $CH_3$ | H | $CH_3$ | $CHF_2$ | $CH_3$ |
| L | O | $CH_3$ | H | $CH_3$ | $CHF_2$ | $CH_3$ |
| M | O | $CH_3$ | H | $CH_3$ | $CHF_2$ | $CH_3$ |
| N | O | $CH_3$ | H | $CH_3$ | $CHF_2$ | $CH_3$ |
| O | O | $CH_3$ | H | $CH_3$ | $CHF_2$ | $CH_3$ |
| P | O | $CH_3$ | H | $CH_3$ | $CHF_2$ | $CH_3$ |
| Q | O | $CH_3$ | H | $CH_3$ | $CHF_2$ | $CH_3$ |
| R | O | $CH_3$ | H | $CH_3$ | $CHF_2$ | $CH_3$ |
| S | O | $CH_3$ | H | $CH_3$ | $CHF_2$ | $CH_3$ |
| T | O | $CH_3$ | H | $CH_3$ | $CHF_2$ | $CH_3$ |
| U | O | $CH_3$ | H | $CH_3$ | $CHF_2$ | $CH_3$ |
| V | O | $CH_3$ | H | $CH_3$ | $CHF_2$ | $CH_3$ |
| W | O | $CH_3$ | H | $CH_3$ | $CHF_2$ | $CH_3$ |
| X | O | $CH_3$ | H | $CH_3$ | $CHF_2$ | $CH_3$ |
| Y | O | $CH_3$ | H | $CH_3$ | $CHF_2$ | $CH_3$ |
| A | O | $C_2H_5$ | H | $CH_3$ | $CHF_2$ | $CH_3$ |
| B | O | $C_2H_5$ | H | $CH_3$ | $CHF_2$ | $CH_3$ |
| C | O | $C_2H_5$ | H | $CH_3$ | $CHF_2$ | $CH_3$ |
| D | O | $C_2H_5$ | H | $CH_3$ | $CHF_2$ | $CH_3$ |
| E | O | $C_2H_5$ | H | $CH_3$ | $CHF_2$ | $CH_3$ |
| F | O | $C_2H_5$ | H | $CH_3$ | $CHF_2$ | $CH_3$ |
| G | O | $C_2H_5$ | H | $CH_3$ | $CHF_2$ | $CH_3$ |
| H | O | $C_2H_5$ | H | $CH_3$ | $CHF_2$ | $CH_3$ |
| I | O | $C_2H_5$ | H | $CH_3$ | $CHF_2$ | $CH_3$ |
| J | O | $C_2H_5$ | H | $CH_3$ | $CHF_2$ | $CH_3$ |
| K | O | $C_2H_5$ | H | $CH_3$ | $CHF_2$ | $CH_3$ |
| L | O | $C_2H_5$ | H | $CH_3$ | $CHF_2$ | $CH_3$ |
| M | O | $C_2H_5$ | H | $CH_3$ | $CHF_2$ | $CH_3$ |
| N | O | $C_2H_5$ | H | $CH_3$ | $CHF_2$ | $CH_3$ |
| O | O | $C_2H_5$ | H | $CH_3$ | $CHF_2$ | $CH_3$ |
| P | O | $C_2H_5$ | H | $CH_3$ | $CHF_2$ | $CH_3$ |
| Q | O | $C_2H_5$ | H | $CH_3$ | $CHF_2$ | $CH_3$ |
| R | O | $C_2H_5$ | H | $CH_3$ | $CHF_2$ | $CH_3$ |
| S | O | $C_2H_5$ | H | $CH_3$ | $CHF_2$ | $CH_3$ |
| T | O | $C_2H_5$ | H | $CH_3$ | $CHF_2$ | $CH_3$ |
| U | O | $C_2H_5$ | H | $CH_3$ | $CHF_2$ | $CH_3$ |
| V | O | $C_2H_5$ | H | $CH_3$ | $CHF_2$ | $CH_3$ |
| W | O | $C_2H_5$ | H | $CH_3$ | $CHF_2$ | $CH_3$ |
| X | O | $C_2H_5$ | H | $CH_3$ | $CHF_2$ | $CH_3$ |
| Y | O | $C_2H_5$ | H | $CH_3$ | $CHF_2$ | $CH_3$ |
| A | $CH_2$ | $CH_3$ | $CH_3$ | $CH_3$ | $CHF_2$ | $CH_3$ |
| B | $CH_2$ | $CH_3$ | $CH_3$ | $CH_3$ | $CHF_2$ | $CH_3$ |
| C | $CH_2$ | $CH_3$ | $CH_3$ | $CH_3$ | $CHF_2$ | $CH_3$ |
| D | $CH_2$ | $CH_3$ | $CH_3$ | $CH_3$ | $CHF_2$ | $CH_3$ |
| E | $CH_2$ | $CH_3$ | $CH_3$ | $CH_3$ | $CHF_2$ | $CH_3$ |
| F | $CH_2$ | $CH_3$ | $CH_3$ | $CH_3$ | $CHF_2$ | $CH_3$ |

TABLE B-continued

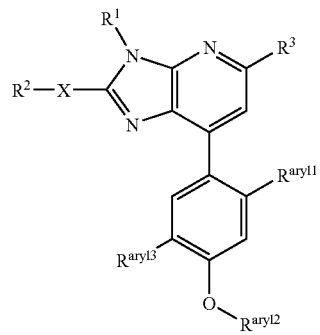

| R[1(a)] | X | R[2] | R[3] | R[aryl1] | R[aryl2] | R[aryl3] |
|---|---|---|---|---|---|---|
| G | $CH_2$ | $CH_3$ | $CH_3$ | $CH_3$ | $CHF_2$ | $CH_3$ |
| H | $CH_2$ | $CH_3$ | $CH_3$ | $CH_3$ | $CHF_2$ | $CH_3$ |
| I | $CH_2$ | $CH_3$ | $CH_3$ | $CH_3$ | $CHF_2$ | $CH_3$ |
| J | $CH_2$ | $CH_3$ | $CH_3$ | $CH_3$ | $CHF_2$ | $CH_3$ |
| K | $CH_2$ | $CH_3$ | $CH_3$ | $CH_3$ | $CHF_2$ | $CH_3$ |
| L | $CH_2$ | $CH_3$ | $CH_3$ | $CH_3$ | $CHF_2$ | $CH_3$ |
| M | $CH_2$ | $CH_3$ | $CH_3$ | $CH_3$ | $CHF_2$ | $CH_3$ |
| N | $CH_2$ | $CH_3$ | $CH_3$ | $CH_3$ | $CHF_2$ | $CH_3$ |
| O | $CH_2$ | $CH_3$ | $CH_3$ | $CH_3$ | $CHF_2$ | $CH_3$ |
| P | $CH_2$ | $CH_3$ | $CH_3$ | $CH_3$ | $CHF_2$ | $CH_3$ |
| Q | $CH_2$ | $CH_3$ | $CH_3$ | $CH_3$ | $CHF_2$ | $CH_3$ |
| R | $CH_2$ | $CH_3$ | $CH_3$ | $CH_3$ | $CHF_2$ | $CH_3$ |
| S | $CH_2$ | $CH_3$ | $CH_3$ | $CH_3$ | $CHF_2$ | $CH_3$ |
| T | $CH_2$ | $CH_3$ | $CH_3$ | $CH_3$ | $CHF_2$ | $CH_3$ |
| U | $CH_2$ | $CH_3$ | $CH_3$ | $CH_3$ | $CHF_2$ | $CH_3$ |
| V | $CH_2$ | $CH_3$ | $CH_3$ | $CH_3$ | $CHF_2$ | $CH_3$ |
| W | $CH_2$ | $CH_3$ | $CH_3$ | $CH_3$ | $CHF_2$ | $CH_3$ |
| X | $CH_2$ | $CH_3$ | $CH_3$ | $CH_3$ | $CHF_2$ | $CH_3$ |
| Y | $CH_2$ | $CH_3$ | $CH_3$ | $CH_3$ | $CHF_2$ | $CH_3$ |

[(a)]See Table A, above.

Particular compounds provided herein further include those having the following structure, with the substituents thereof being set forth in Table C, below.

TABLE C

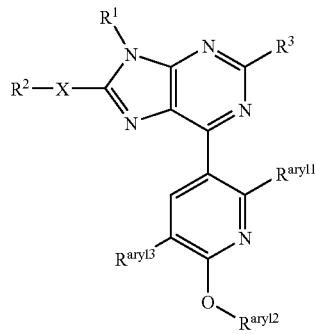

| R[1(a)] | X | R[2] | R[3] | R[aryl1] | R[aryl2] | R[aryl3] |
|---|---|---|---|---|---|---|
| A | $CH_2$ | $CH_3$ | H | Cl | $CF_3$ | H |
| B | $CH_2$ | $CH_3$ | H | Cl | $CF_3$ | H |
| C | $CH_2$ | $CH_3$ | H | Cl | $CF_3$ | H |
| D | $CH_2$ | $CH_3$ | H | Cl | $CF_3$ | H |
| E | $CH_2$ | $CH_3$ | H | Cl | $CF_3$ | H |
| F | $CH_2$ | $CH_3$ | H | Cl | $CF_3$ | H |
| G | $CH_2$ | $CH_3$ | H | Cl | $CF_3$ | H |
| H | $CH_2$ | $CH_3$ | H | Cl | $CF_3$ | H |
| I | $CH_2$ | $CH_3$ | H | Cl | $CF_3$ | H |
| J | $CH_2$ | $CH_3$ | H | Cl | $CF_3$ | H |
| K | $CH_2$ | $CH_3$ | H | Cl | $CF_3$ | H |
| L | $CH_2$ | $CH_3$ | H | Cl | $CF_3$ | H |

TABLE C-continued

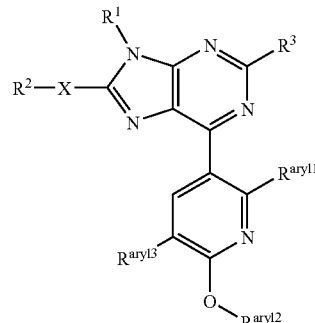

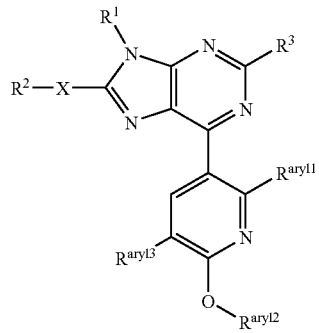

| R[1(a)] | X | R[2] | R[3] | R[aryl1] | R[aryl2] | R[aryl3] |
|---|---|---|---|---|---|---|
| M | CH$_2$ | CH$_3$ | H | Cl | CF$_3$ | H |
| N | CH$_2$ | CH$_3$ | H | Cl | CF$_3$ | H |
| O | CH$_2$ | CH$_3$ | H | Cl | CF$_3$ | H |
| P | CH$_2$ | CH$_3$ | H | Cl | CF$_3$ | H |
| Q | CH$_2$ | CH$_3$ | H | Cl | CF$_3$ | H |
| R | CH$_2$ | CH$_3$ | H | Cl | CF$_3$ | H |
| S | CH$_2$ | CH$_3$ | H | Cl | CF$_3$ | H |
| T | CH$_2$ | CH$_3$ | H | Cl | CF$_3$ | H |
| U | CH$_2$ | CH$_3$ | H | Cl | CF$_3$ | H |
| V | CH$_2$ | CH$_3$ | H | Cl | CF$_3$ | H |
| W | CH$_2$ | CH$_3$ | H | Cl | CF$_3$ | H |
| X | CH$_2$ | CH$_3$ | H | Cl | CF$_3$ | H |
| Y | CH$_2$ | CH$_3$ | H | Cl | CF$_3$ | H |
| A | O | CH$_3$ | H | Cl | CF$_3$ | H |
| B | O | CH$_3$ | H | Cl | CF$_3$ | H |
| C | O | CH$_3$ | H | Cl | CF$_3$ | H |
| D | O | CH$_3$ | H | Cl | CF$_3$ | H |
| E | O | CH$_3$ | H | Cl | CF$_3$ | H |
| F | O | CH$_3$ | H | Cl | CF$_3$ | H |
| G | O | CH$_3$ | H | Cl | CF$_3$ | H |
| H | O | CH$_3$ | H | Cl | CF$_3$ | H |
| I | O | CH$_3$ | H | Cl | CF$_3$ | H |
| J | O | CH$_3$ | H | Cl | CF$_3$ | H |
| K | O | CH$_3$ | H | Cl | CF$_3$ | H |
| L | O | CH$_3$ | H | Cl | CF$_3$ | H |
| M | O | CH$_3$ | H | Cl | CF$_3$ | H |
| N | O | CH$_3$ | H | Cl | CF$_3$ | H |
| O | O | CH$_3$ | H | Cl | CF$_3$ | H |
| P | O | CH$_3$ | H | Cl | CF$_3$ | H |
| Q | O | CH$_3$ | H | Cl | CF$_3$ | H |
| R | O | CH$_3$ | H | Cl | CF$_3$ | H |
| S | O | CH$_3$ | H | Cl | CF$_3$ | H |
| T | O | CH$_3$ | H | Cl | CF$_3$ | H |
| U | O | CH$_3$ | H | Cl | CF$_3$ | H |
| V | O | CH$_3$ | H | Cl | CF$_3$ | H |
| W | O | CH$_3$ | H | Cl | CF$_3$ | H |
| X | O | CH$_3$ | H | Cl | CF$_3$ | H |
| Y | O | CH$_3$ | H | Cl | CF$_3$ | H |
| A | O | C$_2$H$_5$ | H | Cl | CF$_3$ | H |
| B | O | C$_2$H$_5$ | H | Cl | CF$_3$ | H |
| C | O | C$_2$H$_5$ | H | Cl | CF$_3$ | H |
| D | O | C$_2$H$_5$ | H | Cl | CF$_3$ | H |
| E | O | C$_2$H$_5$ | H | Cl | CF$_3$ | H |
| F | O | C$_2$H$_5$ | H | Cl | CF$_3$ | H |
| G | O | C$_2$H$_5$ | H | Cl | CF$_3$ | H |
| H | O | C$_2$H$_5$ | H | Cl | CF$_3$ | H |
| I | O | C$_2$H$_5$ | H | Cl | CF$_3$ | H |
| J | O | C$_2$H$_5$ | H | Cl | CF$_3$ | H |
| K | O | C$_2$H$_5$ | H | Cl | CF$_3$ | H |
| L | O | C$_2$H$_5$ | H | Cl | CF$_3$ | H |
| M | O | C$_2$H$_5$ | H | Cl | CF$_3$ | H |
| N | O | C$_2$H$_5$ | H | Cl | CF$_3$ | H |
| O | O | C$_2$H$_5$ | H | Cl | CF$_3$ | H |
| P | O | C$_2$H$_5$ | H | Cl | CF$_3$ | H |
| Q | O | C$_2$H$_5$ | H | Cl | CF$_3$ | H |
| R | O | C$_2$H$_5$ | H | Cl | CF$_3$ | H |
| S | O | C$_2$H$_5$ | H | Cl | CF$_3$ | H |
| T | O | C$_2$H$_5$ | H | Cl | CF$_3$ | H |
| U | O | C$_2$H$_5$ | H | Cl | CF$_3$ | H |
| V | O | C$_2$H$_5$ | H | Cl | CF$_3$ | H |
| W | O | C$_2$H$_5$ | H | Cl | CF$_3$ | H |
| X | O | C$_2$H$_5$ | H | Cl | CF$_3$ | H |
| Y | O | C$_2$H$_5$ | H | Cl | CF$_3$ | H |
| A | CH$_2$ | CH$_3$ | CH$_3$ | Cl | CF$_3$ | H |
| B | CH$_2$ | CH$_3$ | CH$_3$ | Cl | CF$_3$ | H |
| C | CH$_2$ | CH$_3$ | CH$_3$ | Cl | CF$_3$ | H |
| D | CH$_2$ | CH$_3$ | CH$_3$ | Cl | CF$_3$ | H |
| E | CH$_2$ | CH$_3$ | CH$_3$ | Cl | CF$_3$ | H |
| F | CH$_2$ | CH$_3$ | CH$_3$ | Cl | CF$_3$ | H |
| G | CH$_2$ | CH$_3$ | CH$_3$ | Cl | CF$_3$ | H |
| H | CH$_2$ | CH$_3$ | CH$_3$ | Cl | CF$_3$ | H |
| I | CH$_2$ | CH$_3$ | CH$_3$ | Cl | CF$_3$ | H |
| J | CH$_2$ | CH$_3$ | CH$_3$ | Cl | CF$_3$ | H |
| K | CH$_2$ | CH$_3$ | CH$_3$ | Cl | CF$_3$ | H |
| L | CH$_2$ | CH$_3$ | CH$_3$ | Cl | CF$_3$ | H |
| M | CH$_2$ | CH$_3$ | CH$_3$ | Cl | CF$_3$ | H |
| N | CH$_2$ | CH$_3$ | CH$_3$ | Cl | CF$_3$ | H |
| O | CH$_2$ | CH$_3$ | CH$_3$ | Cl | CF$_3$ | H |
| P | CH$_2$ | CH$_3$ | CH$_3$ | Cl | CF$_3$ | H |
| Q | CH$_2$ | CH$_3$ | CH$_3$ | Cl | CF$_3$ | H |
| R | CH$_2$ | CH$_3$ | CH$_3$ | Cl | CF$_3$ | H |
| S | CH$_2$ | CH$_3$ | CH$_3$ | Cl | CF$_3$ | H |
| T | CH$_2$ | CH$_3$ | CH$_3$ | Cl | CF$_3$ | H |
| U | CH$_2$ | CH$_3$ | CH$_3$ | Cl | CF$_3$ | H |
| V | CH$_2$ | CH$_3$ | CH$_3$ | Cl | CF$_3$ | H |
| W | CH$_2$ | CH$_3$ | CH$_3$ | Cl | CF$_3$ | H |
| X | CH$_2$ | CH$_3$ | CH$_3$ | Cl | CF$_3$ | H |
| Y | CH$_2$ | CH$_3$ | CH$_3$ | Cl | CF$_3$ | H |
| A | CH$_2$ | CH$_3$ | H | CH$_3$ | CF$_3$ | H |
| B | CH$_2$ | CH$_3$ | H | CH$_3$ | CF$_3$ | H |
| C | CH$_2$ | CH$_3$ | H | CH$_3$ | CF$_3$ | H |
| D | CH$_2$ | CH$_3$ | H | CH$_3$ | CF$_3$ | H |
| E | CH$_2$ | CH$_3$ | H | CH$_3$ | CF$_3$ | H |
| F | CH$_2$ | CH$_3$ | H | CH$_3$ | CF$_3$ | H |
| G | CH$_2$ | CH$_3$ | H | CH$_3$ | CF$_3$ | H |
| H | CH$_2$ | CH$_3$ | H | CH$_3$ | CF$_3$ | H |
| I | CH$_2$ | CH$_3$ | H | CH$_3$ | CF$_3$ | H |
| J | CH$_2$ | CH$_3$ | H | CH$_3$ | CF$_3$ | H |
| K | CH$_2$ | CH$_3$ | H | CH$_3$ | CF$_3$ | H |
| L | CH$_2$ | CH$_3$ | H | CH$_3$ | CF$_3$ | H |
| M | CH$_2$ | CH$_3$ | H | CH$_3$ | CF$_3$ | H |
| N | CH$_2$ | CH$_3$ | H | CH$_3$ | CF$_3$ | H |
| O | CH$_2$ | CH$_3$ | H | CH$_3$ | CF$_3$ | H |
| P | CH$_2$ | CH$_3$ | H | CH$_3$ | CF$_3$ | H |
| Q | CH$_2$ | CH$_3$ | H | CH$_3$ | CF$_3$ | H |
| R | CH$_2$ | CH$_3$ | H | CH$_3$ | CF$_3$ | H |
| S | CH$_2$ | CH$_3$ | H | CH$_3$ | CF$_3$ | H |
| T | CH$_2$ | CH$_3$ | H | CH$_3$ | CF$_3$ | H |
| U | CH$_2$ | CH$_3$ | H | CH$_3$ | CF$_3$ | H |
| V | CH$_2$ | CH$_3$ | H | CH$_3$ | CF$_3$ | H |
| W | CH$_2$ | CH$_3$ | H | CH$_3$ | CF$_3$ | H |
| X | CH$_2$ | CH$_3$ | H | CH$_3$ | CF$_3$ | H |
| Y | CH$_2$ | CH$_3$ | H | CH$_3$ | CF$_3$ | H |
| A | O | CH$_3$ | H | CH$_3$ | CF$_3$ | H |
| B | O | CH$_3$ | H | CH$_3$ | CF$_3$ | H |
| C | O | CH$_3$ | H | CH$_3$ | CF$_3$ | H |
| D | O | CH$_3$ | H | CH$_3$ | CF$_3$ | H |
| E | O | CH$_3$ | H | CH$_3$ | CF$_3$ | H |
| F | O | CH$_3$ | H | CH$_3$ | CF$_3$ | H |
| G | O | CH$_3$ | H | CH$_3$ | CF$_3$ | H |

TABLE C-continued

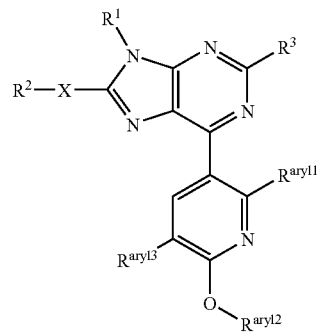

| R[1(a)] | X | R[2] | R[3] | R[aryl1] | R[aryl2] | R[aryl3] |
|---|---|---|---|---|---|---|
| H | O | CH$_3$ | H | CH$_3$ | CF$_3$ | H |
| I | O | CH$_3$ | H | CH$_3$ | CF$_3$ | H |
| J | O | CH$_3$ | H | CH$_3$ | CF$_3$ | H |
| K | O | CH$_3$ | H | CH$_3$ | CF$_3$ | H |
| L | O | CH$_3$ | H | CH$_3$ | CF$_3$ | H |
| M | O | CH$_3$ | H | CH$_3$ | CF$_3$ | H |
| N | O | CH$_3$ | H | CH$_3$ | CF$_3$ | H |
| O | O | CH$_3$ | H | CH$_3$ | CF$_3$ | H |
| P | O | CH$_3$ | H | CH$_3$ | CF$_3$ | H |
| Q | O | CH$_3$ | H | CH$_3$ | CF$_3$ | H |
| R | O | CH$_3$ | H | CH$_3$ | CF$_3$ | H |
| S | O | CH$_3$ | H | CH$_3$ | CF$_3$ | H |
| T | O | CH$_3$ | H | CH$_3$ | CF$_3$ | H |
| U | O | CH$_3$ | H | CH$_3$ | CF$_3$ | H |
| V | O | CH$_3$ | H | CH$_3$ | CF$_3$ | H |
| W | O | CH$_3$ | H | CH$_3$ | CF$_3$ | H |
| X | O | CH$_3$ | H | CH$_3$ | CF$_3$ | H |
| Y | O | CH$_3$ | H | CH$_3$ | CF$_3$ | H |
| A | O | C$_2$H$_5$ | H | CH$_3$ | CF$_3$ | H |
| B | O | C$_2$H$_5$ | H | CH$_3$ | CF$_3$ | H |
| C | O | C$_2$H$_5$ | H | CH$_3$ | CF$_3$ | H |
| D | O | C$_2$H$_5$ | H | CH$_3$ | CF$_3$ | H |
| E | O | C$_2$H$_5$ | H | CH$_3$ | CF$_3$ | H |
| F | O | C$_2$H$_5$ | H | CH$_3$ | CF$_3$ | H |
| G | O | C$_2$H$_5$ | H | CH$_3$ | CF$_3$ | H |
| H | O | C$_2$H$_5$ | H | CH$_3$ | CF$_3$ | H |
| I | O | C$_2$H$_5$ | H | CH$_3$ | CF$_3$ | H |
| J | O | C$_2$H$_5$ | H | CH$_3$ | CF$_3$ | H |
| K | O | C$_2$H$_5$ | H | CH$_3$ | CF$_3$ | H |
| L | O | C$_2$H$_5$ | H | CH$_3$ | CF$_3$ | H |
| M | O | C$_2$H$_5$ | H | CH$_3$ | CF$_3$ | H |
| N | O | C$_2$H$_5$ | H | CH$_3$ | CF$_3$ | H |
| O | O | C$_2$H$_5$ | H | CH$_3$ | CF$_3$ | H |
| P | O | C$_2$H$_5$ | H | CH$_3$ | CF$_3$ | H |
| Q | O | C$_2$H$_5$ | H | CH$_3$ | CF$_3$ | H |
| R | O | C$_2$H$_5$ | H | CH$_3$ | CF$_3$ | H |
| S | O | C$_2$H$_5$ | H | CH$_3$ | CF$_3$ | H |
| T | O | C$_2$H$_5$ | H | CH$_3$ | CF$_3$ | H |
| U | O | C$_2$H$_5$ | H | CH$_3$ | CF$_3$ | H |
| V | O | C$_2$H$_5$ | H | CH$_3$ | CF$_3$ | H |
| W | O | C$_2$H$_5$ | H | CH$_3$ | CF$_3$ | H |
| X | O | C$_2$H$_5$ | H | CH$_3$ | CF$_3$ | H |
| Y | O | C$_2$H$_5$ | H | CH$_3$ | CF$_3$ | H |
| A | CH$_2$ | CH$_3$ | CH$_3$ | CH$_3$ | CF$_3$ | H |
| B | CH$_2$ | CH$_3$ | CH$_3$ | CH$_3$ | CF$_3$ | H |
| C | CH$_2$ | CH$_3$ | CH$_3$ | CH$_3$ | CF$_3$ | H |
| D | CH$_2$ | CH$_3$ | CH$_3$ | CH$_3$ | CF$_3$ | H |
| E | CH$_2$ | CH$_3$ | CH$_3$ | CH$_3$ | CF$_3$ | H |
| F | CH$_2$ | CH$_3$ | CH$_3$ | CH$_3$ | CF$_3$ | H |
| G | CH$_2$ | CH$_3$ | CH$_3$ | CH$_3$ | CF$_3$ | H |
| H | CH$_2$ | CH$_3$ | CH$_3$ | CH$_3$ | CF$_3$ | H |
| I | CH$_2$ | CH$_3$ | CH$_3$ | CH$_3$ | CF$_3$ | H |
| J | CH$_2$ | CH$_3$ | CH$_3$ | CH$_3$ | CF$_3$ | H |
| K | CH$_2$ | CH$_3$ | CH$_3$ | CH$_3$ | CF$_3$ | H |
| L | CH$_2$ | CH$_3$ | CH$_3$ | CH$_3$ | CF$_3$ | H |
| M | CH$_2$ | CH$_3$ | CH$_3$ | CH$_3$ | CF$_3$ | H |
| N | CH$_2$ | CH$_3$ | CH$_3$ | CH$_3$ | CF$_3$ | H |
| O | CH$_2$ | CH$_3$ | CH$_3$ | CH$_3$ | CF$_3$ | H |
| P | CH$_2$ | CH$_3$ | CH$_3$ | CH$_3$ | CF$_3$ | H |
| Q | CH$_2$ | CH$_3$ | CH$_3$ | CH$_3$ | CF$_3$ | H |

TABLE C-continued

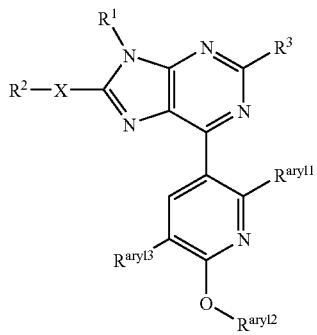

| R[1(a)] | X | R[2] | R[3] | R[aryl1] | R[aryl2] | R[aryl3] |
|---|---|---|---|---|---|---|
| R | CH$_2$ | CH$_3$ | CH$_3$ | CH$_3$ | CF$_3$ | H |
| S | CH$_2$ | CH$_3$ | CH$_3$ | CH$_3$ | CF$_3$ | H |
| T | CH$_2$ | CH$_3$ | CH$_3$ | CH$_3$ | CF$_3$ | H |
| U | CH$_2$ | CH$_3$ | CH$_3$ | CH$_3$ | CF$_3$ | H |
| V | CH$_2$ | CH$_3$ | CH$_3$ | CH$_3$ | CF$_3$ | H |
| W | CH$_2$ | CH$_3$ | CH$_3$ | CH$_3$ | CF$_3$ | H |
| X | CH$_2$ | CH$_3$ | CH$_3$ | CH$_3$ | CF$_3$ | H |
| Y | CH$_2$ | CH$_3$ | CH$_3$ | CH$_3$ | CF$_3$ | H |
| A | CH$_2$ | CH$_3$ | H | Cl | CHF$_2$ | H |
| B | CH$_2$ | CH$_3$ | H | Cl | CHF$_2$ | H |
| C | CH$_2$ | CH$_3$ | H | Cl | CHF$_2$ | H |
| D | CH$_2$ | CH$_3$ | H | Cl | CHF$_2$ | H |
| E | CH$_2$ | CH$_3$ | H | Cl | CHF$_2$ | H |
| F | CH$_2$ | CH$_3$ | H | Cl | CHF$_2$ | H |
| G | CH$_2$ | CH$_3$ | H | Cl | CHF$_2$ | H |
| H | CH$_2$ | CH$_3$ | H | Cl | CHF$_2$ | H |
| I | CH$_2$ | CH$_3$ | H | Cl | CHF$_2$ | H |
| J | CH$_2$ | CH$_3$ | H | Cl | CHF$_2$ | H |
| K | CH$_2$ | CH$_3$ | H | Cl | CHF$_2$ | H |
| L | CH$_2$ | CH$_3$ | H | Cl | CHF$_2$ | H |
| M | CH$_2$ | CH$_3$ | H | Cl | CHF$_2$ | H |
| N | CH$_2$ | CH$_3$ | H | Cl | CHF$_2$ | H |
| O | CH$_2$ | CH$_3$ | H | Cl | CHF$_2$ | H |
| P | CH$_2$ | CH$_3$ | H | Cl | CHF$_2$ | H |
| Q | CH$_2$ | CH$_3$ | H | Cl | CHF$_2$ | H |
| R | CH$_2$ | CH$_3$ | H | Cl | CHF$_2$ | H |
| S | CH$_2$ | CH$_3$ | H | Cl | CHF$_2$ | H |
| T | CH$_2$ | CH$_3$ | H | Cl | CHF$_2$ | H |
| U | CH$_2$ | CH$_3$ | H | Cl | CHF$_2$ | H |
| V | CH$_2$ | CH$_3$ | H | Cl | CHF$_2$ | H |
| W | CH$_2$ | CH$_3$ | H | Cl | CHF$_2$ | H |
| X | CH$_2$ | CH$_3$ | H | Cl | CHF$_2$ | H |
| Y | CH$_2$ | CH$_3$ | H | Cl | CHF$_2$ | H |
| A | O | CH$_3$ | H | Cl | CHF$_2$ | H |
| B | O | CH$_3$ | H | Cl | CHF$_2$ | H |
| C | O | CH$_3$ | H | Cl | CHF$_2$ | H |
| D | O | CH$_3$ | H | Cl | CHF$_2$ | H |
| E | O | CH$_3$ | H | Cl | CHF$_2$ | H |
| F | O | CH$_3$ | H | Cl | CHF$_2$ | H |
| G | O | CH$_3$ | H | Cl | CHF$_2$ | H |
| H | O | CH$_3$ | H | Cl | CHF$_2$ | H |
| I | O | CH$_3$ | H | Cl | CHF$_2$ | H |
| J | O | CH$_3$ | H | Cl | CHF$_2$ | H |
| K | O | CH$_3$ | H | Cl | CHF$_2$ | H |
| L | O | CH$_3$ | H | Cl | CHF$_2$ | H |
| M | O | CH$_3$ | H | Cl | CHF$_2$ | H |
| N | O | CH$_3$ | H | Cl | CHF$_2$ | H |
| O | O | CH$_3$ | H | Cl | CHF$_2$ | H |
| P | O | CH$_3$ | H | Cl | CHF$_2$ | H |
| Q | O | CH$_3$ | H | Cl | CHF$_2$ | H |
| R | O | CH$_3$ | H | Cl | CHF$_2$ | H |
| S | O | CH$_3$ | H | Cl | CHF$_2$ | H |
| T | O | CH$_3$ | H | Cl | CHF$_2$ | H |
| U | O | CH$_3$ | H | Cl | CHF$_2$ | H |
| V | O | CH$_3$ | H | Cl | CHF$_2$ | H |
| W | O | CH$_3$ | H | Cl | CHF$_2$ | H |
| X | O | CH$_3$ | H | Cl | CHF$_2$ | H |
| Y | O | CH$_3$ | H | Cl | CHF$_2$ | H |
| A | O | C$_2$H$_5$ | H | Cl | CHF$_2$ | H |
| B | O | C$_2$H$_5$ | H | Cl | CHF$_2$ | H |

TABLE C-continued

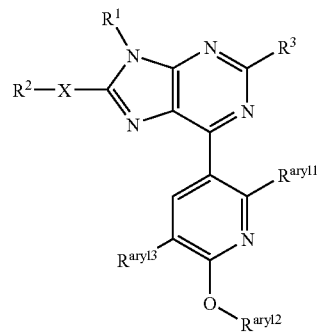

| R[1(a)] | X | R[2] | R[3] | R[aryl1] | R[aryl2] | R[aryl3] |
|---|---|---|---|---|---|---|
| C | O | $C_2H_5$ | H | Cl | $CHF_2$ | H |
| D | O | $C_2H_5$ | H | Cl | $CHF_2$ | H |
| E | O | $C_2H_5$ | H | Cl | $CHF_2$ | H |
| F | O | $C_2H_5$ | H | Cl | $CHF_2$ | H |
| G | O | $C_2H_5$ | H | Cl | $CHF_2$ | H |
| H | O | $C_2H_5$ | H | Cl | $CHF_2$ | H |
| I | O | $C_2H_5$ | H | Cl | $CHF_2$ | H |
| J | O | $C_2H_5$ | H | Cl | $CHF_2$ | H |
| K | O | $C_2H_5$ | H | Cl | $CHF_2$ | H |
| L | O | $C_2H_5$ | H | Cl | $CHF_2$ | H |
| M | O | $C_2H_5$ | H | Cl | $CHF_2$ | H |
| N | O | $C_2H_5$ | H | Cl | $CHF_2$ | H |
| O | O | $C_2H_5$ | H | Cl | $CHF_2$ | H |
| P | O | $C_2H_5$ | H | Cl | $CHF_2$ | H |
| Q | O | $C_2H_5$ | H | Cl | $CHF_2$ | H |
| R | O | $C_2H_5$ | H | Cl | $CHF_2$ | H |
| S | O | $C_2H_5$ | H | Cl | $CHF_2$ | H |
| T | O | $C_2H_5$ | H | Cl | $CHF_2$ | H |
| U | O | $C_2H_5$ | H | Cl | $CHF_2$ | H |
| V | O | $C_2H_5$ | H | Cl | $CHF_2$ | H |
| W | O | $C_2H_5$ | H | Cl | $CHF_2$ | H |
| X | O | $C_2H_5$ | H | Cl | $CHF_2$ | H |
| Y | O | $C_2H_5$ | H | Cl | $CHF_2$ | H |
| A | $CH_2$ | $CH_3$ | $CH_3$ | Cl | $CHF_2$ | H |
| B | $CH_2$ | $CH_3$ | $CH_3$ | Cl | $CHF_2$ | H |
| C | $CH_2$ | $CH_3$ | $CH_3$ | Cl | $CHF_2$ | H |
| D | $CH_2$ | $CH_3$ | $CH_3$ | Cl | $CHF_2$ | H |
| E | $CH_2$ | $CH_3$ | $CH_3$ | Cl | $CHF_2$ | H |
| F | $CH_2$ | $CH_3$ | $CH_3$ | Cl | $CHF_2$ | H |
| G | $CH_2$ | $CH_3$ | $CH_3$ | Cl | $CHF_2$ | H |
| H | $CH_2$ | $CH_3$ | $CH_3$ | Cl | $CHF_2$ | H |
| I | $CH_2$ | $CH_3$ | $CH_3$ | Cl | $CHF_2$ | H |
| J | $CH_2$ | $CH_3$ | $CH_3$ | Cl | $CHF_2$ | H |
| K | $CH_2$ | $CH_3$ | $CH_3$ | Cl | $CHF_2$ | H |
| L | $CH_2$ | $CH_3$ | $CH_3$ | Cl | $CHF_2$ | H |
| M | $CH_2$ | $CH_3$ | $CH_3$ | Cl | $CHF_2$ | H |
| N | $CH_2$ | $CH_3$ | $CH_3$ | Cl | $CHF_2$ | H |
| O | $CH_2$ | $CH_3$ | $CH_3$ | Cl | $CHF_2$ | H |
| P | $CH_2$ | $CH_3$ | $CH_3$ | Cl | $CHF_2$ | H |
| Q | $CH_2$ | $CH_3$ | $CH_3$ | Cl | $CHF_2$ | H |
| R | $CH_2$ | $CH_3$ | $CH_3$ | Cl | $CHF_2$ | H |
| S | $CH_2$ | $CH_3$ | $CH_3$ | Cl | $CHF_2$ | H |
| T | $CH_2$ | $CH_3$ | $CH_3$ | Cl | $CHF_2$ | H |
| U | $CH_2$ | $CH_3$ | $CH_3$ | Cl | $CHF_2$ | H |
| V | $CH_2$ | $CH_3$ | $CH_3$ | Cl | $CHF_2$ | H |
| W | $CH_2$ | $CH_3$ | $CH_3$ | Cl | $CHF_2$ | H |
| X | $CH_2$ | $CH_3$ | $CH_3$ | Cl | $CHF_2$ | H |
| Y | $CH_2$ | $CH_3$ | $CH_3$ | Cl | $CHF_2$ | H |
| A | $CH_2$ | $CH_3$ | H | $CH_3$ | $CHF_2$ | H |
| B | $CH_2$ | $CH_3$ | H | $CH_3$ | $CHF_2$ | H |
| C | $CH_2$ | $CH_3$ | H | $CH_3$ | $CHF_2$ | H |
| D | $CH_2$ | $CH_3$ | H | $CH_3$ | $CHF_2$ | H |
| E | $CH_2$ | $CH_3$ | H | $CH_3$ | $CHF_2$ | H |
| F | $CH_2$ | $CH_3$ | H | $CH_3$ | $CHF_2$ | H |
| G | $CH_2$ | $CH_3$ | H | $CH_3$ | $CHF_2$ | H |
| H | $CH_2$ | $CH_3$ | H | $CH_3$ | $CHF_2$ | H |
| I | $CH_2$ | $CH_3$ | H | $CH_3$ | $CHF_2$ | H |
| J | $CH_2$ | $CH_3$ | H | $CH_3$ | $CHF_2$ | H |
| K | $CH_2$ | $CH_3$ | H | $CH_3$ | $CHF_2$ | H |
| L | $CH_2$ | $CH_3$ | H | $CH_3$ | $CHF_2$ | H |

TABLE C-continued

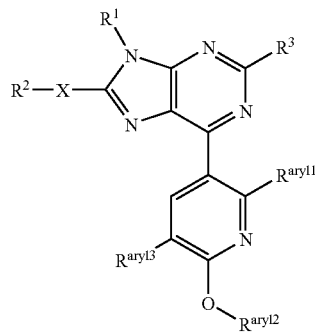

| R[1(a)] | X | R[2] | R[3] | R[aryl1] | R[aryl2] | R[aryl3] |
|---|---|---|---|---|---|---|
| M | $CH_2$ | $CH_3$ | H | $CH_3$ | $CHF_2$ | H |
| N | $CH_2$ | $CH_3$ | H | $CH_3$ | $CHF_2$ | H |
| O | $CH_2$ | $CH_3$ | H | $CH_3$ | $CHF_2$ | H |
| P | $CH_2$ | $CH_3$ | H | $CH_3$ | $CHF_2$ | H |
| Q | $CH_2$ | $CH_3$ | H | $CH_3$ | $CHF_2$ | H |
| R | $CH_2$ | $CH_3$ | H | $CH_3$ | $CHF_2$ | H |
| S | $CH_2$ | $CH_3$ | H | $CH_3$ | $CHF_2$ | H |
| T | $CH_2$ | $CH_3$ | H | $CH_3$ | $CHF_2$ | H |
| U | $CH_2$ | $CH_3$ | H | $CH_3$ | $CHF_2$ | H |
| V | $CH_2$ | $CH_3$ | H | $CH_3$ | $CHF_2$ | H |
| W | $CH_2$ | $CH_3$ | H | $CH_3$ | $CHF_2$ | H |
| X | $CH_2$ | $CH_3$ | H | $CH_3$ | $CHF_2$ | H |
| Y | $CH_2$ | $CH_3$ | H | $CH_3$ | $CHF_2$ | H |
| A | O | $CH_3$ | H | $CH_3$ | $CHF_2$ | H |
| B | O | $CH_3$ | H | $CH_3$ | $CHF_2$ | H |
| C | O | $CH_3$ | H | $CH_3$ | $CHF_2$ | H |
| D | O | $CH_3$ | H | $CH_3$ | $CHF_2$ | H |
| E | O | $CH_3$ | H | $CH_3$ | $CHF_2$ | H |
| F | O | $CH_3$ | H | $CH_3$ | $CHF_2$ | H |
| G | O | $CH_3$ | H | $CH_3$ | $CHF_2$ | H |
| H | O | $CH_3$ | H | $CH_3$ | $CHF_2$ | H |
| I | O | $CH_3$ | H | $CH_3$ | $CHF_2$ | H |
| J | O | $CH_3$ | H | $CH_3$ | $CHF_2$ | H |
| K | O | $CH_3$ | H | $CH_3$ | $CHF_2$ | H |
| L | O | $CH_3$ | H | $CH_3$ | $CHF_2$ | H |
| M | O | $CH_3$ | H | $CH_3$ | $CHF_2$ | H |
| N | O | $CH_3$ | H | $CH_3$ | $CHF_2$ | H |
| O | O | $CH_3$ | H | $CH_3$ | $CHF_2$ | H |
| P | O | $CH_3$ | H | $CH_3$ | $CHF_2$ | H |
| Q | O | $CH_3$ | H | $CH_3$ | $CHF_2$ | H |
| R | O | $CH_3$ | H | $CH_3$ | $CHF_2$ | H |
| S | O | $CH_3$ | H | $CH_3$ | $CHF_2$ | H |
| T | O | $CH_3$ | H | $CH_3$ | $CHF_2$ | H |
| U | O | $CH_3$ | H | $CH_3$ | $CHF_2$ | H |
| V | O | $CH_3$ | H | $CH_3$ | $CHF_2$ | H |
| W | O | $CH_3$ | H | $CH_3$ | $CHF_2$ | H |
| X | O | $CH_3$ | H | $CH_3$ | $CHF_2$ | H |
| Y | O | $CH_3$ | H | $CH_3$ | $CHF_2$ | H |
| A | O | $C_2H_5$ | H | $CH_3$ | $CHF_2$ | H |
| B | O | $C_2H_5$ | H | $CH_3$ | $CHF_2$ | H |
| C | O | $C_2H_5$ | H | $CH_3$ | $CHF_2$ | H |
| D | O | $C_2H_5$ | H | $CH_3$ | $CHF_2$ | H |
| E | O | $C_2H_5$ | H | $CH_3$ | $CHF_2$ | H |
| F | O | $C_2H_5$ | H | $CH_3$ | $CHF_2$ | H |
| G | O | $C_2H_5$ | H | $CH_3$ | $CHF_2$ | H |
| H | O | $C_2H_5$ | H | $CH_3$ | $CHF_2$ | H |
| I | O | $C_2H_5$ | H | $CH_3$ | $CHF_2$ | H |
| J | O | $C_2H_5$ | H | $CH_3$ | $CHF_2$ | H |
| K | O | $C_2H_5$ | H | $CH_3$ | $CHF_2$ | H |
| L | O | $C_2H_5$ | H | $CH_3$ | $CHF_2$ | H |
| M | O | $C_2H_5$ | H | $CH_3$ | $CHF_2$ | H |
| N | O | $C_2H_5$ | H | $CH_3$ | $CHF_2$ | H |
| O | O | $C_2H_5$ | H | $CH_3$ | $CHF_2$ | H |
| P | O | $C_2H_5$ | H | $CH_3$ | $CHF_2$ | H |
| Q | O | $C_2H_5$ | H | $CH_3$ | $CHF_2$ | H |
| R | O | $C_2H_5$ | H | $CH_3$ | $CHF_2$ | H |
| S | O | $C_2H_5$ | H | $CH_3$ | $CHF_2$ | H |
| T | O | $C_2H_5$ | H | $CH_3$ | $CHF_2$ | H |
| U | O | $C_2H_5$ | H | $CH_3$ | $CHF_2$ | H |
| V | O | $C_2H_5$ | H | $CH_3$ | $CHF_2$ | H |

TABLE C-continued

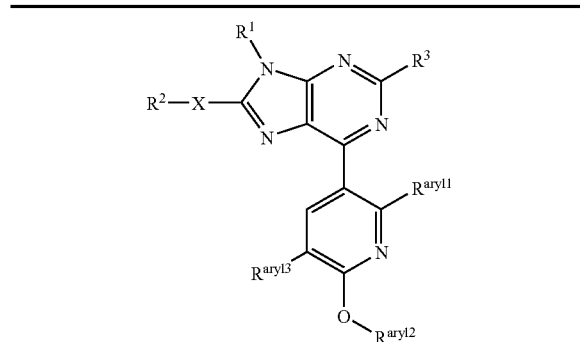

| R[1(a)] | X | R[2] | R[3] | R[aryl1] | R[aryl2] | R[aryl3] |
|---|---|---|---|---|---|---|
| W | O | $C_2H_5$ | H | $CH_3$ | $CHF_2$ | H |
| X | O | $C_2H_5$ | H | $CH_3$ | $CHF_2$ | H |
| Y | O | $C_2H_5$ | H | $CH_3$ | $CHF_2$ | H |
| A | $CH_2$ | $CH_3$ | $CH_3$ | $CH_3$ | $CHF_2$ | H |
| B | $CH_2$ | $CH_3$ | $CH_3$ | $CH_3$ | $CHF_2$ | H |
| C | $CH_2$ | $CH_3$ | $CH_3$ | $CH_3$ | $CHF_2$ | H |
| D | $CH_2$ | $CH_3$ | $CH_3$ | $CH_3$ | $CHF_2$ | H |
| E | $CH_2$ | $CH_3$ | $CH_3$ | $CH_3$ | $CHF_2$ | H |
| F | $CH_2$ | $CH_3$ | $CH_3$ | $CH_3$ | $CHF_2$ | H |
| G | $CH_2$ | $CH_3$ | $CH_3$ | $CH_3$ | $CHF_2$ | H |
| H | $CH_2$ | $CH_3$ | $CH_3$ | $CH_3$ | $CHF_2$ | H |
| I | $CH_2$ | $CH_3$ | $CH_3$ | $CH_3$ | $CHF_2$ | H |
| J | $CH_2$ | $CH_3$ | $CH_3$ | $CH_3$ | $CHF_2$ | H |
| K | $CH_2$ | $CH_3$ | $CH_3$ | $CH_3$ | $CHF_2$ | H |
| L | $CH_2$ | $CH_3$ | $CH_3$ | $CH_3$ | $CHF_2$ | H |
| M | $CH_2$ | $CH_3$ | $CH_3$ | $CH_3$ | $CHF_2$ | H |
| N | $CH_2$ | $CH_3$ | $CH_3$ | $CH_3$ | $CHF_2$ | H |
| O | $CH_2$ | $CH_3$ | $CH_3$ | $CH_3$ | $CHF_2$ | H |
| P | $CH_2$ | $CH_3$ | $CH_3$ | $CH_3$ | $CHF_2$ | H |
| Q | $CH_2$ | $CH_3$ | $CH_3$ | $CH_3$ | $CHF_2$ | H |
| R | $CH_2$ | $CH_3$ | $CH_3$ | $CH_3$ | $CHF_2$ | H |
| S | $CH_2$ | $CH_3$ | $CH_3$ | $CH_3$ | $CHF_2$ | H |
| T | $CH_2$ | $CH_3$ | $CH_3$ | $CH_3$ | $CHF_2$ | H |
| U | $CH_2$ | $CH_3$ | $CH_3$ | $CH_3$ | $CHF_2$ | H |
| V | $CH_2$ | $CH_3$ | $CH_3$ | $CH_3$ | $CHF_2$ | H |
| W | $CH_2$ | $CH_3$ | $CH_3$ | $CH_3$ | $CHF_2$ | H |
| X | $CH_2$ | $CH_3$ | $CH_3$ | $CH_3$ | $CHF_2$ | H |
| Y | $CH_2$ | $CH_3$ | $CH_3$ | $CH_3$ | $CHF_2$ | H |
| A | $CH_2$ | $CH_3$ | H | Cl | $CF_3$ | $CH_3$ |
| B | $CH_2$ | $CH_3$ | H | Cl | $CF_3$ | $CH_3$ |
| C | $CH_2$ | $CH_3$ | H | Cl | $CF_3$ | $CH_3$ |
| D | $CH_2$ | $CH_3$ | H | Cl | $CF_3$ | $CH_3$ |
| E | $CH_2$ | $CH_3$ | H | Cl | $CF_3$ | $CH_3$ |
| F | $CH_2$ | $CH_3$ | H | Cl | $CF_3$ | $CH_3$ |
| G | $CH_2$ | $CH_3$ | H | Cl | $CF_3$ | $CH_3$ |
| H | $CH_2$ | $CH_3$ | H | Cl | $CF_3$ | $CH_3$ |
| I | $CH_2$ | $CH_3$ | H | Cl | $CF_3$ | $CH_3$ |
| J | $CH_2$ | $CH_3$ | H | Cl | $CF_3$ | $CH_3$ |
| K | $CH_2$ | $CH_3$ | H | Cl | $CF_3$ | $CH_3$ |
| L | $CH_2$ | $CH_3$ | H | Cl | $CF_3$ | $CH_3$ |
| M | $CH_2$ | $CH_3$ | H | Cl | $CF_3$ | $CH_3$ |
| N | $CH_2$ | $CH_3$ | H | Cl | $CF_3$ | $CH_3$ |
| O | $CH_2$ | $CH_3$ | H | Cl | $CF_3$ | $CH_3$ |
| P | $CH_2$ | $CH_3$ | H | Cl | $CF_3$ | $CH_3$ |
| Q | $CH_2$ | $CH_3$ | H | Cl | $CF_3$ | $CH_3$ |
| R | $CH_2$ | $CH_3$ | H | Cl | $CF_3$ | $CH_3$ |
| S | $CH_2$ | $CH_3$ | H | Cl | $CF_3$ | $CH_3$ |
| T | $CH_2$ | $CH_3$ | H | Cl | $CF_3$ | $CH_3$ |
| U | $CH_2$ | $CH_3$ | H | Cl | $CF_3$ | $CH_3$ |
| V | $CH_2$ | $CH_3$ | H | Cl | $CF_3$ | $CH_3$ |
| W | $CH_2$ | $CH_3$ | H | Cl | $CF_3$ | $CH_3$ |
| X | $CH_2$ | $CH_3$ | H | Cl | $CF_3$ | $CH_3$ |
| Y | $CH_2$ | $CH_3$ | H | Cl | $CF_3$ | $CH_3$ |
| A | O | $CH_3$ | H | Cl | $CF_3$ | $CH_3$ |
| B | O | $CH_3$ | H | Cl | $CF_3$ | $CH_3$ |
| C | O | $CH_3$ | H | Cl | $CF_3$ | $CH_3$ |
| D | O | $CH_3$ | H | Cl | $CF_3$ | $CH_3$ |
| E | O | $CH_3$ | H | Cl | $CF_3$ | $CH_3$ |
| F | O | $CH_3$ | H | Cl | $CF_3$ | $CH_3$ |
| G | O | $CH_3$ | H | Cl | $CF_3$ | $CH_3$ |
| H | O | $CH_3$ | H | Cl | $CF_3$ | $CH_3$ |
| I | O | $CH_3$ | H | Cl | $CF_3$ | $CH_3$ |
| J | O | $CH_3$ | H | Cl | $CF_3$ | $CH_3$ |
| K | O | $CH_3$ | H | Cl | $CF_3$ | $CH_3$ |
| L | O | $CH_3$ | H | Cl | $CF_3$ | $CH_3$ |
| M | O | $CH_3$ | H | Cl | $CF_3$ | $CH_3$ |
| N | O | $CH_3$ | H | Cl | $CF_3$ | $CH_3$ |
| O | O | $CH_3$ | H | Cl | $CF_3$ | $CH_3$ |
| P | O | $CH_3$ | H | Cl | $CF_3$ | $CH_3$ |
| Q | O | $CH_3$ | H | Cl | $CF_3$ | $CH_3$ |
| R | O | $CH_3$ | H | Cl | $CF_3$ | $CH_3$ |
| S | O | $CH_3$ | H | Cl | $CF_3$ | $CH_3$ |
| T | O | $CH_3$ | H | Cl | $CF_3$ | $CH_3$ |
| U | O | $CH_3$ | H | Cl | $CF_3$ | $CH_3$ |
| V | O | $CH_3$ | H | Cl | $CF_3$ | $CH_3$ |
| W | O | $CH_3$ | H | Cl | $CF_3$ | $CH_3$ |
| X | O | $CH_3$ | H | Cl | $CF_3$ | $CH_3$ |
| Y | O | $CH_3$ | H | Cl | $CF_3$ | $CH_3$ |
| A | O | $C_2H_5$ | H | Cl | $CF_3$ | $CH_3$ |
| B | O | $C_2H_5$ | H | Cl | $CF_3$ | $CH_3$ |
| C | O | $C_2H_5$ | H | Cl | $CF_3$ | $CH_3$ |
| D | O | $C_2H_5$ | H | Cl | $CF_3$ | $CH_3$ |
| E | O | $C_2H_5$ | H | Cl | $CF_3$ | $CH_3$ |
| F | O | $C_2H_5$ | H | Cl | $CF_3$ | $CH_3$ |
| G | O | $C_2H_5$ | H | Cl | $CF_3$ | $CH_3$ |
| H | O | $C_2H_5$ | H | Cl | $CF_3$ | $CH_3$ |
| I | O | $C_2H_5$ | H | Cl | $CF_3$ | $CH_3$ |
| J | O | $C_2H_5$ | H | Cl | $CF_3$ | $CH_3$ |
| K | O | $C_2H_5$ | H | Cl | $CF_3$ | $CH_3$ |
| L | O | $C_2H_5$ | H | Cl | $CF_3$ | $CH_3$ |
| M | O | $C_2H_5$ | H | Cl | $CF_3$ | $CH_3$ |
| N | O | $C_2H_5$ | H | Cl | $CF_3$ | $CH_3$ |
| O | O | $C_2H_5$ | H | Cl | $CF_3$ | $CH_3$ |
| P | O | $C_2H_5$ | H | Cl | $CF_3$ | $CH_3$ |
| Q | O | $C_2H_5$ | H | Cl | $CF_3$ | $CH_3$ |
| R | O | $C_2H_5$ | H | Cl | $CF_3$ | $CH_3$ |
| S | O | $C_2H_5$ | H | Cl | $CF_3$ | $CH_3$ |
| T | O | $C_2H_5$ | H | Cl | $CF_3$ | $CH_3$ |
| U | O | $C_2H_5$ | H | Cl | $CF_3$ | $CH_3$ |
| V | O | $C_2H_5$ | H | Cl | $CF_3$ | $CH_3$ |
| W | O | $C_2H_5$ | H | Cl | $CF_3$ | $CH_3$ |
| X | O | $C_2H_5$ | H | Cl | $CF_3$ | $CH_3$ |
| Y | O | $C_2H_5$ | H | Cl | $CF_3$ | $CH_3$ |
| A | $CH_2$ | $CH_3$ | $CH_3$ | Cl | $CF_3$ | $CH_3$ |
| B | $CH_2$ | $CH_3$ | $CH_3$ | Cl | $CF_3$ | $CH_3$ |
| C | $CH_2$ | $CH_3$ | $CH_3$ | Cl | $CF_3$ | $CH_3$ |
| D | $CH_2$ | $CH_3$ | $CH_3$ | Cl | $CF_3$ | $CH_3$ |
| E | $CH_2$ | $CH_3$ | $CH_3$ | Cl | $CF_3$ | $CH_3$ |
| F | $CH_2$ | $CH_3$ | $CH_3$ | Cl | $CF_3$ | $CH_3$ |
| G | $CH_2$ | $CH_3$ | $CH_3$ | Cl | $CF_3$ | $CH_3$ |
| H | $CH_2$ | $CH_3$ | $CH_3$ | Cl | $CF_3$ | $CH_3$ |
| I | $CH_2$ | $CH_3$ | $CH_3$ | Cl | $CF_3$ | $CH_3$ |
| J | $CH_2$ | $CH_3$ | $CH_3$ | Cl | $CF_3$ | $CH_3$ |
| K | $CH_2$ | $CH_3$ | $CH_3$ | Cl | $CF_3$ | $CH_3$ |
| L | $CH_2$ | $CH_3$ | $CH_3$ | Cl | $CF_3$ | $CH_3$ |
| M | $CH_2$ | $CH_3$ | $CH_3$ | Cl | $CF_3$ | $CH_3$ |
| N | $CH_2$ | $CH_3$ | $CH_3$ | Cl | $CF_3$ | $CH_3$ |
| O | $CH_2$ | $CH_3$ | $CH_3$ | Cl | $CF_3$ | $CH_3$ |
| P | $CH_2$ | $CH_3$ | $CH_3$ | Cl | $CF_3$ | $CH_3$ |
| Q | $CH_2$ | $CH_3$ | $CH_3$ | Cl | $CF_3$ | $CH_3$ |

TABLE C-continued

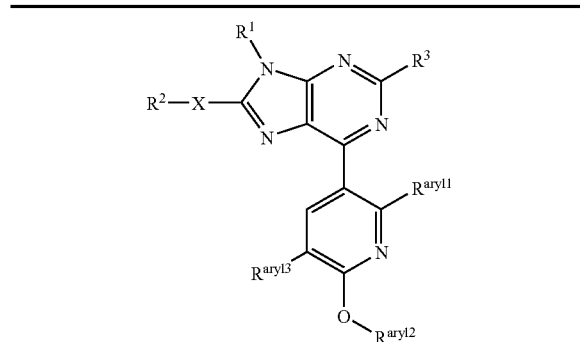

| $R^{1(a)}$ | X | $R^2$ | $R^3$ | $R^{aryl1}$ | $R^{aryl2}$ | $R^{aryl3}$ |
|---|---|---|---|---|---|---|
| R | $CH_2$ | $CH_3$ | $CH_3$ | Cl | $CF_3$ | $CH_3$ |
| S | $CH_2$ | $CH_3$ | $CH_3$ | Cl | $CF_3$ | $CH_3$ |
| T | $CH_2$ | $CH_3$ | $CH_3$ | Cl | $CF_3$ | $CH_3$ |
| U | $CH_2$ | $CH_3$ | $CH_3$ | Cl | $CF_3$ | $CH_3$ |
| V | $CH_2$ | $CH_3$ | $CH_3$ | Cl | $CF_3$ | $CH_3$ |
| W | $CH_2$ | $CH_3$ | $CH_3$ | Cl | $CF_3$ | $CH_3$ |
| X | $CH_2$ | $CH_3$ | $CH_3$ | Cl | $CF_3$ | $CH_3$ |
| Y | $CH_2$ | $CH_3$ | $CH_3$ | Cl | $CF_3$ | $CH_3$ |
| A | $CH_2$ | $CH_3$ | H | $CH_3$ | $CF_3$ | $CH_3$ |
| B | $CH_2$ | $CH_3$ | H | $CH_3$ | $CF_3$ | $CH_3$ |
| C | $CH_2$ | $CH_3$ | H | $CH_3$ | $CF_3$ | $CH_3$ |
| D | $CH_2$ | $CH_3$ | H | $CH_3$ | $CF_3$ | $CH_3$ |
| E | $CH_2$ | $CH_3$ | H | $CH_3$ | $CF_3$ | $CH_3$ |
| F | $CH_2$ | $CH_3$ | H | $CH_3$ | $CF_3$ | $CH_3$ |
| G | $CH_2$ | $CH_3$ | H | $CH_3$ | $CF_3$ | $CH_3$ |
| H | $CH_2$ | $CH_3$ | H | $CH_3$ | $CF_3$ | $CH_3$ |
| I | $CH_2$ | $CH_3$ | H | $CH_3$ | $CF_3$ | $CH_3$ |
| J | $CH_2$ | $CH_3$ | H | $CH_3$ | $CF_3$ | $CH_3$ |
| K | $CH_2$ | $CH_3$ | H | $CH_3$ | $CF_3$ | $CH_3$ |
| L | $CH_2$ | $CH_3$ | H | $CH_3$ | $CF_3$ | $CH_3$ |
| M | $CH_2$ | $CH_3$ | H | $CH_3$ | $CF_3$ | $CH_3$ |
| N | $CH_2$ | $CH_3$ | H | $CH_3$ | $CF_3$ | $CH_3$ |
| O | $CH_2$ | $CH_3$ | H | $CH_3$ | $CF_3$ | $CH_3$ |
| P | $CH_2$ | $CH_3$ | H | $CH_3$ | $CF_3$ | $CH_3$ |
| Q | $CH_2$ | $CH_3$ | H | $CH_3$ | $CF_3$ | $CH_3$ |
| R | $CH_2$ | $CH_3$ | H | $CH_3$ | $CF_3$ | $CH_3$ |
| S | $CH_2$ | $CH_3$ | H | $CH_3$ | $CF_3$ | $CH_3$ |
| T | $CH_2$ | $CH_3$ | H | $CH_3$ | $CF_3$ | $CH_3$ |
| U | $CH_2$ | $CH_3$ | H | $CH_3$ | $CF_3$ | $CH_3$ |
| V | $CH_2$ | $CH_3$ | H | $CH_3$ | $CF_3$ | $CH_3$ |
| W | $CH_2$ | $CH_3$ | H | $CH_3$ | $CF_3$ | $CH_3$ |
| X | $CH_2$ | $CH_3$ | H | $CH_3$ | $CF_3$ | $CH_3$ |
| Y | $CH_2$ | $CH_3$ | H | $CH_3$ | $CF_3$ | $CH_3$ |
| A | O | $CH_3$ | H | $CH_3$ | $CF_3$ | $CH_3$ |
| B | O | $CH_3$ | H | $CH_3$ | $CF_3$ | $CH_3$ |
| C | O | $CH_3$ | H | $CH_3$ | $CF_3$ | $CH_3$ |
| D | O | $CH_3$ | H | $CH_3$ | $CF_3$ | $CH_3$ |
| E | O | $CH_3$ | H | $CH_3$ | $CF_3$ | $CH_3$ |
| F | O | $CH_3$ | H | $CH_3$ | $CF_3$ | $CH_3$ |
| G | O | $CH_3$ | H | $CH_3$ | $CF_3$ | $CH_3$ |
| H | O | $CH_3$ | H | $CH_3$ | $CF_3$ | $CH_3$ |
| I | O | $CH_3$ | H | $CH_3$ | $CF_3$ | $CH_3$ |
| J | O | $CH_3$ | H | $CH_3$ | $CF_3$ | $CH_3$ |
| K | O | $CH_3$ | H | $CH_3$ | $CF_3$ | $CH_3$ |
| L | O | $CH_3$ | H | $CH_3$ | $CF_3$ | $CH_3$ |
| M | O | $CH_3$ | H | $CH_3$ | $CF_3$ | $CH_3$ |
| N | O | $CH_3$ | H | $CH_3$ | $CF_3$ | $CH_3$ |
| O | O | $CH_3$ | H | $CH_3$ | $CF_3$ | $CH_3$ |
| P | O | $CH_3$ | H | $CH_3$ | $CF_3$ | $CH_3$ |
| Q | O | $CH_3$ | H | $CH_3$ | $CF_3$ | $CH_3$ |
| R | O | $CH_3$ | H | $CH_3$ | $CF_3$ | $CH_3$ |
| S | O | $CH_3$ | H | $CH_3$ | $CF_3$ | $CH_3$ |
| T | O | $CH_3$ | H | $CH_3$ | $CF_3$ | $CH_3$ |
| U | O | $CH_3$ | H | $CH_3$ | $CF_3$ | $CH_3$ |
| V | O | $CH_3$ | H | $CH_3$ | $CF_3$ | $CH_3$ |
| W | O | $CH_3$ | H | $CH_3$ | $CF_3$ | $CH_3$ |
| X | O | $CH_3$ | H | $CH_3$ | $CF_3$ | $CH_3$ |
| Y | O | $CH_3$ | H | $CH_3$ | $CF_3$ | $CH_3$ |
| A | O | $C_2H_5$ | H | $CH_3$ | $CF_3$ | $CH_3$ |
| B | O | $C_2H_5$ | H | $CH_3$ | $CF_3$ | $CH_3$ |
| C | O | $C_2H_5$ | H | $CH_3$ | $CF_3$ | $CH_3$ |
| D | O | $C_2H_5$ | H | $CH_3$ | $CF_3$ | $CH_3$ |
| E | O | $C_2H_5$ | H | $CH_3$ | $CF_3$ | $CH_3$ |
| F | O | $C_2H_5$ | H | $CH_3$ | $CF_3$ | $CH_3$ |
| G | O | $C_2H_5$ | H | $CH_3$ | $CF_3$ | $CH_3$ |
| H | O | $C_2H_5$ | H | $CH_3$ | $CF_3$ | $CH_3$ |
| I | O | $C_2H_5$ | H | $CH_3$ | $CF_3$ | $CH_3$ |
| J | O | $C_2H_5$ | H | $CH_3$ | $CF_3$ | $CH_3$ |
| K | O | $C_2H_5$ | H | $CH_3$ | $CF_3$ | $CH_3$ |
| L | O | $C_2H_5$ | H | $CH_3$ | $CF_3$ | $CH_3$ |
| M | O | $C_2H_5$ | H | $CH_3$ | $CF_3$ | $CH_3$ |
| N | O | $C_2H_5$ | H | $CH_3$ | $CF_3$ | $CH_3$ |
| O | O | $C_2H_5$ | H | $CH_3$ | $CF_3$ | $CH_3$ |
| P | O | $C_2H_5$ | H | $CH_3$ | $CF_3$ | $CH_3$ |
| Q | O | $C_2H_5$ | H | $CH_3$ | $CF_3$ | $CH_3$ |
| R | O | $C_2H_5$ | H | $CH_3$ | $CF_3$ | $CH_3$ |
| S | O | $C_2H_5$ | H | $CH_3$ | $CF_3$ | $CH_3$ |
| T | O | $C_2H_5$ | H | $CH_3$ | $CF_3$ | $CH_3$ |
| U | O | $C_2H_5$ | H | $CH_3$ | $CF_3$ | $CH_3$ |
| V | O | $C_2H_5$ | H | $CH_3$ | $CF_3$ | $CH_3$ |
| W | O | $C_2H_5$ | H | $CH_3$ | $CF_3$ | $CH_3$ |
| X | O | $C_2H_5$ | H | $CH_3$ | $CF_3$ | $CH_3$ |
| Y | O | $C_2H_5$ | H | $CH_3$ | $CF_3$ | $CH_3$ |
| A | $CH_2$ | $CH_3$ | $CH_3$ | $CH_3$ | $CF_3$ | $CH_3$ |
| B | $CH_2$ | $CH_3$ | $CH_3$ | $CH_3$ | $CF_3$ | $CH_3$ |
| C | $CH_2$ | $CH_3$ | $CH_3$ | $CH_3$ | $CF_3$ | $CH_3$ |
| D | $CH_2$ | $CH_3$ | $CH_3$ | $CH_3$ | $CF_3$ | $CH_3$ |
| E | $CH_2$ | $CH_3$ | $CH_3$ | $CH_3$ | $CF_3$ | $CH_3$ |
| F | $CH_2$ | $CH_3$ | $CH_3$ | $CH_3$ | $CF_3$ | $CH_3$ |
| G | $CH_2$ | $CH_3$ | $CH_3$ | $CH_3$ | $CF_3$ | $CH_3$ |
| H | $CH_2$ | $CH_3$ | $CH_3$ | $CH_3$ | $CF_3$ | $CH_3$ |
| I | $CH_2$ | $CH_3$ | $CH_3$ | $CH_3$ | $CF_3$ | $CH_3$ |
| J | $CH_2$ | $CH_3$ | $CH_3$ | $CH_3$ | $CF_3$ | $CH_3$ |
| K | $CH_2$ | $CH_3$ | $CH_3$ | $CH_3$ | $CF_3$ | $CH_3$ |
| L | $CH_2$ | $CH_3$ | $CH_3$ | $CH_3$ | $CF_3$ | $CH_3$ |
| M | $CH_2$ | $CH_3$ | $CH_3$ | $CH_3$ | $CF_3$ | $CH_3$ |
| N | $CH_2$ | $CH_3$ | $CH_3$ | $CH_3$ | $CF_3$ | $CH_3$ |
| O | $CH_2$ | $CH_3$ | $CH_3$ | $CH_3$ | $CF_3$ | $CH_3$ |
| P | $CH_2$ | $CH_3$ | $CH_3$ | $CH_3$ | $CF_3$ | $CH_3$ |
| Q | $CH_2$ | $CH_3$ | $CH_3$ | $CH_3$ | $CF_3$ | $CH_3$ |
| R | $CH_2$ | $CH_3$ | $CH_3$ | $CH_3$ | $CF_3$ | $CH_3$ |
| S | $CH_2$ | $CH_3$ | $CH_3$ | $CH_3$ | $CF_3$ | $CH_3$ |
| T | $CH_2$ | $CH_3$ | $CH_3$ | $CH_3$ | $CF_3$ | $CH_3$ |
| U | $CH_2$ | $CH_3$ | $CH_3$ | $CH_3$ | $CF_3$ | $CH_3$ |
| V | $CH_2$ | $CH_3$ | $CH_3$ | $CH_3$ | $CF_3$ | $CH_3$ |
| W | $CH_2$ | $CH_3$ | $CH_3$ | $CH_3$ | $CF_3$ | $CH_3$ |
| X | $CH_2$ | $CH_3$ | $CH_3$ | $CH_3$ | $CF_3$ | $CH_3$ |
| Y | $CH_2$ | $CH_3$ | $CH_3$ | $CH_3$ | $CF_3$ | $CH_3$ |
| A | $CH_2$ | $CH_3$ | H | Cl | $CHF_2$ | $CH_3$ |
| B | $CH_2$ | $CH_3$ | H | Cl | $CHF_2$ | $CH_3$ |
| C | $CH_2$ | $CH_3$ | H | Cl | $CHF_2$ | $CH_3$ |
| D | $CH_2$ | $CH_3$ | H | Cl | $CHF_2$ | $CH_3$ |
| E | $CH_2$ | $CH_3$ | H | Cl | $CHF_2$ | $CH_3$ |
| F | $CH_2$ | $CH_3$ | H | Cl | $CHF_2$ | $CH_3$ |
| G | $CH_2$ | $CH_3$ | H | Cl | $CHF_2$ | $CH_3$ |
| H | $CH_2$ | $CH_3$ | H | Cl | $CHF_2$ | $CH_3$ |
| I | $CH_2$ | $CH_3$ | H | Cl | $CHF_2$ | $CH_3$ |
| J | $CH_2$ | $CH_3$ | H | Cl | $CHF_2$ | $CH_3$ |
| K | $CH_2$ | $CH_3$ | H | Cl | $CHF_2$ | $CH_3$ |
| L | $CH_2$ | $CH_3$ | H | Cl | $CHF_2$ | $CH_3$ |

TABLE C-continued

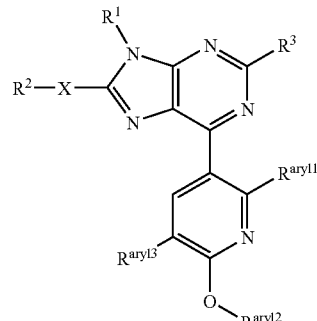

| R[1(a)] | X | R[2] | R[3] | R[aryl1] | R[aryl2] | R[aryl3] |
|---|---|---|---|---|---|---|
| M | $CH_2$ | $CH_3$ | H | Cl | $CHF_2$ | $CH_3$ |
| N | $CH_2$ | $CH_3$ | H | Cl | $CHF_2$ | $CH_3$ |
| O | $CH_2$ | $CH_3$ | H | Cl | $CHF_2$ | $CH_3$ |
| P | $CH_2$ | $CH_3$ | H | Cl | $CHF_2$ | $CH_3$ |
| Q | $CH_2$ | $CH_3$ | H | Cl | $CHF_2$ | $CH_3$ |
| R | $CH_2$ | $CH_3$ | H | Cl | $CHF_2$ | $CH_3$ |
| S | $CH_2$ | $CH_3$ | H | Cl | $CHF_2$ | $CH_3$ |
| T | $CH_2$ | $CH_3$ | H | Cl | $CHF_2$ | $CH_3$ |
| U | $CH_2$ | $CH_3$ | H | Cl | $CHF_2$ | $CH_3$ |
| V | $CH_2$ | $CH_3$ | H | Cl | $CHF_2$ | $CH_3$ |
| W | $CH_2$ | $CH_3$ | H | Cl | $CHF_2$ | $CH_3$ |
| X | $CH_2$ | $CH_3$ | H | Cl | $CHF_2$ | $CH_3$ |
| Y | $CH_2$ | $CH_3$ | H | Cl | $CHF_2$ | $CH_3$ |
| A | O | $CH_3$ | H | Cl | $CHF_2$ | $CH_3$ |
| B | O | $CH_3$ | H | Cl | $CHF_2$ | $CH_3$ |
| C | O | $CH_3$ | H | Cl | $CHF_2$ | $CH_3$ |
| D | O | $CH_3$ | H | Cl | $CHF_2$ | $CH_3$ |
| E | O | $CH_3$ | H | Cl | $CHF_2$ | $CH_3$ |
| F | O | $CH_3$ | H | Cl | $CHF_2$ | $CH_3$ |
| G | O | $CH_3$ | H | Cl | $CHF_2$ | $CH_3$ |
| H | O | $CH_3$ | H | Cl | $CHF_2$ | $CH_3$ |
| I | O | $CH_3$ | H | Cl | $CHF_2$ | $CH_3$ |
| J | O | $CH_3$ | H | Cl | $CHF_2$ | $CH_3$ |
| K | O | $CH_3$ | H | Cl | $CHF_2$ | $CH_3$ |
| L | O | $CH_3$ | H | Cl | $CHF_2$ | $CH_3$ |
| M | O | $CH_3$ | H | Cl | $CHF_2$ | $CH_3$ |
| N | O | $CH_3$ | H | Cl | $CHF_2$ | $CH_3$ |
| O | O | $CH_3$ | H | Cl | $CHF_2$ | $CH_3$ |
| P | O | $CH_3$ | H | Cl | $CHF_2$ | $CH_3$ |
| Q | O | $CH_3$ | H | Cl | $CHF_2$ | $CH_3$ |
| R | O | $CH_3$ | H | Cl | $CHF_2$ | $CH_3$ |
| S | O | $CH_3$ | H | Cl | $CHF_2$ | $CH_3$ |
| T | O | $CH_3$ | H | Cl | $CHF_2$ | $CH_3$ |
| U | O | $CH_3$ | H | Cl | $CHF_2$ | $CH_3$ |
| V | O | $CH_3$ | H | Cl | $CHF_2$ | $CH_3$ |
| W | O | $CH_3$ | H | Cl | $CHF_2$ | $CH_3$ |
| X | O | $CH_3$ | H | Cl | $CHF_2$ | $CH_3$ |
| Y | O | $CH_3$ | H | Cl | $CHF_2$ | $CH_3$ |
| A | O | $C_2H_5$ | H | Cl | $CHF_2$ | $CH_3$ |
| B | O | $C_2H_5$ | H | Cl | $CHF_2$ | $CH_3$ |
| C | O | $C_2H_5$ | H | Cl | $CHF_2$ | $CH_3$ |
| D | O | $C_2H_5$ | H | Cl | $CHF_2$ | $CH_3$ |
| E | O | $C_2H_5$ | H | Cl | $CHF_2$ | $CH_3$ |
| F | O | $C_2H_5$ | H | Cl | $CHF_2$ | $CH_3$ |
| G | O | $C_2H_5$ | H | Cl | $CHF_2$ | $CH_3$ |
| H | O | $C_2H_5$ | H | Cl | $CHF_2$ | $CH_3$ |
| I | O | $C_2H_5$ | H | Cl | $CHF_2$ | $CH_3$ |
| J | O | $C_2H_5$ | H | Cl | $CHF_2$ | $CH_3$ |
| K | O | $C_2H_5$ | H | Cl | $CHF_2$ | $CH_3$ |
| L | O | $C_2H_5$ | H | Cl | $CHF_2$ | $CH_3$ |
| M | O | $C_2H_5$ | H | Cl | $CHF_2$ | $CH_3$ |
| N | O | $C_2H_5$ | H | Cl | $CHF_2$ | $CH_3$ |
| O | O | $C_2H_5$ | H | Cl | $CHF_2$ | $CH_3$ |
| P | O | $C_2H_5$ | H | Cl | $CHF_2$ | $CH_3$ |
| Q | O | $C_2H_5$ | H | Cl | $CHF_2$ | $CH_3$ |
| R | O | $C_2H_5$ | H | Cl | $CHF_2$ | $CH_3$ |
| S | O | $C_2H_5$ | H | Cl | $CHF_2$ | $CH_3$ |
| T | O | $C_2H_5$ | H | Cl | $CHF_2$ | $CH_3$ |
| U | O | $C_2H_5$ | H | Cl | $CHF_2$ | $CH_3$ |
| V | O | $C_2H_5$ | H | Cl | $CHF_2$ | $CH_3$ |

TABLE C-continued

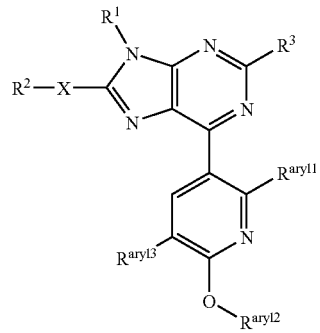

| R[1(a)] | X | R[2] | R[3] | R[aryl1] | R[aryl2] | R[aryl3] |
|---|---|---|---|---|---|---|
| W | O | $C_2H_5$ | H | Cl | $CHF_2$ | $CH_3$ |
| X | O | $C_2H_5$ | H | Cl | $CHF_2$ | $CH_3$ |
| Y | O | $C_2H_5$ | H | Cl | $CHF_2$ | $CH_3$ |
| A | $CH_2$ | $CH_3$ | $CH_3$ | Cl | $CHF_2$ | $CH_3$ |
| B | $CH_2$ | $CH_3$ | $CH_3$ | Cl | $CHF_2$ | $CH_3$ |
| C | $CH_2$ | $CH_3$ | $CH_3$ | Cl | $CHF_2$ | $CH_3$ |
| D | $CH_2$ | $CH_3$ | $CH_3$ | Cl | $CHF_2$ | $CH_3$ |
| E | $CH_2$ | $CH_3$ | $CH_3$ | Cl | $CHF_2$ | $CH_3$ |
| F | $CH_2$ | $CH_3$ | $CH_3$ | Cl | $CHF_2$ | $CH_3$ |
| G | $CH_2$ | $CH_3$ | $CH_3$ | Cl | $CHF_2$ | $CH_3$ |
| H | $CH_2$ | $CH_3$ | $CH_3$ | Cl | $CHF_2$ | $CH_3$ |
| I | $CH_2$ | $CH_3$ | $CH_3$ | Cl | $CHF_2$ | $CH_3$ |
| J | $CH_2$ | $CH_3$ | $CH_3$ | Cl | $CHF_2$ | $CH_3$ |
| K | $CH_2$ | $CH_3$ | $CH_3$ | Cl | $CHF_2$ | $CH_3$ |
| L | $CH_2$ | $CH_3$ | $CH_3$ | Cl | $CHF_2$ | $CH_3$ |
| M | $CH_2$ | $CH_3$ | $CH_3$ | Cl | $CHF_2$ | $CH_3$ |
| N | $CH_2$ | $CH_3$ | $CH_3$ | Cl | $CHF_2$ | $CH_3$ |
| O | $CH_2$ | $CH_3$ | $CH_3$ | Cl | $CHF_2$ | $CH_3$ |
| P | $CH_2$ | $CH_3$ | $CH_3$ | Cl | $CHF_2$ | $CH_3$ |
| Q | $CH_2$ | $CH_3$ | $CH_3$ | Cl | $CHF_2$ | $CH_3$ |
| R | $CH_2$ | $CH_3$ | $CH_3$ | Cl | $CHF_2$ | $CH_3$ |
| S | $CH_2$ | $CH_3$ | $CH_3$ | Cl | $CHF_2$ | $CH_3$ |
| T | $CH_2$ | $CH_3$ | $CH_3$ | Cl | $CHF_2$ | $CH_3$ |
| U | $CH_2$ | $CH_3$ | $CH_3$ | Cl | $CHF_2$ | $CH_3$ |
| V | $CH_2$ | $CH_3$ | $CH_3$ | Cl | $CHF_2$ | $CH_3$ |
| W | $CH_2$ | $CH_3$ | $CH_3$ | Cl | $CHF_2$ | $CH_3$ |
| X | $CH_2$ | $CH_3$ | $CH_3$ | Cl | $CHF_2$ | $CH_3$ |
| Y | $CH_2$ | $CH_3$ | $CH_3$ | Cl | $CHF_2$ | $CH_3$ |
| A | $CH_2$ | $CH_3$ | H | $CH_3$ | $CHF_2$ | $CH_3$ |
| B | $CH_2$ | $CH_3$ | H | $CH_3$ | $CHF_2$ | $CH_3$ |
| C | $CH_2$ | $CH_3$ | H | $CH_3$ | $CHF_2$ | $CH_3$ |
| D | $CH_2$ | $CH_3$ | H | $CH_3$ | $CHF_2$ | $CH_3$ |
| E | $CH_2$ | $CH_3$ | H | $CH_3$ | $CHF_2$ | $CH_3$ |
| F | $CH_2$ | $CH_3$ | H | $CH_3$ | $CHF_2$ | $CH_3$ |
| G | $CH_2$ | $CH_3$ | H | $CH_3$ | $CHF_2$ | $CH_3$ |
| H | $CH_2$ | $CH_3$ | H | $CH_3$ | $CHF_2$ | $CH_3$ |
| I | $CH_2$ | $CH_3$ | H | $CH_3$ | $CHF_2$ | $CH_3$ |
| J | $CH_2$ | $CH_3$ | H | $CH_3$ | $CHF_2$ | $CH_3$ |
| K | $CH_2$ | $CH_3$ | H | $CH_3$ | $CHF_2$ | $CH_3$ |
| L | $CH_2$ | $CH_3$ | H | $CH_3$ | $CHF_2$ | $CH_3$ |
| M | $CH_2$ | $CH_3$ | H | $CH_3$ | $CHF_2$ | $CH_3$ |
| N | $CH_2$ | $CH_3$ | H | $CH_3$ | $CHF_2$ | $CH_3$ |
| O | $CH_2$ | $CH_3$ | H | $CH_3$ | $CHF_2$ | $CH_3$ |
| P | $CH_2$ | $CH_3$ | H | $CH_3$ | $CHF_2$ | $CH_3$ |
| Q | $CH_2$ | $CH_3$ | H | $CH_3$ | $CHF_2$ | $CH_3$ |
| R | $CH_2$ | $CH_3$ | H | $CH_3$ | $CHF_2$ | $CH_3$ |
| S | $CH_2$ | $CH_3$ | H | $CH_3$ | $CHF_2$ | $CH_3$ |
| T | $CH_2$ | $CH_3$ | H | $CH_3$ | $CHF_2$ | $CH_3$ |
| U | $CH_2$ | $CH_3$ | H | $CH_3$ | $CHF_2$ | $CH_3$ |
| V | $CH_2$ | $CH_3$ | H | $CH_3$ | $CHF_2$ | $CH_3$ |
| W | $CH_2$ | $CH_3$ | H | $CH_3$ | $CHF_2$ | $CH_3$ |
| X | $CH_2$ | $CH_3$ | H | $CH_3$ | $CHF_2$ | $CH_3$ |
| Y | $CH_2$ | $CH_3$ | H | $CH_3$ | $CHF_2$ | $CH_3$ |
| A | O | $CH_3$ | H | $CH_3$ | $CHF_2$ | $CH_3$ |
| B | O | $CH_3$ | H | $CH_3$ | $CHF_2$ | $CH_3$ |
| C | O | $CH_3$ | H | $CH_3$ | $CHF_2$ | $CH_3$ |
| D | O | $CH_3$ | H | $CH_3$ | $CHF_2$ | $CH_3$ |
| E | O | $CH_3$ | H | $CH_3$ | $CHF_2$ | $CH_3$ |
| F | O | $CH_3$ | H | $CH_3$ | $CHF_2$ | $CH_3$ |
| G | C | $CH_3$ | H | $CH_3$ | $CHF_2$ | $CH_3$ |

TABLE C-continued

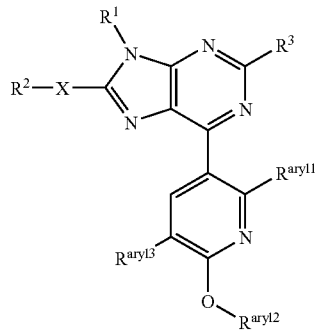

| $R^{1(a)}$ | X | $R^2$ | $R^3$ | $R^{aryl1}$ | $R^{aryl2}$ | $R^{aryl3}$ |
|---|---|---|---|---|---|---|
| H | O | $CH_3$ | H | $CH_3$ | $CHF_2$ | $CH_3$ |
| I | O | $CH_3$ | H | $CH_3$ | $CHF_2$ | $CH_3$ |
| J | O | $CH_3$ | H | $CH_3$ | $CHF_2$ | $CH_3$ |
| K | O | $CH_3$ | H | $CH_3$ | $CHF_2$ | $CH_3$ |
| L | O | $CH_3$ | H | $CH_3$ | $CHF_2$ | $CH_3$ |
| M | O | $CH_3$ | H | $CH_3$ | $CHF_2$ | $CH_3$ |
| N | O | $CH_3$ | H | $CH_3$ | $CHF_2$ | $CH_3$ |
| O | O | $CH_3$ | H | $CH_3$ | $CHF_2$ | $CH_3$ |
| P | O | $CH_3$ | H | $CH_3$ | $CHF_2$ | $CH_3$ |
| Q | O | $CH_3$ | H | $CH_3$ | $CHF_2$ | $CH_3$ |
| R | O | $CH_3$ | H | $CH_3$ | $CHF_2$ | $CH_3$ |
| S | O | $CH_3$ | H | $CH_3$ | $CHF_2$ | $CH_3$ |
| T | O | $CH_3$ | H | $CH_3$ | $CHF_2$ | $CH_3$ |
| U | O | $CH_3$ | H | $CH_3$ | $CHF_2$ | $CH_3$ |
| V | O | $CH_3$ | H | $CH_3$ | $CHF_2$ | $CH_3$ |
| W | O | $CH_3$ | H | $CH_3$ | $CHF_2$ | $CH_3$ |
| X | O | $CH_3$ | H | $CH_3$ | $CHF_2$ | $CH_3$ |
| Y | O | $CH_3$ | H | $CH_3$ | $CHF_2$ | $CH_3$ |
| A | O | $C_2H_5$ | H | $CH_3$ | $CHF_2$ | $CH_3$ |
| B | O | $C_2H_5$ | H | $CH_3$ | $CHF_2$ | $CH_3$ |
| C | O | $C_2H_5$ | H | $CH_3$ | $CHF_2$ | $CH_3$ |
| D | O | $C_2H_5$ | H | $CH_3$ | $CHF_2$ | $CH_3$ |
| E | O | $C_2H_5$ | H | $CH_3$ | $CHF_2$ | $CH_3$ |
| F | O | $C_2H_5$ | H | $CH_3$ | $CHF_2$ | $CH_3$ |
| G | O | $C_2H_5$ | H | $CH_3$ | $CHF_2$ | $CH_3$ |
| H | O | $C_2H_5$ | H | $CH_3$ | $CHF_2$ | $CH_3$ |
| I | O | $C_2H_5$ | H | $CH_3$ | $CHF_2$ | $CH_3$ |
| J | O | $C_2H_5$ | H | $CH_3$ | $CHF_2$ | $CH_3$ |
| K | O | $C_2H_5$ | H | $CH_3$ | $CHF_2$ | $CH_3$ |
| L | O | $C_2H_5$ | H | $CH_3$ | $CHF_2$ | $CH_3$ |
| M | O | $C_2H_5$ | H | $CH_3$ | $CHF_2$ | $CH_3$ |
| N | O | $C_2H_5$ | H | $CH_3$ | $CHF_2$ | $CH_3$ |
| O | O | $C_2H_5$ | H | $CH_3$ | $CHF_2$ | $CH_3$ |
| P | O | $C_2H_5$ | H | $CH_3$ | $CHF_2$ | $CH_3$ |
| Q | O | $C_2H_5$ | H | $CH_3$ | $CHF_2$ | $CH_3$ |
| R | O | $C_2H_5$ | H | $CH_3$ | $CHF_2$ | $CH_3$ |
| S | O | $C_2H_5$ | H | $CH_3$ | $CHF_2$ | $CH_3$ |
| T | O | $C_2H_5$ | H | $CH_3$ | $CHF_2$ | $CH_3$ |
| U | O | $C_2H_5$ | H | $CH_3$ | $CHF_2$ | $CH_3$ |
| V | O | $C_2H_5$ | H | $CH_3$ | $CHF_2$ | $CH_3$ |
| W | O | $C_2H_5$ | H | $CH_3$ | $CHF_2$ | $CH_3$ |
| X | O | $C_2H_5$ | H | $CH_3$ | $CHF_2$ | $CH_3$ |
| Y | O | $C_2H_5$ | H | $CH_3$ | $CHF_2$ | $CH_3$ |
| A | $CH_2$ | $CH_3$ | $CH_3$ | $CH_3$ | $CHF_2$ | $CH_3$ |
| B | $CH_2$ | $CH_3$ | $CH_3$ | $CH_3$ | $CHF_2$ | $CH_3$ |
| C | $CH_2$ | $CH_3$ | $CH_3$ | $CH_3$ | $CHF_2$ | $CH_3$ |
| D | $CH_2$ | $CH_3$ | $CH_3$ | $CH_3$ | $CHF_2$ | $CH_3$ |
| E | $CH_2$ | $CH_3$ | $CH_3$ | $CH_3$ | $CHF_2$ | $CH_3$ |
| F | $CH_2$ | $CH_3$ | $CH_3$ | $CH_3$ | $CHF_2$ | $CH_3$ |
| G | $CH_2$ | $CH_3$ | $CH_3$ | $CH_3$ | $CHF_2$ | $CH_3$ |
| H | $CH_2$ | $CH_3$ | $CH_3$ | $CH_3$ | $CHF_2$ | $CH_3$ |
| I | $CH_2$ | $CH_3$ | $CH_3$ | $CH_3$ | $CHF_2$ | $CH_3$ |
| J | $CH_2$ | $CH_3$ | $CH_3$ | $CH_3$ | $CHF_2$ | $CH_3$ |
| K | $CH_2$ | $CH_3$ | $CH_3$ | $CH_3$ | $CHF_2$ | $CH_3$ |
| L | $CH_2$ | $CH_3$ | $CH_3$ | $CH_3$ | $CHF_2$ | $CH_3$ |
| M | $CH_2$ | $CH_3$ | $CH_3$ | $CH_3$ | $CHF_2$ | $CH_3$ |
| N | $CH_2$ | $CH_3$ | $CH_3$ | $CH_3$ | $CHF_2$ | $CH_3$ |
| O | $CH_2$ | $CH_3$ | $CH_3$ | $CH_3$ | $CHF_2$ | $CH_3$ |
| P | $CH_2$ | $CH_3$ | $CH_3$ | $CH_3$ | $CHF_2$ | $CH_3$ |
| Q | $CH_2$ | $CH_3$ | $CH_3$ | $CH_3$ | $CHF_2$ | $CH_3$ |
| R | $CH_2$ | $CH_3$ | $CH_3$ | $CH_3$ | $CHF_2$ | $CH_3$ |
| S | $CH_2$ | $CH_3$ | $CH_3$ | $CH_3$ | $CHF_2$ | $CH_3$ |
| T | $CH_2$ | $CH_3$ | $CH_3$ | $CH_3$ | $CHF_2$ | $CH_3$ |
| U | $CH_2$ | $CH_3$ | $CH_3$ | $CH_3$ | $CHF_2$ | $CH_3$ |
| V | $CH_2$ | $CH_3$ | $CH_3$ | $CH_3$ | $CHF_2$ | $CH_3$ |
| W | $CH_2$ | $CH_3$ | $CH_3$ | $CH_3$ | $CHF_2$ | $CH_3$ |
| X | $CH_2$ | $CH_3$ | $CH_3$ | $CH_3$ | $CHF_2$ | $CH_3$ |
| Y | $CH_2$ | $CH_3$ | $CH_3$ | $CH_3$ | $CHF_2$ | $CH_3$ |

[a]See Table A, above.

Particular compounds provided herein further include those having the following structure, with the substituents thereof being set forth in Table D, below.

TABLE D

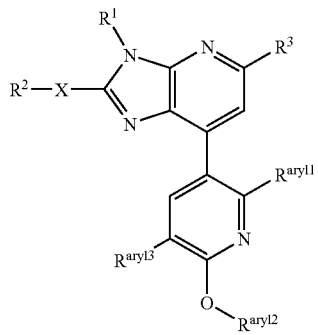

| $R^{1(a)}$ | X | $R^2$ | $R^3$ | $R^{aryl1}$ | $R^{aryl2}$ | $R^{aryl3}$ |
|---|---|---|---|---|---|---|
| A | $CH_2$ | $CH_3$ | H | Cl | $CF_3$ | H |
| B | $CH_2$ | $CH_3$ | H | Cl | $CF_3$ | H |
| C | $CH_2$ | $CH_3$ | H | Cl | $CF_3$ | H |
| D | $CH_2$ | $CH_3$ | H | Cl | $CF_3$ | H |
| E | $CH_2$ | $CH_3$ | H | Cl | $CF_3$ | H |
| F | $CH_2$ | $CH_3$ | H | Cl | $CF_3$ | H |
| G | $CH_2$ | $CH_3$ | H | Cl | $CF_3$ | H |
| H | $CH_2$ | $CH_3$ | H | Cl | $CF_3$ | H |
| I | $CH_2$ | $CH_3$ | H | Cl | $CF_3$ | H |
| J | $CH_2$ | $CH_3$ | H | Cl | $CF_3$ | H |
| K | $CH_2$ | $CH_3$ | H | Cl | $CF_3$ | H |
| L | $CH_2$ | $CH_3$ | H | Cl | $CF_3$ | H |
| M | $CH_2$ | $CH_3$ | H | Cl | $CF_3$ | H |
| N | $CH_2$ | $CH_3$ | H | Cl | $CF_3$ | H |
| O | $CH_2$ | $CH_3$ | H | Cl | $CF_3$ | H |
| P | $CH_2$ | $CH_3$ | H | Cl | $CF_3$ | H |
| Q | $CH_2$ | $CH_3$ | H | Cl | $CF_3$ | H |
| R | $CH_2$ | $CH_3$ | H | Cl | $CF_3$ | H |
| S | $CH_2$ | $CH_3$ | H | Cl | $CF_3$ | H |
| T | $CH_2$ | $CH_3$ | H | Cl | $CF_3$ | H |
| U | $CH_2$ | $CH_3$ | H | Cl | $CF_3$ | H |
| V | $CH_2$ | $CH_3$ | H | Cl | $CF_3$ | H |
| W | $CH_2$ | $CH_3$ | H | Cl | $CF_3$ | H |

TABLE D-continued

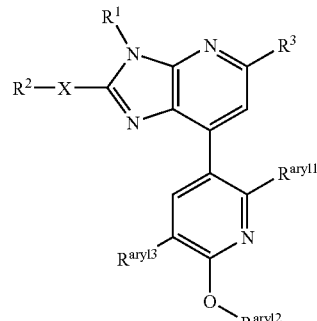

| R[1(a)] | X | R[2] | R[3] | R[aryl1] | R[aryl2] | R[aryl3] |
|---|---|---|---|---|---|---|
| X | CH$_2$ | CH$_3$ | H | Cl | CF$_3$ | H |
| Y | CH$_2$ | CH$_3$ | H | Cl | CF$_3$ | H |
| A | O | CH$_3$ | H | Cl | CF$_3$ | H |
| B | O | CH$_3$ | H | Cl | CF$_3$ | H |
| C | O | CH$_3$ | H | Cl | CF$_3$ | H |
| D | O | CH$_3$ | H | Cl | CF$_3$ | H |
| E | O | CH$_3$ | H | Cl | CF$_3$ | H |
| F | O | CH$_3$ | H | Cl | CF$_3$ | H |
| G | O | CH$_3$ | H | Cl | CF$_3$ | H |
| H | O | CH$_3$ | H | Cl | CF$_3$ | H |
| I | O | CH$_3$ | H | Cl | CF$_3$ | H |
| J | O | CH$_3$ | H | Cl | CF$_3$ | H |
| K | O | CH$_3$ | H | Cl | CF$_3$ | H |
| L | O | CH$_3$ | H | Cl | CF$_3$ | H |
| M | O | CH$_3$ | H | Cl | CF$_3$ | H |
| N | O | CH$_3$ | H | Cl | CF$_3$ | H |
| O | O | CH$_3$ | H | Cl | CF$_3$ | H |
| P | O | CH$_3$ | H | Cl | CF$_3$ | H |
| Q | O | CH$_3$ | H | Cl | CF$_3$ | H |
| R | O | CH$_3$ | H | Cl | CF$_3$ | H |
| S | O | CH$_3$ | H | Cl | CF$_3$ | H |
| T | O | CH$_3$ | H | Cl | CF$_3$ | H |
| U | O | CH$_3$ | H | Cl | CF$_3$ | H |
| V | O | CH$_3$ | H | Cl | CF$_3$ | H |
| W | O | CH$_3$ | H | Cl | CF$_3$ | H |
| X | O | CH$_3$ | H | Cl | CF$_3$ | H |
| Y | O | CH$_3$ | H | Cl | CF$_3$ | H |
| A | O | C$_2$H$_5$ | H | Cl | CF$_3$ | H |
| B | O | C$_2$H$_5$ | H | Cl | CF$_3$ | H |
| C | O | C$_2$H$_5$ | H | Cl | CF$_3$ | H |
| D | O | C$_2$H$_5$ | H | Cl | CF$_3$ | H |
| E | O | C$_2$H$_5$ | H | Cl | CF$_3$ | H |
| F | O | C$_2$H$_5$ | H | Cl | CF$_3$ | H |
| G | O | C$_2$H$_5$ | H | Cl | CF$_3$ | H |
| H | O | C$_2$H$_5$ | H | Cl | CF$_3$ | H |
| I | O | C$_2$H$_5$ | H | Cl | CF$_3$ | H |
| J | O | C$_2$H$_5$ | H | Cl | CF$_3$ | H |
| K | O | C$_2$H$_5$ | H | Cl | CF$_3$ | H |
| L | O | C$_2$H$_5$ | H | Cl | CF$_3$ | H |
| M | O | C$_2$H$_5$ | H | Cl | CF$_3$ | H |
| N | O | C$_2$H$_5$ | H | Cl | CF$_3$ | H |
| O | O | C$_2$H$_5$ | H | Cl | CF$_3$ | H |
| P | O | C$_2$H$_5$ | H | Cl | CF$_3$ | H |
| Q | O | C$_2$H$_5$ | H | Cl | CF$_3$ | H |
| R | O | C$_2$H$_5$ | H | Cl | CF$_3$ | H |
| S | O | C$_2$H$_5$ | H | Cl | CF$_3$ | H |
| T | O | C$_2$H$_5$ | H | Cl | CF$_3$ | H |
| U | O | C$_2$H$_5$ | H | Cl | CF$_3$ | H |
| V | O | C$_2$H$_5$ | H | Cl | CF$_3$ | H |
| W | O | C$_2$H$_5$ | H | Cl | CF$_3$ | H |
| X | O | C$_2$H$_5$ | H | Cl | CF$_3$ | H |
| Y | O | C$_2$H$_5$ | H | Cl | CF$_3$ | H |
| A | CH$_2$ | CH$_3$ | CH$_3$ | Cl | CF$_3$ | H |
| B | CH$_2$ | CH$_3$ | CH$_3$ | Cl | CF$_3$ | H |
| C | CH$_2$ | CH$_3$ | CH$_3$ | Cl | CF$_3$ | H |
| D | CH$_2$ | CH$_3$ | CH$_3$ | Cl | CF$_3$ | H |
| E | CH$_2$ | CH$_3$ | CH$_3$ | Cl | CF$_3$ | H |
| F | CH$_2$ | CH$_3$ | CH$_3$ | Cl | CF$_3$ | H |
| G | CH$_2$ | CH$_3$ | CH$_3$ | Cl | CF$_3$ | H |
| H | CH$_2$ | CH$_3$ | CH$_3$ | Cl | CF$_3$ | H |

TABLE D-continued

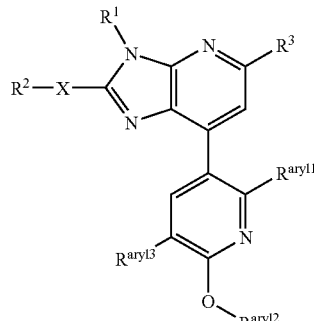

| R[1(a)] | X | R[2] | R[3] | R[aryl1] | R[aryl2] | R[aryl3] |
|---|---|---|---|---|---|---|
| I | CH$_2$ | CH$_3$ | CH$_3$ | Cl | CF$_3$ | H |
| J | CH$_2$ | CH$_3$ | CH$_3$ | Cl | CF$_3$ | H |
| K | CH$_2$ | CH$_3$ | CH$_3$ | Cl | CF$_3$ | H |
| L | CH$_2$ | CH$_3$ | CH$_3$ | Cl | CF$_3$ | H |
| M | CH$_2$ | CH$_3$ | CH$_3$ | Cl | CF$_3$ | H |
| N | CH$_2$ | CH$_3$ | CH$_3$ | Cl | CF$_3$ | H |
| O | CH$_2$ | CH$_3$ | CH$_3$ | Cl | CF$_3$ | H |
| P | CH$_2$ | CH$_3$ | CH$_3$ | Cl | CF$_3$ | H |
| Q | CH$_2$ | CH$_3$ | CH$_3$ | Cl | CF$_3$ | H |
| R | CH$_2$ | CH$_3$ | CH$_3$ | Cl | CF$_3$ | H |
| S | CH$_2$ | CH$_3$ | CH$_3$ | Cl | CF$_3$ | H |
| T | CH$_2$ | CH$_3$ | CH$_3$ | Cl | CF$_3$ | H |
| U | CH$_2$ | CH$_3$ | CH$_3$ | Cl | CF$_3$ | H |
| V | CH$_2$ | CH$_3$ | CH$_3$ | Cl | CF$_3$ | H |
| W | CH$_2$ | CH$_3$ | CH$_3$ | Cl | CF$_3$ | H |
| X | CH$_2$ | CH$_3$ | CH$_3$ | Cl | CF$_3$ | H |
| Y | CH$_2$ | CH$_3$ | CH$_3$ | Cl | CF$_3$ | H |
| A | CH$_2$ | CH$_3$ | H | CH$_3$ | CF$_3$ | H |
| B | CH$_2$ | CH$_3$ | H | CH$_3$ | CF$_3$ | H |
| C | CH$_2$ | CH$_3$ | H | CH$_3$ | CF$_3$ | H |
| D | CH$_2$ | CH$_3$ | H | CH$_3$ | CF$_3$ | H |
| E | CH$_2$ | CH$_3$ | H | CH$_3$ | CF$_3$ | H |
| F | CH$_2$ | CH$_3$ | H | CH$_3$ | CF$_3$ | H |
| G | CH$_2$ | CH$_3$ | H | CH$_3$ | CF$_3$ | H |
| H | CH$_2$ | CH$_3$ | H | CH$_3$ | CF$_3$ | H |
| I | CH$_2$ | CH$_3$ | H | CH$_3$ | CF$_3$ | H |
| J | CH$_2$ | CH$_3$ | H | CH$_3$ | CF$_3$ | H |
| K | CH$_2$ | CH$_3$ | H | CH$_3$ | CF$_3$ | H |
| L | CH$_2$ | CH$_3$ | H | CH$_3$ | CF$_3$ | H |
| M | CH$_2$ | CH$_3$ | H | CH$_3$ | CF$_3$ | H |
| N | CH$_2$ | CH$_3$ | H | CH$_3$ | CF$_3$ | H |
| O | CH$_2$ | CH$_3$ | H | CH$_3$ | CF$_3$ | H |
| P | CH$_2$ | CH$_3$ | H | CH$_3$ | CF$_3$ | H |
| Q | CH$_2$ | CH$_3$ | H | CH$_3$ | CF$_3$ | H |
| R | CH$_2$ | CH$_3$ | H | CH$_3$ | CF$_3$ | H |
| S | CH$_2$ | CH$_3$ | H | CH$_3$ | CF$_3$ | H |
| T | CH$_2$ | CH$_3$ | H | CH$_3$ | CF$_3$ | H |
| U | CH$_2$ | CH$_3$ | H | CH$_3$ | CF$_3$ | H |
| V | CH$_2$ | CH$_3$ | H | CH$_3$ | CF$_3$ | H |
| W | CH$_2$ | CH$_3$ | H | CH$_3$ | CF$_3$ | H |
| X | CH$_2$ | CH$_3$ | H | CH$_3$ | CF$_3$ | H |
| Y | CH$_2$ | CH$_3$ | H | CH$_3$ | CF$_3$ | H |
| A | O | CH$_3$ | H | CH$_3$ | CF$_3$ | H |
| B | O | CH$_3$ | H | CH$_3$ | CF$_3$ | H |
| C | O | CH$_3$ | H | CH$_3$ | CF$_3$ | H |
| D | O | CH$_3$ | H | CH$_3$ | CF$_3$ | H |
| E | O | CH$_3$ | H | CH$_3$ | CF$_3$ | H |
| F | O | CH$_3$ | H | CH$_3$ | CF$_3$ | H |
| G | O | CH$_3$ | H | CH$_3$ | CF$_3$ | H |
| H | O | CH$_3$ | H | CH$_3$ | CF$_3$ | H |
| I | O | CH$_3$ | H | CH$_3$ | CF$_3$ | H |
| J | O | CH$_3$ | H | CH$_3$ | CF$_3$ | H |
| K | O | CH$_3$ | H | CH$_3$ | CF$_3$ | H |
| L | O | CH$_3$ | H | CH$_3$ | CF$_3$ | H |
| M | O | CH$_3$ | H | CH$_3$ | CF$_3$ | H |
| N | O | CH$_3$ | H | CH$_3$ | CF$_3$ | H |
| O | O | CH$_3$ | H | CH$_3$ | CF$_3$ | H |
| P | O | CH$_3$ | H | CH$_3$ | CF$_3$ | H |
| Q | O | CH$_3$ | H | CH$_3$ | CF$_3$ | H |
| R | O | CH$_3$ | H | CH$_3$ | CF$_3$ | H |

TABLE D-continued

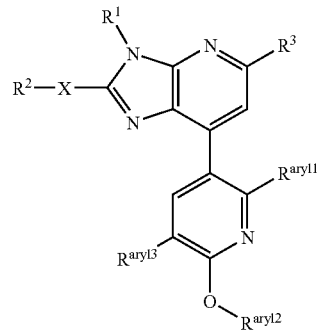

| R[1(a)] | X | R[2] | R[3] | R[aryl1] | R[aryl2] | R[aryl3] |
|---|---|---|---|---|---|---|
| S | O | $CH_3$ | H | $CH_3$ | $CF_3$ | H |
| T | O | $CH_3$ | H | $CH_3$ | $CF_3$ | H |
| U | O | $CH_3$ | H | $CH_3$ | $CF_3$ | H |
| V | O | $CH_3$ | H | $CH_3$ | $CF_3$ | H |
| W | O | $CH_3$ | H | $CH_3$ | $CF_3$ | H |
| X | O | $CH_3$ | H | $CH_3$ | $CF_3$ | H |
| Y | O | $CH_3$ | H | $CH_3$ | $CF_3$ | H |
| A | O | $C_2H_5$ | H | $CH_3$ | $CF_3$ | H |
| B | O | $C_2H_5$ | H | $CH_3$ | $CF_3$ | H |
| C | O | $C_2H_5$ | H | $CH_3$ | $CF_3$ | H |
| D | O | $C_2H_5$ | H | $CH_3$ | $CF_3$ | H |
| E | O | $C_2H_5$ | H | $CH_3$ | $CF_3$ | H |
| F | O | $C_2H_5$ | H | $CH_3$ | $CF_3$ | H |
| G | O | $C_2H_5$ | H | $CH_3$ | $CF_3$ | H |
| H | O | $C_2H_5$ | H | $CH_3$ | $CF_3$ | H |
| I | O | $C_2H_5$ | H | $CH_3$ | $CF_3$ | H |
| J | O | $C_2H_5$ | H | $CH_3$ | $CF_3$ | H |
| K | O | $C_2H_5$ | H | $CH_3$ | $CF_3$ | H |
| L | O | $C_2H_5$ | H | $CH_3$ | $CF_3$ | H |
| M | O | $C_2H_5$ | H | $CH_3$ | $CF_3$ | H |
| N | O | $C_2H_5$ | H | $CH_3$ | $CF_3$ | H |
| O | O | $C_2H_5$ | H | $CH_3$ | $CF_3$ | H |
| P | O | $C_2H_5$ | H | $CH_3$ | $CF_3$ | H |
| Q | O | $C_2H_5$ | H | $CH_3$ | $CF_3$ | H |
| R | O | $C_2H_5$ | H | $CH_3$ | $CF_3$ | H |
| S | O | $C_2H_5$ | H | $CH_3$ | $CF_3$ | H |
| T | O | $C_2H_5$ | H | $CH_3$ | $CF_3$ | H |
| U | O | $C_2H_5$ | H | $CH_3$ | $CF_3$ | H |
| V | O | $C_2H_5$ | H | $CH_3$ | $CF_3$ | H |
| W | O | $C_2H_5$ | H | $CH_3$ | $CF_3$ | H |
| X | O | $C_2H_5$ | H | $CH_3$ | $CF_3$ | H |
| Y | O | $C_2H_5$ | H | $CH_3$ | $CF_3$ | H |
| A | $CH_2$ | $CH_3$ | $CH_3$ | $CH_3$ | $CF_3$ | H |
| B | $CH_2$ | $CH_3$ | $CH_3$ | $CH_3$ | $CF_3$ | H |
| C | $CH_2$ | $CH_3$ | $CH_3$ | $CH_3$ | $CF_3$ | H |
| D | $CH_2$ | $CH_3$ | $CH_3$ | $CH_3$ | $CF_3$ | H |
| E | $CH_2$ | $CH_3$ | $CH_3$ | $CH_3$ | $CF_3$ | H |
| F | $CH_2$ | $CH_3$ | $CH_3$ | $CH_3$ | $CF_3$ | H |
| G | $CH_2$ | $CH_3$ | $CH_3$ | $CH_3$ | $CF_3$ | H |
| H | $CH_2$ | $CH_3$ | $CH_3$ | $CH_3$ | $CF_3$ | H |
| I | $CH_2$ | $CH_3$ | $CH_3$ | $CH_3$ | $CF_3$ | H |
| J | $CH_2$ | $CH_3$ | $CH_3$ | $CH_3$ | $CF_3$ | H |
| K | $CH_2$ | $CH_3$ | $CH_3$ | $CH_3$ | $CF_3$ | H |
| L | $CH_2$ | $CH_3$ | $CH_3$ | $CH_3$ | $CF_3$ | H |
| M | $CH_2$ | $CH_3$ | $CH_3$ | $CH_3$ | $CF_3$ | H |
| N | $CH_2$ | $CH_3$ | $CH_3$ | $CH_3$ | $CF_3$ | H |
| O | $CH_2$ | $CH_3$ | $CH_3$ | $CH_3$ | $CF_3$ | H |
| P | $CH_2$ | $CH_3$ | $CH_3$ | $CH_3$ | $CF_3$ | H |
| Q | $CH_2$ | $CH_3$ | $CH_3$ | $CH_3$ | $CF_3$ | H |
| R | $CH_2$ | $CH_3$ | $CH_3$ | $CH_3$ | $CF_3$ | H |
| S | $CH_2$ | $CH_3$ | $CH_3$ | $CH_3$ | $CF_3$ | H |
| T | $CH_2$ | $CH_3$ | $CH_3$ | $CH_3$ | $CF_3$ | H |
| U | $CH_2$ | $CH_3$ | $CH_3$ | $CH_3$ | $CF_3$ | H |
| V | $CH_2$ | $CH_3$ | $CH_3$ | $CH_3$ | $CF_3$ | H |
| W | $CH_2$ | $CH_3$ | $CH_3$ | $CH_3$ | $CF_3$ | H |
| X | $CH_2$ | $CH_3$ | $CH_3$ | $CH_3$ | $CF_3$ | H |
| Y | $CH_2$ | $CH_3$ | $CH_3$ | $CH_3$ | $CF_3$ | H |
| A | $CH_2$ | $CH_3$ | H | Cl | $CHF_2$ | H |
| B | $CH_2$ | $CH_3$ | H | Cl | $CHF_2$ | H |
| C | $CH_2$ | $CH_3$ | H | Cl | $CHF_2$ | H |
| D | $CH_2$ | $CH_3$ | H | Cl | $CHF_2$ | H |
| E | $CH_2$ | $CH_3$ | H | Cl | $CHF_2$ | H |
| F | $CH_2$ | $CH_3$ | H | Cl | $CHF_2$ | H |
| G | $CH_2$ | $CH_3$ | H | Cl | $CHF_2$ | H |
| H | $CH_2$ | $CH_3$ | H | Cl | $CHF_2$ | H |
| I | $CH_2$ | $CH_3$ | H | Cl | $CHF_2$ | H |
| J | $CH_2$ | $CH_3$ | H | Cl | $CHF_2$ | H |
| K | $CH_2$ | $CH_3$ | H | Cl | $CHF_2$ | H |
| L | $CH_2$ | $CH_3$ | H | Cl | $CHF_2$ | H |
| M | $CH_2$ | $CH_3$ | H | Cl | $CHF_2$ | H |
| N | $CH_2$ | $CH_3$ | H | Cl | $CHF_2$ | H |
| O | $CH_2$ | $CH_3$ | H | Cl | $CHF_2$ | H |
| P | $CH_2$ | $CH_3$ | H | Cl | $CHF_2$ | H |
| Q | $CH_2$ | $CH_3$ | H | Cl | $CHF_2$ | H |
| R | $CH_2$ | $CH_3$ | H | Cl | $CHF_2$ | H |
| S | $CH_2$ | $CH_3$ | H | Cl | $CHF_2$ | H |
| T | $CH_2$ | $CH_3$ | H | Cl | $CHF_2$ | H |
| U | $CH_2$ | $CH_3$ | H | Cl | $CHF_2$ | H |
| V | $CH_2$ | $CH_3$ | H | Cl | $CHF_2$ | H |
| W | $CH_2$ | $CH_3$ | H | Cl | $CHF_2$ | H |
| X | $CH_2$ | $CH_3$ | H | Cl | $CHF_2$ | H |
| Y | $CH_2$ | $CH_3$ | H | Cl | $CHF_2$ | H |
| A | O | $CH_3$ | H | Cl | $CHF_2$ | H |
| B | O | $CH_3$ | H | Cl | $CHF_2$ | H |
| C | O | $CH_3$ | H | Cl | $CHF_2$ | H |
| D | O | $CH_3$ | H | Cl | $CHF_2$ | H |
| E | O | $CH_3$ | H | Cl | $CHF_2$ | H |
| F | O | $CH_3$ | H | Cl | $CHF_2$ | H |
| G | O | $CH_3$ | H | Cl | $CHF_2$ | H |
| H | O | $CH_3$ | H | Cl | $CHF_2$ | H |
| I | O | $CH_3$ | H | Cl | $CHF_2$ | H |
| J | O | $CH_3$ | H | Cl | $CHF_2$ | H |
| K | O | $CH_3$ | H | Cl | $CHF_2$ | H |
| L | O | $CH_3$ | H | Cl | $CHF_2$ | H |
| M | O | $CH_3$ | H | Cl | $CHF_2$ | H |
| N | O | $CH_3$ | H | Cl | $CHF_2$ | H |
| O | O | $CH_3$ | H | Cl | $CHF_2$ | H |
| P | O | $CH_3$ | H | Cl | $CHF_2$ | H |
| Q | O | $CH_3$ | H | Cl | $CHF_2$ | H |
| R | O | $CH_3$ | H | Cl | $CHF_2$ | H |
| S | O | $CH_3$ | H | Cl | $CHF_2$ | H |
| T | O | $CH_3$ | H | Cl | $CHF_2$ | H |
| U | O | $CH_3$ | H | Cl | $CHF_2$ | H |
| V | O | $CH_3$ | H | Cl | $CHF_2$ | H |
| W | O | $CH_3$ | H | Cl | $CHF_2$ | H |
| X | O | $CH_3$ | H | Cl | $CHF_2$ | H |
| Y | O | $CH_3$ | H | Cl | $CHF_2$ | H |
| A | O | $C_2H_5$ | H | Cl | $CHF_2$ | H |
| B | O | $C_2H_5$ | H | Cl | $CHF_2$ | H |
| C | O | $C_2H_5$ | H | Cl | $CHF_2$ | H |
| D | O | $C_2H_5$ | H | Cl | $CHF_2$ | H |
| E | O | $C_2H_5$ | H | Cl | $CHF_2$ | H |
| F | O | $C_2H_5$ | H | Cl | $CHF_2$ | H |
| G | O | $C_2H_5$ | H | Cl | $CHF_2$ | H |
| H | O | $C_2H_5$ | H | Cl | $CHF_2$ | H |
| I | O | $C_2H_5$ | H | Cl | $CHF_2$ | H |
| J | O | $C_2H_5$ | H | Cl | $CHF_2$ | H |
| K | O | $C_2H_5$ | H | Cl | $CHF_2$ | H |
| L | O | $C_2H_5$ | H | Cl | $CHF_2$ | H |
| M | O | $C_2H_5$ | H | Cl | $CHF_2$ | H |

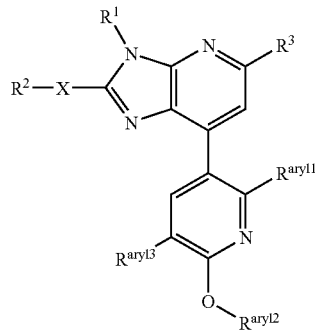

TABLE D-continued

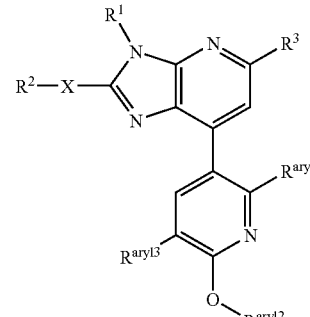

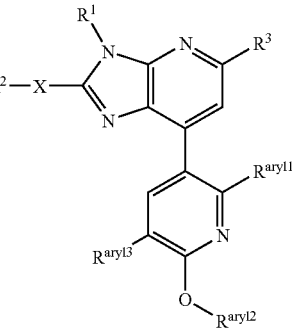

| R[1(a)] | X | R[2] | R[3] | R[aryl1] | R[aryl2] | R[aryl3] |
|---|---|---|---|---|---|---|
| N | O | $C_2H_5$ | H | Cl | $CHF_2$ | H |
| O | O | $C_2H_5$ | H | Cl | $CHF_2$ | H |
| P | O | $C_2H_5$ | H | Cl | $CHF_2$ | H |
| Q | O | $C_2H_5$ | H | Cl | $CHF_2$ | H |
| R | O | $C_2H_5$ | H | Cl | $CHF_2$ | H |
| S | O | $C_2H_5$ | H | Cl | $CHF_2$ | H |
| T | O | $C_2H_5$ | H | Cl | $CHF_2$ | H |
| U | O | $C_2H_5$ | H | Cl | $CHF_2$ | H |
| V | O | $C_2H_5$ | H | Cl | $CHF_2$ | H |
| W | O | $C_2H_5$ | H | Cl | $CHF_2$ | H |
| X | O | $C_2H_5$ | H | Cl | $CHF_2$ | H |
| Y | O | $C_2H_5$ | H | Cl | $CHF_2$ | H |
| A | $CH_2$ | $CH_3$ | $CH_3$ | Cl | $CHF_2$ | H |
| B | $CH_2$ | $CH_3$ | $CH_3$ | Cl | $CHF_2$ | H |
| C | $CH_2$ | $CH_3$ | $CH_3$ | Cl | $CHF_2$ | H |
| D | $CH_2$ | $CH_3$ | $CH_3$ | Cl | $CHF_2$ | H |
| E | $CH_2$ | $CH_3$ | $CH_3$ | Cl | $CHF_2$ | H |
| F | $CH_2$ | $CH_3$ | $CH_3$ | Cl | $CHF_2$ | H |
| G | $CH_2$ | $CH_3$ | $CH_3$ | Cl | $CHF_2$ | H |
| H | $CH_2$ | $CH_3$ | $CH_3$ | Cl | $CHF_2$ | H |
| I | $CH_2$ | $CH_3$ | $CH_3$ | Cl | $CHF_2$ | H |
| J | $CH_2$ | $CH_3$ | $CH_3$ | Cl | $CHF_2$ | H |
| K | $CH_2$ | $CH_3$ | $CH_3$ | Cl | $CHF_2$ | H |
| L | $CH_2$ | $CH_3$ | $CH_3$ | Cl | $CHF_2$ | H |
| M | $CH_2$ | $CH_3$ | $CH_3$ | Cl | $CHF_2$ | H |
| N | $CH_2$ | $CH_3$ | $CH_3$ | Cl | $CHF_2$ | H |
| O | $CH_2$ | $CH_3$ | $CH_3$ | Cl | $CHF_2$ | H |
| P | $CH_2$ | $CH_3$ | $CH_3$ | Cl | $CHF_2$ | H |
| Q | $CH_2$ | $CH_3$ | $CH_3$ | Cl | $CHF_2$ | H |
| R | $CH_2$ | $CH_3$ | $CH_3$ | Cl | $CHF_2$ | H |
| S | $CH_2$ | $CH_3$ | $CH_3$ | Cl | $CHF_2$ | H |
| T | $CH_2$ | $CH_3$ | $CH_3$ | Cl | $CHF_2$ | H |
| U | $CH_2$ | $CH_3$ | $CH_3$ | Cl | $CHF_2$ | H |
| V | $CH_2$ | $CH_3$ | $CH_3$ | Cl | $CHF_2$ | H |
| W | $CH_2$ | $CH_3$ | $CH_3$ | Cl | $CHF_2$ | H |
| X | $CH_2$ | $CH_3$ | $CH_3$ | Cl | $CHF_2$ | H |
| Y | $CH_2$ | $CH_3$ | $CH_3$ | Cl | $CHF_2$ | H |
| A | $CH_2$ | $CH_3$ | H | $CH_3$ | $CHF_2$ | H |
| B | $CH_2$ | $CH_3$ | H | $CH_3$ | $CHF_2$ | H |
| C | $CH_2$ | $CH_3$ | H | $CH_3$ | $CHF_2$ | H |
| D | $CH_2$ | $CH_3$ | H | $CH_3$ | $CHF_2$ | H |
| E | $CH_2$ | $CH_3$ | H | $CH_3$ | $CHF_2$ | H |
| F | $CH_2$ | $CH_3$ | H | $CH_3$ | $CHF_2$ | H |
| G | $CH_2$ | $CH_3$ | H | $CH_3$ | $CHF_2$ | H |
| H | $CH_2$ | $CH_3$ | H | $CH_3$ | $CHF_2$ | H |
| I | $CH_2$ | $CH_3$ | H | $CH_3$ | $CHF_2$ | H |
| J | $CH_2$ | $CH_3$ | H | $CH_3$ | $CHF_2$ | H |
| K | $CH_2$ | $CH_3$ | H | $CH_3$ | $CHF_2$ | H |
| L | $CH_2$ | $CH_3$ | H | $CH_3$ | $CHF_2$ | H |
| M | $CH_2$ | $CH_3$ | H | $CH_3$ | $CHF_2$ | H |
| N | $CH_2$ | $CH_3$ | H | $CH_3$ | $CHF_2$ | H |
| O | $CH_2$ | $CH_3$ | H | $CH_3$ | $CHF_2$ | H |
| P | $CH_2$ | $CH_3$ | H | $CH_3$ | $CHF_2$ | H |
| Q | $CH_2$ | $CH_3$ | H | $CH_3$ | $CHF_2$ | H |
| R | $CH_2$ | $CH_3$ | H | $CH_3$ | $CHF_2$ | H |
| S | $CH_2$ | $CH_3$ | H | $CH_3$ | $CHF_2$ | H |
| T | $CH_2$ | $CH_3$ | H | $CH_3$ | $CHF_2$ | H |
| U | $CH_2$ | $CH_3$ | H | $CH_3$ | $CHF_2$ | H |
| V | $CH_2$ | $CH_3$ | H | $CH_3$ | $CHF_2$ | H |
| W | $CH_2$ | $CH_3$ | H | $CH_3$ | $CHF_2$ | H |
| X | $CH_2$ | $CH_3$ | H | $CH_3$ | $CHF_2$ | H |
| Y | $CH_2$ | $CH_3$ | H | $CH_3$ | $CHF_2$ | H |
| A | O | $CH_3$ | H | $CH_3$ | $CHF_2$ | H |
| B | O | $CH_3$ | H | $CH_3$ | $CHF_2$ | H |
| C | O | $CH_3$ | H | $CH_3$ | $CHF_2$ | H |
| D | O | $CH_3$ | H | $CH_3$ | $CHF_2$ | H |
| E | O | $CH_3$ | H | $CH_3$ | $CHF_2$ | H |
| F | O | $CH_3$ | H | $CH_3$ | $CHF_2$ | H |
| G | O | $CH_3$ | H | $CH_3$ | $CHF_2$ | H |
| H | O | $CH_3$ | H | $CH_3$ | $CHF_2$ | H |
| I | O | $CH_3$ | H | $CH_3$ | $CHF_2$ | H |
| J | O | $CH_3$ | H | $CH_3$ | $CHF_2$ | H |
| K | O | $CH_3$ | H | $CH_3$ | $CHF_2$ | H |
| L | O | $CH_3$ | H | $CH_3$ | $CHF_2$ | H |
| M | O | $CH_3$ | H | $CH_3$ | $CHF_2$ | H |
| N | O | $CH_3$ | H | $CH_3$ | $CHF_2$ | H |
| O | O | $CH_3$ | H | $CH_3$ | $CHF_2$ | H |
| P | O | $CH_3$ | H | $CH_3$ | $CHF_2$ | H |
| Q | O | $CH_3$ | H | $CH_3$ | $CHF_2$ | H |
| R | O | $CH_3$ | H | $CH_3$ | $CHF_2$ | H |
| S | O | $CH_3$ | H | $CH_3$ | $CHF_2$ | H |
| T | O | $CH_3$ | H | $CH_3$ | $CHF_2$ | H |
| U | O | $CH_3$ | H | $CH_3$ | $CHF_2$ | H |
| V | O | $CH_3$ | H | $CH_3$ | $CHF_2$ | H |
| W | O | $CH_3$ | H | $CH_3$ | $CHF_2$ | H |
| X | O | $CH_3$ | H | $CH_3$ | $CHF_2$ | H |
| Y | O | $CH_3$ | H | $CH_3$ | $CHF_2$ | H |
| A | O | $C_2H_5$ | H | $CH_3$ | $CHF_2$ | H |
| B | O | $C_2H_5$ | H | $CH_3$ | $CHF_2$ | H |
| C | O | $C_2H_5$ | H | $CH_3$ | $CHF_2$ | H |
| D | O | $C_2H_5$ | H | $CH_3$ | $CHF_2$ | H |
| E | O | $C_2H_5$ | H | $CH_3$ | $CHF_2$ | H |
| F | O | $C_2H_5$ | H | $CH_3$ | $CHF_2$ | H |
| G | O | $C_2H_5$ | H | $CH_3$ | $CHF_2$ | H |
| H | O | $C_2H_5$ | H | $CH_3$ | $CHF_2$ | H |
| I | O | $C_2H_5$ | H | $CH_3$ | $CHF_2$ | H |
| J | O | $C_2H_5$ | H | $CH_3$ | $CHF_2$ | H |
| K | O | $C_2H_5$ | H | $CH_3$ | $CHF_2$ | H |
| L | O | $C_2H_5$ | H | $CH_3$ | $CHF_2$ | H |
| M | O | $C_2H_5$ | H | $CH_3$ | $CHF_2$ | H |
| N | O | $C_2H_5$ | H | $CH_3$ | $CHF_2$ | H |
| O | O | $C_2H_5$ | H | $CH_3$ | $CHF_2$ | H |
| P | O | $C_2H_5$ | H | $CH_3$ | $CHF_2$ | H |
| Q | O | $C_2H_5$ | H | $CH_3$ | $CHF_2$ | H |
| R | O | $C_2H_5$ | H | $CH_3$ | $CHF_2$ | H |
| S | O | $C_2H_5$ | H | $CH_3$ | $CHF_2$ | H |
| T | O | $C_2H_5$ | H | $CH_3$ | $CHF_2$ | H |
| U | O | $C_2H_5$ | H | $CH_3$ | $CHF_2$ | H |
| V | O | $C_2H_5$ | H | $CH_3$ | $CHF_2$ | H |
| W | O | $C_2H_5$ | H | $CH_3$ | $CHF_2$ | H |
| X | O | $C_2H_5$ | H | $CH_3$ | $CHF_2$ | H |
| Y | O | $C_2H_5$ | H | $CH_3$ | $CHF_2$ | H |
| A | $CH_2$ | $CH_3$ | $CH_3$ | $CH_3$ | $CHF_2$ | H |
| B | $CH_2$ | $CH_3$ | $CH_3$ | $CH_3$ | $CHF_2$ | H |
| C | $CH_2$ | $CH_3$ | $CH_3$ | $CH_3$ | $CHF_2$ | H |
| D | $CH_2$ | $CH_3$ | $CH_3$ | $CH_3$ | $CHF_2$ | H |
| E | $CH_2$ | $CH_3$ | $CH_3$ | $CH_3$ | $CHF_2$ | H |
| F | $CH_2$ | $CH_3$ | $CH_3$ | $CH_3$ | $CHF_2$ | H |
| G | $CH_2$ | $CH_3$ | $CH_3$ | $CH_3$ | $CHF_2$ | H |
| H | $CH_2$ | $CH_3$ | $CH_3$ | $CH_3$ | $CHF_2$ | H |

TABLE D-continued

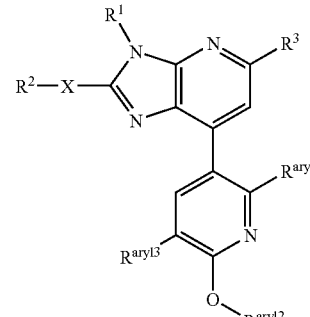

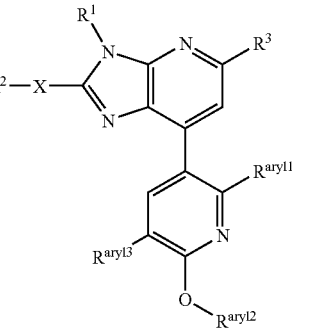

| $R^{1(a)}$ | X | $R^2$ | $R^3$ | $R^{aryl1}$ | $R^{aryl2}$ | $R^{aryl3}$ | $R^{1(a)}$ | X | $R^2$ | $R^3$ | $R^{aryl1}$ | $R^{aryl2}$ | $R^{aryl3}$ |
|---|---|---|---|---|---|---|---|---|---|---|---|---|---|
| I | $CH_2$ | $CH_3$ | $CH_3$ | $CH_3$ | $CHF_2$ | H | S | O | $CH_3$ | H | Cl | $CF_3$ | $CH_3$ |
| J | $CH_2$ | $CH_3$ | $CH_3$ | $CH_3$ | $CHF_2$ | H | T | O | $CH_3$ | H | Cl | $CF_3$ | $CH_3$ |
| K | $CH_2$ | $CH_3$ | $CH_3$ | $CH_3$ | $CHF_2$ | H | U | O | $CH_3$ | H | Cl | $CF_3$ | $CH_3$ |
| L | $CH_2$ | $CH_3$ | $CH_3$ | $CH_3$ | $CHF_2$ | H | V | O | $CH_3$ | H | Cl | $CF_3$ | $CH_3$ |
| M | $CH_2$ | $CH_3$ | $CH_3$ | $CH_3$ | $CHF_2$ | H | W | O | $CH_3$ | H | Cl | $CF_3$ | $CH_3$ |
| N | $CH_2$ | $CH_3$ | $CH_3$ | $CH_3$ | $CHF_2$ | H | X | O | $CH_3$ | H | Cl | $CF_3$ | $CH_3$ |
| O | $CH_2$ | $CH_3$ | $CH_3$ | $CH_3$ | $CHF_2$ | H | Y | O | $CH_3$ | H | Cl | $CF_3$ | $CH_3$ |
| P | $CH_2$ | $CH_3$ | $CH_3$ | $CH_3$ | $CHF_2$ | H | A | O | $C_2H_5$ | H | Cl | $CF_3$ | $CH_3$ |
| Q | $CH_2$ | $CH_3$ | $CH_3$ | $CH_3$ | $CHF_2$ | H | B | O | $C_2H_5$ | H | Cl | $CF_3$ | $CH_3$ |
| R | $CH_2$ | $CH_3$ | $CH_3$ | $CH_3$ | $CHF_2$ | H | C | O | $C_2H_5$ | H | Cl | $CF_3$ | $CH_3$ |
| S | $CH_2$ | $CH_3$ | $CH_3$ | $CH_3$ | $CHF_2$ | H | D | O | $C_2H_5$ | H | Cl | $CF_3$ | $CH_3$ |
| T | $CH_2$ | $CH_3$ | $CH_3$ | $CH_3$ | $CHF_2$ | H | E | O | $C_2H_5$ | H | Cl | $CF_3$ | $CH_3$ |
| U | $CH_2$ | $CH_3$ | $CH_3$ | $CH_3$ | $CHF_2$ | H | F | O | $C_2H_5$ | H | Cl | $CF_3$ | $CH_3$ |
| V | $CH_2$ | $CH_3$ | $CH_3$ | $CH_3$ | $CHF_2$ | H | G | O | $C_2H_5$ | H | Cl | $CF_3$ | $CH_3$ |
| W | $CH_2$ | $CH_3$ | $CH_3$ | $CH_3$ | $CHF_2$ | H | H | O | $C_2H_5$ | H | Cl | $CF_3$ | $CH_3$ |
| X | $CH_2$ | $CH_3$ | $CH_3$ | $CH_3$ | $CHF_2$ | H | I | O | $C_2H_5$ | H | Cl | $CF_3$ | $CH_3$ |
| Y | $CH_2$ | $CH_3$ | $CH_3$ | $CH_3$ | $CHF_2$ | H | J | O | $C_2H_5$ | H | Cl | $CF_3$ | $CH_3$ |
| A | $CH_2$ | $CH_3$ | H | Cl | $CF_3$ | $CH_3$ | K | O | $C_2H_5$ | H | Cl | $CF_3$ | $CH_3$ |
| B | $CH_2$ | $CH_3$ | H | Cl | $CF_3$ | $CH_3$ | L | O | $C_2H_5$ | H | Cl | $CF_3$ | $CH_3$ |
| C | $CH_2$ | $CH_3$ | H | Cl | $CF_3$ | $CH_3$ | M | O | $C_2H_5$ | H | Cl | $CF_3$ | $CH_3$ |
| D | $CH_2$ | $CH_3$ | H | Cl | $CF_3$ | $CH_3$ | N | O | $C_2H_5$ | H | Cl | $CF_3$ | $CH_3$ |
| E | $CH_2$ | $CH_3$ | H | Cl | $CF_3$ | $CH_3$ | O | O | $C_2H_5$ | H | Cl | $CF_3$ | $CH_3$ |
| F | $CH_2$ | $CH_3$ | H | Cl | $CF_3$ | $CH_3$ | P | O | $C_2H_5$ | H | Cl | $CF_3$ | $CH_3$ |
| G | $CH_2$ | $CH_3$ | H | Cl | $CF_3$ | $CH_3$ | Q | O | $C_2H_5$ | H | Cl | $CF_3$ | $CH_3$ |
| H | $CH_2$ | $CH_3$ | H | Cl | $CF_3$ | $CH_3$ | R | O | $C_2H_5$ | H | Cl | $CF_3$ | $CH_3$ |
| I | $CH_2$ | $CH_3$ | H | Cl | $CF_3$ | $CH_3$ | S | O | $C_2H_5$ | H | Cl | $CF_3$ | $CH_3$ |
| J | $CH_2$ | $CH_3$ | H | Cl | $CF_3$ | $CH_3$ | T | O | $C_2H_5$ | H | Cl | $CF_3$ | $CH_3$ |
| K | $CH_2$ | $CH_3$ | H | Cl | $CF_3$ | $CH_3$ | U | O | $C_2H_5$ | H | Cl | $CF_3$ | $CH_3$ |
| L | $CH_2$ | $CH_3$ | H | Cl | $CF_3$ | $CH_3$ | V | O | $C_2H_5$ | H | Cl | $CF_3$ | $CH_3$ |
| M | $CH_2$ | $CH_3$ | H | Cl | $CF_3$ | $CH_3$ | W | O | $C_2H_5$ | H | Cl | $CF_3$ | $CH_3$ |
| N | $CH_2$ | $CH_3$ | H | Cl | $CF_3$ | $CH_3$ | X | O | $C_2H_5$ | H | Cl | $CF_3$ | $CH_3$ |
| O | $CH_2$ | $CH_3$ | H | Cl | $CF_3$ | $CH_3$ | Y | O | $C_2H_5$ | H | Cl | $CF_3$ | $CH_3$ |
| P | $CH_2$ | $CH_3$ | H | Cl | $CF_3$ | $CH_3$ | A | $CH_2$ | $CH_3$ | $CH_3$ | Cl | $CF_3$ | $CH_3$ |
| Q | $CH_2$ | $CH_3$ | H | Cl | $CF_3$ | $CH_3$ | B | $CH_2$ | $CH_3$ | $CH_3$ | Cl | $CF_3$ | $CH_3$ |
| R | $CH_2$ | $CH_3$ | H | Cl | $CF_3$ | $CH_3$ | C | $CH_2$ | $CH_3$ | $CH_3$ | Cl | $CF_3$ | $CH_3$ |
| S | $CH_2$ | $CH_3$ | H | Cl | $CF_3$ | $CH_3$ | D | $CH_2$ | $CH_3$ | $CH_3$ | Cl | $CF_3$ | $CH_3$ |
| T | $CH_2$ | $CH_3$ | H | Cl | $CF_3$ | $CH_3$ | E | $CH_2$ | $CH_3$ | $CH_3$ | Cl | $CF_3$ | $CH_3$ |
| U | $CH_2$ | $CH_3$ | H | Cl | $CF_3$ | $CH_3$ | F | $CH_2$ | $CH_3$ | $CH_3$ | Cl | $CF_3$ | $CH_3$ |
| V | $CH_2$ | $CH_3$ | H | Cl | $CF_3$ | $CH_3$ | G | $CH_2$ | $CH_3$ | $CH_3$ | Cl | $CF_3$ | $CH_3$ |
| W | $CH_2$ | $CH_3$ | H | Cl | $CF_3$ | $CH_3$ | H | $CH_2$ | $CH_3$ | $CH_3$ | Cl | $CF_3$ | $CH_3$ |
| X | $CH_2$ | $CH_3$ | H | Cl | $CF_3$ | $CH_3$ | I | $CH_2$ | $CH_3$ | $CH_3$ | Cl | $CF_3$ | $CH_3$ |
| Y | $CH_2$ | $CH_3$ | H | Cl | $CF_3$ | $CH_3$ | J | $CH_2$ | $CH_3$ | $CH_3$ | Cl | $CF_3$ | $CH_3$ |
| A | O | $CH_3$ | H | Cl | $CF_3$ | $CH_3$ | K | $CH_2$ | $CH_3$ | $CH_3$ | Cl | $CF_3$ | $CH_3$ |
| B | O | $CH_3$ | H | Cl | $CF_3$ | $CH_3$ | L | $CH_2$ | $CH_3$ | $CH_3$ | Cl | $CF_3$ | $CH_3$ |
| C | O | $CH_3$ | H | Cl | $CF_3$ | $CH_3$ | M | $CH_2$ | $CH_3$ | $CH_3$ | Cl | $CF_3$ | $CH_3$ |
| D | O | $CH_3$ | H | Cl | $CF_3$ | $CH_3$ | N | $CH_2$ | $CH_3$ | $CH_3$ | Cl | $CF_3$ | $CH_3$ |
| E | O | $CH_3$ | H | Cl | $CF_3$ | $CH_3$ | O | $CH_2$ | $CH_3$ | $CH_3$ | Cl | $CF_3$ | $CH_3$ |
| F | O | $CH_3$ | H | Cl | $CF_3$ | $CH_3$ | P | $CH_2$ | $CH_3$ | $CH_3$ | Cl | $CF_3$ | $CH_3$ |
| G | O | $CH_3$ | H | Cl | $CF_3$ | $CH_3$ | Q | $CH_2$ | $CH_3$ | $CH_3$ | Cl | $CF_3$ | $CH_3$ |
| H | O | $CH_3$ | H | Cl | $CF_3$ | $CH_3$ | R | $CH_2$ | $CH_3$ | $CH_3$ | Cl | $CF_3$ | $CH_3$ |
| I | O | $CH_3$ | H | Cl | $CF_3$ | $CH_3$ | S | $CH_2$ | $CH_3$ | $CH_3$ | Cl | $CF_3$ | $CH_3$ |
| J | O | $CH_3$ | H | Cl | $CF_3$ | $CH_3$ | T | $CH_2$ | $CH_3$ | $CH_3$ | Cl | $CF_3$ | $CH_3$ |
| K | O | $CH_3$ | H | Cl | $CF_3$ | $CH_3$ | U | $CH_2$ | $CH_3$ | $CH_3$ | Cl | $CF_3$ | $CH_3$ |
| L | O | $CH_3$ | H | Cl | $CF_3$ | $CH_3$ | V | $CH_2$ | $CH_3$ | $CH_3$ | Cl | $CF_3$ | $CH_3$ |
| M | O | $CH_3$ | H | Cl | $CF_3$ | $CH_3$ | W | $CH_2$ | $CH_3$ | $CH_3$ | Cl | $CF_3$ | $CH_3$ |
| N | O | $CH_3$ | H | Cl | $CF_3$ | $CH_3$ | X | $CH_2$ | $CH_3$ | $CH_3$ | Cl | $CF_3$ | $CH_3$ |
| O | O | $CH_3$ | H | Cl | $CF_3$ | $CH_3$ | Y | $CH_2$ | $CH_3$ | $CH_3$ | Cl | $CF_3$ | $CH_3$ |
| P | O | $CH_3$ | H | Cl | $CF_3$ | $CH_3$ | A | $CH_2$ | $CH_3$ | H | $CH_3$ | $CF_3$ | $CH_3$ |
| Q | O | $CH_3$ | H | Cl | $CF_3$ | $CH_3$ | B | $CH_2$ | $CH_3$ | H | $CH_3$ | $CF_3$ | $CH_3$ |
| R | O | $CH_3$ | H | Cl | $CF_3$ | $CH_3$ | C | $CH_2$ | $CH_3$ | H | $CH_3$ | $CF_3$ | $CH_3$ |

TABLE D-continued

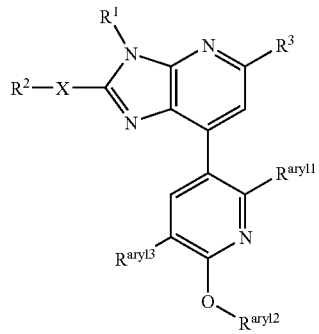

| R[1(a)] | X | R[2] | R[3] | R[aryl1] | R[aryl2] | R[aryl3] |
|---|---|---|---|---|---|---|
| D | $CH_2$ | $CH_3$ | H | $CH_3$ | $CF_3$ | $CH_3$ |
| E | $CH_2$ | $CH_3$ | H | $CH_3$ | $CF_3$ | $CH_3$ |
| F | $CH_2$ | $CH_3$ | H | $CH_3$ | $CF_3$ | $CH_3$ |
| G | $CH_2$ | $CH_3$ | H | $CH_3$ | $CF_3$ | $CH_3$ |
| H | $CH_2$ | $CH_3$ | H | $CH_3$ | $CF_3$ | $CH_3$ |
| I | $CH_2$ | $CH_3$ | H | $CH_3$ | $CF_3$ | $CH_3$ |
| J | $CH_2$ | $CH_3$ | H | $CH_3$ | $CF_3$ | $CH_3$ |
| K | $CH_2$ | $CH_3$ | H | $CH_3$ | $CF_3$ | $CH_3$ |
| L | $CH_2$ | $CH_3$ | H | $CH_3$ | $CF_3$ | $CH_3$ |
| M | $CH_2$ | $CH_3$ | H | $CH_3$ | $CF_3$ | $CH_3$ |
| N | $CH_2$ | $CH_3$ | H | $CH_3$ | $CF_3$ | $CH_3$ |
| O | $CH_2$ | $CH_3$ | H | $CH_3$ | $CF_3$ | $CH_3$ |
| P | $CH_2$ | $CH_3$ | H | $CH_3$ | $CF_3$ | $CH_3$ |
| Q | $CH_2$ | $CH_3$ | H | $CH_3$ | $CF_3$ | $CH_3$ |
| R | $CH_2$ | $CH_3$ | H | $CH_3$ | $CF_3$ | $CH_3$ |
| S | $CH_2$ | $CH_3$ | H | $CH_3$ | $CF_3$ | $CH_3$ |
| T | $CH_2$ | $CH_3$ | H | $CH_3$ | $CF_3$ | $CH_3$ |
| U | $CH_2$ | $CH_3$ | H | $CH_3$ | $CF_3$ | $CH_3$ |
| V | $CH_2$ | $CH_3$ | H | $CH_3$ | $CF_3$ | $CH_3$ |
| W | $CH_2$ | $CH_3$ | H | $CH_3$ | $CF_3$ | $CH_3$ |
| X | $CH_2$ | $CH_3$ | H | $CH_3$ | $CF_3$ | $CH_3$ |
| Y | $CH_2$ | $CH_3$ | H | $CH_3$ | $CF_3$ | $CH_3$ |
| A | O | $CH_3$ | H | $CH_3$ | $CF_3$ | $CH_3$ |
| B | O | $CH_3$ | H | $CH_3$ | $CF_3$ | $CH_3$ |
| C | O | $CH_3$ | H | $CH_3$ | $CF_3$ | $CH_3$ |
| D | O | $CH_3$ | H | $CH_3$ | $CF_3$ | $CH_3$ |
| E | O | $CH_3$ | H | $CH_3$ | $CF_3$ | $CH_3$ |
| F | O | $CH_3$ | H | $CH_3$ | $CF_3$ | $CH_3$ |
| G | O | $CH_3$ | H | $CH_3$ | $CF_3$ | $CH_3$ |
| H | O | $CH_3$ | H | $CH_3$ | $CF_3$ | $CH_3$ |
| I | O | $CH_3$ | H | $CH_3$ | $CF_3$ | $CH_3$ |
| J | O | $CH_3$ | H | $CH_3$ | $CF_3$ | $CH_3$ |
| K | O | $CH_3$ | H | $CH_3$ | $CF_3$ | $CH_3$ |
| L | O | $CH_3$ | H | $CH_3$ | $CF_3$ | $CH_3$ |
| M | O | $CH_3$ | H | $CH_3$ | $CF_3$ | $CH_3$ |
| N | O | $CH_3$ | H | $CH_3$ | $CF_3$ | $CH_3$ |
| O | O | $CH_3$ | H | $CH_3$ | $CF_3$ | $CH_3$ |
| P | O | $CH_3$ | H | $CH_3$ | $CF_3$ | $CH_3$ |
| Q | O | $CH_3$ | H | $CH_3$ | $CF_3$ | $CH_3$ |
| R | O | $CH_3$ | H | $CH_3$ | $CF_3$ | $CH_3$ |
| S | O | $CH_3$ | H | $CH_3$ | $CF_3$ | $CH_3$ |
| T | O | $CH_3$ | H | $CH_3$ | $CF_3$ | $CH_3$ |
| U | O | $CH_3$ | H | $CH_3$ | $CF_3$ | $CH_3$ |
| V | O | $CH_3$ | H | $CH_3$ | $CF_3$ | $CH_3$ |
| W | O | $CH_3$ | H | $CH_3$ | $CF_3$ | $CH_3$ |
| X | O | $CH_3$ | H | $CH_3$ | $CF_3$ | $CH_3$ |
| Y | O | $CH_3$ | H | $CH_3$ | $CF_3$ | $CH_3$ |
| A | O | $C_2H_5$ | H | $CH_3$ | $CF_3$ | $CH_3$ |
| B | O | $C_2H_5$ | H | $CH_3$ | $CF_3$ | $CH_3$ |
| C | O | $C_2H_5$ | H | $CH_3$ | $CF_3$ | $CH_3$ |
| D | O | $C_2H_5$ | H | $CH_3$ | $CF_3$ | $CH_3$ |
| E | O | $C_2H_5$ | H | $CH_3$ | $CF_3$ | $CH_3$ |
| F | O | $C_2H_5$ | H | $CH_3$ | $CF_3$ | $CH_3$ |
| G | O | $C_2H_5$ | H | $CH_3$ | $CF_3$ | $CH_3$ |
| H | O | $C_2H_5$ | H | $CH_3$ | $CF_3$ | $CH_3$ |
| I | O | $C_2H_5$ | H | $CH_3$ | $CF_3$ | $CH_3$ |
| J | O | $C_2H_5$ | H | $CH_3$ | $CF_3$ | $CH_3$ |
| K | O | $C_2H_5$ | H | $CH_3$ | $CF_3$ | $CH_3$ |
| L | O | $C_2H_5$ | H | $CH_3$ | $CF_3$ | $CH_3$ |
| M | O | $C_2H_5$ | H | $CH_3$ | $CF_3$ | $CH_3$ |
| N | O | $C_2H_5$ | H | $CH_3$ | $CF_3$ | $CH_3$ |
| O | O | $C_2H_5$ | H | $CH_3$ | $CF_3$ | $CH_3$ |
| P | O | $C_2H_5$ | H | $CH_3$ | $CF_3$ | $CH_3$ |
| Q | O | $C_2H_5$ | H | $CH_3$ | $CF_3$ | $CH_3$ |
| R | O | $C_2H_5$ | H | $CH_3$ | $CF_3$ | $CH_3$ |
| S | O | $C_2H_5$ | H | $CH_3$ | $CF_3$ | $CH_3$ |
| T | O | $C_2H_5$ | H | $CH_3$ | $CF_3$ | $CH_3$ |
| U | O | $C_2H_5$ | H | $CH_3$ | $CF_3$ | $CH_3$ |
| V | O | $C_2H_5$ | H | $CH_3$ | $CF_3$ | $CH_3$ |
| W | O | $C_2H_5$ | H | $CH_3$ | $CF_3$ | $CH_3$ |
| X | O | $C_2H_5$ | H | $CH_3$ | $CF_3$ | $CH_3$ |
| Y | O | $C_2H_5$ | H | $CH_3$ | $CF_3$ | $CH_3$ |
| A | $CH_2$ | $CH_3$ | $CH_3$ | $CH_3$ | $CF_3$ | $CH_3$ |
| B | $CH_2$ | $CH_3$ | $CH_3$ | $CH_3$ | $CF_3$ | $CH_3$ |
| C | $CH_2$ | $CH_3$ | $CH_3$ | $CH_3$ | $CF_3$ | $CH_3$ |
| D | $CH_2$ | $CH_3$ | $CH_3$ | $CH_3$ | $CF_3$ | $CH_3$ |
| E | $CH_2$ | $CH_3$ | $CH_3$ | $CH_3$ | $CF_3$ | $CH_3$ |
| F | $CH_2$ | $CH_3$ | $CH_3$ | $CH_3$ | $CF_3$ | $CH_3$ |
| G | $CH_2$ | $CH_3$ | $CH_3$ | $CH_3$ | $CF_3$ | $CH_3$ |
| H | $CH_2$ | $CH_3$ | $CH_3$ | $CH_3$ | $CF_3$ | $CH_3$ |
| I | $CH_2$ | $CH_3$ | $CH_3$ | $CH_3$ | $CF_3$ | $CH_3$ |
| J | $CH_2$ | $CH_3$ | $CH_3$ | $CH_3$ | $CF_3$ | $CH_3$ |
| K | $CH_2$ | $CH_3$ | $CH_3$ | $CH_3$ | $CF_3$ | $CH_3$ |
| L | $CH_2$ | $CH_3$ | $CH_3$ | $CH_3$ | $CF_3$ | $CH_3$ |
| M | $CH_2$ | $CH_3$ | $CH_3$ | $CH_3$ | $CF_3$ | $CH_3$ |
| N | $CH_2$ | $CH_3$ | $CH_3$ | $CH_3$ | $CF_3$ | $CH_3$ |
| O | $CH_2$ | $CH_3$ | $CH_3$ | $CH_3$ | $CF_3$ | $CH_3$ |
| P | $CH_2$ | $CH_3$ | $CH_3$ | $CH_3$ | $CF_3$ | $CH_3$ |
| Q | $CH_2$ | $CH_3$ | $CH_3$ | $CH_3$ | $CF_3$ | $CH_3$ |
| R | $CH_2$ | $CH_3$ | $CH_3$ | $CH_3$ | $CF_3$ | $CH_3$ |
| S | $CH_2$ | $CH_3$ | $CH_3$ | $CH_3$ | $CF_3$ | $CH_3$ |
| T | $CH_2$ | $CH_3$ | $CH_3$ | $CH_3$ | $CF_3$ | $CH_3$ |
| U | $CH_2$ | $CH_3$ | $CH_3$ | $CH_3$ | $CF_3$ | $CH_3$ |
| V | $CH_2$ | $CH_3$ | $CH_3$ | $CH_3$ | $CF_3$ | $CH_3$ |
| W | $CH_2$ | $CH_3$ | $CH_3$ | $CH_3$ | $CF_3$ | $CH_3$ |
| X | $CH_2$ | $CH_3$ | $CH_3$ | $CH_3$ | $CF_3$ | $CH_3$ |
| Y | $CH_2$ | $CH_3$ | $CH_3$ | $CH_3$ | $CF_3$ | $CH_3$ |
| A | $CH_2$ | $CH_3$ | H | Cl | $CHF_2$ | $CH_3$ |
| B | $CH_2$ | $CH_3$ | H | Cl | $CHF_2$ | $CH_3$ |
| C | $CH_2$ | $CH_3$ | H | Cl | $CHF_2$ | $CH_3$ |
| D | $CH_2$ | $CH_3$ | H | Cl | $CHF_2$ | $CH_3$ |
| E | $CH_2$ | $CH_3$ | H | Cl | $CHF_2$ | $CH_3$ |
| F | $CH_2$ | $CH_3$ | H | Cl | $CHF_2$ | $CH_3$ |
| G | $CH_2$ | $CH_3$ | H | Cl | $CHF_2$ | $CH_3$ |
| H | $CH_2$ | $CH_3$ | H | Cl | $CHF_2$ | $CH_3$ |
| I | $CH_2$ | $CH_3$ | H | Cl | $CHF_2$ | $CH_3$ |
| J | $CH_2$ | $CH_3$ | H | Cl | $CHF_2$ | $CH_3$ |
| K | $CH_2$ | $CH_3$ | H | Cl | $CHF_2$ | $CH_3$ |
| L | $CH_2$ | $CH_3$ | H | Cl | $CHF_2$ | $CH_3$ |
| M | $CH_2$ | $CH_3$ | H | Cl | $CHF_2$ | $CH_3$ |
| N | $CH_2$ | $CH_3$ | H | Cl | $CHF_2$ | $CH_3$ |
| O | $CH_2$ | $CH_3$ | H | Cl | $CHF_2$ | $CH_3$ |
| P | $CH_2$ | $CH_3$ | H | Cl | $CHF_2$ | $CH_3$ |
| Q | $CH_2$ | $CH_3$ | H | Cl | $CHF_2$ | $CH_3$ |
| R | $CH_2$ | $CH_3$ | H | Cl | $CHF_2$ | $CH_3$ |
| S | $CH_2$ | $CH_3$ | H | Cl | $CHF_2$ | $CH_3$ |
| T | $CH_2$ | $CH_3$ | H | Cl | $CHF_2$ | $CH_3$ |
| U | $CH_2$ | $CH_3$ | H | Cl | $CHF_2$ | $CH_3$ |
| V | $CH_2$ | $CH_3$ | H | Cl | $CHF_2$ | $CH_3$ |
| W | $CH_2$ | $CH_3$ | H | Cl | $CHF_2$ | $CH_3$ |

TABLE D-continued

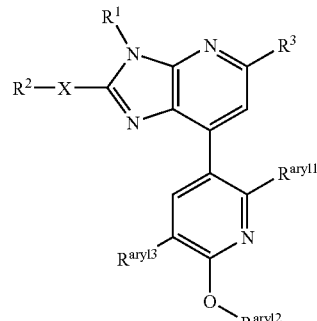

| R[1(a)] | X | R[2] | R[3] | R[aryl1] | R[aryl2] | R[aryl3] |
|---|---|---|---|---|---|---|
| X | $CH_2$ | $CH_3$ | H | Cl | $CHF_2$ | $CH_3$ |
| Y | $CH_2$ | $CH_3$ | H | Cl | $CHF_2$ | $CH_3$ |
| A | O | $CH_3$ | H | Cl | $CHF_2$ | $CH_3$ |
| B | O | $CH_3$ | H | Cl | $CHF_2$ | $CH_3$ |
| C | O | $CH_3$ | H | Cl | $CHF_2$ | $CH_3$ |
| D | O | $CH_3$ | H | Cl | $CHF_2$ | $CH_3$ |
| E | O | $CH_3$ | H | Cl | $CHF_2$ | $CH_3$ |
| F | O | $CH_3$ | H | Cl | $CHF_2$ | $CH_3$ |
| G | O | $CH_3$ | H | Cl | $CHF_2$ | $CH_3$ |
| H | O | $CH_3$ | H | Cl | $CHF_2$ | $CH_3$ |
| I | O | $CH_3$ | H | Cl | $CHF_2$ | $CH_3$ |
| J | O | $CH_3$ | H | Cl | $CHF_2$ | $CH_3$ |
| K | O | $CH_3$ | H | Cl | $CHF_2$ | $CH_3$ |
| L | O | $CH_3$ | H | Cl | $CHF_2$ | $CH_3$ |
| M | O | $CH_3$ | H | Cl | $CHF_2$ | $CH_3$ |
| N | O | $CH_3$ | H | Cl | $CHF_2$ | $CH_3$ |
| O | O | $CH_3$ | H | Cl | $CHF_2$ | $CH_3$ |
| P | O | $CH_3$ | H | Cl | $CHF_2$ | $CH_3$ |
| Q | O | $CH_3$ | H | Cl | $CHF_2$ | $CH_3$ |
| R | O | $CH_3$ | H | Cl | $CHF_2$ | $CH_3$ |
| S | O | $CH_3$ | H | Cl | $CHF_2$ | $CH_3$ |
| T | O | $CH_3$ | H | Cl | $CHF_2$ | $CH_3$ |
| U | O | $CH_3$ | H | Cl | $CHF_2$ | $CH_3$ |
| V | O | $CH_3$ | H | Cl | $CHF_2$ | $CH_3$ |
| W | O | $CH_3$ | H | Cl | $CHF_2$ | $CH_3$ |
| X | O | $CH_3$ | H | Cl | $CHF_2$ | $CH_3$ |
| Y | O | $CH_3$ | H | Cl | $CHF_2$ | $CH_3$ |
| A | O | $C_2H_5$ | H | Cl | $CHF_2$ | $CH_3$ |
| B | O | $C_2H_5$ | H | Cl | $CHF_2$ | $CH_3$ |
| C | O | $C_2H_5$ | H | Cl | $CHF_2$ | $CH_3$ |
| D | O | $C_2H_5$ | H | Cl | $CHF_2$ | $CH_3$ |
| E | O | $C_2H_5$ | H | Cl | $CHF_2$ | $CH_3$ |
| F | O | $C_2H_5$ | H | Cl | $CHF_2$ | $CH_3$ |
| G | O | $C_2H_5$ | H | Cl | $CHF_2$ | $CH_3$ |
| H | O | $C_2H_5$ | H | Cl | $CHF_2$ | $CH_3$ |
| I | O | $C_2H_5$ | H | Cl | $CHF_2$ | $CH_3$ |
| J | O | $C_2H_5$ | H | Cl | $CHF_2$ | $CH_3$ |
| K | O | $C_2H_5$ | H | Cl | $CHF_2$ | $CH_3$ |
| L | O | $C_2H_5$ | H | Cl | $CHF_2$ | $CH_3$ |
| M | O | $C_2H_5$ | H | Cl | $CHF_2$ | $CH_3$ |
| N | O | $C_2H_5$ | H | Cl | $CHF_2$ | $CH_3$ |
| O | O | $C_2H_5$ | H | Cl | $CHF_2$ | $CH_3$ |
| P | O | $C_2H_5$ | H | Cl | $CHF_2$ | $CH_3$ |
| Q | O | $C_2H_5$ | H | Cl | $CHF_2$ | $CH_3$ |
| R | O | $C_2H_5$ | H | Cl | $CHF_2$ | $CH_3$ |
| S | O | $C_2H_5$ | H | Cl | $CHF_2$ | $CH_3$ |
| T | O | $C_2H_5$ | H | Cl | $CHF_2$ | $CH_3$ |
| U | O | $C_2H_5$ | H | Cl | $CHF_2$ | $CH_3$ |
| V | O | $C_2H_5$ | H | Cl | $CHF_2$ | $CH_3$ |
| W | O | $C_2H_5$ | H | Cl | $CHF_2$ | $CH_3$ |
| X | O | $C_2H_5$ | H | Cl | $CHF_2$ | $CH_3$ |
| Y | O | $C_2H_5$ | H | Cl | $CHF_2$ | $CH_3$ |
| A | $CH_2$ | $CH_3$ | $CH_3$ | Cl | $CHF_2$ | $CH_3$ |
| B | $CH_2$ | $CH_3$ | $CH_3$ | Cl | $CHF_2$ | $CH_3$ |
| C | $CH_2$ | $CH_3$ | $CH_3$ | Cl | $CHF_2$ | $CH_3$ |
| D | $CH_2$ | $CH_3$ | $CH_3$ | Cl | $CHF_2$ | $CH_3$ |
| E | $CH_2$ | $CH_3$ | $CH_3$ | Cl | $CHF_2$ | $CH_3$ |
| F | $CH_2$ | $CH_3$ | $CH_3$ | Cl | $CHF_2$ | $CH_3$ |
| G | $CH_2$ | $CH_3$ | $CH_3$ | Cl | $CHF_2$ | $CH_3$ |
| H | $CH_2$ | $CH_3$ | $CH_3$ | Cl | $CHF_2$ | $CH_3$ |

TABLE D-continued

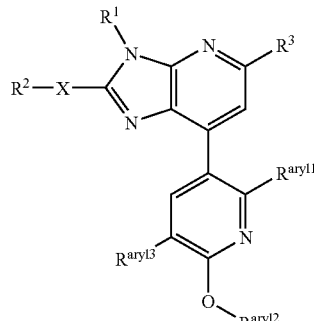

| R[1(a)] | X | R[2] | R[3] | R[aryl1] | R[aryl2] | R[aryl3] |
|---|---|---|---|---|---|---|
| I | $CH_2$ | $CH_3$ | $CH_3$ | Cl | $CHF_2$ | $CH_3$ |
| J | $CH_2$ | $CH_3$ | $CH_3$ | Cl | $CHF_2$ | $CH_3$ |
| K | $CH_2$ | $CH_3$ | $CH_3$ | Cl | $CHF_2$ | $CH_3$ |
| L | $CH_2$ | $CH_3$ | $CH_3$ | Cl | $CHF_2$ | $CH_3$ |
| M | $CH_2$ | $CH_3$ | $CH_3$ | Cl | $CHF_2$ | $CH_3$ |
| N | $CH_2$ | $CH_3$ | $CH_3$ | Cl | $CHF_2$ | $CH_3$ |
| O | $CH_2$ | $CH_3$ | $CH_3$ | Cl | $CHF_2$ | $CH_3$ |
| P | $CH_2$ | $CH_3$ | $CH_3$ | Cl | $CHF_2$ | $CH_3$ |
| Q | $CH_2$ | $CH_3$ | $CH_3$ | Cl | $CHF_2$ | $CH_3$ |
| R | $CH_2$ | $CH_3$ | $CH_3$ | Cl | $CHF_2$ | $CH_3$ |
| S | $CH_2$ | $CH_3$ | $CH_3$ | Cl | $CHF_2$ | $CH_3$ |
| T | $CH_2$ | $CH_3$ | $CH_3$ | Cl | $CHF_2$ | $CH_3$ |
| U | $CH_2$ | $CH_3$ | $CH_3$ | Cl | $CHF_2$ | $CH_3$ |
| V | $CH_2$ | $CH_3$ | $CH_3$ | Cl | $CHF_2$ | $CH_3$ |
| W | $CH_2$ | $CH_3$ | $CH_3$ | Cl | $CHF_2$ | $CH_3$ |
| X | $CH_2$ | $CH_3$ | $CH_3$ | Cl | $CHF_2$ | $CH_3$ |
| Y | $CH_2$ | $CH_3$ | $CH_3$ | Cl | $CHF_2$ | $CH_3$ |
| A | $CH_2$ | $CH_3$ | H | $CH_3$ | $CHF_2$ | $CH_3$ |
| B | $CH_2$ | $CH_3$ | H | $CH_3$ | $CHF_2$ | $CH_3$ |
| C | $CH_2$ | $CH_3$ | H | $CH_3$ | $CHF_2$ | $CH_3$ |
| D | $CH_2$ | $CH_3$ | H | $CH_3$ | $CHF_2$ | $CH_3$ |
| E | $CH_2$ | $CH_3$ | H | $CH_3$ | $CHF_2$ | $CH_3$ |
| F | $CH_2$ | $CH_3$ | H | $CH_3$ | $CHF_2$ | $CH_3$ |
| G | $CH_2$ | $CH_3$ | H | $CH_3$ | $CHF_2$ | $CH_3$ |
| H | $CH_2$ | $CH_3$ | H | $CH_3$ | $CHF_2$ | $CH_3$ |
| I | $CH_2$ | $CH_3$ | H | $CH_3$ | $CHF_2$ | $CH_3$ |
| J | $CH_2$ | $CH_3$ | H | $CH_3$ | $CHF_2$ | $CH_3$ |
| K | $CH_2$ | $CH_3$ | H | $CH_3$ | $CHF_2$ | $CH_3$ |
| L | $CH_2$ | $CH_3$ | H | $CH_3$ | $CHF_2$ | $CH_3$ |
| N | $CH_2$ | $CH_3$ | H | $CH_3$ | $CHF_2$ | $CH_3$ |
| N | $CH_2$ | $CH_3$ | H | $CH_3$ | $CHF_2$ | $CH_3$ |
| O | $CH_2$ | $CH_3$ | H | $CH_3$ | $CHF_2$ | $CH_3$ |
| P | $CH_2$ | $CH_3$ | H | $CH_3$ | $CHF_2$ | $CH_3$ |
| Q | $CH_2$ | $CH_3$ | H | $CH_3$ | $CHF_2$ | $CH_3$ |
| R | $CH_2$ | $CH_3$ | H | $CH_3$ | $CHF_2$ | $CH_3$ |
| S | $CH_2$ | $CH_3$ | H | $CH_3$ | $CHF_2$ | $CH_3$ |
| T | $CH_2$ | $CH_3$ | H | $CH_3$ | $CHF_2$ | $CH_3$ |
| U | $CH_2$ | $CH_3$ | H | $CH_3$ | $CHF_2$ | $CH_3$ |
| V | $CH_2$ | $CH_3$ | H | $CH_3$ | $CHF_2$ | $CH_3$ |
| W | $CH_2$ | $CH_3$ | H | $CH_3$ | $CHF_2$ | $CH_3$ |
| X | $CH_2$ | $CH_3$ | H | $CH_3$ | $CHF_2$ | $CH_3$ |
| Y | $CH_2$ | $CH_3$ | H | $CH_3$ | $CHF_2$ | $CH_3$ |
| A | O | $CH_3$ | H | $CH_3$ | $CHF_2$ | $CH_3$ |
| B | O | $CH_3$ | H | $CH_3$ | $CHF_2$ | $CH_3$ |
| C | O | $CH_3$ | H | $CH_3$ | $CHF_2$ | $CH_3$ |
| D | O | $CH_3$ | H | $CH_3$ | $CHF_2$ | $CH_3$ |
| E | O | $CH_3$ | H | $CH_3$ | $CHF_2$ | $CH_3$ |
| F | O | $CH_3$ | H | $CH_3$ | $CHF_2$ | $CH_3$ |
| G | C | $CH_3$ | H | $CH_3$ | $CHF_2$ | $CH_3$ |
| H | O | $CH_3$ | H | $CH_3$ | $CHF_2$ | $CH_3$ |
| I | O | $CH_3$ | H | $CH_3$ | $CHF_2$ | $CH_3$ |
| J | O | $CH_3$ | H | $CH_3$ | $CHF_2$ | $CH_3$ |
| K | O | $CH_3$ | H | $CH_3$ | $CHF_2$ | $CH_3$ |
| L | O | $CH_3$ | H | $CH_3$ | $CHF_2$ | $CH_3$ |
| M | O | $CH_3$ | H | $CH_3$ | $CHF_2$ | $CH_3$ |
| N | O | $CH_3$ | H | $CH_3$ | $CHF_2$ | $CH_3$ |
| O | O | $CH_3$ | H | $CH_3$ | $CHF_2$ | $CH_3$ |
| P | O | $CH_3$ | H | $CH_3$ | $CHF_2$ | $CH_3$ |
| Q | O | $CH_3$ | H | $CH_3$ | $CHF_2$ | $CH_3$ |
| R | O | $CH_3$ | H | $CH_3$ | $CHF_2$ | $CH_3$ |

TABLE D-continued

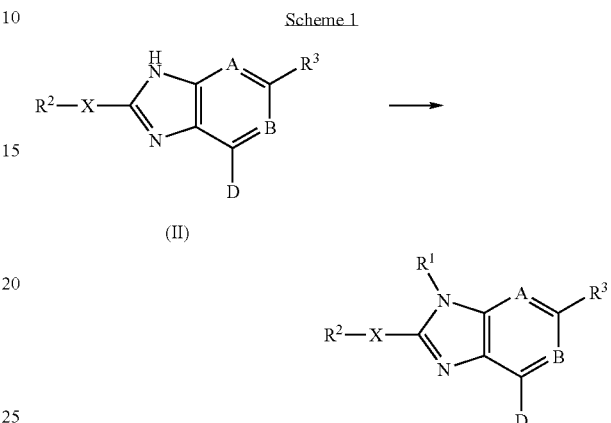

| $R^{1(a)}$ | X | $R^2$ | $R^3$ | $R^{aryl1}$ | $R^{aryl2}$ | $R^{aryl3}$ |
|---|---|---|---|---|---|---|
| S | O | $CH_3$ | H | $CH_3$ | $CHF_2$ | $CH_3$ |
| T | O | $CH_3$ | H | $CH_3$ | $CHF_2$ | $CH_3$ |
| U | O | $CH_3$ | H | $CH_3$ | $CHF_2$ | $CH_3$ |
| V | O | $CH_3$ | H | $CH_3$ | $CHF_2$ | $CH_3$ |
| W | O | $CH_3$ | H | $CH_3$ | $CHF_2$ | $CH_3$ |
| X | O | $CH_3$ | H | $CH_3$ | $CHF_2$ | $CH_3$ |
| Y | O | $CH_3$ | H | $CH_3$ | $CHF_2$ | $CH_3$ |
| A | O | $C_2H_5$ | H | $CH_3$ | $CHF_2$ | $CH_3$ |
| B | O | $C_2H_5$ | H | $CH_3$ | $CHF_2$ | $CH_3$ |
| C | O | $C_2H_5$ | H | $CH_3$ | $CHF_2$ | $CH_3$ |
| D | O | $C_2H_5$ | H | $CH_3$ | $CHF_2$ | $CH_3$ |
| E | O | $C_2H_5$ | H | $CH_3$ | $CHF_2$ | $CH_3$ |
| F | O | $C_2H_5$ | H | $CH_3$ | $CHF_2$ | $CH_3$ |
| G | O | $C_2H_5$ | H | $CH_3$ | $CHF_2$ | $CH_3$ |
| H | O | $C_2H_5$ | H | $CH_3$ | $CHF_2$ | $CH_3$ |
| I | O | $C_2H_5$ | H | $CH_3$ | $CHF_2$ | $CH_3$ |
| J | O | $C_2H_5$ | H | $CH_3$ | $CHF_2$ | $CH_3$ |
| K | O | $C_2H_5$ | H | $CH_3$ | $CHF_2$ | $CH_3$ |
| L | O | $C_2H_5$ | H | $CH_3$ | $CHF_2$ | $CH_3$ |
| M | O | $C_2H_5$ | H | $CH_3$ | $CHF_2$ | $CH_3$ |
| N | O | $C_2H_5$ | H | $CH_3$ | $CHF_2$ | $CH_3$ |
| O | O | $C_2H_5$ | H | $CH_3$ | $CHF_2$ | $CH_3$ |
| P | O | $C_2H_5$ | H | $CH_3$ | $CHF_2$ | $CH_3$ |
| Q | O | $C_2H_5$ | H | $CH_3$ | $CHF_2$ | $CH_3$ |
| R | O | $C_2H_5$ | H | $CH_3$ | $CHF_2$ | $CH_3$ |
| S | O | $C_2H_5$ | H | $CH_3$ | $CHF_2$ | $CH_3$ |
| T | O | $C_2H_5$ | H | $CH_3$ | $CHF_2$ | $CH_3$ |
| U | O | $C_2H_5$ | H | $CH_3$ | $CHF_2$ | $CH_3$ |
| V | O | $C_2H_5$ | H | $CH_3$ | $CHF_2$ | $CH_3$ |
| W | O | $C_2H_5$ | H | $CH_3$ | $CHF_2$ | $CH_3$ |
| X | O | $C_2H_5$ | H | $CH_3$ | $CHF_2$ | $CH_3$ |
| Y | O | $C_2H_5$ | H | $CH_3$ | $CHF_2$ | $CH_3$ |
| A | $CH_2$ | $CH_3$ | $CH_3$ | $CH_3$ | $CHF_2$ | $CH_3$ |
| B | $CH_2$ | $CH_3$ | $CH_3$ | $CH_3$ | $CHF_2$ | $CH_3$ |
| C | $CH_2$ | $CH_3$ | $CH_3$ | $CH_3$ | $CHF_2$ | $CH_3$ |
| D | $CH_2$ | $CH_3$ | $CH_3$ | $CH_3$ | $CHF_2$ | $CH_3$ |
| E | $CH_2$ | $CH_3$ | $CH_3$ | $CH_3$ | $CHF_2$ | $CH_3$ |
| F | $CH_2$ | $CH_3$ | $CH_3$ | $CH_3$ | $CHF_2$ | $CH_3$ |
| G | $CH_2$ | $CH_3$ | $CH_3$ | $CH_3$ | $CHF_2$ | $CH_3$ |
| H | $CH_2$ | $CH_3$ | $CH_3$ | $CH_3$ | $CHF_2$ | $CH_3$ |
| I | $CH_2$ | $CH_3$ | $CH_3$ | $CH_3$ | $CHF_2$ | $CH_3$ |
| J | $CH_2$ | $CH_3$ | $CH_3$ | $CH_3$ | $CHF_2$ | $CH_3$ |
| K | $CH_2$ | $CH_3$ | $CH_3$ | $CH_3$ | $CHF_2$ | $CH_3$ |
| L | $CH_2$ | $CH_3$ | $CH_3$ | $CH_3$ | $CHF_2$ | $CH_3$ |
| M | $CH_2$ | $CH_3$ | $CH_3$ | $CH_3$ | $CHF_2$ | $CH_3$ |
| N | $CH_2$ | $CH_3$ | $CH_3$ | $CH_3$ | $CHF_2$ | $CH_3$ |
| O | $CH_2$ | $CH_3$ | $CH_3$ | $CH_3$ | $CHF_2$ | $CH_3$ |
| P | $CH_2$ | $CH_3$ | $CH_3$ | $CH_3$ | $CHF_2$ | $CH_3$ |
| Q | $CH_2$ | $CH_3$ | $CH_3$ | $CH_3$ | $CHF_2$ | $CH_3$ |
| R | $CH_2$ | $CH_3$ | $CH_3$ | $CH_3$ | $CHF_2$ | $CH_3$ |
| S | $CH_2$ | $CH_3$ | $CH_3$ | $CH_3$ | $CHF_2$ | $CH_3$ |
| T | $CH_2$ | $CH_3$ | $CH_3$ | $CH_3$ | $CHF_2$ | $CH_3$ |
| U | $CH_2$ | $CH_3$ | $CH_3$ | $CH_3$ | $CHF_2$ | $CH_3$ |
| V | $CH_2$ | $CH_3$ | $CH_3$ | $CH_3$ | $CHF_2$ | $CH_3$ |
| W | $CH_2$ | $CH_3$ | $CH_3$ | $CH_3$ | $CHF_2$ | $CH_3$ |
| X | $CH_2$ | $CH_3$ | $CH_3$ | $CH_3$ | $CHF_2$ | $CH_3$ |
| Y | $CH_2$ | $CH_3$ | $CH_3$ | $CH_3$ | $CHF_2$ | $CH_3$ |

(a)See Table A, above.

Compounds of formula (I), including, but not limited to, the preferred compounds described hereinabove, are prepared by a number of means well known to ordinarily skilled artisans given the teachings of this invention. These include the following synthetic routes and schemes, readily understood by those of ordinary skill in the art.

For example, compounds of formula (I) are prepared by the reaction shown in Scheme 1.

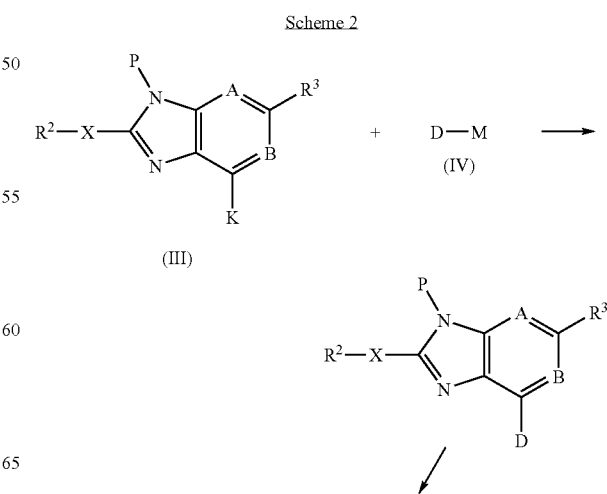

A compound of formula (II) is, for example, alkylated on the imidazole nitrogen atom with an appropriate reagent. Typical conditions for this transformation include treatment of compound (II) with a base, such as sodium hydride, potassium tert-butoxide, sodium hexamethyldisilazide, etc., followed by a reagent J—$R^1$, where J represents a halide (chloride, bromide or iodide) or pseudohalide (tosylate, mesylate, triflate, etc.), at an appropriate temperature (0° C. or room temperature, with warming if necessary) in a solvent such as tetrahydrofuran, dimethylformamide or dimethylsulfoxide. Alternatively, this reaction is performed using the Mitsunobu conditions (Mitsunobu, *Synthesis* 1981, pp. 1–28). The compound (II) is treated with an alcohol compound $R^1OH$, along with a phosphine (triphenyl, tributyl, etc.) and a phosphine-activating reagent such as diethyl azodicarboxylate.

Compounds of Formula (II) are, for example, prepared according to the route shown in Scheme 2.

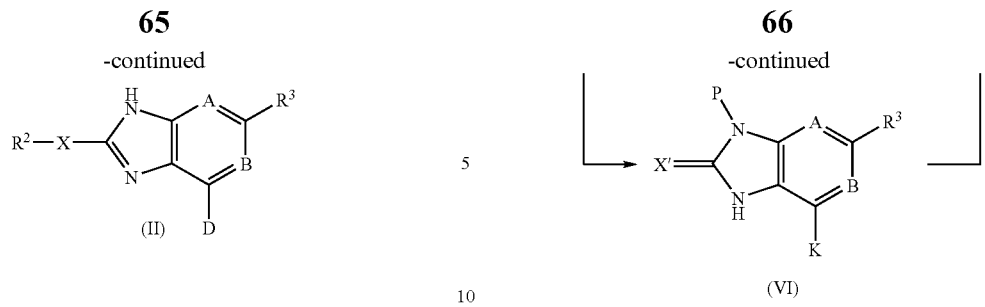

A compound of Formula (III) is coupled to an aromatic compound of Formula (IV), with elimination of the elements of M—K; for compound (III), K represents a halide, pseudohalide (such as mesylate, tosylate or triflate), or thiomethyl, and P represents a protecting group (if the conditions of the reaction warrant protection of the imidazole N—H; otherwise, P can be H). Suitable P groups may include benzyl, 4-methoxybenzyl, methoxymethyl, trimethylsilylethoxymethyl, tert-butoxycarbonyl or benzyloxycarbonyl. For compound (IV), M represents groups such as lithium, bromomagnesium, chlorozinc, (dihydroxy) boron, (dialkoxy)boron, trialkylstannyl and the like. The coupling reaction may be performed in the presence of an appropriate catalyst, such as tetrakis(triphenylphosphine) palladium, bis(triphenylphosphine)palladium dichloride, [1,3-bis(diphenylphosphino)propane]nickel dichloride, etc.

Two particularly useful methods involve the coupling of chloroheterocycles with in-situ-prepared arylzinc reagents according to the method of Negishi et al. (*J. Org. Chem*. 1977, 42, 1821), and the coupling with arylboronic esters according to the method of Suzuki et al. (*Chem. Letters* 1989, 1405). Appropriate solvents for reactions of this type usually include tetrahydrofuran, diethyl ether, dimethylformamide, or dimethylsulfoxide. Typical temperatures range from ambient up to the boiling point of the solvent. Once coupled, the P group may be removed to afford compound (II). Conditions for the removal of the protecting groups are well known to those familiar to the art of organic synthesis; e.g. hydrogenation to remove benzyl or benzyloxycarbonyl, a fluoride source (such as tetrabutylammonium fluoride) to remove silylethoxymethyl, an acid source (such as trifluoroacetic acid) to remove tert-butoxycarbonyl or 4-methoxybenzyl, etc.

Compounds of formula (III) can be prepared according to the plan shown in Scheme 3.

Scheme 3

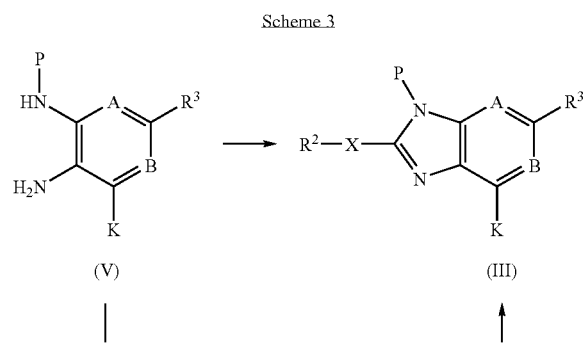

A diamine compound of formula (V) (in this case, P is a group such as benzyl, which can be introduced already attached to the nitrogen atom; otherwise, P could represent H initially, and another protecting group being introduced in a later step) is used in a cyclocondensation reaction to make the imidazole ring. The conditions used will, of course, depend on the X group chosen, and may include the intermediacy of the compound (VI). A review of imidazole-forming reactions may be found in *Comprehensive Heterocyclic Chemistry* (Pergamon Press, 1984) vol. 5, pp. 457–498.

Preparation of compounds of formula (V) wherein both A and B are nitrogen atoms may proceed according to the route of Scheme 4.

Scheme 4

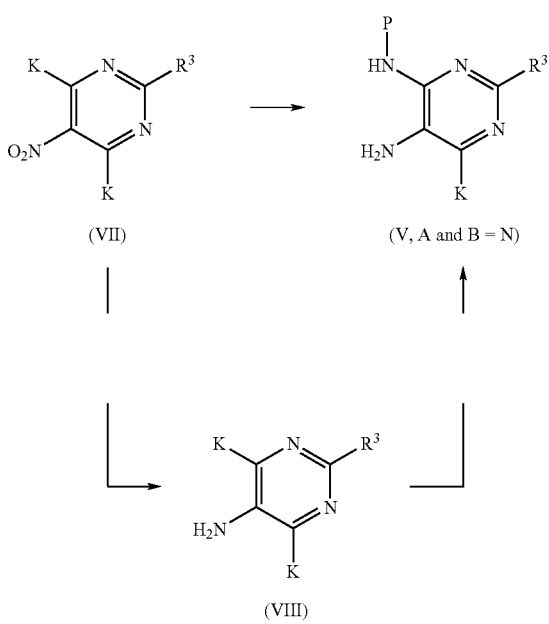

A compound of formula (VII) may be available from commercial sources, particularly for K=chloride. Compounds bearing pseudohalide K groups may be available from the corresponding dihydroxy compounds by treatment with an appropriate activating reagent, such as an organosulfonic anhydride or sulfonyl chloride.

Compound (VII) may be converted to (V) by either (i) monoalkylation with a compound P—NH$_2$, followed by reduction of the nitro group; (ii) reduction of the nitro group, to give an amine compound of formula (VIII), followed by monoalkylation with a compound P—NH$_2$; or (iii) use of a source of ammonia (ammonia gas, ammonium hydroxide, etc.) in either route, followed by protection of the amine group with the group P. Pyrimidine chemistry of this type is well represented in the literature, and is reviewed in *Comprehensive Heterocyclic Chemistry*, vol. 6. Alkylation of chloropyrimidines with amine compounds can be accomplished under either acidic (e.g. HCl or acetic) or basic (trialkylamines, potassium tert-butoxide, etc.) conditions. Nitro groups in compounds of this type can be reduced to amino groups using one of any number of conditions, including catalytic hydrogenation, tin dichloride, sodium dithionite, zinc metal, iron powder, etc.

Preparation of compounds of formula (V) wherein either A or B represent nitrogen atoms is shown in Scheme 5.

do this involves treatment of the dicyclohexylamine salt of compound (X) with phosphorus oxychloride to give (XI) wherein K=Cl.

Alternatively, both the hydroxy and pyridone groups in compound (X) can be activated at the same time, using stronger conditions such as phosphorus oxychloride and heat, or excess toluenesulfonic anhydride, to give compound (XII). Compound (XI) may be converted to the protected amine compound (XIII) using the same general route discussed above for the pyrimidines. Selective monoalkylation using compound (XII) is also possible, but will probably give mixtures of regioisomeric products (XIV) and (XV).

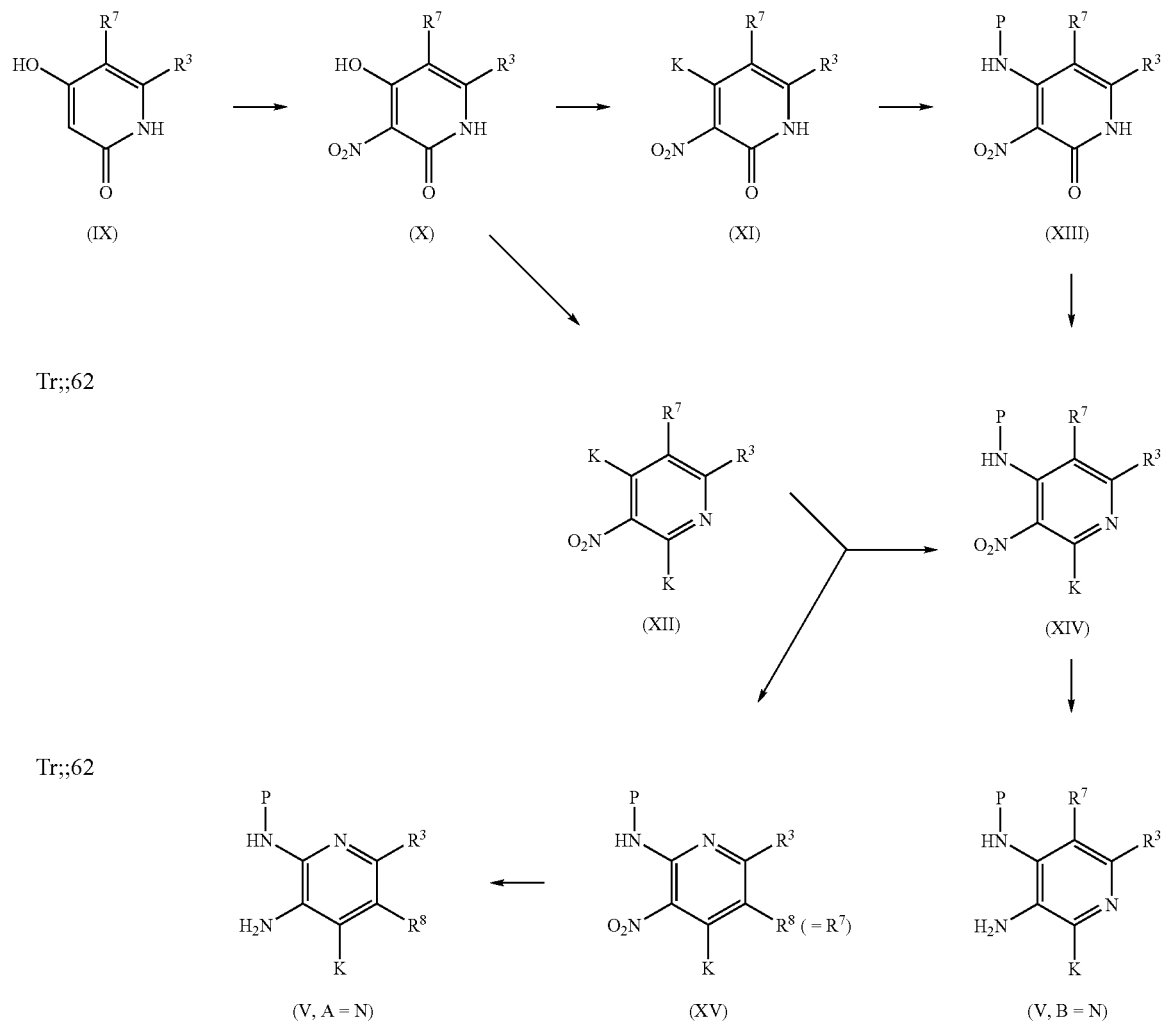

Scheme 5

An hydroxypyridone compound of formula (IX) can be nitrated to give compound (X), employing conditions such as concentrated or fuming nitric acid, optionally in the presence of concentrated sulfuric or acetic acid. The hydroxypyridone can be selectively monoactivated with a K group to give a compound of formula (XI); one method to The nitro groups in these compounds can then be reduced as discussed above, to give compounds of formula (V), wherein either A or B is nitrogen.

An alternative approach to the method involving introduction of the $R^1$ group at the final step is shown in Scheme 6.

Scheme 6

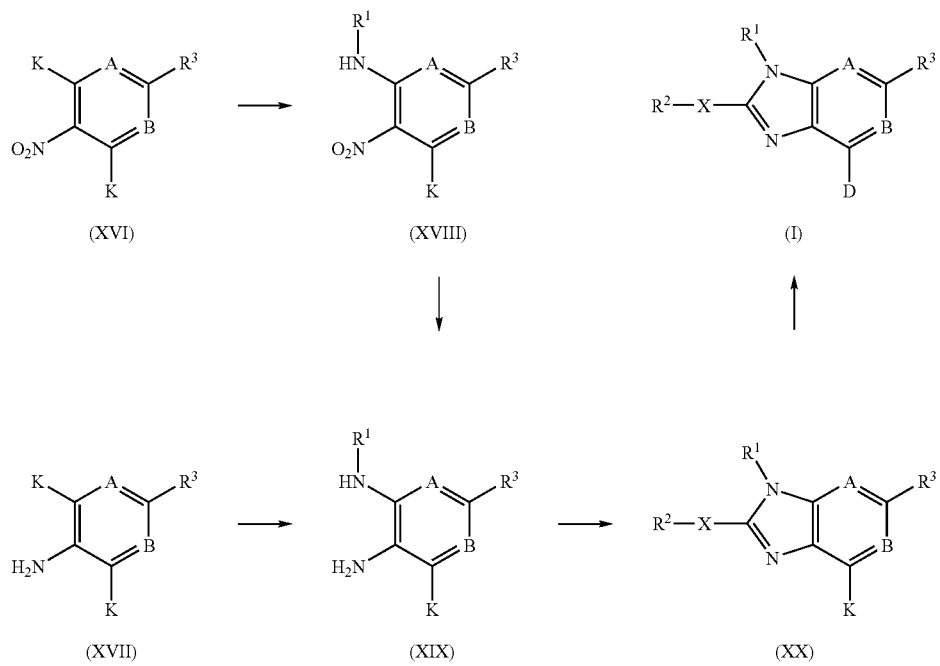

This is particularly useful in the cases where $R^1$ represents a group where alkylation of compound (II) is impractical (e.g. a very bulky $R^1$ group), but can also be used in a general manner. Here, compounds of formula (XVI) or (XVII) (either amino- or nitro-pyridines or pyrimidines) are alkylated with an amine reagent $R^1$—$NH_2$, under either acidic or basic conditions as described above.

Nitro compound (XVIII) can be converted to amine compound (XIX) by nitro reduction reactions described earlier. Compound (XIX) can be cyclized to imidazole compound (XX). As above, this reaction will depend upon the choice of X group. For example, for X=$CHR^9$, one can use an orthoester reagent such as $R^2CH(R^9)C(OR)_3$, with heating in neat solution or high-boiling solvents, and the optional presence of an acid catalyst (such as hydrochloric or sulfuric acid) (see Montgomery and Temple, *J. Org. Chem*. 1960, 25, 395). For X=$NR^{10}$, the cyclization is performed using reagents such as an guanidine reagent of the structure $R^2R^{10}N$—C(=NH)$NH_2$ or a urea-derived reagent of the structure $R^2R^{10}N$—C(=NH)D, where D represents a group like $OCH_3$, $SCH_3$ or $SO_2CH_3$. For X=O, the ring is formed using a reagent of the structure $(R^2O)_4C$ (with acetic acid catalysis), provided one has access to the reagent with the $R^2$ group of choice (see Brown and Lynn, *J. Chem. Soc. Perkin Trans. I* 1974, 349). Alternatively, the diamine (XIX) is treated with phosgene, followed by O-alkylation to introduce the $R^2$ group (such as a reagent like $R^2$—I or $R^2$—Br).

A similar route can be used for X=S, which would use thiophosgene or some similar reagent, followed by S-alkylation with the $R^2$ group. The sulfur atom in this compound (and sulfide groups throughout the molecule in general) can be oxidized to either the sulfoxide or sulfone if desired by treatment with an appropriate oxidizing agent such as potassium permanganate, potassium peroxomonosulfate or m-chloroperbenzoic acid. Finally, compound (XX) can be used in an aryl coupling reaction as described above to replace the K group with the desired aryl group in compound (I).

Methods of synthesis of compounds $R^1$—OH, $R^1$—J and $R^1$—$NH_2$ are related, in that the alcohol can be used in the synthesis of the other two compounds, as is shown in Scheme 7.

Scheme 7

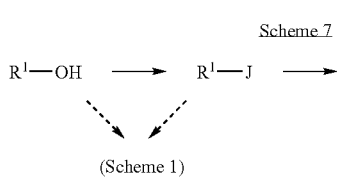

(Scheme 1)

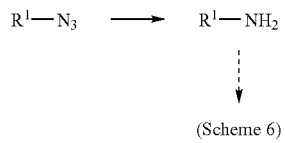

(Scheme 6)

For example, the hydroxy group may be converted to the following J groups, using the indicated reagents (this route is not limited to these J groups): methanesulfonate, using methanesulfonyl chloride or anhydride and an appropriate base; toluenesulfonate, using toluenesulfonyl chloride or anhydride and an appropriate base; iodide; using iodine/triphenylphosphine; bromide, using phosphorus tribromide or carbon tetrabromide/triphenylphosphine; or trifluoromethanesulfonate, using trifluoromethane-sulfonic anhydride and an appropriate base.

Both compounds $R^1$—OH and $R^1$—J are used in the methods portrayed in Scheme 1. Conversion of $R^1$—J to $R^1$—$N_3$ requires the use of an azide source, such as sodium azide, and a solvent such as dimethylsulfoxide or dimethylformamide, or water and a phase-transfer catalyst (such as tetrabutylammonium hydrogen sulfate). Reduction of the azide compound $R^1$—$N_3$ to $R^1$—$NH_2$ may be accomplished using reagents such as sodium borohydride or triphenylphosphine, or hydrogen gas and a catalyst (such as palladium on carbon). The amine $R^1$—$NH_2$ may then be employed in the methods portrayed in Scheme 6.

In the cases where the compound $R^1$—OH could be represented by a structure of formula (XXI) (Scheme 8), wherein $R^{1a}$ and $R^{1b}$ represents substructures which, taken together with the carbinol methine group, comprise the entire group $R^1$, this compound may be prepared by addition to a carbonyl compound.

An homologous approach may also be employed in the synthesis of alcohols $R^1$—OH, involving the ring-opening reaction of cyclic ether compounds with organometallic reagents (Scheme 9).

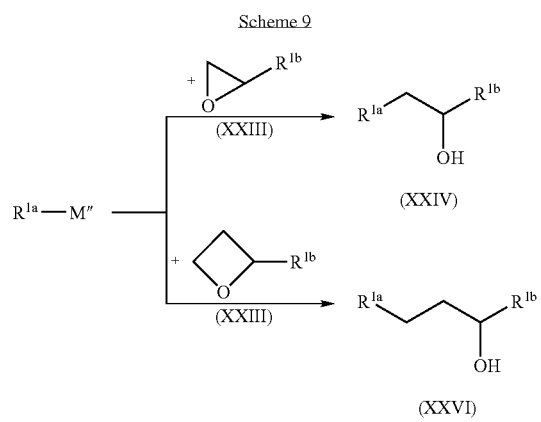

Here, an organometallic reagent $R^{1a}$—M″ is used, where M″ represents metals such as Mg, Zn or Cu. Especially useful is

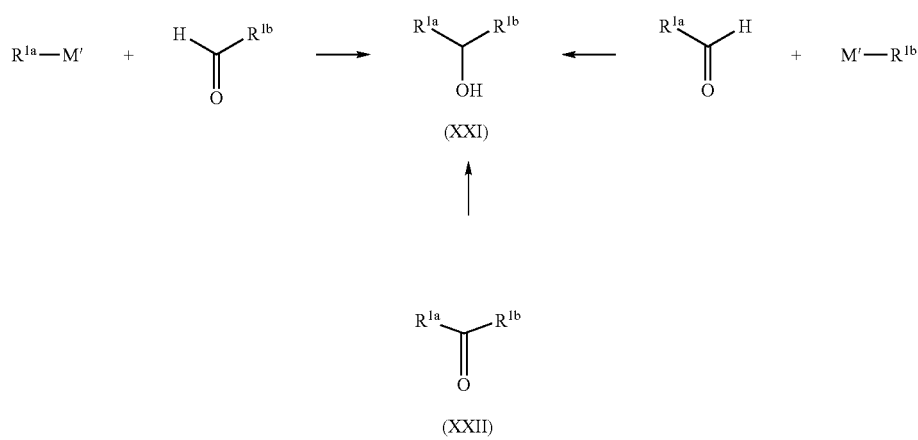

This route is particularly useful in the case where $R^{1a}$ or $R^{1b}$ represents a cycloalkyl group, such as cyclopropyl. An organometallic reagent (where M′ represents a metallic group, such as Li, CuCN, CuI, MgCl, MgBr, MgI, ZnCl, CrCl, etc.) can be allowed to react with an aldehyde reagent to prepare the alcohol compound of formula (XXI).

Alternatively, a ketone of formula (XXII) may be treated with a reducing agent, such as sodium borohydride, lithium aluminum hydride, etc., which will also generate the alcohol of formula (XXI). Standard methods of ketone synthesis may be used where appropriate in the preparation of compounds for formula (XXII), which will be familiar to those skilled in the art of organic synthesis.

the method described in Huynh, et al., Tetrahedron Letters 1979, (17), pp. 1503–1506, where organomagnesium reagents are allowed to react with cyclic ethers with catalysis provided by copper(I) iodide. Use of an epoxide compound of formula (XXIII) in this manner would result in synthesis of an alcohol compound of formula (XXIV), and use of an oxetane compound of formula (XXV) would generate an alcohol of formula (XXVI). Both compounds (XXIV) and (XXVI) are variants of $R^1$—OH.

Synthesis of compound $R^1$—$NH_2$ with formula (XXVII) is portrayed in Scheme 10.

Scheme 10

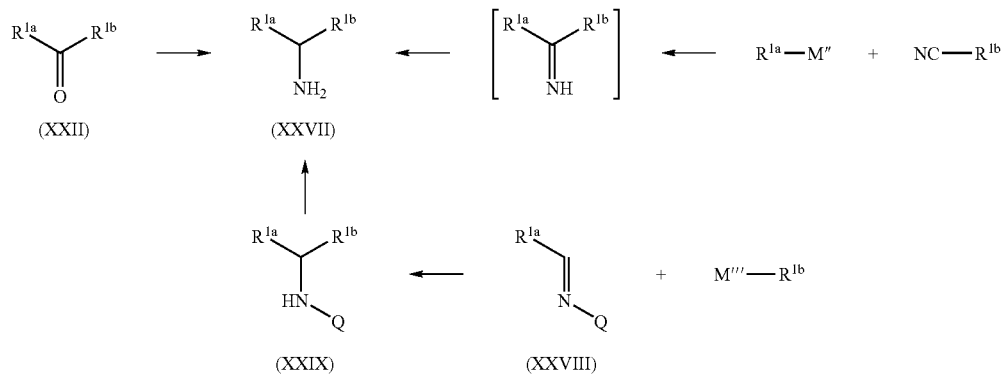

A simple reductive amination of ketone (XXII) will produce amine (XXVII). This reaction may be performed using anhydrous ammonia in the presence of hydrogen and a catalyst.

Alternatively, addition of an organometallic reagent to a nitrile compound gives an imine, which may be treated in situ with a reducing agent (such as sodium cyanoborohydride) to give the corresponding amine (XXVII). Finally, a compound of formula (XXVIII), wherein Q is an optionally-substituted oxygen atom (i.e. an oxime) or nitrogen atom (i.e. a hydrazone), may be allowed to react with an organometallic reagent $R^{1b}$—M'''. Here, metallic groups M''' such as MgBr, CuCl or $CeCl_2$ have been used in additions to oximes or hydrazones. The intermediate addition products of formula (XXIX) may be subjected to reductive cleavage (using conditions such as sodium/liquid ammonia or catalytic hydrogenation), which will afford amines (XXVII).

Amino acids, either naturally-occurring or synthetic, are potential sources of useful starting materials for the synthesis of the compounds of this invention. Scheme 11 shows some possible applications of this approach.

Scheme 11

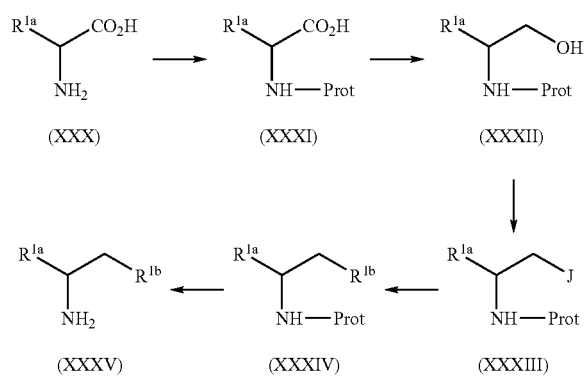

Protected amino acids of formula (XXXI) are prepared from the parent compounds of formula (XXX); useful protecting groups ("Prot") include tert-butoxycarbonyl, benzyloxycarbonyl and triphenylmethyl. Standard texts in peptide chemistry describe this protection. The carboxylic acid group may be reduced using reagents such as lithium borohydride, which gives alcohol (XXXII). The hydroxy group may be converted to a leaving group "J" as described before. The compound of formula (XXXIII) may be treated with appropriate reagents to produce a wide variety of functional groups included in the scope of this invention (compound (XXXIV)); displacement of J with cyanide (sodium cyanide in warm dimethylformamide may be used here) gives a nitrile, displacement of J with a mercaptan (in the presence of a base, such as potassium carbonate) gives a disulfide, displacement of J with a secondary amine gives a tertiary amine, etc.

Haloalkoxy-substituted aromatic groups (i.e., as ring D, either phenyl or pyridyl, having one or more haloalkoxy groups as substituents on the ring) may be introduced at several positions in the synthesis. For example, a reagent D—M (compound IV) may be prepared, wherein M is a metal suitable for cross-coupling with a heterocyclic compound (formula III, see above). In this case, the D group bears the haloalkoxy group, which is prepared according to methods discussed below. Alternatively, the complete molecule of Formula (I) with a phenolic OH substituent on the D group is treated with appropriate reagents to effect incorporation of the haloalkoxy functionality.

Phenolic groups are converted to haloalkoxy groups by haloalkyl alkylating reagents. For example, treatment of sodium phenolates (available from phenols upon treatment with basic reagents such as sodium hydride in appropriate solvents) with reagents such as 2,2,2-trifluoroethyl methanesulfonate (according to the method of F. Camps, J. Coll, A. Messeguer and M. A. Pericas, *Synthesis* 1980, p. 727) or 2,2,2-trifluoroethyl p-toluenesulfonate (according to the method of D. Preschler, T. Thiele and R. Ruhmann, *J. Fluorine Chem.* 1996, 79, p. 145–148) gives the corresponding aryl group substituted with a 2,2,2-trifluoroethoxy group. Many trifluoromethoxy-substituted aromatic reagents are available from commercial sources, which may be used to prepare compounds of the formula type IV by standard organic chemistry. Where the appropriate starting material is not available, phenolic OH groups are converted into trifluoromethoxy groups by treatment with reagents such as trifluoroacetic acid (according to Grinberg, et al., *Izv. Akad. Nauk SSSR, Ser. Khim.* 1997, p. 1505–1508) or carbon tetrachloride and antimony trifluoride with catalytic antimony pentachloride (according to Dow Chemical Co., U.S. Pat. No. 4,950,802).

Trifluoromethoxy aryl compounds are also made by conversion of a phenol to an intermediate group and subsequent fluorination to the desired product. Examples: are 1) the reaction of dithiocarbonates with 1,3-dibromo -5,5-dimethylpyrrolidine-2,4-dione/pyridinium fluoride (according to M. Kuroboshi, K. Suzuki and T. Hiyama, *Tetrahedron Lett.* 1992, 33, p. 4173–4176); 2) the reaction of aryl thiochloroformates with molybdenum hexafluoride (according to F. Mathey and J. Bensoam, *Tetrahedron Lett.* 1973); and 3) the reaction of aryl fluoroformates with sulfur tetrafluoride/HF/sodium fluoride (according to W. A. Sheppard, *J. Org. Chem.* 1964, 29), all which afford trifluoromethoxy aryl compounds. Difluoromethoxy groups are prepared from phenols by treatment with chlorodifluoromethane in the presence of sodium hydroxide (according to S. V. Shelyazhenko, Y. A. Fialkov and L. M. Yagupol'skii, *J. Org. Chem.* (*Russia*) 1992, p. 1317–1323). Shelyazhenko et al. also teaches the chlorination of such difluoromethoxy aryl groups to give aryl chlorodifluoromethoxy compounds. Other haloalkoxy compounds may be prepared by Mitsunobu-type coupling of phenols with halo-substituted alcohols (employing reagents like diethyl azodicarboxylate and triphenylphosphine).

Also provided herein are compositions comprising the compounds of this invention, particularly pharmaceutical compositions comprising pharmaeutically acceptable carriers and therapeutically effective amounts of the compounds provided herein. "Pharmaceutically acceptable carriers" are media generally accepted in the art for the delivery of biologically active agents to mammals, e.g., humans. Such carriers are generally formulated according to a number of factors well within the purview of those of ordinary skill in the art to determine and account for. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically acceptable carriers, and factors involved in their selection, are found in a variety of readily available sources, e.g., *Remington's Pharmaceutical Sciences,* 17th ed., Mack Publishing Company, Easton, Pa., 1985, the contents of which are incorporated herein by reference.

"Therapeutically effective amounts" of biologically active agents are amounts effective to lessen, inhibit or prevent diseases and disorders in mammals, or the symptoms thereof. Such amounts include optimal and suboptimal doses, and can be determined in a variety of ways known to ordinarily skilled artisans, e.g., by administering various amounts of a particular agent to an animal afflicted with a particular condition and then determining the effect on the animal. Typically, therapeutically effective amounts of biologically active agents range from about 0.1 mg per kg of a mammal being treated to about 100 mg per kg, although amounts outside this range can also be therapeutically effective under a variety of conditions.

In particular, therapeutically effective amounts of the compounds of this invention are amounts effective to antagonize, or lower, levels of corticotropin releasing factor (CRF) in mammals, thereby alleviating in the mammals conditions characterized by abnormally high levels of CRF expression. In this regard, CRF is known to have a broad extrahyopthalamic distribution in the CNS, contributing therein to a wide spectrum of autonomic, behavioral and physiological effects (see, e.g., Vale et al., 1983; Koob, 1985; and, De Souza et al., 1985). For example, CRF concentrations are significantly increased in the cerebrospinal fluid of patients afflicted with affective disorder or major depression (see, e.g., Nemeroff et al., 1984; Banki et al., 1987; France et al., 1988; Arato et al., 1989), and thus, antagonism of CRF should ameliorate these conditions.

Moreover, excessive levels of CRF are known to produce anxiogenic effects in animal models (see, e.g., Britton et al., 1982; Berridge and Dunn, 1986 and 1987), and, CRF antagonists are known to produce anxiolytic effects; accordingly, therapeutically effective amounts of compounds provided herein are, for example, determined by assessing the anxiolytic effects of varying amounts of the compounds in such animal models. Furthermore, clinical data provides evidence that CRF has a role in psychiatric disorders and neurological diseases including depression, anxiety-related disorders and feeding disorders; a role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system (see, e.g., E. B. De Souza, 1988).

Neurochemical, endocrine and receptor binding studies have all demonstrated interactions between CRF and benzodiazepine anxiolytics, providing further evidence for the involvement of CRF in these disorders. Chlordiazepoxide attenuates the "anxiogenic" effects of CRF in both the conflict test [K. T. Britton et al., *Psychopharmacology* 86:170 (1985); K. T. Britton et al., *Psychopharmacology* 94:306 (1988)] and in the acoustic startle test [N. R. Swerdlow et al., *Psychopharmacology* 88:147 (1986)] in rats. The benzodiazepine receptor antagonist (Ro15–1788), which was without behavioral activity alone in the operant conflict test, reversed the effects of CRF in a dose-dependent manner while the benzodiazepine inverse agonist (FG7142) enhanced the actions of CRF [K. T. Britton et al., *Psychopharmacology* 94:306 (1988)].

The contents of the above-cited disclosures are incorporated herein by reference.

Accordingly, antagonism of CRF by compounds of this invention is an effective means of treating conditions such as affective disorder, depression and anxiety. Additional treatable conditions include, without limitation: headache, irritable bowel syndrome, post-traumatic stress disorder, supranuclear palsy, immune suppression, Alzheimer's disease, Huntington's disease, Parkinson's disease, progressive supranuclear palsy, amyotrophic lateral sclerosis, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis and hypoglycemia. Therefore, this invention further provides a method of treating such conditions, said method comprising administering to mammals afflicted with the conditions a dose of a pharmaceutical composition provided herein.

The following examples describe experimental procedures used to prepare particular compounds provided by this invention and set forth in Tables 1 and 2 hereinbelow. However, those of ordinary skill in the art will readily understand that these examples are not intended to be limiting, and are merely illustrative of the invention as defined in the claims which follow thereafter.

EXAMPLES

Part I

The following Table I sets forth exemplary compounds provided herein (wherein A and B are each N and ring D is a phenyl ring). The compounds are listed in the table sequentially, by example number, along with melting point ("m. p.") data; or, where the compound is listed as an "oil" in the column for "m. p.," spectral data is provided following the table. These compounds were synthesized according to the schemes set forth hereinabove; specific examples of reaction conditions and materials by which two of the compounds, 6-(2-Chloro-4-trifluoromethoxyphenyl)-9-dicyclopropylmethyl-8-ethylpurine (Example 8) and 6-(2-Chloro-4-difluoromethoxyphenyl)-8-ethyl-9-(2-pentyl)purine (Example 11), were made are provided.

TABLE 1

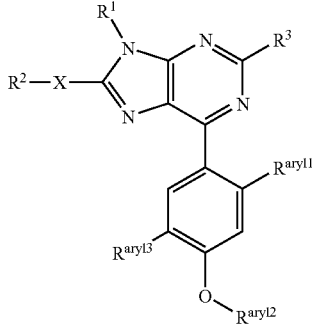

| Ex. No. | $R^{1a}$ | X | $R^2$ | $R^3$ | $R^{aryl1}$ | $R^{aryl2}$ | $R^{aryl3}$ | m.p.[b] |
|---|---|---|---|---|---|---|---|---|
| 1 | B | $CH_2$ | $CH_3$ | H | Cl | $CF_3$ | H | oil |
| 2 | C | $CH_2$ | $CH_3$ | H | Cl | $CF_3$ | H | oil |
| 3 | E | $CH_2$ | $CH_3$ | H | Cl | $CF_3$ | H | oil |
| 4 | F | $CH_2$ | $CH_3$ | H | Cl | $CF_3$ | H | oil |
| 5 | K | $CH_2$ | $CH_3$ | H | Cl | $CF_3$ | H | 103–104 |
| 6 | L | $CH_2$ | $CH_3$ | H | Cl | $CF_3$ | H | 88–92 |
| 7 | V | $CH_2$ | $CH_3$ | H | Cl | $CF_3$ | H | oil |
| 8 | Y | $CH_2$ | $CH_3$ | H | Cl | $CF_3$ | H | 119–120 |
| 9 | L | $CH_2$ | $CH_3$ | H | $CH_3$ | $CF_3$ | H | 77–78 |
| 10 | A | O | $CH_3$ | H | $CH_3$ | $CF_3$ | H | 99–100 |
| 11 | B | $CH_2$ | $CH_3$ | H | Cl | $CHF_2$ | H | oil |
| 12 | C | $CH_2$ | $CH_3$ | H | Cl | $CHF_2$ | H | oil |
| 13 | D | $CH_2$ | $CH_3$ | H | Cl | $CHF_2$ | H | oil |
| 14 | E | $CH_2$ | $CH_3$ | H | Cl | $CHF_2$ | H | oil |
| 15 | G | $CH_2$ | $CH_3$ | H | Cl | $CHF_2$ | H | oil |
| 16 | I | $CH_2$ | $CH_3$ | H | Cl | $CHF_2$ | H | oil |
| 17 | J | $CH_2$ | $CH_3$ | H | Cl | $CHF_2$ | H | oil |
| 18 | L | $CH_2$ | $CH_3$ | H | Cl | $CHF_2$ | H | 89–90 |
| 19 | N | $CH_2$ | $CH_3$ | H | Cl | $CHF_2$ | H | oil |
| 20 | R | $CH_2$ | $CH_3$ | H | Cl | $CHF_2$ | H | oil |
| 21 | V | $CH_2$ | $CH_3$ | H | Cl | $CHF_2$ | H | oil |
| 22 | W | $CH_2$ | $CH_3$ | H | Cl | $CHF_2$ | H | 139–142 |
| 23 | X | $CH_2$ | $CH_3$ | H | Cl | $CHF_2$ | H | oil |
| 24 | Y | O | $CH_3$ | H | Cl | $CHF_2$ | H | 115–117 |
| 25 | Z | $CH_2$ | $CH_3$ | H | Cl | $CHF_2$ | H | oil |
| 26 | AA | $CH_2$ | $CH_3$ | H | Cl | $CHF_2$ | H | oil |
| 27 | BB | $CH_2$ | $CH_3$ | H | Cl | $CHF_2$ | H | oil |
| 28 | G | $CH_2$ | $CH_3$ | H | Cl | $CF_3$ | H | 76–79 |
| 29 | N | O | $CH_3$ | H | Cl | $CHF_2$ | H | 110–112 |
| 30 | CC | $CH_2$ | $CH_3$ | H | Cl | $CHF_2$ | H | 121–122 |
| 31 | CC | O | $CH_3$ | H | Cl | $CHF_2$ | H | 90–91 |
| 32 | Y | $CH_2$ | $CH_3$ | H | Cl | $CHF_2$ | H | 116–117 |

[a]Key to $R^1$ codes: A = 2-butyl; B = 2-pentyl; C = 2-hexyl; D = 2-heptyl; E = 3-pentyl; F = 3-hexyl; G = 3-heptyl; H = 1-methoxy-3-pentyl; I = 4-heptyl; J = 1-cyclopropyl-1-ethyl; K = 1-cyclopropyl-1-propyl; L = 1-cyclopropyl-1-butyl; M = 1-cyclopropyl-3-methoxy-1-propyl; N = 1-cyclobutyl-1-ethyl; O = 1-cyclobutyl-1-propyl; P = 1-cyclobutyl-1-butyl; Q = 1-cyclobutyl-3-methoxy-1-propyl; R = 1-cyclopentyl-1-ethyl; S = 1-cyclopentyl-1-propyl; T = 1-cyclopentyl-1-butyl; U = 1-cyclopentyl-3-methoxy-1-propyl; V = ?-cyclopropylbenzyl; W = 1-phenyl-2-butyn-1-yl; X = 1-cyclopropyl-2-butyn-1-yl; Y = dicyclopropylmethyl; Z = 2-hexyn-4-yl; AA = cyclopentyl; BB = 1-cyclopropyl-2-propyl; CC = dicyclobutylmethyl
[b]Melting point data; for compounds listed as oils, spectral data is provided hereinbelow.

Spectral Data:

Example 1

TLC $R_F$ 0.41 (25:75 ethyl acetate-hexane). $^1$H NMR (300 MHz, CDCl$_3$): Δ 8.96 (1H, s), 7.76 (1H, d, J=8.4 Hz), 7.45–7.44 (1H, m), 7.27 (1H, dm, J=8 Hz), 4.61–4.51 (1H, m), 2.98 (2H, dq, J=7.5, 1.6 Hz), 2.48–2.35 (1H, m), 2.10–1.98 (1H, m), 1.75 (3H, d, J=7.0 Hz), 1.41 (3H, t, J=7.5 Hz), 1.35–1.22 (2H, m), 0.93 (3H, t, J=7.2 Hz). MS (NH$_3$-CI): m/e calculated for C$_{19}$H$_{21}$ClF$_3$N$_4$O: 413.1349, found 413.1344; 416 (8), 415 (35), 414 (24), 413 (100).

Example 2

TLC $R_F$ 0.45 (25:75 ethyl acetate-hexane). $^1$H NMR (300 MHz, CDCl$_3$): Δ 8.96 (1H, s), 7.77 (1H, d, J=8.4 Hz), 7.44 (1H, m), 7.27 (1H, dm, J=8 Hz), 4.57–4.49 (1H, m), 2.97 (2H, dq, J=7.7, 1.7 Hz), 2.47–2.36 (1H, m), 2.12–2.02 (1H, m), 1.75 (3H, d, J=7.0 Hz), 1.41 (3H, t, J=7.7 Hz), 1.33–1.21 (4H, m), 0.86 (3H, t, J=7.3 Hz). MS (NH$_3$-CI): m/e calculated for C$_{20}$H$_{23}$ClF$_3$N$_4$O: 427.1509, found 427.1507; 430 (8), 429 (35), 428 (25), 427 (100).

Example 3

TLC $R_F$ 0.44 (25:75 ethyl acetate-hexane). $^1$H NMR (300 MHz, CDCl$_3$): Δ 8.95 (1H, s), 7.80 (1H, d, J=8.4 Hz), 7.45–7.44 (1H, m), 7.30 (1H, dm, J=8 Hz), 4.23–4.17 (1H, m), 2.97 (2H, q, J=7.6 Hz), 2.54–2.39 (2H, m), 2.14–2.00 (2H, m), 1.43 (3H, t, J=7.6 Hz), 0.84 (6H, t, J=7.3 Hz). MS (NH$_3$-CI): m/e calculated for C$_{19}$H$_{21}$ClF$_3$N$_4$O: 413.1368, found 413.1373; 416 (8), 415 (34), 414 (24), 413 (100).

Example 4

TLC $R_F$ 0.48 (25:75 ethyl acetate-hexane). $^1$H NMR (300 MHz, CDCl$_3$): Δ 8.95 (1H, s), 7.79 (1H, d, J=8.4 Hz), 7.45–7.43 (1H, m), 7.27 (1H, dm, J=8 Hz), 4.35–4.25 (1H, m), 2.96 (2H, q, J=7.4 Hz), 2.42 (2H, br), 2.12–1.93 (2H, m), 1.43 (3H, t, J=7.4 Hz), 1.37–1.22 (2H, m), 0.91 (3H, t, J=7.2 Hz), 0.83 (3H, t, J=7.5 Hz). MS (NH$_3$-CI) m/e calculated for C$_{20}$H$_{23}$ClF$_3$N$_4$O: 427.1514, found 427.1515; 430 (8), 429 (34), 428 (25), 427 (100).

Example 5 see Table 1 for melting point data.

Example 6

TLC R$_F$ 0.50 (25:75 ethyl acetate-hexane). $^1$H NMR (300 MHz, CDCl$_3$): Δ 8.96 (1H, s), 7.80 (1H, d, J=8.4 Hz), 7.45–7.43 (1H, m), 7.31–7.27 (1H, dm, J=8 Hz), 3.80–3.73 (1H, m), 2.93 (2H, q, J=7.3 Hz), 2.40 (1H, br), 2.25–2.14 (1H, m), 1.95 (1H, br), 1.42 (3H, t, J=7.5 Hz), 1.35–1.10 (2H, m), 0.92 (3H, t, J=7.3 Hz), 0.91–0.80 (1H, m), 0.53–0.44 (2H, m), 0.24–0.14 (1H, m). MS (NH$_3$-CI): m/e calculated for C$_{21}$H$_{23}$ClF$_3$N$_4$O: 439.1519, found 439.1524; 442 (8), 441 (34), 440 (26), 439 (100).

Example 7

TLC R$_F$ 0.46 (25:75 ethyl acetate-hexane). $^1$H NMR (300 MHz, CDCl$_3$): Δ 8.98 (1H, s), 7.83 (1H, d, J=8.4 Hz), 7.46–7.27 (7H, m), 5.13 (1H, d, J=10.7 Hz), 2.88–2.62 (2H, m), 2.15 (1H, br), 1.26 (3H, t, J=7.5 Hz), 1.12–1.02 (1H, m), 0.78–0.62 (2H, m), 0.54–0.44 (1H, m). MS (NH$_3$-CI): m/e calculated for C$_{24}$H$_{21}$ClF$_3$N$_4$O: 473.1361, found 473.1365; 476 (9), 475 (36), 474 (29), 473 (100).

Example 8 see Table 1 for melting point data.

Example 9 see Table 1 for melting point data.

Example 10 see Table 1 for melting point data.

Example 11

TLC R$_F$ 0.14 (20:80 ethyl acetate-hexane). $^1$H NMR (300 MHz, CDCl$_3$): Δ 8.96 (1H, s), 7.73 (1H, d, J=8.5 Hz), 7.34 (1H, d, J=2.5 Hz), 7.18 (1H, dd, J=8.5, 2.5 Hz), 6.57 (1H, t, J=73.2 Hz), 4.60–4.50 (1H, m), 2.97 (2H, dq, J=7.5, 1.7 Hz), 2.47–2.35 (1H, m), 2.10–1.98 (1H, m), 1.74 (3H, d, J=6.6 Hz), 1.41 (3H, t, J=7.5 Hz), 1.39–1.22 (2H, m), 0.93 (3H, t, J=7.2 Hz). $^{19}$F NMR (300 MHz, CDCl$_3$): ? –81.6 (2F, d, J=73.2 Hz). MS (AP): m/e calc'd for C$_{19}$H$_{22}$ClF$_2$N$_4$O: 395.1450, found 395.1446; 395 (100).

Example 12

TLC R$_F$ 0.15 (20:80 ethyl acetate-hexane). $^1$H NMR (300 MHz, CDCl$_3$): Δ 8.96 (1H, s), 7.74 (1H, d, J=8.5 Hz), 7.35 (1H, d, J=2.5 Hz), 7.18 (1H, dd, J=8.5, 2.5 Hz), 6.57 (1H, t, J=73.2 Hz), 4.60–4.49 (1H, m), 2.97 (2H, dq, J=7.7, 1.8 Hz), 2.49–2.36 (1H, m), 2.12–2.00 (1H, m), 1.75 (3H, t, J=7.0 Hz), 1.41 (3H, t, J=7.5 Hz), 1.40–1.23 (4H, m), 0.86 (3H, t, J=7.2 Hz). MS (AP): m/e calc'd for C$_{20}$H$_{24}$ClF$_2$N$_4$O: 409.1606, found 409.1590; 409 (100).

Example 13

TLC R$_F$ 0.18 (20:80 ethyl acetate-hexane). $^1$H NMR (300 MHz, CDCl$_3$): Δ 8.96 (1H, s), 7.74 (1H, d, J=8.4 Hz), 7.34 (1H, d, J=2.1 Hz), 7.18 (1H, dd, J=8.4, 2.1 Hz), 6.57 (1H, t, J=73.2 Hz), 4.60–4.49 (1H, m), 2.97 (2H, dq, J=7.7, 1.8 Hz), 2.47–2.35 (1H, m), 2.11–1.99 (1H, m), 1.74 (3H, d, J=6.6 Hz), 1.41 (3H, t, J=7.7 Hz), 1.37–1.20 (6H, m), 0.84 (3H, t, J=7.0 Hz). MS (AP): m/e calc'd for C$_{21}$H$_{26}$ClF$_2$N$_4$O: 423.1763, found 423.1764; 423 (100).

Example 14

TLC R$_F$ 0.15 (20:80 ethyl acetate-hexane). $^1$H NMR (300 MHz, CDCl$_3$): Δ 8.94 (1H, s), 7.77 (1H, d, J=8.5 Hz), 7.35 (1H, d, J=2.6 Hz), 7.19 (1H, dd, J=8.5, 2.6 Hz), 6.57 (1H, t, J=73.0 Hz), 4.21 (1H, br), 2.96 (1H, q, J=7.4 Hz), 2.53–2.39 (2H, m), 2.15–2.00 (2H, m), 1.43 (3H, t, J=7.4 Hz), 0.83 (6H, t, J=7.5 Hz). MS (AP): m/e calc'd for C$_{19}$H$_{22}$ClF$_2$N$_4$O: 395.1450, found 395.1437; 395 (100).

Example 15

TLC R$_F$ 0.22 (20:80 ethyl acetate-hexane). $^1$H NMR (300 MHz, CDCl3): Δ 8.95 (1H, s), 7.78 (1H, d, J=8.4 Hz), 7.35 (1H, d, J=2.5 Hz), 7.19 (1H, dd, J=8.4, 2.5 Hz), 6.58 (1H, t, J=73.2 Hz), 4.27 (1H, br), 2.95 (2H, q, J=7.7 Hz), 2.41 (2H, br), 2.11–1.98 (2H, m), 1.43 (3H, t, J=7.7 Hz), 1.39–1.20 (4H, m), 0.85 (3H, t, J=7.3 Hz), 0.82 (3H, t, J=7.3 Hz). MS (AP): m/e calc'd for C$_{21}$H$_{26}$ClF$_2$N$_4$O: 423.1763, found 423.1758; 423 (100).

Example 16

TLC R$_F$ 0.29 (20:80 ethyl acetate-hexane). $^1$H NMR (300 MHz, CDCl$_3$): Δ 8.95 (1H, s), 7.77 (1H, d, J=8.4 Hz), 7.35 (1H, d, J=2.2 Hz), 7.19 (1H, dd, J=8.4, 2.2 Hz), 6.57 (1H, t, J=73.2 Hz), 4.38 (1H, br), 2.95 (2H, q, J=7.3 Hz), 2.39 (2H, br), 2.05–1.92 (2H, m), 1.43 (3H, t, J=7.3 Hz), 1.38–1.21 (2H, m), 1.19–1.02 (2H, m), 0.91 (6H, t, J=7.3 Hz). MS (AP): m/e calc'd for C$_{21}$H$_{26}$ClF$_2$N$_4$O: 423.1763, found 423.1752; 423 (100).

Example 17

TLC R$_F$ 0.11 (20:80 ethyl acetate-hexane). $^1$H NMR (300 MHz, CDCl$_3$): Δ 8.96 (1H, s), 7.75 (1H, d, J=8.8 Hz), 7.35 (1H, d, J=2.6 Hz), 7.19 (1H, dd, J=8.8, 2.6 Hz), 6.57 (1H, t, J=73.0 Hz), 3.81–3.71 (1H, m), 3.00–2.90 (2H, m), 2.09–1.99 (1H, m), 1. 82 (3H, d, J=7.0 Hz), 1.40 (3H, t, J=7.5 Hz), 0.88–0.78 (1H, m), 0.58–0.41 (2H, m), 0.30–0.20 (1H, m). MS (AP): m/e calc'd for C$_{19}$H$_{20}$ClF$_2$N$_4$O: 393.1293, found 393.1281; 393 (100).

Example 18 see Table 1 for melting point data.

Example 19

TLC R$_F$ 0.26 (30:70 ethyl acetate-hexane). $^1$H NMR (300 MHz, CDCl$_3$): Δ 8.95 (1H, s), 7.74 (1H, d, J=8.4 Hz), 7.35 (1H, d, J=2.2 Hz), 7.18 (1H, dd, J=8.4, 2.2 Hz), 6.57 (1H, t, J=73.2 Hz), 4.44 (1H, br), 3.57 (1H, br), 3.01 (2H, dq, J=7.3, 1.5 Hz), 2.28 (1H, br), 1.98–1.70 (4H, m), 1.63 (3H, d, J=7.0 Hz), 1.62–1.50 (1H, m), 1.43 (3H, t, J=7.3 Hz). MS (AP): m/e calc'd for C$_{20}$H$_{22}$ClF$_2$N$_4$O: 407.1450, found 407.1450; 407 (100).

Example 20

TLC R$_F$ 0.11 (20:80 ethyl acetate-hexane). $^1$H NMR (300 MHz, CDCl$_3$): Δ 8.95 (1H, s), 7.75 (1H, d, J=8.4 Hz), 7.34 (1H, d, J=2.2 Hz), 7.18 (1H, dd, J=8.4, 2.2 Hz), 6.57 (1H, t, J=73.0 Hz), 4.22 (1H, br), 3.15 (1H, br), 3.03–2.94 (2H, m), 2.11–2.00 (1H, m), 1.74 (3H, d, J=6.6 Hz), 1.72–1.49 (3H, m), 1.42 (3H, t, J=7.5 Hz), 1.38–1.25 (4H, m). MS (AP): m/e calc'd for $C_{21}H_{24}ClF_2N_4O$: 421.1606, found 421.1603; 421 (100).

Example 21

TLC $R_F$ 0.20 (20:80 ethyl acetate-hexane). $^1$H NMR (300 MHz, CDCl$_3$): Δ 8.98 (1H, s), 7.80 (1H, d, J=8.4 Hz), 7.48–7.27 (6H, m), 7.19 (1H, dd, J=8.4, 2.2 Hz), 6.58 (1H, t, J=73.0 Hz), 5.13 (1H, br d, J=10.6 Hz), 2.89–2.61 (2H, m), 1.26 (3H, t, J=7.3 Hz), 1.12–1.02 (1H, m), 0.78–0.58 (3H, m), 0.38–0.28 (1H, m). MS (AP): m/e calc'd for $C_{24}H_{22}ClF_2N_4O$: 455.1451, found 455.1448; 455 (100).

Example 22

TLC $R_F$ 0.21 (20:80 ethyl acetate-hexane). $^1$H NMR (300 MHz, CDCl$_3$): Δ 9.04 (1H, s), 7.78 (1H, d, J=8.4 Hz), 7.46–7.30 (6H, m), 7.20 (1H, dd, J=8.4, 2.2 Hz), 7.19 (1H, d, J=2.6 Hz), 6.58 (1H, t, J=73.0 Hz), 2.98 (1H, dq, J=15.9, 7.5 Hz), 2.65 (1H, dq, J=15.9, 7.5 Hz), 2.00 (3H, d, J=2.6 Hz), 1.16 (3H, t, J=7.5 Hz). MS (AP): m/e calc'd for $C_{24}H_{20}ClF_2N_4O$: 453.1293, found 453.1298; 453 (100).

Example 23

TLC $R_F$ 0.16 (20:80 ethyl acetate-hexane). $^1$H NMR (300 MHz, CDCl$_3$): Δ 8.97 (1H, s), 7.75 (1H, d, J=8.4 Hz), 7.35 (1H, d, J=2.2 Hz), 7.19 (1H, dd, J=8.4, 2.2 Hz), 6.58 (1H, t, J=73.0 Hz), 5.19 (1H, dq, J=8.2, 2.2 Hz), 3.35–3.07 (2H, m), 1.88 (3H, d, J=2.2 Hz), 1.70–1.59 (1H, m), 1.48 (3H, t, J=7.5 Hz), 0.88–0.78 (2H, m), 0.60–0.45 (2H, m). MS (AP): m/e calc'd for $C_{21}H_{20}ClF_2N_4O$: 417.1294, found 417.1301; 417 (100).

Example 24 see Table 1 for melting point data.

Example 25

TLC $R_F$ 0.13 (20:80 ethyl acetate-hexane). 1H NMR (300 MHz, CDCl$_3$): Δ 8.99 (1H, s), 7.74 (1H, d, J=8.4 Hz), 7.35 (1H, d, J=2.2 Hz), 7.19 (1H, dd, J=8.4, 2.2 Hz), 6.58 (1H, t, J=73.0 Hz), 5.50 (1H, tq, J=7.8, 2.2 Hz), 3.19 (1H, dq, J=15.6, 7.5 Hz), 3.06 (1H, dq, J=15.6, 7.5 Hz), 2.35–2.09 (2H, m), 1.88 (3H, d, J=2.2 Hz), 1.46 (3H, t, J=7.5 Hz), 1.01 (3H, t, J=7.5 Hz). MS (AP): m/e calc'd for $C_{20}H_{20}ClF_2N_4O$: 405.1294, found 405.1291; 405 (100).

Example 26

TLC $R_F$ 0.36 (25:75 ethyl acetate-hexane). $^1$H NMR (300 MHz, CDCl$_3$): Δ 8.96 (1H, s), 7.73 (1H, d, J=8.4 Hz), 7.44 (1H, d, J=1.1 Hz), 7.28 (1H, dd, J=8.4, 1.1 hz), 4.79 (1H, -pentet, J=8.4 Hz), 3.01 (2H, q, J=7.7 Hz), 2.62–2.50 (2H, m), 2.23–2.07 (2H, m), 1.89–1.77 (2H, m), 1.66–1.49 (2H, m), 1.41 (3H, t, J=7.7 Hz). MS (NH$_3$-CI): m/e calculated for $C_{19}H_{19}ClF_3N_4O$: 411.1205, found 411.1208; 414 (7), 413 (34), 412 (24), 411 (100).

Example 27

TLC $R_F$ 0.30 (30:70 ethyl acetate-hexane). $^1$H NMR (300 MHz, CDCl$_3$): Δ 8.95 (1H, s), 7.73 (1H, d, J=8.5 Hz), 7.34 (1H, d, J=2.1 Hz), 7.19 (1H, dd, J=8.5, 2.1 Hz), 6.57 (1H, t, J=73.3 Hz), 4.65–4.58 (1H, m), 3.02 (2H, q, J=7.6 Hz), 2.48–2.38 (1H, m), 1.85–1.76 (1H, m), 1.80 (3H, d, J=7.0 Hz), 1.42 (3H, t, J=7.6 Hz), 0.49–0.41 (2H, m), 0.38–0.26 (1H, m), 0.15–0.07 (1H, m), −0.13–0.21 (1H, m). MS (API): m/e 410 (7), 409 (35), 408 (22), 407 (100). Analysis calculated for $C_{20}H_{21}ClF_2N_4O$: C, 59.04; H, 5.20; N, 13.77; found: C, 58.76; H, 5.09; N, 13.72.

Example 28 see Table 1 for melting point data.

Example 29 see Table 1 for melting point data.

Example 30 see Table 1 for melting point data.

Example 31 see Table 1 for melting point data.

Example 32 see Table 1 for melting point data.

Synthesis:
Preparation of 6-(2-Chloro-4-trifluoromethoxyphenyl)-9-dicyclopropylmethyl-8-ethylpurine (Example 8)

Part A. A solution of 4-trifluoromethoxyaniline (12.0 mL, 88.8 mmol) and N-chlorosuccinimide (13.04 g, 97.7 mmol) in acetonitrile (90 mL) was heated to reflux for 12 h. After cooling, the solution was filtered and evaporated, and the residual material was separated by column chromatography (silica gel, 10:90 ethyl acetate-hexane) to afford the product, 2-chloro-4-trifluoromethoxyaniline, as a liquid. The product was further purified by distillation to afford 18.14 g (85.7 mmol, 97%) pure product, b.p. 50–60° C./5 mm Hg (bulb-to-bulb). $^1$H NMR (300 MHz, CDCl$_3$): Δ 7.16 (1H, d, J=2.5 Hz), 6.96 (1H, dd, J=8.8, 2.5 Hz), 6.73 (1H, d, J=8.8 Hz), 4.08 (2H, br s). MS (H$_2$O-GC/MS): m/e 214 (27), 213 (17), 212 (100).

Part B. A solution of the aniline from Part A (17.97 g, 84.9 mmol) in concentrated hydrochloric acid (50 mL) was cooled to −5° C., and treated with a saturated aqueous solution of sodium nitrite (6.45 g, 93.5 mmol) After stirring for 30 min., the solution was diluted with 50 mL cyclohexane and 50 mL dichloromethane, and the resulting mixture was stirred vigorously while a saturated aqueous solution of potassium iodide (28.2 g, 170 mmol) was added dropwise. The resulting solution was allowed to stir for 12 h, then was partitioned between water and dichloromethane. The organic phase was washed with 1 N aqueous sodium bisulfite solution and brine. The three aqueous phases were back-extracted in sequence with dichloromethane, and the organic phases were combined, dried over anhydrous magnesium sulfate, filtered and evaporated. The product was purified by distillation to afford the product, 3-chloro-4-iodo-trifluoroanisole (21.38 g, 66.3 mmol, 78%). b.p. 60–70° C./1 mm Hg (bulb-to-bulb). $^1$H NMR (300 MHz, CDCl$_3$): Δ 7.87 (1H, d, J=8.8 Hz), 7.35 (1H, d, J=2.5 Hz), 6.87 (1H, J=ddd, J=8.8 Hz, 2.5H, 0.7 Hz). MS (H$_2$O-GC/MS): m/e 324 (31), 323 (10), 322 (100).

Part C. A solution of the iodide from Part B (17.5 g, 54.3 mmol) in THF (50 mL) was cooled to −90° C., and treated dropwise with a hexane solution of n-butyllithium (38.0 mL, 1.6 M, 60.8 mmol). After stirring for 30 min., the resulting solution was treated by syringe with triisopropylborate (14.0 mL, 60.6 mmol) and allowed to warm to ambient temperature with stirring for 10 h. The solution was treated with 6 N hydrochloric acid and water (20 mL each), and stirred for 1 h. Then, the mixture was partitioned between water and ethyl acetate and separated. The aqueous phase was extracted with additional ethyl acetate, and the extracts were combined, dried over magnesium sulfate, filtered and evaporated. The residual material was triturated with hexane and filtered, and the filtrate allowed to stand to give a second crop of solid product, which was 2-chloro-4-trifluoromethoxybenzeneboronic acid (3.95 g, 16.5 mmol, 30%). m.p. 160–162° C. $^1$H NMR (300 MHz, CDCl$_3$): Δ 8.00 (1H, d, J=8.1 Hz), 7.24 (1H, d, J=1.1 Hz), 7.19 (1H, dd, J=8.1, 1.1 Hz), 5.31 (2H, s). MS (H$_2$O-GC/MS, as ethylene glycol ester): m/e 267 (100).

Part D. A solution of dicyclopropyl ketone (50 g) in absolute methanol (150 mL) in an autoclave vessel was charged with W4 Raney nickel (12 g, washed free of water and in methanol slurry) and then anhydrous ammonia (17 g). The mixture was subjected to 120 atm of hydrogen at 150–160° C. for 5 hours, then cooled and excess gasses purged. The resulting slurry was filtered through celite, and the filtrate was distilled to about one-third the original volume (atmospheric pressure, Vigreaux column). The pot solution was cooled to 0° C., diluted with 3 volumes diethyl ether, and treated with 4 N hydrochloric acid solution in anhydrous dioxane until precipitate formation ceased. The solid product (dicyclopropylmethylamine hydrochloride) was collected by filtration, washed with excess diethyl ether, and dried under vacuum (45.22 g, 306 mmol, 67%). $^1$H NMR (300 MHz, methanol-d$_4$): Δ 1. 94 (1H, t, J=9.3 Hz), 1.11–0.99 (2H, m), 0.75–0.59 (4H, m), 0.48–0.37 (4H, m). MS (NH$_3$-DCI): m/e 114 (5), 113 (100).

Part E. A solution of 5-amino-4,6-dichloropyrimidine (5.00 g, 30.5 mmol) and diisopropylethylamine (12.0 mL, 68.9 mmol) in ethanol (100 mL) was treated with the amine from Part D (3.81 g, 25.8 mmol), and heated to reflux for 72 h. The resulting mixture was cooled and poured into water (300 mL), which was extracted with ethyl acetate (2×300 mL). The extracts were washed with brine, combined, dried over sodium sulfate, filtered and evaporated. The residual oil was separated by column chromatography (30:70 ethyl acetate-hexane), and the desired product, 5-amino-4-chloro-6-dicyclopropylmethylaminopyrimidine, was triturated with warm ether-hexane, collected by filtration, and dried under vacuum (3.15 g, 13.2 mmol, 43%). m.p. 137–138° C. TLC R$_F$ 0.17 (30:70 ethyl acetate-hexane). $^1$H NMR (300 MHz, CDCl$_3$): Δ 8.01 (1H, s), 4.95 (1H, br d, J=7.3 Hz), 3.45 (1H, q, J=7.0 Hz), 3.37 (2H, br s), 1.06–0.94 (2H, m), 0.59–0.32 (8H, m). MS (NH$_3$-CI): m/e 243 (1), 242 (5), 241 (36), 240 (16), 239 (100).

Part F. A solution of the diamine from Part E (1.80 g, 7.54 mmol) and 1 drop concentrated hydrochloric acid in triethyl orthopropionate (12 mL) was heated to 100° C. for 6 hours. The excess orthoester was removed by distillation (partial vacuum, short-path), and the pot residue solidified to give the product, N-(4-chloro-6-dicyclopropylmethylaminopyrimidin-5-yl)-O-ethyl-propionimidate. $^1$H NMR (300 MHz, CDCl$_3$): Δ 8.08 (1H, s), 4.84 (1H, br d, J=8.0 Hz), 4.35 (2H, br), 3.45 (1H, q, J=7.7 Hz), 2.14 (2H, q, J=7.3 Hz), 1.41 (3H, t, J=7.1 Hz), 1.08 (3H, t, J=7.7 Hz), 1.03–0.93 (2H, m), 0.58–0.27 (8H, m). MS (NH$_3$-CI): m/e 327 (1), 326 (7), 325 (36), 324 (21), 323 (100).

Part G. A solution of the imidate compound prepared in Part F above and p-toluenesulfonic acid monohydrate (50 mg) in diphenyl ether (10 mL) was heated to 170° C. for 2 hours. The resulting mixture was cooled and separated by column chromatography (silica gel, hexane to remove diphenyl ether, then 30:70 ethyl acetate-hexane) to afford the product, 6-chloro-9-dicyclopropylmethyl-8-ethylpurine, as a solid (1.42 g, 5.13 mmol, 68% for both steps F and G).

m.p. 99–100° C. TLC R$_F$ 0.26 (30:70 ethyl acetate-hexane). $^1$H NMR (300 MHz, CDCl$_3$): Δ 8.63 (1H, s), 2.99 (2H, br), 1.92 (1H, br), 1.50 (3H, t, J=7.3 Hz), 0.87–0.78 (2H, m), 0.50–0.39 (4H, m), 0.20–0.10 (4H, m). MS (NH$_3$-CI): m/e 280 (6), 279 (36), 278 (19), 277 (100).

Part H. A solution of the purine chloride from Part G (870 mg, 3.14 =mol), the boronic acid from Part C (980 mg, 4.08 mmol), triphenylphosphine (190 mg, 0.724 mmol) and 2 M aqueous sodium carbonate solution (4 mL, 8 mmol) in dimethoxyethane (15 mL) was degassed by three successive cycles of vacuum pumping/purging with dry nitrogen. To this mixture was added palladium (II) acetate 40 mg, 0.178 mmol), and the mixture was degassed again as described above and heated to reflux for 12 h. After cooling, the mixture was poured into water and extracted twice with ethyl acetate. The extracts were washed in sequence with 1) a 15% w/w aqueous solution of 1,3,5-triazine-2,4,6-trithiol trisodium salt, and 2) saturated brine, combined, dried over anhydrous sodium sulfate, filtered and evaporated. The residual material was separated by column chromatography (15:85 ethyl acetate-hexane) to afford the solid title product, which was purified further by recrystallization from ether-hexane (first crop 500 mg, 1.14 mmol, 30%). m.p. 119–120° C. (ether-hexane). TLC R$_F$ 0.43 (30:70 ethyl acetate-hexane). $^1$H NMR (300 MHz, CDCl$_3$): Δ 8.95 (1H, s), 7.80 (1H, d, J=8.4 Hz), 7.46–7.44 (1H, m), 7.31–7.25 (1H, m), 3.92 (1H, v br), 2.98 (2H, br), 1.95 (2H, br), 1.44 (3H, br t, J=7 Hz), 0.92–0.82 (2H, m), 0.63–0.53 (2H, m), 0.52–0.42 (2H, m), 0.28–0.18 (2H, m). MS (NH$_3$-CI): m/e 440 (8), 439 (35), 438 (26), 437 (100). Analysis calculated for C$_{21}$H$_{20}$ClF$_3$N$_4$O: C, 57.74; H, 4.60; N, 12.83; found: C, 57.80; H, 4.57; N, 12.43.

Preparation of 6-(2-Chloro-4-difluoromethoxyphenyl)-8-ethyl-9-(2-pentyl)purine (Example 10)

Part A. A solution of 5-amino-4,6-dichloropyrimidine (24.6 g, 150 mmol), 4-methoxybenzylamine (20.0 mL, 150 mmol) and diisopropylethylamine (30.0 mL, 172 mmol) in ethanol (200 mL) was heated to ref lux for 4 days. After cooling, the solution was evaporated and the residue partitioned between water and ethyl acetate. The organic layer was washed with more water and brine, and the three aqueous phases were back-extracted in sequence with ethyl acetate. The extracts were combined, dried over sodium sulfate, filtered and evaporated. The resulting solid was triturated with ether, collected by filtration and dried under vacuum to afford pure product, 5-amino-4-chloro-6-(4-methoxybenzylamino)pyrimidine. m.p. 187–188° C. TLC R$_F$ 0.11 (30:70 ethyl acetate-hexane). $^1$H NMR (300 MHz, CDCl$_3$): Δ 8.12 (1H, s), 7.33 (2H! d, J=9.0 Hz), 6.89 (2H, d, J=9.0 Hz), 5. 01 (1H, br), 4. 61 (2H, d, J=5. 1 Hz), 3. 81 (3H, s), 3.35 (2H, br). MS (NH$_3$-CI): m/e 268 (4), 267 (31), 266 (15), 265 (100).

Part B. A solution of the diamine from Part A in triethyl orthopropionate (5 eq.) was treated with a catalytic quantity of concentrated hydrochloric acid and warmed to 60° C. for 10 h. Volatile components of the mixture were removed by distillation, and the resulting residue was taken up in mesitylene (0.5 H) and treated with p-toluenesulfonic acid monohydrate (0.05 eq.). This solution was heated to reflux under a Dean-Stark trap, and the trap tube (containing solvent and ethanol) was periodically drained f or a period of 1 h. The solution was cooled and evaporated, and the residual material was separated by column chromatography (silica gel, 30:70 ethyl acetate-hexane) to afford the product, 6-chloro-8-ethyl-9-(4-methoxybenzyl)purine, as a solid, m.p. 101–103° C.

Part C. A solution of 4- bromo-3-chlorophenol (15.81 g, 76.2 mmol) in isopropanol (150 mL) was treated with 20% w/w aqueous sodium hydroxide solution (150 mL), and heated to reflux while chlorodifluoromethane was bubbled in via a needle. After 2 h, the gas flow was shut off, and the solution was cooled and evaporated. The resulting mixture was extracted twice with ethyl acetate, and the extracts were washed with water and brine, combined, dried over magnesium sulfate, filtered and evaporated. The resulting liquid was purified by elution through a short column of silica gel (5:95 ethyl acetate-hexane), and evaporation afforded the product, 4-bromo-3-chloro-difluoroanisole (14.1 g, 54.8 mmol, 72%). TLC $R_F$ 0.49 (5:95 ethyl acetate-hexane). $^1$H NMR (300 MHz, CDCl$_3$): Δ 7.60 (1H, d, J=8.8 Hz), 7.27 (1H, d, J=2.6 Hz), 6.93 (1H, dd, J=3.8, 2.6 Hz), 6.49 (1H, t, J=72.9 Hz). MS (H$_2$O-GC/MS): m/e 259 (22), 239 (100).

Part D. A solution of the bromide from Part C (14.1 g, 54.8 mmol) and triisopropylborate (13.9 mL, 60.2 mmol) in 60 mL THF was cooled to −78° C. under nitrogen, and a hexane solution of n-butyllithium (37.5 mL, 1.6 M, 60.0 mmol) was added slowly dropwise. The mixture was allowed to warm to ambient temperature with stirring over 12 h, then was quenched by the addition of 20 mL 6 N hydrochloric acid and 20 mL water. The resulting mixture was extracted twice with ethyl acetate, and the extracts were washed with brine, combined, dried over magnesium sulfate, filtered and evaporated. The resulting solid was triturated with cyclohexane, filtered and dried under vacuum to afford the product, 2-chloro-4-difluoromethoxybenzeneboronic acid (5.61 g, 25.2 mmol, 46%). m.p. 167–169° C. (cyclohexane). $^1$H NMR (300 MHz, CDCl$_3$): Δ 7.97 (1H, d, J=8.4 Hz), 7.15 (1H, d, J=2.2 Hz), 7.07 (1H, dd, J=8.4, 2.2 Hz), 6.59 (1H, t, J=73.0 Hz), 5.29 (2H, s). MS (H$_2$O-GC/MS): m/e 249 (100).

Part E. A solution of the purine chloride from Part B (1.24 g, 4.50 mmol), the boronic acid from Part D (1.50 g, 6.75 mmol), triphenylphosphine (238 mg, 0.907 mmol) and 2 M aqueous sodium carbonate solution (7 mL, 14 mmol) in dimethoxyethane (23 mL) was degassed as described above, then treated with palladium (II) acetate (51 mg, 0.227 mmol). The solution was degassed a second time, and then heated to reflux for 12 h. After cooling, the solution was poured into water. This was extracted twice with ethyl acetate, and the extracts were washed in sequence with 15% w/w aqueous 1,3,5-triazine-2,4,6-trithiol trisodium salt solution and saturated aqueous brine. The extracts were combined, dried over sodium sulfate, filtered and evaporated. The residual material was separated by column chromatography (silica gel, 25:75 ethyl acetate-hexane) to afford the product, 6-(2-chloro-4-difluoromethoxyphenyl)-8-ethyl-9-(4-methoxybenzyl)purine, as an oil (1.44 g, 3.24 mmol, 72%). TLC $R_F$ 0.24 (50:50 ethyl acetate-hexane). $^1$H NMR (300 MHz, CDCl$_3$): Δ 9.03 (1H, s), 7.76 (1H, d, J=8.8 Hz), 7.35 (1H, d, J=2.2 Hz), 7.20 (1H, dd, J=8.8, 2.2 Hz), 7.19 (2H, d, J=8.8 Hz), 6.86 (2H, d, J=8.8 Hz), 6.57 (1H, t, J=73.0 Hz), 5.44 (2H, s), 3.79 (3H, s), 2.89 (2H, q, J=7.7 Hz), 1.32 (3H, t, J=7.7 Hz). MS (AP): m/e 445 (100).

Part F. A solution of the 4-methoxybenzyl compound from Part E (1.33 g, 2.99 mmol) in trifluoroacetic acid (10 mL) was heated to reflux for 12 h. The solution was cooled and evaporated, and the residue taken up in saturated aqueous sodium bicarbonate. This mixture was extracted twice with ethyl acetate, and the extracts were washed with brine, combined, dried over sodium sulfate, filtered and evaporated. The residue was separated by column chromatography (silica gel, ethyl acetate) to afford the product, 6-(2-chloro-4-difluoromethoxyphenyl)-8-ethylpurine, as an oil (940 mg, 2.89 mmol, 97%). TLC $R_F$ 0.06 (50:50 ethyl acetate-hexane). $^1$H NMR (300 MHz, CDCl$_3$): Δ 10.62 (1H, br s), 9.17 (0.2H, s), 9.01 (0.8H, s), 7.74 (1H, d, J=8.4 Hz), 7.37 (0.2H, d, J=2.6 Hz), 7.36 (0.8H, d, J=2.6 Hz), 7.21 (1H, dd, J=8.4, 2.6 Hz), 6.62 (0.2H, t, J=72.3 Hz), 6.57 (0.8H, t, J=72.9 Hz), 3.07 (2H, q, J=7.3 Hz), 1.52 (3H, t, J=7.3 Hz). MS (AP): m/e 325 (100).

Part G. A solution of triphenylphosphine in THF was cooled to −30° C., and treated with 1 eq. of diethyl azodicarboxylate. This solution was stirred for 30 min., and an aliquot containing 0.36 mmol of the reagents was extracted by syringe and delivered to a septum vial containing the purine from Part F (0.241 mmol) and 2-pentanol (32 mg, 0.36 mmol). The vial was shaken for 10 h, then the contents were evaporated by a stream of nitrogen and the residue applied to a solid phase extraction cartridge containing 2 g of silica gel 60 (Supelco). The cartridge was eluted with 10:90 ethyl acetate-hexane, and the fractions collected which contained the product were combined and evaporated to afford the title product (35 mg, 0.089 mmol, 37%) as an oil. TLC $R_F$ 0.14 (20:80 ethyl acetate-hexane). $^1$H NMR (300 MHz, CDCl$_3$): Δ 8.96 (1H, s), 7.73 (1H, d, J=8.5 Hz), 7.34 (1H, d, J=2.5 Hz), 7.18 (1H, dd, J=8.5, 2.5 Hz), 6.57 (1H, t, J=73.2 Hz), 4.60–4.50 (1H, m), 2.97 (2H, dq, J=7.5, 1.7 Hz), 2.47–2.35 (1H, m), 2.10–1.98 (1H, m), 1.74 (3H, d, J=6.6 Hz), 1.41 (3H, t, J=7.5 Hz), 1.39–1.22 (2H, m), 0.93 (3H, t, J=7.2 Hz). MS (AP): m/e calculated for C$_{19}$H$_{22}$ClF$_2$N$_4$O: 395.1450, found 395.1444; 395 (100).

Part II

The following Table 2 sets forth exemplary compounds provided herein (wherein A is N, B is CH and ring D is a phenyl ring); $R^1$ substituents are as set forth in Table 1 above. The compounds are set forth sequentially, by example number, along with melting point ("m. p.") data (degrees C.); or, where the compound is listed as an "oil" in the column for "m. p.," spectral data is provided following the table. The compounds were synthesized according to the schemes set forth hereinabove.

TABLE 2

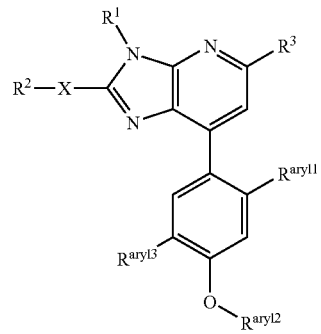

| Ex. No. | $R^1$ | X | $R^2$ | $R^3$ | $R^{aryl1}$ | $R^{aryl2}$ | $R^{aryl3}$ | m.p. |
|---|---|---|---|---|---|---|---|---|
| 33 | A | CH$_2$ | CH$_3$ | H | Cl | CF$_3$ | H | oil |
| 34 | E | CH$_2$ | CH$_3$ | H | Cl | CF$_3$ | H | 57–58 |
| 35 | H | CH$_2$ | CH$_3$ | H | Cl | CF$_3$ | H | oil |
| 36 | J | CH$_2$ | CH$_3$ | H | Cl | CF$_3$ | H | oil |
| 37 | K | CH$_2$ | CH$_3$ | H | Cl | CF$_3$ | H | oil |
| 38 | M | CH$_2$ | CH$_3$ | H | Cl | CF$_3$ | H | oil |
| 39 | Q | CH$_2$ | CH$_3$ | H | Cl | CF$_3$ | H | oil |
| 40 | H | O | CH$_3$ | H | Cl | CF$_3$ | H | oil |
| 41 | J | O | CH$_3$ | H | Cl | CF$_3$ | H | oil |
| 42 | K | O | CH$_3$ | H | Cl | CF$_3$ | H | oil |
| 43 | M | O | CH$_3$ | H | Cl | CF$_3$ | H | oil |
| 44 | A | CH$_2$ | CH$_3$ | H | CH$_3$ | CF$_3$ | H | 70–71 |

TABLE 2-continued

[Structure: Imidazopyridine core with R¹ on N, R²—X at 2-position, R³ at 5-position, and aryl group at 7-position bearing R^aryl1, R^aryl2 (via O linker), R^aryl3]

| Ex. No. | R¹ | X | R² | R³ | R^aryl1 | R^aryl2 | R^aryl3 | m.p. |
|---|---|---|---|---|---|---|---|---|
| 45 | K | CH₂ | CH₃ | H | CH₃ | CF₃ | H | oil |
| 46 | M | CH₂ | CH₃ | H | CH₃ | CF₃ | H | oil |
| 47 | Q | CH₂ | CH₃ | H | CH₃ | CF₃ | H | oil |
| 48 | A | CH₂ | CH₃ | H | Cl | CHF₂ | H | 77–78 |
| 49 | B | CH₂ | CH₃ | H | Cl | CHF₂ | H | oil |
| 50 | H | CH₂ | CH₃ | H | Cl | CHF₂ | H | oil |
| 51 | J | CH₂ | CH₃ | H | Cl | CHF₂ | H | oil |
| 52 | K | CH₂ | CH₃ | H | Cl | CHF₂ | H | oil |
| 53 | N | CH₂ | CH₃ | H | Cl | CHF₂ | H | oil |
| 54 | A | CH₂ | CH₃ | H | CH₃ | CHF₂ | H | oil |
| 55 | B | CH₂ | CH₃ | H | CH₃ | CHF₂ | H | oil |

Spectral Data:

Example 33

$^1$H NMR (300 MHz, CDCl₃): Δ 8.33 (1H, d, J=5.1 Hz), 7.68 (1H, d, J=8.4 Hz), 7.42 (1H, d, J=1.5 Hz), 7.25 (1H, dd, J=8.4, 1.5 Hz), 7.22 (1H, d, J=5.1 Hz) 4.54–4.42 (1H, m), 2.96 (2H, q, J=7.5 Hz), 2.55–2.39 (1H, m), 2.16–2.02 (1H, m), 1.76 (3H, d, J=7.0 Hz), 1.39 (3H, t, J=7.5 Hz), 0.86 (3H, t, J=7.5 Hz).

Example 34 see Table 2 for melting point data.

Example 35

$^1$H NMR (300 MHz, CDCl₃): Δ 8.30 (1H, d, J=4.8 Hz), 7.73 (1H, d, J=8.8 Hz), 7.44–7.41 (1H, m), 7.26 (1H, br d, J=8 Hz), 7.23 (1H, d, J=4.8 Hz), 4.48 (1H, br), 3.38–3.29 (1H, m), 3.24 (3H, s), 2.97 (2H, q, J=7.7 Hz), 2.95 (1H, br), 2.80 (1H, br), 2.57 (1H, br), 2.30–2.19 (1H, m), 2.14–2.00 ((H, m), 1.40 (3H, t, J=7.7 Hz), 0.84 (3H, t, J=7.3 Hz). Analysis calculated for C₂₁H₂₃ClF₃N₃O₂: C, 57.08; H, 5.26; N, 9.52; found: C, 57.20; H, 4.93; N, 9.20.

Example 36

$^1$H NMR (300 MHz, CDCl₃): Δ 8.34 (1H, d, J=5.1 Hz), 7.69 (1H, d, J=8.4 Hz), 7.44–7.41 (1H, m), 7.29–7.24 (1H, m), 7.23 (1H, d, J=5.1 Hz), 3.87–3.77 (1H, m), 2.95 (2H, dq, J=7.5, 3.1 Hz), 2.10–2.00 (1H, m), 1.82 (3H, d, J=7.0 Hz), 1.38 (3H, t, J=7.5 Hz), 0.83–0.73 (1H, m), 0.54–0.39 (2H, m), 0.29–0.22 (1H, m). Analysis calculated for C₂₀H₁₉ClF₃N₃O: C, 58.61; H, 4.67; N, 10.25; found: C, 58.51; H, 4.55; N, 10.08.

Example 37

$^1$H NMR (300 MHz, CDCl₃): Δ 8.32 (1H, d, J=5.1 Hz), 7.72 (1H, d, J=8.5 Hz), 7.43–7.41 (1H, m), 7.29–7.22 (2H, m), 3.58 (1H, br), 2.92 (2H, q, J=7.5 Hz), 2.51–2.39 (1H, m), 2.31–2.19 (1H, m), 1.98 (1H, br), 1.39 (3H, t, J=7.5 Hz), 0.87 (3H, t, J=7.5 Hz), 0.85–0.75 (1H, m), 0.50–0.40 (2H, m), 0.26–0.16 (1H, m). $^{13}$C NMR (300 MHz, CDCl₃): ? 158.0, 149.1, 141.8, 135.3, 134.1, 133.9, 133.3, 133.0, 122.7, 122.1, 119.1, 118.5, 77.2, 63.9, 27.1, 22.2, 15.0, 12.7, 11.4, 6.0, 3.7. MS (NH3-Cl): m/e 427 (8), 426 (35), 425 (26), 424 (100); Analysis calculated for C₂₁H₂₁ClF₃N₃O: C, 59.51; H, 4.99; N, 9.91; found: C, 59.40; H, 4.91; N, 9.69.

Example 38

$^1$H NMR (300 MHz, CDCl₃): Δ 8.32 (1H, d, J=5.1 Hz), 7.73 (1H, d, J=8.4 Hz), 7.43–7.26 (2H, m), 7.25 (1H, d, J=5.1 Hz), 4.98–4.82 (1H, m), 3.47–3.37 (1H, m), 3.23 (3H, s), 3.01–2.75 (3H, m), 2.55–2.40 (1H, m), 1.70–1.55 (2H, m), 1.38 (3H, t, J=7.7 Hz), 0.82–0.72 (1H, m), 0.50–0.40 (2H, m), 0.30–0.20 (1H, m).

Example 39

$^1$H NMR (300 MHz, CDCl₃): ? 8.29 (1H, d, J=5.1 Hz), 7.74 (1H, d, J=8.8 Hz), 7.42 (1H, narrow m), 7.27–7.20 (2H, m), 4.45 (1H, dt, J=11.0, 3.6 Hz), 3.73–3.62 (1H, m), 3.36–3.29 (1H, m), 3.24 (3H, s), 3.00 (2H, q, J=7.5 Hz), 2.86 (1H, dt, J=10.1, 3.1 Hz), 2.75–2.65 (1H, m), 2.50–1.50 (7H, m), 1.44 (3H, t, J=7.5 Hz).

Example 40

$^1$H NMR (300 MHz, CDCl₃): Δ 8.19 (1H, d, J=5.1 Hz), 7.70 (1H, d, J=8.4 Hz), 7.44–7.41 (1H, m), 7.24 (1H, br d, J=8 Hz), 7.17 (1H, d, J=5.1 Hz), 4.71–4.61 (1H, m), 4.16 (3H, s), 3.38–3.28 (1H, m), 3.20 (3H, s), 3.19–3.11 (1H, m), 2.58–2.47 (1H, m), 2.33–2.09 (2H, m), 1.98–1.87 (1H, m), 0.82 (3H, t, J=7.3 Hz). Analysis calculated for C₂₀H₂₁ClF₃N₃O₃: C, 54.12; H, 4.78; N, 9.48; found: C, 53.75; H, 4.80; N, 9.34.

Example 41

$^1$H NMR (300 MHz, CDCl₃): Δ 8.18 (1H, d, J=5.1 Hz), 7.69 (1H, d, J=8.4 Hz), 7.44–7.41 (1H, m), 7.24 (1H, br d, J=8 Hz), 7.17 (1H, d, J=5.1 Hz), 4.17 (3H, S), 3.89 (1H, dq, J=10.2, 7.0 Hz), 1.80–1.70 (1H, m), 1.70 (3H, d, J=7.0 Hz), 0.73–0.63 (1H, m), 0.47–0.27 (3H, m). Analysis calculated for C₁₉H₁₇ClF₃N₃O₂: C, 55.42; H, 4.16; N, 10.20; found: C, 55.38; H, 4.02; N, 10.05.

Example 42

$^1$H NMR (300 MHz, CDCl₃): Δ 8.17 (1H, d, J=5.1 Hz), 7.71 (1H, d, J=8.8 Hz), 7.44–7.41 (1H, m), 7.24 (1H, dm, J=8 Hz), 7.17 (1H, d, J=5.1 Hz), 4.16 (3H, s), 3.64 (1H, dt, J=9.9, 5.9 Hz), 2.39–2.25 (1H, m), 2.17–2.05 (1H, m), 1.79–1.66 (1H, m), 0.85 (3H, t, J=7.3 Hz), 0.78–0.68 (1H, m), 0.49–0.36 (2H, m), 0.29–0.20 (1H, m). Analysis calculated for C₂₀H₁₉ClF₃N₃O₂: C, 56.41; H, 4.51; N, 9.88; found: C, 56.44; H, 4.35; N, 10.18.

Example 43

$^1$H NMR (300 MHz, CDCl₃): Δ 8.18 (1H, d, J=5.1 Hz), 7.71 (1H, d, J=8.4 Hz), 7.44–7.41 (1H, m), 7.24 (1H, br d, J=8 Hz), 7.17 (1H, d, J=5.1 Hz), 4.16 (3H, s), 3.95–3.85 (1H, m), 3.45–3.35 (1H, m), 3.25–3.15 (1H, m), 3.21 (3H, s), 2.63–2.52 (1H, m), 2.44–2.31 (1H, m), 1.81–1.71 (1H, m), 0.78–0.68 (1H, m), 0.50–0.38 (2H, m), 0.35–0.25 (1H, m).

Example 44 see Table 2 for melting point data.

Example 45

¹H NMR (300 MHz, CDCl₃): Δ 8.31 (1H, d, J=5.1 Hz), 7.45 (1H, d, J=8.4 Hz), 7.21 (1H, br s), 7.17 (1H, br d, J=8 Hz), 7.04 (1H, d, J=5.1 Hz), 3.56 (1H, br), 2.92 (2H, q, J=7.5 Hz), 2.46 (1H, br), 2.32 (3H, s), 2.31–2.19 (1H, m), 1.96 (1H, br), 1.39 (3H, t, J=7.5 Hz), 0.86 (3H, t, J=7.5 Hz), 0.85–0.76 (1H, m), 0.50–0.40 (2H, m), 0.25–0.15 (1H, m).

Example 46

¹H NMR (300 MHz, CDCl₃): Δ 8.30 (1H, d, J=5.1 Hz), 7.46 (1H, d, J=8.0 Hz), 7.18 (1H, br s), 7.15 (1H, br d, J=8 Hz), 7.04 (1H, d, J=5.1 Hz), 3.75 (1H, br), 3.44–3.34 (1H, m), 3.23 (3H, s), 3.00–2.75 (4H, m), 2.52–2.40 (1H, m), 2.33 (3H, s), 2.18 (1H, br), 1.37 (3H, t, J=7.5 Hz), 0.81–0.72 (1H, m), 0.51–0.41 (2H, m), 0.30–0.20 (1H, m).

Example 47

¹H NMR (300 MHz, CDCl₃): Δ 8.27 (1H, d, J=5.1 Hz), 7.45 (1H, d, J=8.0 Hz), 7.17–7.13 (2H, m), 7.02 (1H, d, J=5.1 Hz), 4.44 (1H, dt, J=11.0, 3.3 Hz), 3.78–3.62 (1H, m), 3.36–3.26 (1H, m), 3.23 (3H, s), 2.99 (2H, q, J=7.5 Hz), 2.86 (1H, dt, J=10.2, 2.5 Hz), 2.78–2.65 (1H, m), 2.30 (3H, s), 2.29–2.20 (1H, m), 2.18–2.08 (1H, m), 1.92–1.79 (3H, m), 1.77–1.67 (1H, m), 1.66–1.56 (1H, m), 1.44 (3H, t, J=7.5 Hz).

Example 48 see Table 2 for melting point data.

Example 49

¹H NMR (300 MHz, CDCl₃): Δ 8.33 (1H, d, J=4.8 Hz), 7.65 (1H, d, J=8.4 Hz), 7.33 (1H, d, J=2.2 Hz), 7.22 (1H, d, J=4.8 Hz), 7.16 (1H, dd, J=8.4, 2.2 Hz), 6.56 (1H, t, J=73.2 Hz), 4.62–4.54 (1H, m), 2.96 (2H, dq, J=7.5, 1.0 Hz), 2.50–2.38 (1H, m), 2.10–1.98 (1H, m), 1.75 (3H, d, J=7.0 Hz), 1.38 (3H, t, J=7.5 Hz), 1.37–1.27 (1H, m), 1.23–1.13 (1H, m), 0.92 (3H, t, J=7.3 Hz).

Example 50

¹H NMR (300 MHz, CDCl₃): Δ 8.29 (1H, d, J=5.1 Hz), 7.69 (1H, d, J=8.8 Hz), 7.34 (1H, d, J=2.5 Hz), 7.23 (1H, d, J=5.1 Hz), 7.17 (1H, dd, J=8.8, 2.5 Hz), 6.56 (1H, t, J=73.4 Hz), 4.49 (1H, br), 3.38–3.31 (1H, m), 3.24 (3H, s), 2.96 (2H, q, J=7.5 Hz), 2.95–2.75 (2H, br), 2.54 (1H, br), 2.29–2.19 (1H, m), 2.16–2.00 (1H, m), 1.40 (3H, t, J=7.5 Hz), 0.84 (3H, t, J=7.3 Hz).

Example 51

¹H NMR (300 MHz, CDCl₃): Δ 8.33 (1H, d, J=5.1 Hz), 7.66 (1H, d, J=8.4 Hz), 7.34 (1H, d, J=2.6 Hz), 7.23 (1H, d, J=5.1 Hz), 7.16 (1H, dd, J=8.4, 2.6 Hz), 6.56 (1H, t, J=73.2 Hz), 3.83–3.77 (1H, m), 2.94 (2H, dq, J=7.5, 3.3 Hz), 2.09–1.99 (1H, m), 1.82 (3H, d, J=7.0 Hz), 1.37 (3H, t, J=7.5 Hz), 0.81–0.71 (1H, m), 0.53–0.39 (2H, m), 0.30–0.20 (1H, m).

Example 52

¹H NMR (300 MHz, CDCl₃): Δ 8.32 (1H, d, J=5.1 Hz), 7.70 (1H, d, J=8.4 Hz), 7.34 (1H, d, J=2.2 Hz), 7.24 (1H, d, J=5.1 Hz), 7.17 (1H, dd, J=8.4, 2.2 Hz), 6.57 (1H, t, J=73.2 Hz), 3.58 (1H, br), 2.92 (2H, q, J=7.5 Hz), 2.54–2.39 (1H, m), 2.34–2.19 (1H, m), 1.98 (1H, br), 1.39 (3H, t, J=7.5 Hz), 0.87 (3H, t, J=7.5 Hz), 0.86–0.76 (1H, m), 0.52–0.41 (2H, m), 0.26–0.16 (1H, m).

Example 53

¹H NMR (300 MHz, CDCl₃): Δ 8.32 (1H, d, J=5.1 Hz), 7.66 (1H, d, J=8.8 Hz), 7.33 (1H, d, J=2.2 Hz), 7.22 (1H, d, J=5.1 Hz), 7.16 (1H, dd, J=8.8, 2.2 Hz), 6.56 (1H, t, J=73.2 Hz), 4.49 (1H, br), 3.59 (1H, br), 2.99 (2H, q, J=7.5 Hz), 2.31–2.21 (1H, m), 1.97–1.69 (4H, m), 1.62 (3H, d, J=7.3 Hz), 1.61–1.51 (1H, m), 1.41 (3H, t, J=7.5 Hz).

Example 54

¹H NMR (300 MHz, CDCl₃): Δ 8.30 (1H, d, J=5 Hz), 7.41 (1H, d, J=8 Hz), 7.10–7.00 (3H, m), 6.55 (1H, t, J=73 Hz), 4.54–4.42 (1H, m), 2.96 (2H, q, J=7 Hz), 2.53–2.39 (1H, m), 2.16–2.01 (1H, m), 1.78 (3H, d, J=7 Hz), 1.39 (3H, t, J=7 Hz), 0.84 (3H, t, J=7 Hz).

Example 55

¹H NMR (300 MHz, CDCl₃): Δ 8.30 (1H, d, J=4.8 Hz), 7.40 (1H, d, J=8.4 Hz), 7.10–7.00 (1H, m), 7.02 (1H, d, J=4.8 Hz), 6.55 (1H, t, J=74.1 Hz), 4.65–4.52 (1H, m), 2.94 (2H, dq, J=7.5, 1.2 Hz), 2.48–2.34 (1H, m), 2.29 (3H, s), 2.09–1.98 (1H, m), 1.75 (3H, d, J=7.0 Hz), 1.37 (3H, t, J=7.5 Hz), 1.36–1.26 (1H, m), 1.22–1.09 (1H, m), 0.91 (3H, t, J=7.3 Hz).

Synthesis:

Part III

The following Table 3 sets forth exemplary compounds provided herein (wherein A is CH, B is N and ring D is a phenyl ring); R¹ substituents are as set forth in Table 1 above. The compounds are set forth sequentially, by example number, along with melting point ("m. p.") data (degrees C); or, where the compounds is listed as an "oil" in the column for "m. p.," spectral data is provided following the table. The compounds were synthesized according to the schemes set forth hereinabove.

TABLE 3

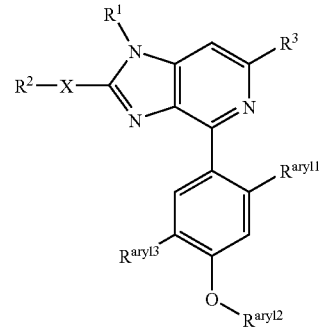

| Ex. No. | R¹ | X | R² | R³ | $R^{aryl1}$ | $R^{aryl2}$ | $R^{aryl3}$ | m.p. |
|---|---|---|---|---|---|---|---|---|
| 56 | B | $CH_2$ | $CH_3$ | H | Cl | $CHF_2$ | H | oil |
| 57 | B | $CH_2$ | $CH_3$ | H | Cl | $CF_3$ | H | oil |

Example 56

¹H NMR (CDCl₃): δ 8.43 (d, J=5.9 Hz, 1H), 7.66 (d, J=8.7 Hz, 1H), 7.43 (d, J=5.5 Hz, 1H), 7.32 (d, J=2.6 Hz,

1H), 7.15 (doublet of doublets, J=2.5 Hz, J=2.2 Hz, 1H), 6.55 (t, J=73.6 Hz, 1H), 4.47 (m, 1H), 2.95 (m, 2H), 2.1 (m, 1H), 1.9 (m, 1H), 1.66 (d, J=6.9 Hz, 3H), 1.37 (t, J=7.7 Hz, 3H), 1.3 (m, 1H), 1.14 (m, 1H), 0.923 (t, J=7.3 Hz, 3H).

Example 57

$^1$H-NMR (CDCl$_3$) δ 0.93 (3H, t, J=7.4 Hz), 1.16 (1H, m), 1.35 (1H, m), 1.38 (3H, t, J=7.5 Hz), 1.67 (3H, d, J=7 Hz), 1.95 (1H, m), 2.11 (1H, m), 2.95 (2H, m), 4.48 (1H, m), 7.24 (broad), 7.41 (1H, broad s), 7.44 (1H, d, J=5.9 Hz), 7.69 (1H, d, J=8.5 Hz), 8.43 (1H, d, J=5.9 Hz).

What is claimed is:

1. A compound of formula (I)

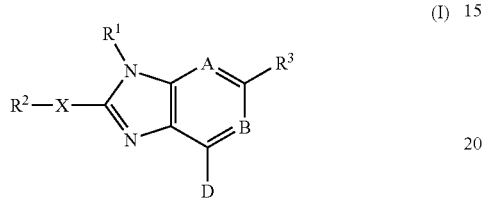

or a stereoisomer or pharmaceutically acceptable salt thereof, wherein:

A is N and B is C—R$^8$,

D is an aryl ring, wherein:

said aryl ring is selected from the group consisting of phenyl, naphthyl, indanyl and indenyl;

said aryl ring is substituted by 1–2 C$_{1-4}$ haloalkoxy groups; and, said aryl ring is substituted by 1–2 moieties selected independently from C$_{1-6}$ alkyl, C$_{3-6}$ cycloalkyl, C$_{2-6}$ alkenyl, C$_{2-6}$ alkynyl, halogen, C$_{1-4}$ haloalkyl, OH, C$_{1-4}$ alkoxy, (C$_{1-4}$ alkoxy)-C$_{1-4}$ alkoxy, CN, SH, C$_{1-4}$ alkylthio, C$_{1-4}$ alkylsulfinyl, C$_{1-4}$ alkylsulfonyl, COR$^{17}$, CO$_2$R$^{17}$ and NR$^{17}$R$^{19}$;

X is CH—R$^9$, N—R$^{10}$, O, S(O)$_n$ or a bond;

n is equal to 0, 2 or 3;

R$^1$ is selected from the group consisting of H, C$_{1-10}$ alkyl, C$_{2-10}$ alkenyl, C$_{2-10}$ alkynyl, C$_{3-8}$ cycloalkyl, C$_{4-12}$ cycloalkylalkyl or (C$_{1-4}$ alkoxy)-C$_{1-4}$ alkyl, each optionally substituted with 1 to 3 substituents selected independently from the group consisting of C$_{1-6}$ alkyl, C$_{3-6}$ cycloalkyl, C$_{4-8}$ cycloalkyl, aryl, halogen, C$_{1-4}$ haloalkyl, cyano, —OR$^{13}$, —S(O)$_m$R$^{14}$, —COR$^{13}$, —CO$_2$R$^{13}$, —NR$_{15}$COR$^{13}$, —N(COR$^{13}$)$_2$, NR$^{15}$CONR$^{13}$R$^{16}$, —NR$^{15}$CO$_2$R$^{14}$, —NR$^{13}$R$^{16}$, and —CONR$^{13}$R$^{16}$;

m is equal to 0, 1, or 2;

R$^2$ is C$_{1-4}$ alkyl or C$_{3-8}$ cycloalkyl, each optionally substituted with 1–3 substituents selected from hydroxy, halo and C$_{1-4}$ alkoxy, or where X is a bond, R$^2$ is optionally cyano;

R$^3$ and R$^8$ are each independently selected from the group consisting of H, C$_{1-4}$ alkyl, C$_{3-8}$ cycloalkyl, C$_{1-4}$alkoxy, C$_{1-4}$alkylthio, C$_{1-4}$alkylsulfinyl, C$_{1-4}$ alkylsulfonyl, amino, C$_{1-4}$ alkylamino, C$_{2-8}$dialkylamino, phenyl and phenyl substituted by 1–3 groups selected from C$_{1-7}$alkyl, C$_{3-8}$cycloalkyl, halogen, nitro, C$_{1-4}$alkoxy, C$_{1-4}$alkylthio and C$_{2-8}$ dialkylamino;

R$^9$ and R$^{10}$ are each independently H, C$_{1-4}$ alkyl or C$_{3-8}$cycloalkyl;

R$^{13}$ and R$^{16}$ are selected independently from the group consisting of at each occurrence thereof from H, C$_{1-4}$ alkyl, C$_{1-4}$haloalkyl, C$_{2-8}$alkoxyalkyl, C$_{3-6}$cycloalkyl, C$_{4-12}$cycloalkylalkyl, aryl, and (aryl)C$_{1-4}$alkyl;

R$^{14}$ is selected from the group consisting of C$_{1-4}$alkyl, C$_{1-4}$haloalkyl, C$_{2-8}$alkoxyalkyl, C$_{3-6}$cycloalkyl, C$_{4-12}$cycloalkylalkyl, aryl, and (aryl)C$_{1-4}$ alkyl, R$^{15}$ is independently at each occurrence thereof selected from the group consisting of H, C$_{1-4}$alkyl, C$_{3-7}$cycloalkyl, C$_{4-12}$cycloalkylalkyl, benzyl and benzyl substituted with 1–3 groups chosen from C$_{1-4}$alkyl, halogen, nitro, C$_{1-4}$alkoxy, and dimethylamino; and, R$^{17}$, R$^{18}$ and R$^{19}$ are selected independently at each occurrence from the group consisting of H, C$_{1-6}$ alkyl, C$_{3-10}$cycloalkyl and C$_{4-16}$cycloalkylalkyl.

2. The compound of claim 1, wherein R$^8$ is H.

3. The compound of claim 2, wherein D is phenyl.

4. The compound of claim 3, wherein the phenyl ring is substituted with a haloalkoxy group on the carbon atom of the ring which is furthest away on the ring from the carbon atom of the ring which is the point of attachment of the ring to the imidazopyridine ring.

5. The compound of claim 4, wherein the haloalkoxy group is —OCHF$_2$ or —OCF$_3$.

6. The compound of claim 3, wherein the phenyl ring comprises an additional substituent on the carbon atom of the ring which is adjacent on the ring to the carbon atom of the ring which is the point of attachment of the ring to the imidazopyridine ring.

7. The compound of claim 6, wherein the substituent is selected from C$_{1-6}$ alkyl, halogen, C$_{1-4}$ haloalkyl, C$_{1-4}$alkoxy, (methoxy)-C$_{1-4}$alkoxy, CN, C$_{1-4}$alkylthio, C$_{1-4}$alkylsulfinyl and C$_{1-4}$ alkylsulfonyl groups.

8. The compound of claim 7, wherein the substituent is Cl or CH$_3$.

9. The compound of claim 3, wherein the carbon atom of the phenyl ring which is adjacent to the atom that is furthest away on the ring from the carbon atom of the ring that is the point of attachment of the ring to the imidazopyridine ring and which is located on the phenyl ring between the furthest away carbon atom and the point of attachment carbon atom is unsubstituted.

10. The compound of claim 3, wherein the carbon atom of the phenyl ring which is adjacent to the atom that is furthest away on the ring from the carbon atom of the ring that is the point of attachment of the ring to the imidazopyridine ring and which is located on the phenyl ring between the furthest away carbon atom and the point of attachment carbon atom is substituted.

11. The compound of claim 10, wherein the substituent is selected from C$_{1-6}$alkyl, halogen, C$_{1-4}$haloalkyl and C$_{1-4}$ alkoxy.

12. The compound of claim 11, wherein the substituent is CH$_3$.

13. The compound of claim 3, wherein the phenyl ring is substituted with:

(i) —OCHF$_2$ or —OCF$_3$ on the carbon atom of the ring which is furthest away on the ring from the carbon atom of the ring which is the point of attachment of the ring to the imidazopyridine ring;

(ii) Cl or CH$_3$ on the carbon atom of the ring which is adjacent on the ring to the carbon atom of the ring which is the point of attachment of the ring to the imidazopyridine ring; and, (iii) CH$_3$ on the carbon atom of the ring which is adjacent to the atom that is furthest away on the ring from the carbon atom of the ring that is the point of attachment of the ring to the imidazopyridine ring and which is located on the ring between the furthest away carbon atom and the point of attachment carbon atom.

14. The compound of claim 3, wherein $R^1$ is $C_{1-7}$alkyl, $C_{5-7}$cycloalkyl, or $C_{2-7}$alkynyl, each of which is optionally substituted $C_{3-5}$ cycloalkyl, $C_{1-2}$alkoxy, phenyl or phenyl substituted with 1–3 CN, $C_{1-3}$alkoxy, or $C_{1-3}$alkyl groups.

15. The compound of claim 14, wherein $R^1$ is 2-butyl, 2-pentyl, 2-hexyl, 2-heptyl, 3-pentyl, 3-hexyl, 3-heptyl, 1-methoxy-3-pentyl, 4-heptyl, 1-cyclopropyl-1-ethyl, 1-cyclopropyl-1-propyl, 1-cyclopropyl-1-butyl, 1-cyclopropyl-3-methoxy-1-propyl, 1-cyclobutyl-1-ethyl, 1-cyclobutyl-1-propyl, 1-cyclobutyl-1-butyl, 1-cyclobutyl-3-methoxy-1-propyl, 1-cyclopentyl-1-ethyl, 1-cyclopentyl-1-propyl, 1-cyclopentyl-1-butyl, 1-cyclopentyl-3-methoxy-1-propyl, alpha-cyclopropylbenzyl, 1-phenyl-2-butyn-1-yl, 1-cyclopropyl-2-butyn-1-yl or dicyclopropylmethyl.

16. The compound of claim 3, wherein $R^2$ is $CH_3$ or $C_2H_5$.

17. The compound of claim 3, wherein $R^3$ is H or $CH_3$.

18. The compound of claim 3, wherein X is O or CH—$R^9$ and wherein $R^9$ is H.

19. The compound of claim 3, wherein:

$R^1$ is 2-butyl, 2-pentyl, 2-hexyl, 2-heptyl, 3-pentyl, 3-hexyl, 3-heptyl, 1-methoxy-3-pentyl, 4-heptyl, 1-cyclopropyl-1-ethyl, 1-cyclopropyl-1-propyl, 1-cyclopropyl-1-butyl, 1-cyclopropyl-3-methoxy-1-propyl, 1-cyclobutyl-1-ethyl, 1-cyclobutyl-1-propyl, 1-cyclobutyl-1-butyl, 1-cyclobutyl-3-methoxy-1-propyl, 1-cyclopentyl-1-ethyl, 1-cyclopentyl-1-propyl, 1-cyclopentyl-1-butyl, 1-cyclopentyl-3-methoxy-1-propyl, alpha-cyclopropylbenzyl, 1-phenyl-2-butyn-1-yl, 1-cyclopropyl-2-butyn-1-yl or dicyclopropylmethyl;

$R^2$ is $CH_3$ or $C_2H_5$;

$R^3$ is H or $CH_3$;

X is $CH_2$ or O; and, the phenyl ring is substituted with:
 (i) —$OCHF_2$ or —$OCF_3$ on the carbon atom of the ring which is furthest away on the ring from the carbon atom of the ring which is the point of attachment of the ring to the imidazopyridine ring;
 (ii) Cl or $CH_3$ on the carbon atom of the ring which is adjacent on the ring to the carbon atom of the ring which is the point of attachment of the ring to the imidazopyridine ring; and,
 (iii) $CH_3$ on the carbon atom of the ring which is adjacent to the atom that is furthest away on the ring from the carbon atom of the ring that is the point of attachment of the ring to the imidazopyridine ring and which is located on the ring between the furthest away carbon atom and the point of attachment carbon atom.

20. A pharmaceutical composition comprising a pharmaceutically acceptable carrier and a therapeutically effective amount of the compound of claim 1.

21. A method of treating a mammal afflicted with depression, said method comprising administering to the mammal a therapeutically effective amount of the pharmaceutical composition of claim 20.

* * * * *

UNITED STATES PATENT AND TRADEMARK OFFICE
CERTIFICATE OF CORRECTION

PATENT NO. : 7,045,529 B2 Page 1 of 1
APPLICATION NO. : 09/738666
DATED : May 16, 2006
INVENTOR(S) : Richard G. Wilde et al.

It is certified that error appears in the above-identified patent and that said Letters Patent is hereby corrected as shown below:

On the cover page, item [54]

The title should read:   Imidazopyrimidinyl and Imidazopyridinyl Derivatives and Cover page, item (73)  Assignee should read:  Bristol-Myers Squibb Pharma Company Signed and Sealed this Ninth Day of January, 2007

JON W. DUDAS
*Director of the United States Patent and Trademark Office*